US009303266B2

(12) United States Patent
Flasinski

(10) Patent No.: US 9,303,266 B2
(45) Date of Patent: Apr. 5, 2016

(54) PLANT REGULATORY ELEMENTS AND USES THEREOF

(71) Applicant: Monsanto Technology LLC, St. Louis, MO (US)

(72) Inventor: Stanislaw Flasinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 22 days.

(21) Appl. No.: 14/133,599

(22) Filed: Dec. 18, 2013

(65) Prior Publication Data

US 2014/0189909 A1 Jul. 3, 2014

Related U.S. Application Data

(60) Provisional application No. 61/739,720, filed on Dec. 19, 2012.

(51) Int. Cl.
*C12N 15/82* (2006.01)

(52) U.S. Cl.
CPC .................................. *C12N 15/8216* (2013.01)

(58) Field of Classification Search
None
See application file for complete search history.

(56) References Cited

U.S. PATENT DOCUMENTS

| | | | | |
|---|---|---|---|---|
| 5,510,474 | A * | 4/1996 | Quail et al. | 536/24.1 |
| 6,054,574 | A | 4/2000 | Quail et al. | |
| 7,371,848 | B2 * | 5/2008 | Conner et al. | 536/24.1 |
| 8,168,859 | B2 | 5/2012 | Abbitt | |
| 2007/0061917 | A1 | 3/2007 | McCutchen et al. | |
| 2009/0138985 | A1 | 5/2009 | Martinell et al. | |
| 2010/0058495 | A1 * | 3/2010 | Abbitt | 800/278 |
| 2011/0023183 | A1 | 1/2011 | Stewart et al. | |
| 2012/0198584 | A1 | 8/2012 | Nuccio | |
| 2012/0246763 | A1 | 9/2012 | Flasinski | |

FOREIGN PATENT DOCUMENTS

| | | | |
|---|---|---|---|
| WO | WO 89/12059 | A1 | 12/1989 |
| WO | WO 98/44781 | A1 | 10/1998 |
| WO | WO 01/94394 | A2 | 12/2001 |
| WO | WO 2009/149304 | A2 | 10/2009 |
| WO | WO 2012/158535 | A1 | 11/2012 |

OTHER PUBLICATIONS

Donald & Cashmore, EMBO J 9:1717-26 (1990).*
Kim et al., Plant Mol Biol 24:105-17 (1994).*
Dolferus et al., Plant Physiol 105:1075-87 (1994).*
Potenza et al., In Vitro Cell Dev Biol Plant 40:1-22 (2004).*
Callis et al., Genes Dev 1:1183-200 (1987).*
Christensen & Quail, Transgen Res 5:213-18 (1996).*
Benfey et al., "The CaMV 35S enhancer contains at least two domains which can confer different developmental and tissue-specific expression patterns," *EMBO J.*, 8(8):2195-2202, 1989.
Callis et al., "Introns increase gene expression in cultured maize cells," *Genes & Dev.* 1:1183-1200, 1987.
Cho et al., "Regulation of root-hair initiation and expansin gene expression in arabidopsis," *The Plant Cell*, 14:3237-3253, 2002.
Christiansen et al., "Maize polyubiquitin genes: structure, thermal perturbation of expression and transcript splicing, and promoter activity following transfer to protoplasts by electroporation," *Plant Mol. Biol*, 18:675-689, 1992.
Jeon et al., "Tissue-Preferential Expression of a Rice a-Tubulin Gene, OsTubA1, Mediated by the First Intron," *Plant Physiol.* 123:1005-1014, 2000.
Kim et al., "A 20 nucleotide upstream element is essential for the nopaline synthase (nos) promoter activity," *Plant Mol. Biol.*, 24:105-117, 1994.
Mascarenhas et al., "Intron-mediated enhancement of heterologous gene expression in maize," *Plant Mol. Biol* 15:913-920, 1990.
Odell et al., "Identification of DNA sequences required for activity of the cauliflower mosaic virus 35S promoter," *Nature*, 313:810-812, 1985.
Piechulla et al., "Identification of tomato Lhc promoter regions necessary for circadian expression," *Plant Mol. Biol.*, 38:655-662, 1998.
Vasil et al., "Increased Gene Expression by the First Intron of Maize Shrunken-1 Locus in Grass Species," *Plant Physiol.* 91:1575-1579, 1989.
Welsch et al., "Structural and functional characterization of the phytoene synthase promoter from arabidopsis thaliana," *Planta*, 216:523-534, 2003.
International Search Report and Written Opinion for International Application No. PCT/US2013/075813, dated Jun. 10, 2014.

* cited by examiner

*Primary Examiner* — David H Kruse
*Assistant Examiner* — Russell Boggs
(74) *Attorney, Agent, or Firm* — Dentons US LLP; Carine M. Doyle, Esq.

(57) ABSTRACT

The invention provides novel recombinant DNA molecules and constructs useful for modulating gene expression in plants, plant cells, seeds, and progeny plants. The invention also provides transgenic plants, plant cells, plant parts, seeds, and progeny plants comprising the recombinant DNA molecules of the invention, along with methods of their use.

18 Claims, 9 Drawing Sheets

P-AGRne.Ubq1-1:1:5
(SEQ ID NO: 2; 2005bp)

P-AGRne.Ubq1-1:1:4
(SEQ ID NO: 6; 999 bp)

P-AGRne.Ubq1-1:1:6
(SEQ ID NO: 8; 752 bp)

P-ARUdo.Ubq2-1:1:4
(SEQ ID NO: 24; 2033 bp)

P-ARUdo.Ubq2-1:1:6
(SEQ ID NO: 28; 2004 bp)

P-ARUdo.Ubq2-1:1:5
(SEQ ID NO: 31; 1001 bp)

P-ARUdo.Ubq2-1:1:7
(SEQ ID NO: 33; 695 bp)

▬▬▬▬▬▬▬▬▬▬▬▬ P-BOUgr.Ubq1-1:1:2
(SEQ ID NO: 35; 2371 bp)

▬▬▬▬▬▬▬▬▬ P-BOUgr.Ubq1-1:1:3
(SEQ ID NO: 39; 1999 bp)

▬▬▬▬ P-BOUgr.Ubq1-1:1:5
(SEQ ID NO: 42; 1022 bp)

▬▬▬ P-BOUgr.Ubq1-1:1:6
(SEQ ID NO: 44; 760 bp)

P-BOUgr.Ubq2-1:1:4
(SEQ ID NO: 46; 2100 bp)

P-BOUgr.Ubq2-1:1:7
(SEQ ID NO: 50; 2043 bp)

P-BOUgr.Ubq2-1:1:5
(SEQ ID NO: 53; 2002 bp)

P-BOUgr.Ubq2-1:1:6
(SEQ ID NO: 56; 1024 bp)

P-BOUgr.Ubq2-1:1:8
(SEQ ID NO: 61; 749 bp)

P-MISsi.Ubq1-1:1:2
(SEQ ID NO: 63; 5359bp)

P-MISsi.Ubq1-1:1:11
(SEQ ID NO: 67; 2423bp)

P-MISsi.Ubq1-1:1:10
(SEQ ID NO: 71; 1447bp)

P-MISsi.Ubq1-1:1:13
(SEQ ID NO: 73; 899bp)

P-MISsi.Ubq1-1:1:14
(SEQ ID NO: 75; 691bp)

P-MISsi.Ubq1-1:1:9
(SEQ ID NO: 77; 506bp)

P-SCHsc.Ubq1-1:1:12
(SEQ ID NO: 79; 2831 bp)

P-SCHsc.Ubq1-1:1:11
(SEQ ID NO: 83; 2033 bp)

P-SCHsc.Ubq1-1:1:10
(SEQ ID NO: 85; 1046 bp)

P-SCHsc.Ubq1-1:1:14
(SEQ ID NO: 87; 547 bp)

P-SORnu.Ubq1-1:1:4
(SEQ ID NO: 89; 2218 bp)

P-SORnu.Ubq1-1:1:5
(SEQ ID NO: 93; 1964 bp)

P-SORnu.Ubq1-1:1:6
(SEQ ID NO: 96; 1023 bp)

P-SORnu.Ubq1-1:1:7
(SEQ ID NO: 98; 724 bp)

Expression Cassette Configuration 1

Promoter
or
chimeric
promoter    Leader   Intron    Coding Region   3' UTR
    [A]       [B]     [C]          [D]          [E]

Expression Cassette Configuration 2

Promoter
or
chimeric
promoter   Leader   Intron   Leader   Coding Region   3' UTR
   [F]      [G]     [H]       [I]          [J]         [K]

Expression Cassette Configuration 3

Promoter
or
chimeric              Coding                              3'
promoter   Leader    Region    Intron   Coding Region   UTR
   [L]      [M]       [N]       [O]          [P]         [Q]

PLANT REGULATORY ELEMENTS AND USES THEREOF

REFERENCE TO RELATED APPLICATIONS

This application claims the benefit of U.S. provisional application Ser. No. 61/739,720, filed Dec. 19, 2012, which is incorporated by reference herein in its entirety.

INCORPORATION OF SEQUENCE LISTING

The sequence listing that is contained in the file named "MONS323USseq-corrected.txt", which is 352,256 bytes (as measured in Microsoft Windows®) and was created on Mar. 6, 2014, is filed herewith by electronic submission and is incorporated by reference herein.

FIELD OF THE INVENTION

The invention relates to the field of plant molecular biology, plant genetic engineering, and DNA molecules useful for modulating gene expression in plants.

BACKGROUND

Regulatory elements are genetic elements that regulate gene activity by modulating the transcription of an operably linked transcribable DNA molecule. Such elements include promoters, leaders, enhancers, introns, and 3' untranslated regions, and are useful in the field of plant molecular biology and plant genetic engineering.

SUMMARY OF THE INVENTION

The invention provides novel regulatory elements for use in plants and constructs comprising the regulatory elements. The invention also provides transgenic plant cells, plants, plant parts, and seeds comprising the regulatory elements. In one embodiment, the invention provides the regulatory elements disclosed herein operably linked to a transcribable DNA molecule. In certain embodiments, the transcribable DNA molecule is heterologous with respect to a regulatory element sequence provided herein. Also provided herein are methods for making and using the regulatory elements disclosed herein, including constructs comprising the regulatory elements, and transgenic plants, plant cells, plant parts, and seeds comprising the regulatory elements operably linked to a transcribable DNA molecule that is heterologous with respect to the regulatory element.

Thus, in one aspect, the invention provides a recombinant DNA molecule comprising a DNA sequence selected from the group consisting of: a) a DNA sequence with at least about 85 percent sequence identity to any of SEQ ID NOs: 1-98 and 168-171; b) a DNA sequence comprising any of SEQ ID NOs: 1-98 and 168-171; and c) a fragment of any of SEQ ID NOs: 1-98 and 168-171, wherein the fragment has gene-regulatory activity; wherein the DNA sequence is operably linked to a heterologous transcribable DNA molecule. By "heterologous transcribable DNA molecule," it is meant that the transcribable DNA molecule is heterologous with respect to the DNA sequence. In specific embodiments, the recombinant DNA molecule comprises a DNA sequence having at least 90 percent, at least 91 percent, at least 92 percent, at least 93 percent, at least 94 percent, at least about 95 percent, at least 96 percent, at least 97 percent, at least 98 percent, or at least 99 percent sequence identity to the DNA sequence of any of SEQ ID NOs: 1-98 and 168-171. In particular embodiments, the heterologous transcribable DNA molecule comprises a gene of agronomic interest, such as a gene capable of conferring herbicide resistance or pest resistance in plants. In still other embodiments, the invention provides a construct comprising a recombinant DNA molecule as provided herein.

In another aspect, provided herein are transgenic plant cells comprising a recombinant DNA molecule comprising a DNA sequence selected from the group consisting of: a) a DNA sequence with at least about 85 percent sequence identity to any of SEQ ID NOs: 1-98 and 168-171; b) a DNA sequence comprising any of SEQ ID NOs: 1-98 and 168-171; and c) a fragment of any of SEQ ID NOs: 1-98 and 168-171, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a dicotyledonous plant cell.

In still yet another aspect, further provided herein is a transgenic plant, or part thereof, comprising a recombinant DNA molecule comprising a DNA sequence selected from the group consisting of: a) a DNA sequence with at least about 85 percent sequence identity to any of SEQ ID NOs: 1-98 and 168-171; b) a DNA sequence comprising any of SEQ ID NOs: 1-98 and 168-171; and c) a fragment of any of SEQ ID NOs: 1-98 and 168-171, wherein the fragment has gene-regulatory activity; wherein the DNA sequence is operably linked to a heterologous transcribable DNA molecule. In specific embodiments, the transgenic plant is a progeny plant of any generation relative to a starting transgenic plant and comprises the recombinant DNA molecule. A transgenic seed comprising the recombinant DNA molecule that produces such a transgenic plant when grown is also provided by the invention.

In still yet another aspect, the invention provides a method of expressing a transcribable DNA molecule, such as a gene of agronomic interest, in a transgenic plant by obtaining a transgenic plant containing a recombinant DNA molecule of the invention and cultivating the plant.

Also provided herein is a method of providing a transgenic plant by transforming a plant cell with a recombinant DNA molecule of the invention to produce a transformed plant cell, and regenerating the transformed plant cell to produce a transgenic plant.

BRIEF DESCRIPTION OF THE FIGURES

FIG. 1 shows an alignment of a 2005 base pair (bp) promoter P-AGRne.Ubq1-1:1:5 (SEQ ID NO: 2), contained in the regulatory expression element group (EXP) EXP-AGRne.Ubq1:1:7 (SEQ ID NO: 1), with promoter variants of P-AGRne.Ubq1-1:1:5. Deletion, for instance of the 5' end of P-AGRne.Ubq1-1:1:5, produced the promoter P-AGRne.Ubq1-1:1:4 (SEQ ID NO: 6), a 999 bp sequence that is contained in EXP-AGRne.Ubq1:1:8 (SEQ ID NO: 5). Another promoter variant shown in FIG. 1 is P-AGRne.Ubq1-1:1:6 (SEQ ID NO: 8), a 762 bp sequence contained in EXP-AGRne.Ubq1:1:9 (SEQ ID NO: 7).

FIG. 2 shows an alignment of a 4114 bp promoter P-ARUdo.Ubq1-1:1:4 (SEQ ID NO: 10), contained in the regulatory expression element group EXP-ARUdo.Ubq1:1:4 (SEQ ID NO: 9), with promoter variants of P-ARUdo.Ubq1-1:1:4. Included in the alignment are a 2012 bp promoter P-ARUdo.Ubq1-1:1:5 (SEQ ID NO: 14); a 1000 bp promoter P-ARUdo.Ubq1-1:1:6 (SEQ ID NO: 17); and a 755 bp promoter P-ARUdo.Ubq1-1:1:8 (SEQ ID NO: 22).

Figure 1:
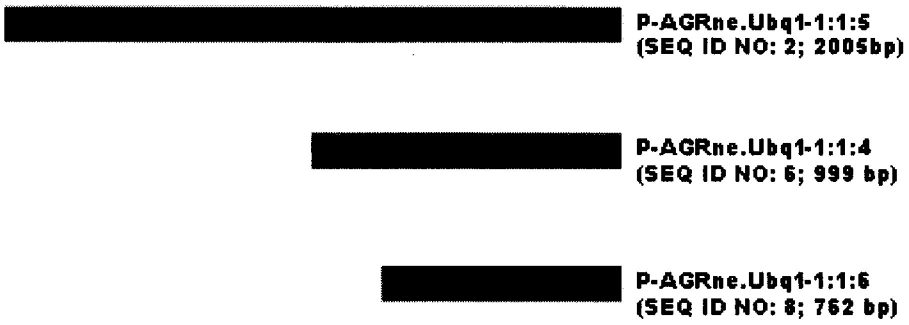
FIG. 1: Shows an alignment of multiple promoter variants of various sizes corresponding to promoter elements from *Agrostis nebulosa*. In particular.
Figure 2:
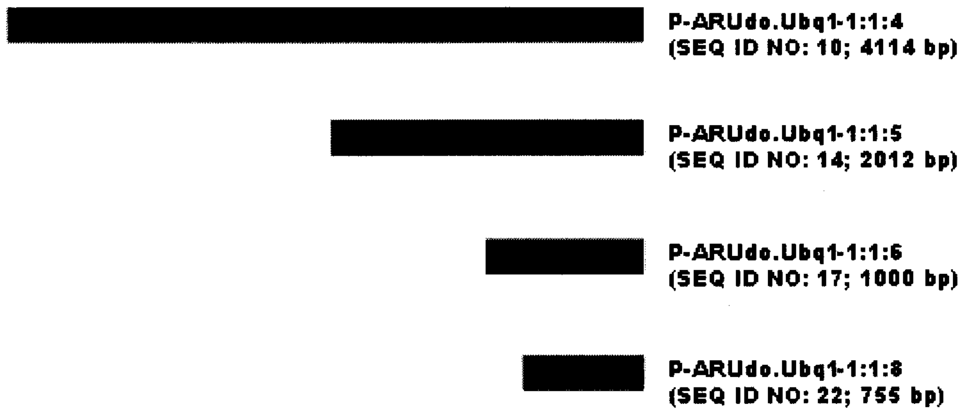
FIG. 2: Shows an alignment of multiple promoter variants of various sizes corresponding to promoter elements from *Arundo donax*. In particular.
Figure 3:
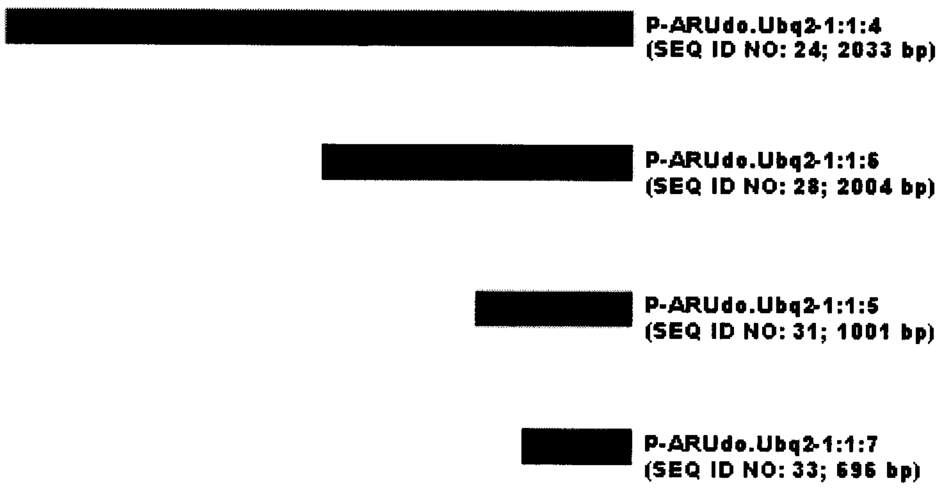

FIG. 3: Shows an alignment of multiple promoter variants of various sizes corresponding to promoter elements from *Arundo donax*. In particular, FIG. 3 shows an alignment of a 2033 bp promoter P-ARUdo.Ubq2-1:1:4 (SEQ ID NO: 24) with promoter variants of P-ARUdo.Ubq2-1:1:4. Included in the alignment are a 2004 bp promoter P-ARUdo.Ubq2-1:1:6 (SEQ ID NO: 28); a 1001 bp promoter P-ARUdo.Ubq2-1:1:5 (SEQ ID NO: 31); and a 696 bp promoter P-ARUdo.Ubq2-1:1:7 (SEQ ID NO: 33).

Figure 4:
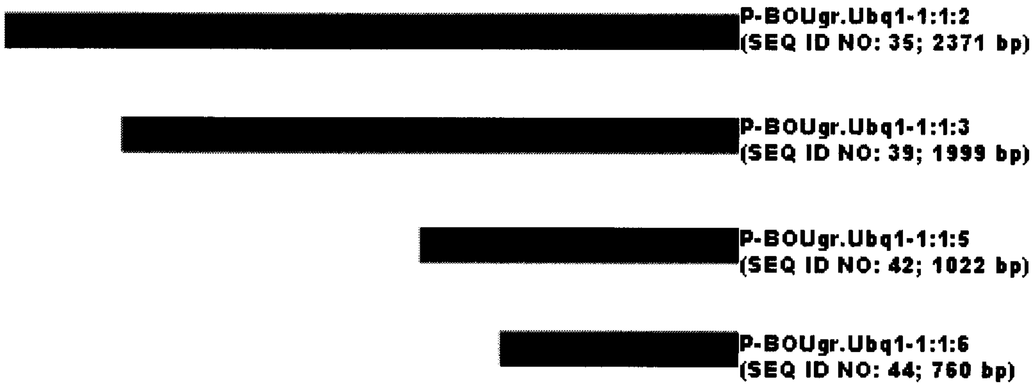

FIG. 4: Shows an alignment of multiple promoter variants of various sizes corresponding to promoter elements from *Bouteloua gracilis*. In particular, FIG. 4 shows an alignment of a 2371 bp promoter P-BOUgr.Ubq1-1:1:2 (SEQ ID NO: 35) with promoter variants of the 5' end of P-BOUgr.Ubq1-1:1:2. Included in the alignment are a 1999 bp promoter P-BOUgr.Ubq1-1:1:3 (SEQ ID NO: 39); a 1022 bp promoter P-BOUgr.Ubq1-1:1:5 (SEQ ID NO: 42); and a 760 bp promoter P-BOUgr.Ubq1-1:1:6 (SEQ ID NO: 44).

Figure 5:
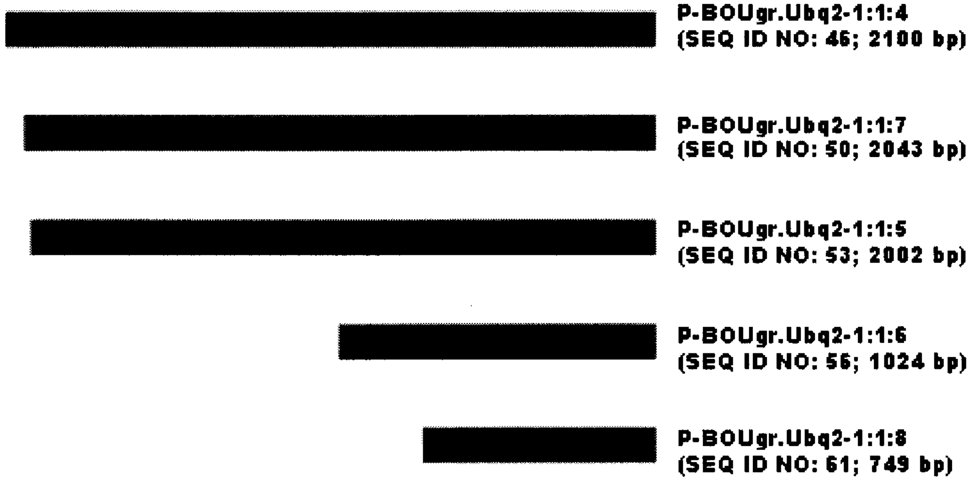

FIG. 5: Shows an alignment of multiple promoter variants of various sizes corresponding to promoter elements from *Bouteloua gracilis*. In particular, FIG. 5 shows alignment of a 2100 bp promoter element, P-BOUgr.Ubq2-1:1:4 (SEQ ID NO: 46) with promoter variants of P-BOUgr.Ubq2-1:1:4. Included in the alignment are a 2043 bp promoter P-BOUgr.Ubq2-1:1:7 (SEQ ID NO: 50); a 2002 bp promoter P-BOUgr.Ubq2-1:1:5 (SEQ ID NO: 53); a 1024 bp promoter P-BOUgr.Ubq2-1:1:6 (SEQ ID NO: 56); and a 749 bp promoter P-BOUgr.Ubq2-1:1:8 (SEQ ID NO: 61).

Figure 6:
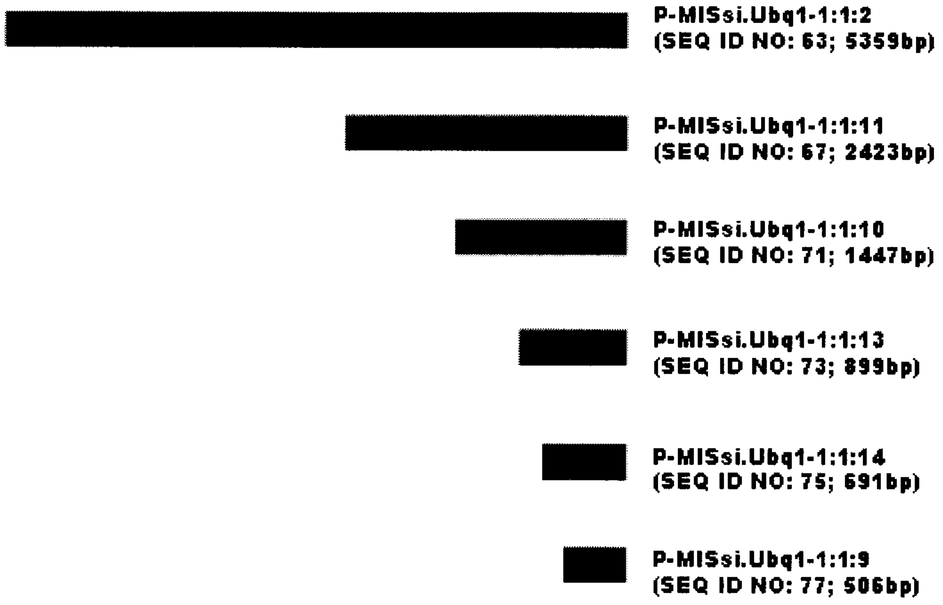

FIG. 6: Shows an alignment of multiple promoter variants of various sizes corresponding to promoter elements from *Miscanthus sinesis*. In particular, FIG. 6 shows an alignment of a 5359 bp promoter element, P-MISsi.Ubq1-1:1:2 (SEQ ID NO: 63) with promoter variants of P-MISsi.Ubq1-1:1:2. Included in the alignment are a 2423 bp promoter P-MISsi.Ubq1-1:1:11 (SEQ ID NO: 67); a 1447 bp promoter P-MISsi.Ubq1-1:1:10 (SEQ ID NO: 71); a 899 bp promoter P-MISsi.Ubq1-1:1:13 (SEQ ID NO: 73); a 691 bp promoter P-MISsi.Ubq1-1:1:14 (SEQ ID NO: 75); and a 506 bp promoter P-MISsi.Ubq1-1:1:9 (SEQ ID NO: 77).

Figure 7:
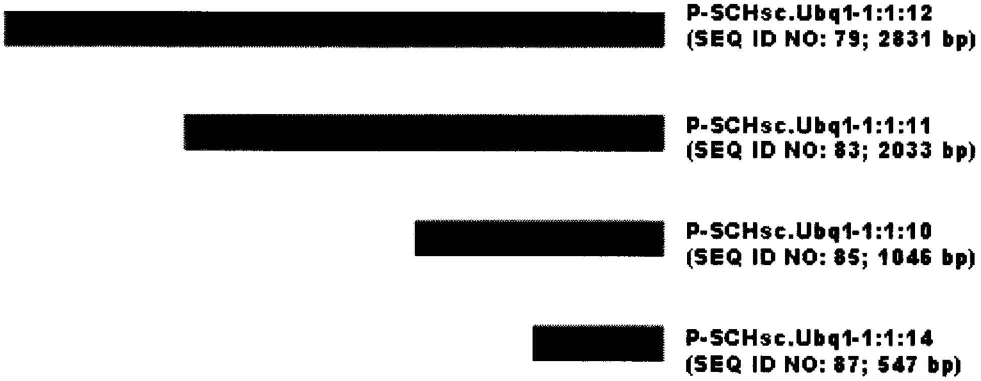

FIG. 7: Shows an alignment of multiple promoter variants of various sizes corresponding to promoter elements from *Schizachyium scoparium*. In particular, FIG. 7 shows an alignment of a 2831 bp promoter element, P-SCHsc.Ubq1-1:1:12 (SEQ ID NO: 79) with promoter variants of P-SCHsc.Ubq1-1:1:12. Included in the alignment are a 2033 bp promoter P-SCHsc.Ubq1-1:1:11 (SEQ ID NO: 83); a 1046 bp promoter P-SCHsc.Ubq1-1:1:10 (SEQ ID NO: 85); and a 547 bp promoter P-SCHsc.Ubq1-1:1:14 (SEQ ID NO: 87).

Figure 8:
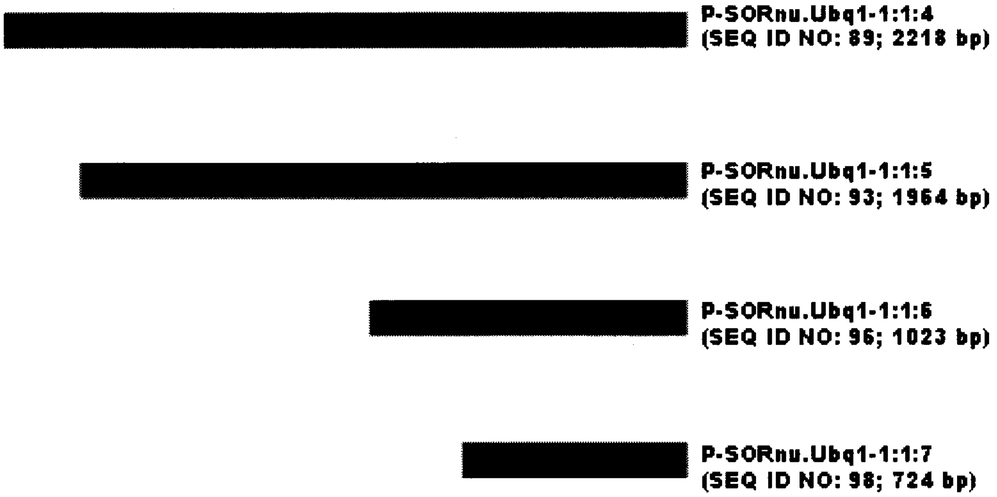

FIG. 8: Shows an alignment of multiple promoter variants of various sizes corresponding to promoter elements from *Sorghastrum nutans*. In particular, FIG. 8 shows an alignment of a 2218 bp promoter element, P-SORnu.Ubq1-1:1:4 (SEQ ID NO: 89) with promoter variants of P-SORnu.Ubq1-1:1:4. Included in the alignment are a 1964 bp promoter P-SORnu.Ubq1-1:1:5 (SEQ ID NO: 93); a 1023 bp promoter P-SORnu.Ubq1-1:1:6 (SEQ ID NO: 96); and a 724 bp promoter P—SORnu.Ubq1-1:1:7 (SEQ ID NO: 98).

Figure 9:
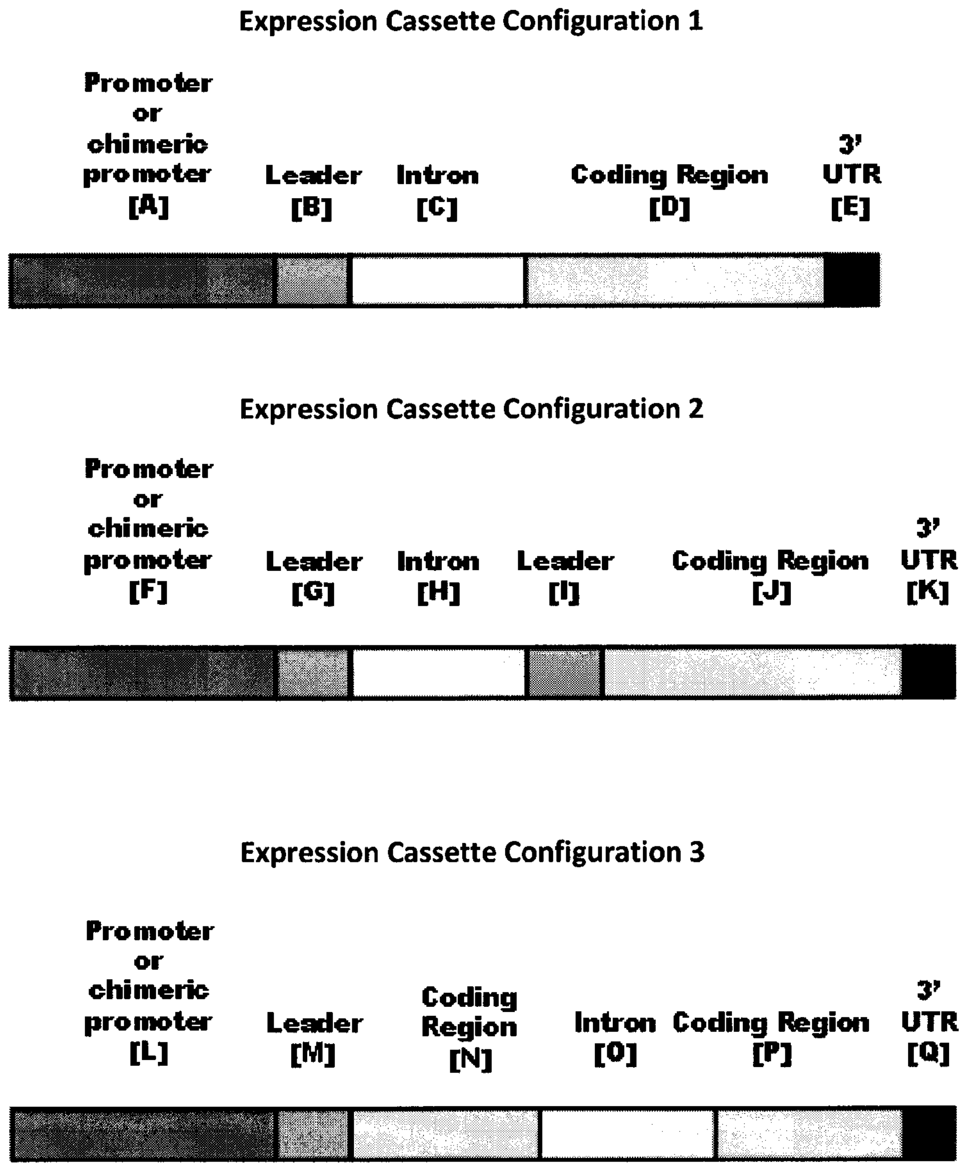

FIG. 9: Shows expression cassette configurations of the invention.

BRIEF DESCRIPTION OF THE SEQUENCES

SEQ ID NOs: 1, 5, 7, 9, 13, 16, 18, 19, 21, 23, 27, 30, 32, 34, 38, 41, 43, 45, 49, 52, 55, 58, 60, 62, 66, 70, 72, 74, 76, 78, 82, 84, 86, 88, 92, 95, 97, 99, 103, 106, 108, 110, 114, 116, 118, 120, 122, 126, 128, 132, 134, 138, 140, 144, 148, 150 and 168 are DNA sequences of regulatory expression element groups (EXPs) comprising a promoter sequence operably linked 5' to a leader sequence which is operably linked 5' to an intron sequence.

SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98, 100, 104, 107, 109, 111, 117, 119, 121, 123, 129, 135, 141, 145, 151 and 169 are promoter sequences.

SEQ ID NOs: 3, 11, 25, 36, 47, 64, 68, 80, 90, 101, 112, 124, 130, 136, 142, 146, 152 and 170 are leader sequences.

SEQ ID NOs: 4, 12, 15, 20, 26, 29, 37, 40, 48, 51, 54, 57, 59, 65, 69, 81, 91, 94, 102, 105, 113, 115, 125, 127, 131, 133, 137, 139, 143, 147, 149, 153 and 171 are intron sequences.

DETAILED DESCRIPTION OF THE INVENTION

The invention provides DNA molecules having gene-regulatory activity in plants. The nucleotide sequences of these DNA molecules are provided as SEQ ID NOs: 1-98 and 168-171. These DNA molecules are, for instance, capable of affecting the expression of an operably linked transcribable DNA molecule in plant tissues, and therefore regulating gene expression of an operably linked transgene in transgenic plants. The invention also provides methods of modifying, producing, and using the same. The invention also provides compositions that include transgenic plant cells, plants, plant parts, and seeds containing recombinant DNA molecules of the invention, and methods for preparing and using the same.

The following definitions and methods are provided to better define the invention and to guide those of ordinary skill in the art in the practice of the invention. Unless otherwise noted, terms are to be understood according to conventional usage by those of ordinary skill in the relevant art.

DNA Molecules

As used herein, the term "DNA" or "DNA molecule" refers to a double-stranded DNA molecule of cellular or synthetic origin, i.e., a polymer of deoxyribonucleotide bases. As used herein, the term "DNA sequence" refers to the nucleotide sequence of a DNA molecule. The nomenclature used herein corresponds to that of by Title 37 of the United States Code of Federal Regulations §1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation.

As used herein, the term "sequence identity" refers to the extent to which two optimally aligned DNA sequences are identical. An optimal sequence alignment is created by manually aligning two DNA sequences, e.g., a reference sequence and another DNA sequence, to maximize the number of nucleotide matches in the sequence alignment with appropriate internal nucleotide insertions, deletions, or gaps. As used herein, the term "reference sequence" refers to a DNA sequence provided as SEQ ID NOs: 1-98 and 168-171.

As used herein, the term "percent sequence identity" or "percent identity" or "% identity" is the identity fraction multiplied by 100. The "identity fraction" for a DNA sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a DNA sequence that when optimally aligned to a reference sequence, provided herein as SEQ ID NOs: 1-98 and 168-171, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence.

Regulatory Elements

Regulatory elements such as promoters, leaders, enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, and introns that function in plants are therefore useful for modifying plant phenotypes through genetic engineering.

As used herein, a "regulatory expression element group" or "EXP" sequence may refer to a group of operably linked regulatory elements, such as enhancers, promoters, leaders, and introns. Thus, a regulatory expression element group may be comprised, for instance, of a promoter operably linked 5' to a leader sequence, which is in turn operably linked 5' to an intron sequence.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may originate from the 5' untranslated region (5' UTR) of a gene. Alternately, promoters may be synthetically produced or manipulated DNA molecules. Promoters may also be chimeric. Chimeric promoters are produced through the fusion of two or more heterologous DNA molecules. Promoters useful in practicing the invention include SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169, including fragments or variants thereof. In specific embodiments of the invention, such DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

In one embodiment, fragments are provided of a promoter sequence disclosed herein. Promoter fragments may comprise promoter activity, as described above, and may be useful alone or in combination with other promoters and promoter fragments, such as in constructing chimeric promoters. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. Methods for producing such fragments from a starting promoter molecule are well known in the art.

Compositions derived from any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169, such as internal or 5' deletions, for example, can be produced using well known methods in the art to improve or alter expression, including by removing elements that have either positive or negative effects on expression; duplicating elements that have positive or negative effects on expression; and/or duplicating or removing elements that have tissue- or cell-specific effects on expression. Compositions derived from any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169 comprised of 3' deletions in which the TATA box element or equivalent DNA sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169 and fragments or enhancers derived therefrom can be used to make chimeric regulatory element compositions comprised of any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169 and the fragments or enhancers derived therefrom operably linked to other enhancers and promoters.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule from the untranslated 5' region (5' UTR) of a gene and defined generally as a DNA segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Promoter molecules of the invention may thus be operably linked to their native leader or may be operably linked to a heterologous leader. Leaders useful in practicing the invention include SEQ ID NOs: 3, 11, 25, 36, 47, 64, 68, 80, 90 and 170 or fragments or variants thereof. In specific embodiments, such DNA sequences may be defined as being capable of acting as a leader in a host cell, including, for example, a transgenic plant cell. In one embodiment, such DNA sequences may be decoded as comprising leader activity.

The leader sequences (5' UTR) presented as SEQ ID NOs: 3, 11, 25, 36, 47, 64, 68, 80, 90 and 170 may be comprised of regulatory elements or may adopt secondary structures that can have an effect on transcription or translation of an operably linked DNA molecule. The leader sequences presented as SEQ ID NOs: 3, 11, 25, 36, 47, 64, 68, 80, 90 and 170 can be used in accordance with the invention to make chimeric regulatory elements that affect transcription or translation of an operably linked DNA molecule. In addition, the leader sequences presented as SEQ ID NOs: 3, 11, 25, 36, 47, 64, 68, 80, 90 and 170 can be used to make chimeric leader sequences that affect transcription or translation of an operably linked DNA molecule.

As used herein, the term "intron" refers to a DNA molecule that may be isolated or identified from the genomic copy of a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from petunia (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, that splicing per se is not required, as IME in dicotyledonous plants has been shown by point mutations within the splice sites of the pat1 gene from *A. thaliana*. Multiple uses of the same intron in one plant has been shown to exhibit disadvantages. In those cases, it is necessary to have a collection of basic control elements for the construction of appropriate recombinant DNA elements.

Introns useful in practicing the invention include SEQ ID NOs: 4, 12, 15, 20, 26, 29, 37, 40, 48, 51, 54, 57, 59, 65, 69, 81, 91, 94 and 171. Compositions derived from any of the introns presented as SEQ ID NOs: 4, 12, 15, 20, 26, 29, 37, 40, 48, 51, 54, 57, 59, 65, 69, 81, 91, 94 and 171 can be comprised of internal deletions or duplications of cis regulatory elements; and/or alterations of the 5' and 3' DNA sequences comprising the intron/exon splice junctions can be used to improve expression or specificity of expression when operably linked to a promoter+leader or chimeric promoter+ leader and coding sequence. When modifying intron/exon boundary sequences, it may be beneficial to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The DNA sequence around the 5' or 3' end splice junction sites of the intron can thus be modified in this manner. Introns and intron variants altered as described herein and through methods known in the art, can be tested empirically as described in the working examples to determine an intron's effect on expression of an operably linked DNA molecule.

As used herein, the term "3' transcription termination molecule," "3' untranslated region" or "3' UTR" herein refers to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR.

From a practical standpoint, it is typically beneficial that a 3' UTR used in an expression cassette possesses the following characteristics. The 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. The 3'

UTR should not cause a reduction in the transcriptional activity imparted by the promoter, leader, enhancers, and introns that are used to drive expression of the DNA molecule. In plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

As used herein, the term "enhancer" or "enhancer element" refers to a cis-acting regulatory element, a.k.a. cis-element, which confers an aspect of the overall expression pattern, but is usually insufficient alone to drive transcription, of an operably linked DNA sequence. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated polymerase chain reaction (PCR), and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention.

As used herein, the term "chimeric" refers to a single DNA molecule produced by fusing a first DNA molecule to a second DNA molecule, where neither the first nor the second DNA molecule would normally be contained in that configuration, i.e., fused to the other. The chimeric DNA molecule is thus a new DNA molecule not otherwise normally contained in nature. As used herein, the term "chimeric promoter" refers to a promoter produced through such manipulation of DNA molecules. A chimeric promoter may combine two or more DNA fragments, for example, the fusion of a promoter to an enhancer element. Thus, the design, construction, and use of chimeric promoters according to the methods disclosed herein for modulating the expression of operably linked transcribable DNA molecules are encompassed by the invention.

As used herein, the term "variant" refers to a second DNA molecule, such as a regulatory element, that is similar in composition, but not identical to, a first DNA molecule, and wherein the second DNA molecule still maintains the general functionality, i.e., same or similar expression pattern, for instance through more or less or equivalent transcriptional or translational activity, of the first DNA molecule. A variant may be a shortened or truncated version of the first DNA molecule and/or an altered version of the DNA sequence of the first DNA molecule, such as one with different restriction enzyme sites and/or internal deletions, substitutions, and/or insertions. Regulatory element "variants" also encompass variants arising from mutations that occur during or as a result of bacterial and plant cell transformation. In the invention, a DNA sequence provided as SEQ ID NOs: 1-98 and 168-171 may be used to create variants that are similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, a DNA sequence provided as SEQ ID NOs: 1-98 and 168-171 may provide a regulatory element reference sequence, wherein the constituent elements that comprise the reference sequence may be joined by methods known in the art and may comprise substitutions, deletions, and/or insertions of one or more nucleotides or mutations that naturally occur in bacterial and plant cell transformation.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* AB1, C58, or LBA4404; however, other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast proteins.

Transcribable DNA Molecules

As used herein, the term "transcribable DNA molecule" refers to any DNA molecule capable of being transcribed into a RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a promoter of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs: 1-98 and 168-

171, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Examples of genes of agronomic interest known in the art include those for herbicide resistance (U.S. Pat. Nos. 6,803, 501; 6,448,476; 6,248,876; 6,225,114; 6,107,549; 5,866,775; 5,804,425; 5,633,435; and 5,463,175), increased yield (U.S. Pat. Nos. USRE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653, 280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013, 864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444, 876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822, 141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171, 640), biopolymers (U.S. Pat. Nos. USRE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689, 041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Expression of a transcribable DNA molecule in a plant cell can also be used to suppress plant pests feeding on the plant cell, for example, compositions isolated from coleopteran pests and compositions isolated from nematode pests. Plant pests include, but are not limited to, arthropod pests, nematode pests, and fungal or microbial pests.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), green fluorescent protein (GFP), proteins that confer antibiotic resistance, and proteins that confer herbicide tolerance.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also includes progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants, of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, Calif., 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique*, (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of Regulatory Elements

Novel ubiquitin regulatory elements, or regulatory expression element group (EXP) sequences, were identified and isolated from genomic DNA of the monocot Cloud grass (*Agrostis nebulosa*), giant reed (*Arundo donax*), Blue grama (*Bouteloua gracilis*), Chinese silvergrass (*Miscanthus sinesis*), Little bluestem (*Schizachyium scoparium*), Yellow Indiangrass (*Sorghastrum nutans*) and Coix (*Coix lacryma-jobi*).

Ubiquitin 1 transcript sequences were identified from each of the above species. The 5' untranslated region (5' UTR) of each of the Ubiquitin 1 transcripts was used to design primers to amplify the corresponding regulatory elements for the identified Ubiquitin gene, which comprises a promoter, leader (5' UTR), and first intron operably linked. The primers were used with GenomeWalker™ (Clontech Laboratories, Inc, Mountain View, Calif.) libraries constructed following the manufacturer's protocol to clone the 5' region of the corresponding genomic DNA sequence. Ubiquitin regulatory elements were also isolated from the monocots *Setaria italica, Setaria viridis*, and *Zea mays* subsp. *Mexicana* (Teosinte) using GenomeWalker™ libraries as described above. In addition, ubiquitin regulatory elements were isolated from the monocot *Sorghum bicolor* using public sequences that are homologs to the Ubiquitin 4, 6, and 7 genes.

Using the identified sequences, a bioinformatic analysis was conducted to identify regulatory elements within the amplified DNA. Using the results of this analysis, regulatory elements were defined within the DNA sequences and primers designed to amplify the regulatory elements. The corresponding DNA molecule for each regulatory element was amplified using standard polymerase chain reaction (PCR) conditions with primers containing unique restriction enzyme sites and genomic DNA isolated from *A. nebulosa, A donax, B. gracilis, M. sinesis, S. scoparium, S. nutans*, and *C. lacryma-jobi*. The resulting DNA fragments were ligated into base plant expression vectors and sequenced. An analysis of the regulatory element transcription start site (TSS) and intron/exon splice junctions was then done using transformed plant protoplasts. Briefly, the protoplasts were transformed with the plant expression vectors comprising the cloned DNA fragments operably linked to a heterologous transcribable DNA molecule and the 5' RACE System for Rapid Amplification of cDNA Ends, Version 2.0 (Invitrogen, Carlsbad, Calif. 92008) was used to confirm the regulatory element TSS and intron/exon splice junctions by analyzing the sequence of the messenger RNA (mRNA) transcripts produced thereby.

DNA sequences of the identified EXPs are provided herein as SEQ ID NOs: 1, 5, 7, 9, 13, 16, 18, 19, 21, 23, 27, 30, 32, 34, 38, 41, 43, 45, 49, 52, 55, 58, 60, 62, 66, 70, 72, 74, 76, 78, 82, 84, 86, 88, 92, 95, 97, 99, 103, 106, 108, 110, 114, 116, 118, 120, 122, 126, 128, 132, 134, 138, 140, 144, 148, 150 and 168, as listed in Table 1 below. Promoter sequences are provided herein as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98, 100, 104, 107, 109, 111, 117, 119, 121, 123, 129, 135, 141, 145, 151 and 169. Leader sequences are provided herein as SEQ ID NOs: 3, 11, 25, 36, 47, 64, 68, 80, 90, 101, 112, 124, 130, 136, 142, 146, 152 and 170. Intron sequences are provided herein as SEQ ID NOs: 4, 12, 15, 20, 26, 29, 37, 40, 48, 51, 54, 57, 59, 65, 69, 81, 91, 94, 102, 105, 113, 115, 125, 127, 131, 133, 137, 139, 143, 147, 149, 153 and 171.

TABLE 1

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| EXP-AGRne.Ubq1:1:7 | 1 | 3143 | *A. nebulosa* | EXP: P-AGRne.Ubq1-1:1:5 (SEQ ID NO: 2); L-AGRne.Ubq1-1:1:1 (SEQ ID NO: 3); I-AGRne.Ubq1-1:1:3 (SEQ ID NO: 4) |
| P-AGRne.Ubq1-1:1:5 | 2 | 2005 | *A. nebulosa* | Promoter |
| L-AGRne.Ubq1-1:1:1 | 3 | 85 | *A. nebulosa* | Leader |
| I-AGRne.Ubq1-1:1:3 | 4 | 1053 | *A. nebulosa* | Intron |
| EXP-AGRne.Ubq1:1:8 | 5 | 2137 | *A. nebulosa* | EXP: P-AGRne.Ubq1-1:1:4 (SEQ ID NO: 6); L-AGRne.Ubq1-1:1:1 (SEQ ID NO: 3); I-AGRne.Ubq1-1:1:3 (SEQ ID NO: 4) |
| P-AGRne.Ubq1-1:1:4 | 6 | 999 | *A. nebulosa* | Promoter |
| EXP-AGRne.Ubq1:1:9 | 7 | 1900 | *A. nebulosa* | EXP: P-AGRne.Ubq1-1:1:6 (SEQ ID NO: 8); L-AGRne.Ubq1-1:1:1 (SEQ ID NO: 3); I-AGRne.Ubq1-1:1:3 (SEQ ID NO: 4) |
| P-AGRne.Ubq1-1:1:6 | 8 | 762 | *A. nebulosa* | Promoter |
| EXP-ARUdo.Ubq1:1:4 | 9 | 5068 | *A. donax* | EXP: P-ARUdo.Ubq1-1:1:4 (SEQ ID NO: 10); L-ARUdo.Ubq1-1:1:1 (SEQ ID NO: 11); I-ARUdo.Ubq1-1:1:2 (SEQ ID NO: 12) |
| P-ARUdo.Ubq1-1:1:4 | 10 | 4114 | *A. donax* | Promoter |
| L-ARUdo.Ubq1-1:1:1 | 11 | 85 | *A. donax* | Leader |
| I-ARUdo.Ubq1-1:1:2 | 12 | 869 | *A. donax* | Intron |
| EXP-ARUdo.Ubq1:1:8 | 13 | 2969 | *A. donax* | EXP: P-ARUdo.Ubq1-1:1:5 (SEQ ID NO: 14); L-ARUdo.Ubq1-1:1:1 (SEQ ID NO: 11); I-ARUdo.Ubq1-1:1:3 (SEQ ID NO: 15) |
| P-ARUdo.Ubq1-1:1:5 | 14 | 2012 | *A. donax* | Promoter |
| I-ARUdo.Ubq1-1:1:3 | 15 | 872 | *A. donax* | Intron |
| EXP-ARUdo.Ubq1:1:6 | 16 | 1954 | *A. donax* | EXP: P-ARUdo.Ubq1-1:1:6 (SEQ ID NO: 17); L-ARUdo.Ubq1-1:1:1 (SEQ ID NO: 11); I-ARUdo.Ubq1-1:1:2 (SEQ ID NO: 12) |
| P-ARUdo.Ubq1-1:1:6 | 17 | 1000 | *A. donax* | Promoter |
| EXP-ARUdo.Ubq1:1:9 | 18 | 1957 | *A. donax* | EXP: P-ARUdo.Ubq1-1:1:6 (SEQ ID NO: 17); L-ARUdo.Ubq1-1:1:1 (SEQ ID NO: 11); I-ARUdo.Ubq1-1:1:3 (SEQ ID NO: 15) |
| EXP-ARUdo.Ubq1:1:12 | 19 | 1957 | *A. donax* | EXP: P-ARUdo.Ubq1-1:1:6 (SEQ ID NO: 17); L-ARUdo.Ubq1-1:1:1 (SEQ ID NO: 11); I-ARUdo.Ubq1-1:1:4 (SEQ ID NO: 20) |
| I-ARUdo.Ubq1-1:1:4 | 20 | 872 | *A. donax* | Intron |
| EXP-ARUdo.Ubq1:1:11 | 21 | 1712 | *A. donax* | EXP: P-ARUdo.Ubq1-1:1:8 (SEQ ID NO: 22); L-ARUdo.Ubq1-1:1:1 (SEQ ID NO: 11); I-ARUdo.Ubq1-1:1:3 (SEQ ID NO: 15) |
| P-ARUdo.Ubq1-1:1:8 | 22 | 755 | *A. donax* | Promoter |
| EXP-ARUdo.Ubq2:1:4 | 23 | 3276 | *A. donax* | EXP: P-ARUdo.Ubq2-1:1:4 (SEQ ID NO: 24); L-ARUdo.Ubq2-1:1:1 (SEQ ID NO: 25); I-ARUdo.Ubq2-1:1:1 (SEQ ID NO: 26) |
| P-ARUdo.Ubq2-1:1:4 | 24 | 2033 | *A. donax* | Promoter |
| L-ARUdo.Ubq2-1:1:1 | 25 | 88 | *A. donax* | Leader |
| I-ARUdo.Ubq2-1:1:1 | 26 | 1155 | *A. donax* | Intron |
| EXP-ARUdo.Ubq2:1:8 | 27 | 3250 | *A. donax* | EXP: P-ARUdo.Ubq2-1:1:6 (SEQ ID NO: 28); L-ARUdo.Ubq2-1:1:1 (SEQ ID NO: 25); I-ARUdo.Ubq2-1:1:2 (SEQ ID NO: 29) |
| P-ARUdo.Ubq2-1:1:6 | 28 | 2004 | *A. donax* | Promoter |
| I-ARUdo.Ubq2-1:1:2 | 29 | 1158 | *A. donax* | Intron |
| EXP-ARUdo.Ubq2:1:9 | 30 | 2247 | *A. donax* | EXP: P-ARUdo.Ubq2-1:1:5 (SEQ ID NO: 31); L-ARUdo.Ubq2-1:1:1 (SEQ ID NO: 25); I-ARUdo.Ubq2-1:1:2 (SEQ ID NO: 29) |
| P-ARUdo.Ubq2-1:1:5 | 31 | 1001 | *A. donax* | Promoter |
| EXP-ARUdo.Ubq2:1:10 | 32 | 1942 | *A. donax* | EXP: P-ARUdo.Ubq2-1:1:7 (SEQ ID NO: 33); L-ARUdo.Ubq2-1:1:1 (SEQ ID NO: 25); I-ARUdo.Ubq2-1:1:2 (SEQ ID NO: 29) |
| P-ARUdo.Ubq2-1:1:7 | 33 | 696 | *A. donax* | Promoter |
| EXP-BOUgr.Ubq1:1:1 | 34 | 3511 | *B. gracilis* | EXP: P-BOUgr.Ubq1-1:1:2 (SEQ ID NO: 35); L-BOUgr.Ubq1-1:1:1 (SEQ ID NO: 36); I-BOUgr.Ubq1-1:1:2 (SEQ ID NO: 37) |
| P-BOUgr.Ubq1-1:1:2 | 35 | 2371 | *B. gracilis* | Promoter |

TABLE 1-continued

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| L-BOUgr.Ubq1-1:1:1 | 36 | 86 | *B. gracilis* | Leader |
| I-BOUgr.Ubq1-1:1:2 | 37 | 1054 | *B. gracilis* | Intron |
| EXP-BOUgr.Ubq1:1:6 | 38 | 3142 | *B. gracilis* | EXP: P-BOUgr.Ubq1-1:1:3 (SEQ ID NO: 39); L-BOUgr.Ubq1-1:1:1 (SEQ ID NO: 36); I-BOUgr.Ubq1-1:1:3 (SEQ ID NO: 40) |
| P-BOUgr.Ubq1-1:1:3 | 39 | 1999 | *B. gracilis* | Promoter |
| I-BOUgr.Ubq1-1:1:3 | 40 | 1057 | *B. gracilis* | Intron |
| EXP-BOUgr.Ubq1:1:7 | 41 | 2165 | *B. gracilis* | EXP: P-BOUgr.Ubq1-1:1:5 (SEQ ID NO: 42); L-BOUgr.Ubq1-1:1:1 (SEQ ID NO: 36); I-BOUgr.Ubq1-1:1:3 (SEQ ID NO: 40) |
| P-BOUgr.Ubq1-1:1:5 | 42 | 1022 | *B. gracilis* | Promoter |
| EXP-BOUgr.Ubq1:1:8 | 43 | 1903 | *B. gracilis* | EXP: P-BOUgr.Ubq1-1:1:6 (SEQ ID NO: 44); L-BOUgr.Ubq1-1:1:1 (SEQ ID NO: 36); I-BOUgr.Ubq1-1:1:3 (SEQ ID NO: 40) |
| P-BOUgr.Ubq1-1:1:6 | 44 | 760 | *B. gracilis* | Promoter |
| EXP-BOUgr.Ubq2:1:11 | 45 | 3234 | *B. gracilis* | EXP: P-BOUgr.Ubq2-1:1:4 (SEQ ID NO: 46); L-BOUgr.Ubq2-1:1:1 (SEQ ID NO: 47); I-BOUgr.Ubq2-1:1:3 (SEQ ID NO: 48) |
| P-BOUgr.Ubq2-1:1:4 | 46 | 2100 | *B. gracilis* | Promoter |
| L-BOUgr.Ubq2-1:1:1 | 47 | 91 | *B. gracilis* | Leader |
| I-BOUgr.Ubq2-1:1:3 | 48 | 1043 | *B. gracilis* | Intron |
| EXP-BOUgr.Ubq2:1:7 | 49 | 3176 | *B. gracilis* | EXP: P-BOUgr.Ubq2-1:1:7 (SEQ ID NO: 50); L-BOUgr.Ubq2-1:1:1 (SEQ ID NO: 47); I-BOUgr.Ubq2-1:1:1 (SEQ ID NO: 51) |
| P-BOUgr.Ubq2-1:1:7 | 50 | 2043 | *B. gracilis* | Promoter |
| I-BOUgr.Ubq2-1:1:1 | 51 | 1042 | *B. gracilis* | Intron |
| EXP-BOUgr.Ubq2:1:14 | 52 | 3139 | *B. gracilis* | EXP: P-BOUgr.Ubq2-1:1:5 (SEQ ID NO: 53); L-BOUgr.Ubq2-1:1:1 (SEQ ID NO: 47); I-BOUgr.Ubq2-1:1:4 (SEQ ID NO: 54) |
| P-BOUgr.Ubq2-1:1:5 | 53 | 2002 | *B. gracilis* | Promoter |
| I-BOUgr.Ubq2-1:1:4 | 54 | 1046 | *B. gracilis* | Intron |
| EXP-BOUgr.Ubq2:1:15 | 55 | 2160 | *B. gracilis* | EXP: P-BOUgr.Ubq2-1:1:6 (SEQ ID NO: 56); L-BOUgr.Ubq2-1:1:1 (SEQ ID NO: 47); I-BOUgr.Ubq2-1:1:5 (SEQ ID NO: 57) |
| P-BOUgr.Ubq2-1:1:6 | 56 | 1024 | *B. gracilis* | Promoter |
| I-BOUgr.Ubq2-1:1:5 | 57 | 1045 | *B. gracilis* | Intron |
| EXP-BOUgr.Ubq2:1:16 | 58 | 2160 | *B. gracilis* | EXP: P-BOUgr.Ubq2-1:1:6 (SEQ ID NO: 56); L-BOUgr.Ubq2-1:1:1 (SEQ ID NO: 47); I-BOUgr.Ubq2-1:1:6 (SEQ ID NO: 59) |
| I-BOUgr.Ubq2-1:1:6 | 59 | 1045 | *B. gracilis* | Intron |
| EXP-BOUgr.Ubq2:1:17 | 60 | 1885 | *B. gracilis* | EXP: P-BOUgr.Ubq2-1:1:8 (SEQ ID NO: 61); L-BOUgr.Ubq2-1:1:1 (SEQ ID NO: 47); I-BOUgr.Ubq2-1:1:6 (SEQ ID NO: 59) |
| P-BOUgr.Ubq2-1:1:8 | 61 | 749 | *B. gracilis* | Promoter |
| EXP-MISsi.Ubq1:1:2 | 62 | 6813 | *M. sinesis* | EXP: P-MISsi.Ubq1-1:1:2 (SEQ ID NO: 63); L-MISsi.Ubq1-1:1:1 (SEQ ID NO: 64); I-MISsi.Ubq1-1:1:1 (SEQ ID NO: 65) |
| P-MISsi.Ubq1-1:1:2 | 63 | 5359 | *M. sinesis* | Promoter |
| L-MISsi.Ubq1-1:1:1 | 64 | 63 | *M. sinesis* | Leader |
| I-MISsi.Ubq1-1:1:1 | 65 | 1391 | *M. sinesis* | Intron |
| EXP-MISsi.Ubq1:1:9 | 66 | 4402 | *M. sinesis* | EXP: P-MISsi.Ubq1-1:1:11 (SEQ ID NO: 67); L-MISsi.Ubq1-1:1:2 (SEQ ID NO: 68); I-MISsi.Ubq1-1:1:3 (SEQ ID NO: 69) |
| P-MISsi.Ubq1-1:1:11 | 67 | 2423 | *M. sinesis* | Promoter |
| L-MISsi.Ubq1-1:1:2 | 68 | 55 | *M. sinesis* | Leader |
| I-MISsi.Ubq1-1:1:3 | 69 | 1924 | *M. sinesis* | Intron |
| EXP-MISsi.Ubq1:1:8 | 70 | 3426 | *M. sinesis* | EXP: P-MISsi.Ubq1-1:1:10 (SEQ ID NO: 71); L-MISsi.Ubq1-1:1:2 (SEQ ID NO: 68); I-MISsi.Ubq1-1:1:3 (SEQ ID NO: 69) |
| P-MISsi.Ubq1-1:1:10 | 71 | 1447 | *M. sinesis* | Promoter |
| EXP-MISsi.Ubq1:1:10 | 72 | 2878 | *M. sinesis* | EXP: P-MISsi.Ubq1-1:1:13 (SEQ ID NO: 73); L-MISsi.Ubq1-1:1:2 (SEQ ID NO: 68); I-MISsi.Ubq1-1:1:3 (SEQ ID NO: 69) |
| P-MISsi.Ubq1-1:1:13 | 73 | 899 | *M. sinesis* | Promoter |
| EXP-MISsi.Ubq1:1:11 | 74 | 2670 | *M. sinesis* | EXP: P-MISsi.Ubq1-1:1:14 (SEQ ID NO: 75); L-MISsi.Ubq1-1:1:2 (SEQ ID NO: 68); I-MISsi.Ubq1-1:1:3 (SEQ ID NO: 69) |
| P-MISsi.Ubq1-1:1:14 | 75 | 691 | *M. sinesis* | Promoter |
| EXP-MISsi.Ubq1:1:7 | 76 | 2485 | *M. sinesis* | EXP: P-MISsi.Ubq1-1:1:9 (SEQ ID NO: 77); L-MISsi.Ubq1-1:1:2 (SEQ ID NO: 68); I-MISsi.Ubq1-1:1:3 (SEQ ID NO: 69) |
| P-MISsi.Ubq1-1:1:9 | 77 | 506 | *M. sinesis* | Promoter |
| EXP-SCHsc.Ubq1:1:9 | 78 | 4079 | *S. scoparium* | EXP: P-SCHsc.Ubq1-1:1:12 (SEQ ID NO: 79); L-SCHsc.Ubq1-1:1:3 (SEQ ID NO: 80); I-SCHsc.Ubq1-1:1:2 (SEQ ID NO: 81) |
| P-SCHsc.Ubq1-1:1:12 | 79 | 2831 | *S. scoparium* | Promoter |
| L-SCHsc.Ubq1-1:1:3 | 80 | 95 | *S. scoparium* | Leader |
| I-SCHsc.Ubq1-1:1:2 | 81 | 1153 | *S. scoparium* | Intron |
| EXP-SCHsc.Ubq1:1:8 | 82 | 3281 | *S. scoparium* | EXP: P-SCHsc.Ubq1-1:1:11 (SEQ ID NO: 83); L-SCHsc.Ubq1-1:1:3 (SEQ ID NO: 80); I-SCHsc.Ubq1-1:1:2 (SEQ ID NO: 81) |
| P-SCHsc.Ubq1-1:1:11 | 83 | 2033 | *S. scoparium* | Promoter |
| EXP-SCHsc.Ubq1:1:7 | 84 | 2294 | *S. scoparium* | EXP: P-SCHsc.Ubq1-1:1:10 (SEQ ID NO: 85); L-SCHsc.Ubq1-1:1:3 (SEQ ID NO: 80); I-SCHsc.Ubq1-1:1:2 (SEQ ID NO: 81) |
| P-SCHsc.Ubq1-1:1:10 | 85 | 1046 | *S. scoparium* | Promoter |
| EXP-SCHsc.Ubq1:1:10 | 86 | 1795 | *S. scoparium* | EXP: P-SCHsc.Ubq1-1:1:14 (SEQ ID NO: 87); L-SCHsc.Ubq1-1:1:3 (SEQ ID NO: 80); I-SCHsc.Ubq1-1:1:2 (SEQ ID NO: 81) |
| P-SCHsc.Ubq1-1:1:14 | 87 | 547 | *S. scoparium* | Promoter |
| EXP-SORnu.Ubq1:1:2 | 88 | 3357 | *S. nutans* | EXP: P-SORnu.Ubq1-1:1:4 (SEQ ID NO: 89); L-SORnu.Ubq1-1:1:1 (SEQ ID NO: 90); I-SORnu.Ubq1-1:1:1 (SEQ ID NO: 91) |
| P-SORnu.Ubq1-1:1:4 | 89 | 2218 | *S. nutans* | Promoter |

TABLE 1-continued

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| L-SORnu.Ubq1-1:1:1 | 90 | 86 | *S. nutans* | Leader |
| I-SORnu.Ubq1-1:1:1 | 91 | 1053 | *S. nutans* | Intron |
| EXP-SORnu.Ubq1:1:6 | 92 | 3106 | *S. nutans* | EXP: P-SORnu.Ubq1-1:1:5 (SEQ ID NO: 93); L-SORnu.Ubq1-1:1:1 (SEQ ID NO: 90); I-SORnu.Ubq1-1:1:2 (SEQ ID NO: 94) |
| P-SORnu.Ubq1-1:1:5 | 93 | 1964 | *S. nutans* | Promoter |
| I-SORnu.Ubq1-1:1:2 | 94 | 1056 | *S. nutans* | Intron |
| EXP-SORnu.Ubq1:1:7 | 95 | 2165 | *S. nutans* | EXP: P-SORnu.Ubq1-1:1:6 (SEQ ID NO: 96); L-SORnu.Ubq1-1:1:1 (SEQ ID NO: 90); I-SORnu.Ubq1-1:1:2 (SEQ ID NO: 94) |
| P-SORnu.Ubq1-1:1:6 | 96 | 1023 | *S. nutans* | Promoter |
| EXP-SORnu.Ubq1:1:8 | 97 | 1866 | *S. nutans* | EXP: P-SORnu.Ubq1-1:1:7 (SEQ ID NO: 98); L-SORnu.Ubq1-1:1:1 (SEQ ID NO: 90); I-SORnu.Ubq1-1:1:2 (SEQ ID NO: 94) |
| P-SORnu.Ubq1-1:1:7 | 98 | 724 | *S. nutans* | Promoter |
| EXP-SETit.Ubq1:1:10 | 99 | 2625 | *S. italica* | EXP: P-SETit.Ubq1-1:1:4 (SEQ ID NO: 100); L-SETit.Ubq1-1:1:1 (SEQ ID NO: 101); I-SETit.Ubq1-1:1:3 (SEQ ID NO: 102) |
| P-SETit.Ubq1-1:1:4 | 100 | 1492 | *S. italica* | Promoter |
| L-SETit.Ubq1-1:1:1 | 101 | 127 | *S. italica* | Leader |
| I-SETit.Ubq1-1:1:3 | 102 | 1006 | *S. italica* | Intron |
| EXP-SETit.Ubq1:1:5 | 103 | 2625 | *S. italica* | EXP: P-SETit.Ubq1-1:1:1 (SEQ ID NO: 104); L-SETit.Ubq1-1:1:1 (SEQ ID NO: 101); I-SETit.Ubq1-1:1:2 (SEQ ID NO: 105) |
| P-SETit.Ubq1-1:1:1 | 104 | 1492 | *S. italica* | Promoter |
| I-SETit.Ubq1-1:1:2 | 105 | 1006 | *S. italica* | Intron |
| EXP-SETit.Ubq1:1:7 | 106 | 2167 | *S. italica* | EXP: P-SETit.Ubq1-1:1:2 (SEQ ID NO: 107); L-SETit.Ubq1-1:1:1 (SEQ ID NO: 101); I-SETit.Ubq1-1:1:2 (SEQ ID NO: 105) |
| P-SETit.Ubq1-1:1:2 | 107 | 1034 | *S. italica* | Promoter |
| EXP-SETit.Ubq1:1:6 | 108 | 1813 | *S. italica* | EXP: P-SETit.Ubq1-1:1:3 (SEQ ID NO: 109); L-SETit.Ubq1-1:1:1 (SEQ ID NO: 101); I-SETit.Ubq1-1:1:2 (SEQ ID NO: 105) |
| P-SETit.Ubq1-1:1:3 | 109 | 680 | *S. italica* | Promoter |
| EXP-Sv.Ubq1:1:7 | 110 | 2634 | *S. viridis* | EXP: P-Sv.Ubq1-1:1:1 (SEQ ID NO: 111); L-Sv.Ubq1-1:1:2 (SEQ ID NO: 112); I-Sv.Ubq1-1:1:2 (SEQ ID NO: 113) |
| P-Sv.Ubq1-1:1:1 | 111 | 1493 | *S. viridis* | Promoter |
| L-Sv.Ubq1-1:1:2 | 112 | 127 | *S. viridis* | Leader |
| I-Sv.Ubq1-1:1:2 | 113 | 1014 | *S. viridis* | Intron |
| EXP-Sv.Ubq1:1:11 | 114 | 2634 | *S. viridis* | EXP: P-Sv.Ubq1-1:1:1 (SEQ ID NO: 111); L-Sv.Ubq1-1:1:2 (SEQ ID NO: 112); I-Sv.Ubq1-1:1:3 (SEQ ID NO: 115) |
| I-Sv.Ubq1-1:1:3 | 115 | 1014 | *S. viridis* | Intron |
| EXP-Sv.Ubq1:1:8 | 116 | 2176 | *S. viridis* | EXP: P-Sv.Ubq1-1:1:2 (SEQ ID NO: 117); L-Sv.Ubq1-1:1:2 (SEQ ID NO: 112); I-Sv.Ubq1-1:1:2 (SEQ ID NO: 113) |
| P-Sv.Ubq1-1:1:2 | 117 | 1035 | *S. viridis* | Promoter |
| EXP-Sv.Ubq1:1:10 | 118 | 1822 | *S. viridis* | EXP: P-Sv.Ubq1-1:1:4 (SEQ ID NO: 119); L-Sv.Ubq1-1:1:2 (SEQ ID NO: 112); I-Sv.Ubq1-1:1:2 (SEQ ID NO: 113) |
| P-Sv.Ubq1-1:1:4 | 119 | 681 | *S. viridis* | Promoter |
| EXP-Sv.Ubq1:1:12 | 120 | 1822 | *S. viridis* | EXP: P-Sv.Ubq1-1:1:3 (SEQ ID NO: 121); L-Sv.Ubq1-1:1:2 (SEQ ID NO: 112); I-Sv.Ubq1-1:1:3 (SEQ ID NO: 115) |
| P-Sv.Ubq1-1:1:3 | 121 | 681 | *S. viridis* | Promoter |
| EXP-Zm.UbqM1:1:6 (Allele-1) | 122 | 1925 | *Z. mays* subsp. *Mexicana* | EXP: P-Zm.UbqM1-1:1:1 (SEQ ID NO: 123); L-Zm.UbqM1-1:1:1 (SEQ ID NO: 124); I-Zm.UbqM1-1:1:13 (SEQ ID NO: 125) |
| P-Zm.UbqM1-1:1:1 (Allele-1) | 123 | 850 | *Z. mays* subsp. *Mexicana* | Promoter |
| L-Zm.UbqM1-1:1:1 (Allele-1) | 124 | 78 | *Z. mays* subsp. *Mexicana* | Leader |
| I-Zm.UbqM1-1:1:13 (Allele-1) | 125 | 997 | *Z. mays* subsp. *Mexicana* | Intron |
| EXP-Zm.UbqM1:1:10 (Allele-1) | 126 | 1925 | *Z. mays* subsp. *Mexicana* | EXP: P-Zm.UbqM1-1:1:1 (SEQ ID NO: 123); L-Zm.UbqM1-1:1:1 (SEQ ID NO: 124); I-Zm.UbqM1-1:1:17 (SEQ ID NO: 127) |
| I-Zm.UbqM1-1:1:17 (Allele-1) | 127 | 997 | *Z. mays* subsp. *Mexicana* | Intron |
| EXP-Zm.UbqM1:1:7 (Allele-2) | 128 | 1974 | *Z. mays* subsp. *Mexicana* | EXP: P-Zm.UbqM1-1:1:4 (SEQ ID NO: 129); L-Zm.UbqM1-1:1:5 (SEQ ID NO: 130); I-Zm.UbqM1-1:1:14 (SEQ ID NO: 131) |
| P-Zm.UbqM1-1:1:4 (Allele-2) | 129 | 887 | *Z. mays* subsp. *Mexicana* | Promoter |
| L-Zm.UbqM1-1:1:5 (Allele-2) | 130 | 77 | *Z. mays* subsp. *Mexicana* | Leader |
| I-Zm.UbqM1-1:1:14 (Allele-2) | 131 | 1010 | *Z. mays* subsp. *Mexicana* | Intron |
| EXP-Zm.UbqM1:1:12 (Allele-2) | 132 | 1974 | *Z. mays* subsp. *Mexicana* | EXP: P-Zm.UbqM1-1:1:4 (SEQ ID NO: 129); L-Zm.UbqM1-1:1:5 (SEQ ID NO: 130); I-Zm.UbqM1-1:1:19 (SEQ ID NO: 133) |
| I-Zm.UbqM1-1:1:19 (Allele-2) | 133 | 1010 | *Z. mays* subsp. *Mexicana* | Intron |
| EXP-Zm.UbqM1:1:8 (Allele-2) | 134 | 2008 | *Z. mays* subsp. *Mexicana* | EXP: P-Zm.UbqM1-1:1:5 (SEQ ID NO: 135); L-Zm.UbqM1-1:1:4 (SEQ ID NO: 136); I-Zm.UbqM1-1:1:15 (SEQ ID NO: 137) |
| P-Zm.UbqM1-1:1:5 (Allele-2) | 135 | 877 | *Z. mays* subsp. *Mexicana* | Promoter |
| L-Zm.UbqM1-1:1:4 (Allele-2) | 136 | 78 | *Z. mays* subsp. *Mexicana* | Leader |

TABLE 1-continued

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| I-Zm.UbqM1-1:1:15 (Allele-2) | 137 | 1053 | *Z. mays* subsp. *Mexicana* | Intron |
| EXP-Zm.UbqM1:1:11 (Allele-2) | 138 | 2008 | *Z. mays* subsp. *Mexicana* | EXP: P-Zm.UbqM1-1:1:5 (SEQ ID NO: 135); L-Zm.UbqM1-1:1:4 (SEQ ID NO: 136); I-Zm.UbqM1-1:1:18 (SEQ ID NO: 139) |
| I-Zm.UbqM1-1:1:18 (Allele-2) | 139 | 1053 | *Z. mays* subsp. *Mexicana* | Intron |
| EXP-Sb.Ubq4:1:2 | 140 | 1635 | *S. bicolor* | EXP: P-Sb.Ubq4-1:1:1 (SEQ ID NO: 141); L-Sb.Ubq4-1:1:1 (SEQ ID NO: 142); I-Sb.Ubq4-1:1:2 (SEQ ID NO: 143) |
| P-Sb.Ubq4-1:1:1 | 141 | 401 | *S. bicolor* | Promoter |
| L-Sb.Ubq4-1:1:1 | 142 | 154 | *S. bicolor* | Leader |
| I-Sb.Ubq4-1:1:2 | 143 | 1080 | *S. bicolor* | Intron |
| EXP-Sb.Ubq6:1:2 | 144 | 2067 | *S. bicolor* | EXP: P-Sb.Ubq6-1:1:1 (SEQ ID NO: 145); L-Sb.Ubq6-1:1:1 (SEQ ID NO: 146); I-Sb.Ubq6-1:1:2 (SEQ ID NO: 147) |
| P-Sb.Ubq6-1:1:1 | 145 | 855 | *S. bicolor* | Promoter |
| L-Sb.Ubq6-1:1:1 | 146 | 136 | *S. bicolor* | Leader |
| I-Sb.Ubq6-1:1:2 | 147 | 1076 | *S. bicolor* | Intron |
| EXP-Sb.Ubq6:1:3 | 148 | 2067 | *S. bicolor* | EXP: P-Sb.Ubq6-1:1:1 (SEQ ID NO: 145); L-Sb.Ubq6-1:1:1 (SEQ ID NO: 146); I-Sb.Ubq6-1:1:3 (SEQ ID NO: 149) |
| I-Sb.Ubq6-1:1:3 | 149 | 1076 | *S. bicolor* | Intron |
| EXP-Sb.Ubq7:1:2 | 150 | 2003 | *S. bicolor* | EXP: P-Sb.Ubq7-1:1:1 (SEQ ID NO: 151); L-Sb.Ubq7-1:1:1 (SEQ ID NO: 152); I-Sb.Ubq7-1:1:2 (SEQ ID NO: 153) |
| P-Sb.Ubq7-1:1:1 | 151 | 565 | *S. bicolor* | Promoter |
| L-Sb.Ubq7-1:1:1 | 152 | 77 | *S. bicolor* | Leader |
| I-Sb.Ubq7-1:1:2 | 153 | 1361 | *S. bicolor* | Intron |
| EXP-Cl.Ubq10 | 168 | 1790 | *C. lacryma-jobi* | EXP: P-Cl.UBQ10 (SEQ ID NO: 169); L-Cl.UBQ10 (SEQ ID NO: 170); I-Cl.UBQ10 (SEQ ID NO: 171) |
| P-Cl.Ubq10 | 169 | 481 | *C. lacryma-jobi* | Promoter |
| L-Cl.Ubq10 | 170 | 93 | *C. lacryma-jobi* | Leader |
| I-Cl.Ubq10 | 171 | 1216 | *C. lacryma-jobi* | Intron |

As shown in Table 1, for example, the regulatory EXP sequence designated EXP-AGRne.Ubq1:1:7 (SEQ ID NO: 1), with components isolated from *A. nebulosa*, comprises a promoter element, P-AGRne.Ubq1-1:1:5 (SEQ ID NO: 2), operably linked 5' to a leader element, L-AGRne.Ubq1-1:1:1 (SEQ ID NO: 3), operably linked 5' to an intron element, I-AGRne.Ubq1-1:1:3 (SEQ ID NO: 4). Other EXP sequences are linked similarly, as outlined in Table 1.

As shown in Table 1, the sequence listing, and FIGS. 1-8, variants of promoter sequences from *A. nebulosa, A donax, B. gracilis, M. sinesis, S. scoparium*, and *S. nutans* were engineered, which comprise shorter promoter fragments of, for instance, P-AGRne.Ubq1-1:1:5 (SEQ ID NO:2), P-ARUdo.Ubq1-1:1:4 (SEQ ID NO:10), or other respective promoters from other species, and for instance resulting in P-AGRne.Ubq1-1:1:4 (SEQ ID NO: 6) and P-ARUdo.Ubq1-1:1:5 (SEQ ID NO: 14), as well as other promoter fragments.

Also listed in Table 1 are three allelic variants isolated using the same primer sets designed for amplification of genomic DNA from *Z. mays* subsp. *mexicana*. Allelic variants of the *Z. mays* subsp. *mexicana* EXP sequences are comprised of DNA sequences that share some identity within various regions of other DNA sequences, but insertions, deletions, and nucleotide mismatches may also be apparent within each promoter, leader and/or intron of each of the EXP sequences. The EXP sequences designated EXP-Zm.UbqM1:1:6 (SEQ ID NO: 122) and EXP-Zm.UbqM1:1:10 (SEQ ID NO: 126) represent a first allele (Allele-1) of the *Z. mays* subsp. *mexicana* Ubq1 gene regulatory expression element group, with the only difference between the two EXP sequences occurring in the last 3' nucleotides of each respective intron following the sequence 5'-AG-3' of the 3' intron splice junction. The EXP sequences designated EXP-Zm.UbqM1:1:7 (SEQ ID NO: 128) and EXP-Zm.UbqM1:1:12 (SEQ ID NO: 132) represent a second allele (Allele-2) of the *Z. mays* subsp. *mexicana* Ubq1 gene regulatory expression element group, with the only difference between the two EXP sequences occurring in the last 3' nucleotides of each respective intron following the sequence 5"-AG-3' of the 3' intron splice junction. The EXP sequences EXP-Zm.UbqM1:1:8 (SEQ ID NO: 134) and EXP-Zm.UbqM1:1:11 (SEQ ID NO: 138) represent a third allele (Allele-3) of the *Z. mays* subsp. *mexicana* Ubq1 gene regulatory expression element group, with the only difference between the two EXP sequences occurring in the last 3' nucleotides of each respective intron following the sequence 5'-AG-3' of the 3' intron splice junction.

Example 2

Analysis of Regulatory Elements Driving GUS in Corn Protoplasts Using GUS Expression Cassette Amplicons Corn leaf protoplasts were transformed with DNA amplicons derived from plant expression vectors containing an EXP sequence, driving expression of the β-glucuronidase transgene (GUS), and compared to leaf protoplasts in which expression of GUS is driven by known constitutive promoters in a series of experiments presented below.

In a first set of experiments, corn protoplast cells derived from leaf tissue were transformed as above with amplicons produced from amplification of GUS expression cassettes comprising plant expression vectors to compare expression of a transgene (GUS) driven by one of EXP-AGRne.Ubq1:1:7 (SEQ ID NO: 1), EXP-AGRne.Ubq1:1:8 (SEQ ID NO: 5), EXP-AGRne.Ubq1:1:9 (SEQ ID NO: 7), EXP-ARUdo.Ubq1:1:8 (SEQ ID NO: 13), EXP-ARUdo.Ubq1:1:9 (SEQ ID NO: 18), EXP-ARUdo.Ubq1:1:11 (SEQ ID NO:

20), EXP-ARUdo.Ubq2:1:8 (SEQ ID NO: 26), EXP-ARUdo.Ubq2:1:9 (SEQ ID NO: 29), EXP-ARUdo.Ubq2:1:10 (SEQ ID NO: 31), EXP-BOUgr.Ubq1:1:6 (SEQ ID NO: 37), EXP-BOUgr.Ubq1:1:7 (SEQ ID NO: 40), EXP-BOUgr.Ubq1:1:8 (SEQ ID NO: 42), EXP-BOUgr.Ubq2:1:14 (SEQ ID NO: 51), EXP-BOUgr.Ubq2:1:16 (SEQ ID NO: 57), EXP-BOUgr.Ubq2:1:17 (SEQ ID NO: 59), EXP-MISsi.Ubq1:1:8 (SEQ ID NO: 69), EXP-MISsi.Ubq1:1:10 (SEQ ID NO: 71), EXP-MISsi.Ubq1:1:11 (SEQ ID NO: 73), EXP-MISsi.Ubq1:1:7 (SEQ ID NO: 75), EXP-SCHsc.Ubq1:1:9 (SEQ ID NO: 77), EXP-SCHsc.Ubq1:1:7 (SEQ ID NO: 83), EXP-SCHsc.Ubq1:1:10 (SEQ ID NO: 85), EXP-SORnu.Ubq1:1:6 (SEQ ID NO: 91), EXP-SORnu.Ubq1:1:7 (SEQ ID NO: 94), EXP-SORnu.Ubq1:1:8 (SEQ ID NO: 96), EXP-SETit.Ubq1:1:5 (SEQ ID NO: 102), EXP-SETit.Ubq1:1:7 (SEQ ID NO: 105), EXP-SETit.Ubq1:1:6 (SEQ ID NO: 107), EXP-Sv.Ubq1:1:7 (SEQ ID NO: 109), EXP-Sv.Ubq1:1:8 (SEQ ID NO: 115), EXP-Sv.Ubq1:1:10 (SEQ ID NO: 117), EXP-Zm.UbqM1:1:6 (SEQ ID NO: 121), EXP-Zm.UbqM1:1:7 (SEQ ID NO: 127), EXP-Zm.UbqM1:1:8 (SEQ ID NO: 133), Exp-Sb.Ubq4:1:2 (SEQ ID NO: 139), and Exp-Sb.Ubq6:1:2 (SEQ ID NO: 143) with that of known constitutive promoters. Each EXP sequence comprising the amplification template from which the expression cassette amplicon is produced was cloned using methods known in the art into a plant expression vector shown in Table 2 below under the heading of "Amplicon Template." The resulting plant expression vectors comprise a expression cassette comprised of a EXP sequence, operably linked 5' to a coding sequence for GUS that either contains a processable intron ("GUS-2", SEQ ID NO: 154), or a contiguous GUS coding sequence ("GUS-1", SEQ ID NO: 153), operably linked 5' to a 3' UTR T-AGRtu.nos-1:1:13 (SEQ ID NO: 157) or T-Ta.Hsp17-1:1:1 (SEQ ID NO: 158). Amplicons were produced using methods known to those skilled in the art using the plasmid construct templates presented in Table 2 below. Briefly, a 5' oligonucleotide primer was designed to anneal to the promoter sequence and a 3' oligonucleotide primer, which anneals at the 3' end of the 3' UTR, was used for amplification of each expression cassette. Successive 5' deletions were introduced into the promoter sequences comprising the expression cassettes, giving rise to different EXP sequences, by the use of different oligonucleotide primers which were designed to anneal at different positions within the promoter sequence comprising each amplicon template.

TABLE 2

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145942 | pMON25455 | EXP-Os.Act1:1:9 | 162 | GUS-1 | T-AGRtu.nos-1:1:13 |
| PCR0145943 | pMON65328 | EXP-CaMV.35S-enh + Ta.Lhcb1 + Os.Act1:1:1 | 161 | GUS-2 | T-Ta.Hsp17-1:1:1 |
| PCR0145935 | pMON140890 | EXP-AGRne.Ubq1:1:7 | 1 | GUS-1 | T-AGRtu.nos-1:1:13 |
| PCR0145827 | pMON140890 | EXP-AGRne.Ubq1:1:8 | 5 | GUS-1 | T-AGRtu.nos-1:1:13 |
| PCR0145828 | pMON140890 | EXP-AGRne.Ubq1:1:9 | 7 | GUS-1 | T-AGRtu.nos-1:1:13 |
| PCR0145939 | pMON140894 | EXP-ARUdo.Ubq1:1:8 | 13 | GUS-1 | T-AGRtu.nos-1:1:13 |
| PCR0145837 | pMON140894 | EXP-ARUdo.Ubq1:1:9 | 18 | GUS-1 | T-AGRtu.nos-1:1:13 |
| PCR0145838 | pMON140894 | EXP-ARUdo.Ubq1:1:11 | 21 | GUS-1 | T-AGRtu.nos-1:1:13 |
| PCR0145940 | pMON140895 | EXP-ARUdo.Ubq2:1:8 | 27 | GUS-1 | T-AGRtu.nos-1:1:13 |
| PCR0145841 | pMON140895 | EXP-ARUdo.Ubq2:1:9 | 30 | GUS-1 | T-AGRtu.nos-1:1:13 |
| PCR0145842 | pMON140895 | EXP-ARUdo.Ubq2:1:10 | 32 | GUS-1 | T-AGRtu.nos-1:1:13 |
| PCR0145936 | pMON140891 | EXP-BOUgr.Ubq1:1:6 | 38 | GUS-1 | T-AGRtu.nos-1:1:13 |
| PCR0145829 | pMON140891 | EXP-BOUgr.Ubq1:1:7 | 41 | GUS-1 | T-AGRtu.nos-1:1:13 |
| PCR0145831 | pMON140891 | EXP-BOUgr.Ubq1:1:8 | 43 | GUS-1 | T-AGRtu.nos-1:1:13 |

TABLE 2-continued

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145937 | pMON140892 | EXP-BOUgr.Ubq2:1:14 | 52 | GUS-1 | T-AGRtu.nos-1:1:13 |
| PCR0145833 | pMON140892 | EXP-BOUgr.Ubq2:1:16 | 58 | GUS-1 | T-AGRtu.nos-1:1:13 |
| PCR0145836 | pMON140892 | EXP-BOUgr.Ubq2:1:17 | 60 | GUS-1 | T-AGRtu.nos-1:1:13 |
| PCR0145898 | pMON136265 | EXP-MISsi.Ubq1:1:8 | 70 | GUS-1 | T-AGRtu.nos-1:1:13 |
| PCR0145823 | pMON136265 | EXP-MISsi.Ubq1:1:10 | 72 | GUS-1 | T-AGRtu.nos-1:1:13 |
| PCR0145824 | pMON136265 | EXP-MISsi.Ubq1:1:11 | 74 | GUS-1 | T-AGRtu.nos-1:1:13 |
| PCR0145899 | pMON136260 | EXP-MISsi.Ubq1:1:7 | 76 | GUS-1 | T-AGRtu.nos-1:1:13 |
| PCR0145894 | pMON136262 | EXP-SCHsc.Ubq1:1:9 | 78 | GUS-1 | T-AGRtu.nos-1:1:13 |
| PCR0145895 | pMON136257 | EXP-SCHsc.Ubq1:1:7 | 84 | GUS-1 | T-AGRtu.nos-1:1:13 |
| PCR0145813 | pMON136257 | EXP-SCHsc.Ubq1:1:10 | 86 | GUS-1 | T-AGRtu.nos-1:1:13 |
| PCR0145938 | pMON140893 | EXP-SORnu.Ubq1:1:6 | 92 | GUS-1 | T-AGRtu.nos-1:1:13 |
| PCR0145839 | pMON140893 | EXP-SORnu.Ubq1:1:7 | 95 | GUS-1 | T-AGRtu.nos-1:1:13 |
| PCR0145840 | pMON140893 | EXP-SORnu.Ubq1:1:8 | 97 | GUS-1 | T-AGRtu.nos-1:1:13 |
| PCR0145900 | pMON140877 | EXP-SETit.Ubq1:1:5 | 103 | GUS-1 | T-AGRtu.nos-1:1:13 |
| PCR0145928 | pMON140877 | EXP-SETit.Ubq1:1:7 | 106 | GUS-1 | T-AGRtu.nos-1:1:13 |
| PCR0145905 | pMON140877 | EXP-SETit.Ubq1:1:6 | 108 | GUS-1 | T-AGRtu.nos-1:1:13 |
| PCR0145909 | pMON140878 | EXP-Sv.Ubq1:1:7 | 110 | GUS-1 | T-AGRtu.nos-1:1:13 |
| PCR0145929 | pMON140878 | EXP-Sv.Ubq1:1:8 | 116 | GUS-1 | T-AGRtu.nos-1:1:13 |
| PCR0145911 | pMON140878 | EXP-Sv.Ubq1:1:10 | 118 | GUS-1 | T-AGRtu.nos-1:1:13 |
| PCR0145914 | pMON140881 | EXP-Zm.UbqM1:1:6 | 122 | GUS-1 | T-AGRtu.nos-1:1:13 |
| PCR0145916 | pMON140883 | EXP-Zm.UbqM1:1:7 | 128 | GUS-1 | T-AGRtu.nos-1:1:13 |
| PCR0145915 | pMON140882 | EXP-Zm.UbqM1:1:8 | 134 | GUS-1 | T-AGRtu.nos-1:1:13 |
| PCR0145921 | pMON140887 | Exp-Sb.Ubq4:1:2 | 140 | GUS-1 | T-AGRtu.nos-1:1:13 |

TABLE 2-continued

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145920 | pMON140886 | Exp-Sb.Ubq6:1:2 | 144 | GUS-1 | T-AGRtu.nos-1:1:13 |

Plasmid constructs listed as amplicon templates in Table 2 served as templates for amplification of transgene expression cassettes comprising the listed EXP sequences of Table 2. Control plasmids used to generate GUS transgene amplicons for comparison were constructed as previously described with the constitutive EXP sequences EXP-Os.Act1:1:9 (SEQ ID NO: 162) and EXP-CaMV.35S-enh+Ta.Lhcb1+Os.Act1:1:1 (SEQ ID NO: 161). An empty vector not designed for transgene expression was used as a negative control to assess background GUS and luciferase expression.

Two plasmids, for use in co-transformation and normalization of data, were also constructed using methods known in the art. Each plasmid contained a specific luciferase coding sequence that was driven by a constitutive EXP sequence. The plant vector pMON19437 comprises a expression cassette with a constitutive promoter operably linked 5' to an intron, (EXP-CaMV.35S-enh+Zm.DnaK:1:1, SEQ ID NO: 163), operably linked 5' to a firefly (*Photinus pyralis*) luciferase coding sequence (LUCIFERASE:1:3, SEQ ID NO: 156), operably linked 5' to a 3' UTR from the *Agrobacterium tumefaciens* nopaline synthase gene (T-AGRtu.nos-1:1:13, SEQ ID NO: 158). The plant vector pMON63934 comprises a expression cassette with a constitutive EXP sequence (EXP-CaMV.35S-enh-Lhcb1, SEQ ID NO: 164), operably linked 5' to a sea pansy (*Renilla reniformis*) luciferase coding sequence (CR-Ren.hRenilla Lucife-0:0:1, SEQ ID NO: 157), operably linked 5' to a 3' UTR from the *Agrobacterium tumefaciens* nopaline synthase gene (T-AGRtu.nos-1:1:13, SEQ ID NO: 158).

Corn leaf protoplasts were transformed using a PEG-based transformation method, which is well known in the art. Protoplast cells were transformed with pMON19437 plasmid DNA, pMON63934 plasmid DNA, and the amplicons presented in Table 2, and were incubated overnight in total darkness. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). One or two transformations for each EXP sequence were performed and the mean expression values for each EXP sequence determined from several samples from each transformation experiment. Sample measurements were made using four replicates of each EXP sequence construct transformation, or alternatively, three replicates of each EXP sequence amplicon per one of two transformation experiments. The mean GUS and luciferase expression levels are provided in Table 3. In this table, the firefly luciferase values (e.g., from expression of pMON19437) are provided in the column labeled "FLuc" and the *Renilla* luciferase values are provided as in the column labeled "RLuc."

TABLE 3

Mean GUS and Luciferase activity in transformed corn leaf protoplast cells.

| EXP Sequence | SEQ ID NO: | GUS | FLuc | RLuc |
|---|---|---|---|---|
| EMPTY | | 5 | 7840.58 | 205661 |
| EXP-Os.Act1:1:9 | 162 | 1540.25 | 2671.83 | 105417 |
| EXP-CaMV.35S-enh + Ta.Lhcb1 + Os.Act1:1:1 | 161 | 12530.8 | 3067.08 | 137723 |
| EXP-AGRne.Ubq1:1:7 | 1 | 39665 | 3645.83 | 137384 |
| EXP-AGRne.Ubq1:1:8 | 5 | 22805.5 | 4183.58 | 140991 |
| EXP-AGRne.Ubq1:1:9 | 7 | 5861.5 | 887.08 | 34034.3 |
| EXP-ARUdo.Ubq1:1:8 | 13 | 26965.5 | 1052.33 | 37774.8 |
| EXP-ARUdo.Ubq1:1:9 | 18 | 66126 | 3251.08 | 114622 |
| EXP-ARUdo.Ubq1:1:11 | 21 | 136163 | | 453851 |
| EXP-ARUdo.Ubq2:1:8 | 27 | 13222.3 | 2203.58 | 72339.1 |
| EXP-ARUdo.Ubq2:1:9 | 30 | 30095 | 6538.58 | 229201 |
| EXP-ARUdo.Ubq2:1:10 | 32 | 16448.5 | 1842.58 | 65325.1 |
| EXP-BOUgr.Ubq1:1:6 | 38 | 32544.3 | 2765.08 | 80330.8 |
| EXP-BOUgr.Ubq1:1:7 | 41 | 3826.33 | 697.11 | 20709 |
| EXP-BOUgr.Ubq1:1:8 | 43 | 9935.5 | 3372.58 | 110965 |
| EXP-BOUgr.Ubq2:1:14 | 52 | 17828 | 1575.83 | 62286.8 |
| EXP-BOUgr.Ubq2:1:16 | 58 | 54970.3 | 3389.08 | 117616 |
| EXP-BOUgr.Ubq2:1:17 | 60 | 48601.3 | 7139.08 | 245785 |
| EXP-MISsi.Ubq1:1:8 | 70 | 11788.3 | 3264.58 | 87751.6 |
| EXP-MISsi.Ubq1:1:10 | 72 | 33329.5 | 2388.58 | 81000.6 |
| EXP-MISsi.Ubq1:1:11 | 74 | 4723.75 | 3135.33 | 98059.1 |
| EXP-MISsi.Ubq1:1:7 | 76 | 4499 | 3073.58 | 84015.1 |
| EXP-SCHsc.Ubq1:1:9 | 78 | 5972 | 1703.33 | 62310.6 |
| EXP-SCHsc.Ubq1:1:7 | 84 | 24173.5 | 5306.08 | 155122 |
| EXP-SCHsc.Ubq1:1:10 | 86 | 7260 | 1171.08 | 38698.1 |
| EXP-SORnu.Ubq1:1:6 | 92 | 3966.5 | 4175.08 | 129365 |
| EXP-SORnu.Ubq1:1:7 | 95 | 23375.5 | 616.83 | 25125.3 |
| EXP-SORnu.Ubq1:1:8 | 97 | 8431.75 | 1630.08 | 55095.6 |
| EXP-SETit.Ubq1:1:5 | 103 | 20496.5 | 2358.83 | 88695.8 |
| EXP-SETit.Ubq1:1:7 | 106 | 75728.5 | 4723.08 | 185224 |
| EXP-SETit.Ubq1:1:6 | 108 | 44148.3 | 4962.08 | 161216 |
| EXP-Sv.Ubq1:1:7 | 110 | 15043.8 | 1888.33 | 74670.6 |
| EXP-Sv.Ubq1:1:8 | 116 | 31997.8 | 3219.83 | 113787 |
| EXP-Sv.Ubq1:1:10 | 118 | 38952.8 | 7011.33 | 220209 |
| EXP-Zm.UbqM1:1:6 | 122 | 30528.3 | 2453.58 | 90113.1 |
| EXP-Zm.UbqM1:1:8 | 134 | 34986.3 | 2553.78 | 105725 |
| Exp-Sb.Ubq4:1:2 | 140 | 9982.25 | 2171.58 | 72593.8 |
| Exp-Sb.Ubq6:1:2 | 144 | 33689 | 3879.58 | 114710 |

To compare the relative activity of each EXP sequence, GUS values were expressed as a ratio of GUS to luciferase activity and normalized with respect to the expression levels observed for EXP-Os.Act1:1:1 and EXP-CaMV.35S-enh+Ta.Lhcb1+Os.Act1:1:1. Table 4 below shows the GUS/RLuc ratios of expression normalized with respect to EXP-Os.Act1:1:1 and EXP-CaMV.35S-enh+Ta.Lhcb1+Os.Act1:1:1 driven expression in corn protoplasts. Table 5 below shows the GUS/FLuc ratios of expression normalized with respect to EXP-Os.Act1:1:1 and EXP-CaMV.35S-enh+Ta.Lhcb1+Os.Act1:1:1 driven expression in corn protoplasts.

TABLE 4

GUS/RLuc and GUS/FLuc ratios of expression normalized with respect to EXP-CaMV.35S-enh + Ta.Lhcb1 + Os.Act1:1:1 (SEQ ID NO: 161) in corn protoplasts.

| EXP Sequence | SEQ ID NO: | GUS/FLuc Relative to EXP-CaMV.35S-enh + Ta.Lhcb1 + Os.Act1:1:1 | GUS/RLuc Relative to EXP-CaMV.35S-enh + Ta.Lhcb1 + Os.Act1:1:1 |
|---|---|---|---|
| EXP-Os.Act1:1:9 | 162 | 0.14 | 0.16 |
| EXP-CaMV.35S-enh + Ta.Lhcb1 + Os.Act1:1:1 | 161 | 1 | 1 |
| EXP-AGRne.Ubq1:1:7 | 1 | 2.66 | 3.17 |
| EXP-AGRne.Ubq1:1:8 | 5 | 1.33 | 1.78 |
| EXP-AGRne.Ubq1:1:9 | 7 | 1.62 | 1.89 |
| EXP-ARUdo.Ubq1:1:8 | 13 | 6.27 | 7.85 |
| EXP-ARUdo.Ubq1:1:9 | 18 | 4.98 | 6.34 |
| EXP-ARUdo.Ubq1:1:11 | 21 | | 3.3 |
| EXP-ARUdo.Ubq2:1:8 | 27 | 1.47 | 2.01 |
| EXP-ARUdo.Ubq2:1:9 | 30 | 1.13 | 1.44 |
| EXP-ARUdo.Ubq2:1:10 | 32 | 2.18 | 2.77 |
| EXP-BOUgr.Ubq1:1:6 | 38 | 2.88 | 4.45 |
| EXP-BOUgr.Ubq1:1:7 | 41 | 1.34 | 2.03 |
| EXP-BOUgr.Ubq1:1:8 | 43 | 0.72 | 0.98 |
| EXP-BOUgr.Ubq2:1:14 | 52 | 2.77 | 3.15 |
| EXP-BOUgr.Ubq2:1:16 | 58 | 3.97 | 5.14 |
| EXP-BOUgr.Ubq2:1:17 | 60 | 1.67 | 2.17 |
| EXP-MISsi.Ubq1:1:8 | 70 | 0.88 | 1.48 |
| EXP-MISsi.Ubq1:1:10 | 72 | 3.42 | 4.52 |
| EXP-MISsi.Ubq1:1:11 | 74 | 0.37 | 0.53 |
| EXP-MISsi.Ubq1:1:7 | 76 | 0.36 | 0.59 |
| EXP-SCHsc.Ubq1:1:9 | 78 | 0.86 | 1.05 |
| EXP-SCHsc.Ubq1:1:7 | 84 | 1.12 | 1.71 |
| EXP-SCHsc.Ubq1:1:10 | 86 | 1.52 | 2.06 |
| EXP-SORnu.Ubq1:1:6 | 92 | 0.23 | 0.34 |
| EXP-SORnu.Ubq1:1:7 | 95 | 9.28 | 10.23 |
| EXP-SORnu.Ubq1:1:8 | 97 | 1.27 | 1.68 |
| EXP-SETit.Ubq1:1:5 | 103 | 2.13 | 2.54 |
| EXP-SETit.Ubq1:1:7 | 106 | 3.92 | 4.49 |
| EXP-SETit.Ubq1:1:6 | 108 | 2.18 | 3.01 |
| EXP-Sv.Ubq1:1:7 | 110 | 1.95 | 2.21 |
| EXP-Sv.Ubq1:1:8 | 116 | 2.43 | 3.09 |
| EXP-Sv.Ubq1:1:10 | 118 | 1.36 | 1.94 |
| EXP-Zm.UbqM1:1:6 | 122 | 3.05 | 3.72 |
| EXP-Zm.UbqM1:1:8 | 134 | 3.35 | 3.64 |
| Exp-Sb.Ubq4:1:2 | 140 | 1.13 | 1.51 |
| Exp-Sb.Ubq6:1:2 | 144 | 2.13 | 3.23 |

TABLE 5

GUS/RLuc and GUS/FLuc ratios of expression normalized with respect to EXP-Os.Act1:1:9 (SEQ ID NO: 162) in corn leaf protoplasts.

| EXP Sequence | SEQ ID NO: | GUS/FLuc Relative to EXP-Os.Act1:1:9 | GUS/RLuc Relative to EXP-Os.Act1:1:9 |
|---|---|---|---|
| EXP-Os.Act1:1:9 | 162 | 1 | 1 |
| EXP-CaMV.35S-enh + Ta.Lhcb1 + Os.Act1:1:1 | 161 | 7.09 | 6.23 |
| EXP-AGRne.Ubq1:1:7 | 1 | 18.87 | 19.76 |
| EXP-AGRne.Ubq1:1:8 | 5 | 9.46 | 11.07 |
| EXP-AGRne.Ubq1:1:9 | 7 | 11.46 | 11.79 |
| EXP-ARUdo.Ubq1:1:8 | 13 | 44.45 | 48.86 |
| EXP-ARUdo.Ubq1:1:9 | 18 | 35.28 | 39.48 |
| EXP-ARUdo.Ubq1:1:11 | 21 | | 20.53 |
| EXP-ARUdo.Ubq2:1:8 | 27 | 10.41 | 12.51 |
| EXP-ARUdo.Ubq2:1:9 | 30 | 7.98 | 8.99 |
| EXP-ARUdo.Ubq2:1:10 | 32 | 15.49 | 17.23 |
| EXP-BOUgr.Ubq1:1:6 | 38 | 20.42 | 27.73 |
| EXP-BOUgr.Ubq1:1:7 | 41 | 9.52 | 12.65 |
| EXP-BOUgr.Ubq1:1:8 | 43 | 5.11 | 6.13 |
| EXP-BOUgr.Ubq2:1:14 | 52 | 19.63 | 19.59 |
| EXP-BOUgr.Ubq2:1:16 | 58 | 28.14 | 31.99 |

TABLE 5-continued

GUS/RLuc and GUS/FLuc ratios of expression normalized with respect to EXP-Os.Act1:1:9 (SEQ ID NO: 162) in corn leaf protoplasts.

| EXP Sequence | SEQ ID NO: | GUS/FLuc Relative to EXP-Os.Act1:1:9 | GUS/RLuc Relative to EXP-Os.Act1:1:9 |
|---|---|---|---|
| EXP-BOUgr.Ubq2:1:17 | 60 | 11.81 | 13.53 |
| EXP-MISsi.Ubq1:1:8 | 70 | 6.26 | 9.19 |
| EXP-MISsi.Ubq1:1:10 | 72 | 24.21 | 28.16 |
| EXP-MISsi.Ubq1:1:11 | 74 | 2.61 | 3.3 |
| EXP-MISsi.Ubq1:1:7 | 76 | 2.54 | 3.67 |
| EXP-SCHsc.Ubq1:1:9 | 78 | 6.08 | 6.56 |
| EXP-SCHsc.Ubq1:1:7 | 84 | 7.9 | 10.67 |
| EXP-SCHsc.Ubq1:1:10 | 86 | 10.75 | 12.84 |
| EXP-SORnu.Ubq1:1:6 | 92 | 1.65 | 2.1 |
| EXP-SORnu.Ubq1:1:7 | 95 | 65.74 | 63.67 |
| EXP-SORnu.Ubq1:1:8 | 97 | 8.97 | 10.47 |
| EXP-SETit.Ubq1:1:5 | 103 | 15.07 | 15.82 |
| EXP-SETit.Ubq1:1:7 | 106 | 27.81 | 27.98 |
| EXP-SETit.Ubq1:1:6 | 108 | 15.43 | 18.74 |
| EXP-Sv.Ubq1:1:7 | 110 | 13.82 | 13.79 |
| EXP-Sv.Ubq1:1:8 | 116 | 17.24 | 19.25 |
| EXP-Sv.Ubq1:1:10 | 118 | 9.64 | 12.11 |
| EXP-Zm.UbqM1:1:6 | 122 | 21.58 | 23.19 |
| EXP-Zm.UbqM1:1:8 | 134 | 23.76 | 22.65 |
| Exp-Sb.Ubq4:1:2 | 140 | 7.97 | 9.41 |
| Exp-Sb.Ubq6:1:2 | 144 | 15.06 | 20.1 |

As can be seen in Tables 9 and 10, all of the EXP sequences were capable of driving GUS transgene expression in corn cells. Average GUS expression was higher for all of the EXP sequences relative to EXP-Os.Act1:1:9. The EXP sequences, EXP-AGRne.Ubq1:1:7 (SEQ ID NO: 1), EXP-AGRne.Ubq1:1:8 (SEQ ID NO: 5), EXP-AGRne.Ubq1:1:9 (SEQ ID NO: 7), EXP-ARUdo.Ubq1:1:8 (SEQ ID NO: 13), EXP-ARUdo.Ubq1:1:9 (SEQ ID NO: 18), EXP-ARUdo.Ubq1:1:11 (SEQ ID NO: 21), EXP-ARUdo.Ubq2:1:8 (SEQ ID NO: 27), EXP-ARUdo.Ubq2:1:9 (SEQ ID NO: 30), EXP-ARUdo.Ubq2:1:10 (SEQ ID NO: 32), EXP-BOUgr.Ubq1:1:6 (SEQ ID NO: 38), EXP-BOUgr.Ubq1:1:7 (SEQ ID NO: 41), EXP-BOUgr.Ubq2:1:14 (SEQ ID NO: 52), EXP-BOUgr.Ubq2:1:16 (SEQ ID NO: 58), EXP-BOUgr.Ubq2:1:17 (SEQ ID NO: 60), EXP-MISsi.Ubq1:1:10 (SEQ ID NO: 72), EXP-SCHsc.Ubq1:1:7 (SEQ ID NO: 84), EXP-SCHsc.Ubq1:1:10 (SEQ ID NO: 86), EXP-SORnu.Ubq1:1:7 (SEQ ID NO: 95), EXP-SORnu.Ubq1:1:8 (SEQ ID NO: 97), EXP-SETit.Ubq1:1:5 (SEQ ID NO: 103), EXP-SETit.Ubq1:1:7 (SEQ ID NO: 106), EXP-SETit.Ubq1:1:6 (SEQ ID NO: 108), EXP-Sv.Ubq1:1:7 (SEQ ID NO: 110), EXP-Sv.Ubq1:1:8 (SEQ ID NO: 116), EXP-Sv.Ubq1:1:10 (SEQ ID NO: 118), EXP-Zm.UbqM1:1:6 (SEQ ID NO: 122), EXP-Zm.UbqM1:1:8 (SEQ ID NO: 134), EXP-Sb.Ubq4:1:2 (SEQ ID NO: 140), and EXP-Sb.Ubq6:1:2 (SEQ ID NO: 144) demonstrated GUS expression levels above that of EXP-CaMV.35S-enh+Ta.Lhcb1+Os.Act1:1:1.

In a second set of experiments, a GUS expression cassette amplicon comprising the EXP sequence EXP-Zm.UbqM1:1:7 (SEQ ID NO: 128) was compared to the control amplicons, PCR0145942 (EXP-Os.Act1:1:9, SEQ ID NO: 162) and PCR0145944 (EXP-CaMV.35S-enh+Zm.DnaK:1:1, SEQ ID NO: 161) with respect to GUS expression. GUS expression driven by the EXP sequence EXP-Zm.UbqM1:1:7 was higher than that of the two controls. Table 6 below shows the mean GUS and luciferase values determined for each amplicon. Table 7 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 6

Mean GUS and Luciferase activity in transformed corn leaf protoplast cells.

| EXP Sequence | SEQ ID NO: | GUS | FLuc | RLuc |
|---|---|---|---|---|
| EXP-Os.Act1:1:9 | 162 | 1512.25 | 11333.75 | 190461.00 |
| EXP-CaMV.35S-enh + Ta.Lhcb1 + Os.Act1:1:1 | 161 | 41176.50 | 13885.75 | 330837.25 |
| EXP-Zm.UbqM1:1:7 | 128 | 79581.50 | 15262.50 | 330755.75 |

TABLE 7

GUS/RLuc and GUS/FLuc ratios of expression normalized with respect to EXP-Os.Act1:1:9 (SEQ ID NO: 161) and EXP-CaMV.35S-enh + Zm.DnaK:1:1 (SEQ ID NO: 160) in corn leaf protoplasts.

| EXP Sequence | SEQ ID NO: | GUS | FLuc | RLuc |
|---|---|---|---|---|
| EXP-Os.Act1:1:9 | 162 | 1512.25 | 11333.75 | 190461.00 |
| EXP-CaMV.35S-enh + Ta.Lhcb1 + Os.Act1:1:1 | 161 | 41176.50 | 13885.75 | 330837.25 |
| EXP-Zm.UbqM1:1:7 | 128 | 79581.50 | 15262.50 | 330755.75 |

The efficacy of regulatory elements driving GUS expression from amplicons can be similarly studied in sugarcane leaf protoplasts. For instance, sugarcane protoplasts may be transformed with DNA amplicons derived from plant expression vectors containing an EXP sequence, driving expression of the GUS transgene, and compared to leaf protoplast in which expression of GUS is driven by known constitutive promoters.

Example 3

Analysis of Regulatory Elements Driving GUS in Wheat Protoplasts Using GUS Expression Cassette Amplicons Wheat leaf protoplasts were transformed with DNA amplicons derived from plant expression vectors containing an EXP sequence, driving expression of the GUS transgene, and compared to leaf protoplast in which expression of GUS was driven by known constitutive promoters.

Wheat protoplast cells derived from leaf tissue were transformed using methods known in the art with amplicons produced from amplification of GUS expression cassettes comprising plant expression vectors to compare expression of a transgene (GUS) driven by the EXP sequences listed in Table 3 with that of known constitutive promoters with methodology as described in a previous example (Example 2), using the same GUS expression cassette amplicons as that used for assay in corn in Example 2 above. Control GUS expression cassette amplicons and Luciferase plasmids used for wheat protoplast transformation were also the same as those presented in the previous example and provided in Table 3 above in Example 2. Likewise, negative controls were used for the determination of GUS and Luciferase background, as described above. Wheat leaf protoplasts were transformed using a PEG-based transformation method, as described in Example 2 above. Table 8 lists mean GUS and LUC activity seen in transformed wheat leaf protoplast cells, and Table 9 and 10 shows normalized GUS/FLuc and GUS/RLuc ratios of expression in wheat protoplasts relative to the constitutive EXP controls.

TABLE 8

Mean GUS and Luciferase activity in transformed wheat leaf protoplast cells.

| EXP Sequence | SEQ ID NO: | GUS | FLuc | RLuc |
|---|---|---|---|---|
| EMPTY | | 262.56 | 1109.78 | 61422.1 |
| EXP-Os.Act1:1:9 | 162 | 2976.33 | 730.11 | 53334.8 |
| EXP-CaMV.35S-enh + Ta.Lhcb1 + Os.Act1:1:1 | 161 | 29299.3 | 741.78 | 50717.4 |
| EXP-AGRne.Ubq1:1:7 | 1 | 27078.3 | 754.44 | 44235.8 |
| EXP-AGRne.Ubq1:1:8 | 5 | 22082.7 | 958.11 | 55774.8 |
| EXP-AGRne.Ubq1:1:9 | 7 | 13882.7 | 699.78 | 49273.4 |
| EXP-ARUdo.Ubq1:1:8 | 13 | 65628 | 791.44 | 56358.8 |
| EXP-ARUdo.Ubq1:1:9 | 18 | 87615 | 801.44 | 53246.4 |
| EXP-ARUdo.Ubq1:1:11 | 21 | 19224.3 | 143.44 | 14104.1 |
| EXP-ARUdo.Ubq2:1:8 | 27 | 25453.3 | 835.11 | 57679.4 |
| EXP-ARUdo.Ubq2:1:9 | 30 | 26720.7 | 702.44 | 47455.4 |
| EXP-ARUdo.Ubq2:1:10 | 32 | 37089.3 | 859.11 | 57814.4 |
| EXP-BOUgr.Ubq1:1:6 | 38 | 35146 | 995.44 | 64418.8 |
| EXP-BOUgr.Ubq1:1:7 | 41 | 18077 | 857.78 | 55793.4 |
| EXP-BOUgr.Ubq1:1:8 | 43 | 11723.7 | 938.44 | 59362.1 |
| EXP-BOUgr.Ubq2:1:14 | 52 | 38109.3 | 875.11 | 58048.1 |
| EXP-BOUgr.Ubq2:1:16 | 58 | 37384 | 860.44 | 52447.8 |
| EXP-BOUgr.Ubq2:1:17 | 60 | 24090.7 | 968.78 | 53057.8 |
| EXP-MISsi.Ubq1:1:8 | 70 | 16456.7 | 1021.78 | 61684.1 |
| EXP-MISsi.Ubq1:1:10 | 72 | 42816.7 | 839.78 | 46688.1 |
| EXP-MISsi.Ubq1:1:11 | 74 | 20625.7 | 987.78 | 61842.1 |
| EXP-MISsi.Ubq1:1:7 | 76 | 4913.67 | 764.78 | 64720.1 |
| EXP-SCHsc.Ubq1:1:9 | 78 | 9726 | 937.11 | 54725.4 |
| EXP-SCHsc.Ubq1:1:7 | 84 | 13374.7 | 1112.44 | 73815.4 |
| EXP-SCHsc.Ubq1:1:10 | 86 | 13650 | 936.78 | 62242.1 |
| EXP-SORnu.Ubq1:1:6 | 92 | 8188.17 | 753.83 | 50572.5 |
| EXP-SORnu.Ubq1:1:7 | 95 | 83233.7 | 854.44 | 54410.1 |
| EXP-SORnu.Ubq1:1:8 | 97 | 21904.7 | 1011.83 | 60852 |
| EXP-SETit.Ubq1:1:5 | 103 | 39427.7 | 908.78 | 57463.1 |
| EXP-SETit.Ubq1:1:7 | 106 | 108091 | 809.44 | 49330.4 |
| EXP-SETit.Ubq1:1:6 | 108 | 58703 | 809.11 | 46110.1 |
| EXP-Sv.Ubq1:1:7 | 110 | 29330 | 684.11 | 43367.1 |
| EXP-Sv.Ubq1:1:8 | 116 | 53359 | 698.11 | 40076.4 |
| EXP-Sv.Ubq1:1:10 | 118 | 49122.7 | 901.44 | 53180.8 |
| EXP-Zm.UbqM1:1:6 | 122 | 37268 | 945.78 | 54088.1 |
| EXP-Zm.UbqM1:1:8 | 134 | 51408 | 677.78 | 47297.4 |
| Exp-Sb.Ubq4:1:2 | 140 | 35660.3 | 1114.11 | 62591.1 |
| Exp-Sb.Ubq6:1:2 | 144 | 27543 | 915.11 | 57826.4 |

TABLE 9

GUS/RLuc and GUS/FLuc ratios of expression normalized with respect to EXP-CaMV.35S-enh + Ta.Lhcb1 + Os.Act1:1:1 (SEQ ID NO: 161) in wheat protoplasts.

| EXP Sequence | SEQ ID NO: | GUS | FLuc | RLuc |
|---|---|---|---|---|
| EMPTY | | 262.56 | 1109.78 | 61422.1 |
| EXP-Os.Act1:1:9 | 162 | 2976.33 | 730.11 | 53334.8 |
| EXP-CaMV.35S-enh + Ta.Lhcb1 + Os.Act1:1:1 | 161 | 29299.3 | 741.78 | 50717.4 |
| EXP-AGRne.Ubq1:1:7 | 1 | 27078.3 | 754.44 | 44235.8 |
| EXP-AGRne.Ubq1:1:8 | 5 | 22082.7 | 958.11 | 55774.8 |
| EXP-AGRne.Ubq1:1:9 | 7 | 13882.7 | 699.78 | 49273.4 |
| EXP-ARUdo.Ubq1:1:8 | 13 | 65628 | 791.44 | 56358.8 |
| EXP-ARUdo.Ubq1:1:9 | 18 | 87615 | 801.44 | 53246.4 |
| EXP-ARUdo.Ubq1:1:11 | 21 | 19224.3 | 143.44 | 14104.1 |
| EXP-ARUdo.Ubq2:1:8 | 27 | 25453.3 | 835.11 | 57679.4 |
| EXP-ARUdo.Ubq2:1:9 | 30 | 26720.7 | 702.44 | 47455.4 |
| EXP-ARUdo.Ubq2:1:10 | 32 | 37089.3 | 859.11 | 57814.4 |
| EXP-BOUgr.Ubq1:1:6 | 38 | 35146 | 995.44 | 64418.8 |
| EXP-BOUgr.Ubq1:1:7 | 41 | 18077 | 857.78 | 55793.4 |
| EXP-BOUgr.Ubq1:1:8 | 43 | 11723.7 | 938.44 | 59362.1 |
| EXP-BOUgr.Ubq2:1:14 | 52 | 38109.3 | 875.11 | 58048.1 |
| EXP-BOUgr.Ubq2:1:16 | 58 | 37384 | 860.44 | 52447.8 |
| EXP-BOUgr.Ubq2:1:17 | 60 | 24090.7 | 968.78 | 53057.8 |
| EXP-MISsi.Ubq1:1:8 | 70 | 16456.7 | 1021.78 | 61684.1 |
| EXP-MISsi.Ubq1:1:10 | 72 | 42816.7 | 839.78 | 46688.1 |
| EXP-MISsi.Ubq1:1:11 | 74 | 20625.7 | 987.78 | 61842.1 |

TABLE 9-continued

GUS/RLuc and GUS/FLuc ratios of expression normalized with respect to EXP-CaMV.35S-enh + Ta.Lhcb1 + Os.Act1:1:1 (SEQ ID NO: 161) in wheat protoplasts.

| EXP Sequence | SEQ ID NO: | GUS | FLuc | RLuc |
|---|---|---|---|---|
| EXP-MISsi.Ubq1:1:7 | 76 | 4913.67 | 764.78 | 64720.1 |
| EXP-SCHsc.Ubq1:1:9 | 78 | 9726 | 937.11 | 54725.4 |
| EXP-SCHsc.Ubq1:1:7 | 84 | 13374.7 | 1112.44 | 73815.4 |
| EXP-SCHsc.Ubq1:1:10 | 86 | 13650 | 936.78 | 62242.1 |
| EXP-SORnu.Ubq1:1:6 | 92 | 8188.17 | 753.83 | 50572.5 |
| EXP-SORnu.Ubq1:1:7 | 95 | 83233.7 | 854.44 | 54410.1 |
| EXP-SORnu.Ubq1:1:8 | 97 | 21904.7 | 1011.83 | 60852 |
| EXP-SETit.Ubq1:1:5 | 103 | 39427.7 | 908.78 | 57463.1 |
| EXP-SETit.Ubq1:1:7 | 106 | 108091 | 809.44 | 49330.4 |
| EXP-SETit.Ubq1:1:6 | 108 | 58703 | 809.11 | 46110.1 |
| EXP-Sv.Ubq1:1:7 | 110 | 29330 | 684.11 | 43367.1 |
| EXP-Sv.Ubq1:1:8 | 116 | 53359 | 698.11 | 40076.4 |
| EXP-Sv.Ubq1:1:10 | 118 | 49122.7 | 901.44 | 53180.8 |
| EXP-Zm.UbqM1:1:6 | 122 | 37268 | 945.78 | 54088.1 |
| EXP-Zm.UbqM1:1:8 | 134 | 51408 | 677.78 | 47297.4 |
| Exp-Sb.Ubq4:1:2 | 140 | 35660.3 | 1114.11 | 62591.1 |
| Exp-Sb.Ubq6:1:2 | 144 | 27543 | 915.11 | 57826.4 |

TABLE 10

GUS/RLuc and GUS/FLuc ratios of expression normalized with respect to EXP-Os.Act1:1:9 (SEQ ID NO: 162) in corn leaf protoplasts.

| EXP Sequence | SEQ ID NO: | GUS/FLuc Relative to EXP-Os.Act1:1:9 | GUS/RLuc Relative to EXP-Os.Act1:1:9 |
|---|---|---|---|
| EXP-Os.Act1:1:9 | 162 | 1 | 1 |
| EXP-CaMV.35S-enh + Ta.Lhcb1 + Os.Act1:1:1 | 161 | 9.69 | 10.35 |
| EXP-AGRne.Ubq1:1:7 | 1 | 8.8 | 10.97 |
| EXP-AGRne.Ubq1:1:8 | 5 | 5.65 | 7.09 |
| EXP-AGRne.Ubq1:1:9 | 7 | 4.87 | 5.05 |
| EXP-ARUdo.Ubq1:1:8 | 13 | 20.34 | 20.87 |
| EXP-ARUdo.Ubq1:1:9 | 18 | 26.82 | 29.49 |
| EXP-ARUdo.Ubq1:1:11 | 21 | 32.88 | 24.43 |
| EXP-ARUdo.Ubq2:1:8 | 27 | 7.48 | 7.91 |
| EXP-ARUdo.Ubq2:1:9 | 30 | 9.33 | 10.09 |
| EXP-ARUdo.Ubq2:1:10 | 32 | 10.59 | 11.5 |
| EXP-BOUgr.Ubq1:1:6 | 38 | 8.66 | 9.78 |
| EXP-BOUgr.Ubq1:1:7 | 41 | 5.17 | 5.81 |
| EXP-BOUgr.Ubq1:1:8 | 43 | 3.06 | 3.54 |
| EXP-BOUgr.Ubq2:1:14 | 52 | 10.68 | 11.76 |
| EXP-BOUgr.Ubq2:1:16 | 58 | 10.66 | 12.77 |
| EXP-BOUgr.Ubq2:1:17 | 60 | 6.1 | 8.14 |
| EXP-MISsi.Ubq1:1:8 | 70 | 3.95 | 4.78 |
| EXP-MISsi.Ubq1:1:10 | 72 | 12.51 | 16.43 |
| EXP-MISsi.Ubq1:1:11 | 74 | 5.12 | 5.98 |
| EXP-MISsi.Ubq1:1:7 | 76 | 1.58 | 1.36 |
| EXP-SCHsc.Ubq1:1:9 | 78 | 2.55 | 3.18 |
| EXP-SCHsc.Ubq1:1:7 | 84 | 2.95 | 3.25 |
| EXP-SCHsc.Ubq1:1:10 | 86 | 3.57 | 3.93 |
| EXP-SORnu.Ubq1:1:6 | 92 | 2.66 | 2.9 |
| EXP-SORnu.Ubq1:1:7 | 95 | 23.9 | 27.41 |
| EXP-SORnu.Ubq1:1:8 | 97 | 5.31 | 6.45 |
| EXP-SETit.Ubq1:1:5 | 103 | 10.64 | 12.3 |
| EXP-SETit.Ubq1:1:7 | 106 | 32.76 | 39.26 |
| EXP-SETit.Ubq1:1:6 | 108 | 17.8 | 22.81 |
| EXP-Sv.Ubq1:1:7 | 110 | 10.52 | 12.12 |
| EXP-Sv.Ubq1:1:8 | 116 | 18.75 | 23.86 |
| EXP-Sv.Ubq1:1:10 | 118 | 13.37 | 16.55 |
| EXP-Zm.UbqM1:1:6 | 122 | 9.67 | 12.35 |
| EXP-Zm.UbqM1:1:8 | 134 | 18.61 | 19.48 |
| Exp-Sb.Ubq4:1:2 | 140 | 7.85 | 10.21 |
| Exp-Sb.Ubq6:1:2 | 144 | 7.38 | 8.54 |

As can be seen in Tables 9 and 10 above, all of the EXP sequences were capable of driving GUS transgene expression in wheat cells. All of the EXP sequences drove GUS expression at levels higher than that of EXP-Os.Act1:1:9 in wheat cells. The EXP sequences EXP-ARUdo.Ubq1:1:8 (SEQ ID NO: 13), EXP-ARUdo.Ubq1:1:9 (SEQ ID NO: 18), EXP-ARUdo.Ubq1:1:11 (SEQ ID NO: 21), EXP-ARUdo.Ubq2:1:10 (SEQ ID NO: 32), EXP-BOUgr.Ubq2:1:14 (SEQ ID NO: 52), EXP-BOUgr.Ubq2:1:16 (SEQ ID NO: 58), EXP-BOUgr.Ubq2:1:17 (SEQ ID NO: 60), EXP-MISsi.Ubq1:1:10 (SEQ ID NO: 72), EXP-SORnu.Ubq1:1:7 (SEQ ID NO: 95), EXP-SETit.Ubq1:1:5 (SEQ ID NO: 103), EXP-SETit.Ubq1:1:7 (SEQ ID NO: 106), EXP-SETit.Ubq1:1:6 (SEQ ID NO: 108), EXP-Sv.Ubq1:1:7 (SEQ ID NO: 110), EXP-Sv.Ubq1:1:8 (SEQ ID NO: 116), EXP-Sv.Ubq1:1:10 (SEQ ID NO: 118), EXP-Zm.UbqM1:1:6 (SEQ ID NO: 122), and EXP-Zm.UbqM1:1:8 (SEQ ID NO: 134) demonstrated levels of GUS expression equal to or greater than GUS expression driven by EXP-CaMV.35S-enh+Ta.Lhcb1+Os.Act1:1:1 in wheat cells.

In a second set of experiments, the amplicon GUS expression cassette comprising EXP-ARUdo.Ubq1:1:11 (SEQ ID NO: 21) was compared to the controls EXP-Os.Act1:1:9 (SEQ ID NO: 162) and EXP-CaMV.35S-enh-FZm.DnaK:1:1 (SEQ ID NO: 161). Table 11 below shows the mean GUS and luciferase values determined for each amplicon. Table 12 below shows the GUS/RLuc ratios of expression normalized with respect to EXP-Os.Act1:1:9 and EXP-CaMV.35S-enh+Zm.DnaK:1:1 driven expression in wheat protoplasts.

TABLE 11

Mean GUS and Luciferase activity in transformed wheat leaf protoplast cells.

| EXP Sequence | SEQ ID NO: | GUS | RLuc |
|---|---|---|---|
| EMPTY | | 20.75 | 187112.50 |
| EXP-Os.Act1:1:9 | 162 | 1234.00 | 176970.50 |
| EXP-CaMV.35S-enh + Ta.Lhcb1 + Os.Act1:1:1 | 161 | 12883.50 | 119439.00 |
| EXP-ARUdo.Ubq1:1:11 | 21 | 30571.50 | 135037.50 |

TABLE 12

GUS/RLuc and GUS/FLuc ratios of expression normalized with respect to EXP-Os.Act1:1:9 (SEQ ID NO: 161) and EXP-CaMV.35S-enh + Zm.DnaK:1:1 (SEQ ID NO: 160) in wheat leaf protoplasts.

| EXP Sequence | SEQ ID NO: | GUS/RLuc Relative to EXP-Os.Act1:1:9 | GUS/RLuc Relative to EXP-CaMV.35S-enh + Ta.Lhcb1 + Os.Act1:1:1 |
|---|---|---|---|
| EXP-Os.Act1:1:9 | 162 | 1.00 | 0.06 |
| EXP-CaMV.35S-enh + Ta.Lhcb1 + Os.Act1:1:1 | 161 | 15.47 | 1.00 |
| EXP-ARUdo.Ubq1:1:11 | 21 | 32.47 | 2.10 |

As can be seen in Table 12 above, GUS expression driven by EXP-ARUdo.Ubq1:1:11 (SEQ ID NO: 21) was higher than both constitutive controls, EXP-Os.Act1:1:9 and EXP-CaMV.35S-enh+Zm.DnaK:1:1.

Example 4

Analysis of Regulatory Elements Driving GUS in Corn and Wheat Protoplasts

Corn and Wheat leaf protoplasts were transformed with plant expression vectors containing an EXP sequence driving expression of the β-glucuronidase (GUS) transgene and compared to GUS expression in leaf protoplasts in which expression of GUS is driven by known constitutive promoters.

Expression of a transgene driven by EXP-Cl.Ubq10 (SEQ ID NO: 168) was compared with expression from known constitutive promoters. The foregoing EXP sequences were cloned into plant expression vectors as shown in Table 13 below to yield vectors in which an EXP sequence is operably linked 5' to a GUS reporter that contained a processable intron (referred to as GUS-2, SEQ ID NO: 160) derived from the potato light-inducible tissue-specific ST-LS1 gene (GenBank Accession: X04753) or a contiguous GUS coding sequence (GUS-1, SEQ ID NO: 159), which was operably linked 5' to a 3' UTR derived from the *A. tumefaciens* Nopaline synthase gene (T-AGRtu.nos-1:1:13, SEQ ID NO: 161) or the wheat Hsp17 gene (T-Ta.Hsp17-1:1:1, SEQ ID NO: 162).

TABLE 13

GUS plant expression plasmid construct and corresponding EXP sequence, GUS coding sequence and 3' UTR used for transformation of corn leaf protoplasts. "SEQ ID NO:" refers to given EXP sequence.

| EXP Sequence | SEQ ID NO: | GUS/RLuc Relative to EXP-Os.Act1:1:9 | GUS/RLuc Relative to EXP-CaMV.35S-enh + Ta.Lhcb1 + Os.Act1:1:1 |
|---|---|---|---|
| EXP-Os.Act1:1:9 | 162 | 1.00 | 0.06 |
| EXP-CaMV.35S-enh + Ta.Lhcb1 + Os.Act1:1:1 | 161 | 15.47 | 1.00 |
| EXP-ARUdo.Ubq1:1:11 | 21 | 32.47 | 2.10 |

Two plasmids, for use in co-transformation and normalization of data, were also constructed using methods known in the art. Each plasmid contained a specific luciferase coding sequence that was driven by a constitutive EXP sequence. The plant vector pMON19437 comprises an expression cassette with a constitutive promoter operably linked 5' to an intron, (EXP-CaMV.35S-enh+Zm.DnaK:1:1, SEQ ID NO: 163), operably linked 5' to a firefly (*Photinus pyralis*) luciferase coding sequence (LUCIFERASE:1:3, SEQ ID NO: 156), operably linked 5' to a 3' UTR from the *Agrobacterium tumefaciens* nopaline synthase gene (T-AGRtu.nos-1:1:13, SEQ ID NO: 158). The plant vector pMON63934 comprises an expression cassette with a constitutive EXP sequence (EXP-CaMV.35S-enh-Lhcb1, SEQ ID NO: 164), operably linked 5' to a sea pansy (*Renilla reniformis*) luciferase coding sequence (CR-Ren.hRenilla Lucife-0:0:1, SEQ ID NO: 157), operably linked 5' to a 3' UTR from the *Agrobacterium tumefaciens* nopaline synthase gene (T-AGRtu.nos-1:1:13, SEQ ID NO: 158).

Corn leaf protoplasts were transformed using a PEG-based transformation method, which is well known in the art. Protoplast cells were transformed with pMON19437 plasmid DNA, pMON63934 plasmid DNA, and the plasmids presented in Table 13 and incubated overnight in total darkness. Measurements of both GUS and luciferase were conducted in a similar manner as that described in Example 2 above. One or two transformations for each EXP sequence were performed and the mean expression values for each EXP sequence determined from several samples from each transformation experiment. Sample measurements were made using four replicates of each EXP sequence construct transformation, or alternatively, three replicates of each EXP sequence construct per one of two transformation experiments. The mean GUS and luciferase expression levels are provided in Table 14. In this table, the firefly luciferase values (e.g., from expression of pMON19437) are provided in the column labeled "FLuc" and the *Renilla* luciferase values are provided as in the column labeled "RLuc."

TABLE 14

Mean GUS and Luciferase activity in transformed corn leaf protoplast cells.

| EXP Sequence | SEQ ID NO: | GUS | FLuc | RLuc |
|---|---|---|---|---|
| EXP-Os.Act1:1:9 | 162 | 83997.3 | 80983 | 61619 |
| EXP-CaMV.35S-enh + Ta.Lhcb1 + Os.Act1:1:1 | 161 | 248832 | 83589.8 | 72064.3 |
| EXP-Cl.Ubq10 | 168 | 30790.8 | 65807.5 | 34846.3 |

Table 15 below shows the GUS/FLuc and GUS/RLuc ratios of expression normalized with respect to EXP-Os.Act1:1:9 and EXP-CaMV.35S-enh+Zm.DnaK:1:1 driven expression in corn protoplasts.

TABLE 15

GUS/FLuc and GUS/RLuc ratios of expression normalized with respect to EXP-Os.Act1:1:9 (SEQ ID NO: 161) and EXP-CaMV.35S-enh + Zm.DnaK:1:1 (SEQ ID NO: 160) in wheat leaf protoplasts.

| EXP Sequence | SEQ ID NO: | GUS/Fluc normalized with respect to EXP-Os.Act1:1:9 | GUS/Rluc normalized with respect to EXP-Os.Act1:1:9 | GUS/Fluc normalized with respect to EXP-CaMV.35S-enh + Ta.Lhcb1 + Os.Act1:1:1 | GUS/Rluc normalized with respect to EXP-CaMV.35S-enh + Ta.Lhcb1 + Os.Act1:1:1 |
|---|---|---|---|---|---|
| EXP-Os.Act1:1:9 | 162 | 1.00 | 1.00 | 0.35 | 0.39 |
| EXP-CaMV.35S-enh + Ta.Lhcb1 + Os.Act1:1:1 | 161 | 2.87 | 2.53 | 1.00 | 1.00 |
| EXP-Cl.Ubq10 | 168 | 0.45 | 0.65 | 0.16 | 0.26 |

As can be seen in Table 15 above, EXP-Cl.Ubq10 (SEQ ID NO: 168) was able to drive expression of GUS, but was at a level lower than that of both constitutive controls.

The plasmids listed in Table 13 above were also used to transform wheat leaf protoplast cells in a similar manner as that for corn leaf protoplasts described above. Mean GUS and luciferase values are shown in Table 16 below. Table 17 below shows the GUS/FLuc and GUS/RLuc ratios of expression normalized with respect to EXP-CaMV.35S-enh+Zm.DnaK:1:1 driven expression in corn protoplasts.

TABLE 16

Mean GUS and Luciferase activity in transformed corn leaf protoplast cells.

| EXP Sequence | SEQ ID NO: | GUS | FLuc | RLuc |
|---|---|---|---|---|
| EXP-CaMV.35S-enh + Ta.Lhcb1 + Os.Act1:1:1 | 161 | 134145 | 1076.67 | 6858.67 |
| EXP-Cl.Ubq10 | 168 | 104669 | 888.67 | 4516 |

TABLE 17

GUS/FLuc and GUS/RLuc ratios of expression normalized with respect to EXP-CaMV.35S-enh + Zm.DnaK:1:1 (SEQ ID NO: 160) in wheat leaf protoplasts.

| EXP Sequence | SEQ ID NO: | GUS/Fluc normalized with respect to EXP-CaMV.35S-enh + Ta.Lhcb1 + Os.Act1:1:1 | GUS/Rluc normalized with respect to EXP-CaMV.35S-enh + Ta.Lhcb1 + Os.Act1:1:1 |
|---|---|---|---|
| EXP-CaMV.35S-enh + Ta.Lhcb1 + Os.Act1:1:1 | 161 | 1.00 | 1.00 |
| EXP-Cl.Ubq10 | 168 | 0.95 | 1.19 |

As can be seen in Table 17 above, EXP-Cl.Ubq10 (SEQ ID NO: 168) expressed GUS at a similar level as that of EXP-CaMV.35S-enh+Zm.DnaK:1:1 (SEQ ID NO: 160) in wheat protoplast cells.

Example 5

Analysis of Regulatory Elements Driving GUS in Transgenic Corn

Corn plants were transformed with plant expression vectors containing a EXP sequences driving expression of the GUS transgene, and the resulting plants were analyzed for GUS protein expression. The ubiquitin EXP sequences were cloned into plant binary transformation plasmid constructs using methods known in the art.

The resulting plant expression vectors contain a right border region from *A. tumefaciens*, a first expression cassette to assay the EXP sequence operably linked to a coding sequence for GUS that possesses the processable intron GUS-2, described above, operably linked 5' to the 3' UTR from the rice lipid transfer protein gene (T-Os.LTP-1:1:1, SEQ ID NO: 159); a second transgene selection cassette used for selection of transformed plant cells that confers resistance to the herbicide glyphosate (driven by the rice Actin 1 promoter), and a left border region from *A. tumefaciens*. The resulting plasmids were used to transform corn plants. Table 18 lists the plasmid designations, the EXP sequences and the SEQ ID NOs, which are also described in Table 1.

TABLE 18

Binary plant transformation plasmids and the associated EXP sequences.

| Plasmid Construct | EXP sequence | SEQ ID NO: |
|---|---|---|
| pMON140869 | EXP-AGRne.Ubq1:1:7 | 1 |
| pMON140870 | EXP-AGRne.Ubq1:1:8 | 5 |
| pMON142650 | EXP-ARUdo.Ubq1:1:8 | 13 |
| pMON142651 | EXP-ARUdo.Ubq1:1:9 | 18 |
| pMON142652 | EXP-ARUdo.Ubq2:1:8 | 27 |
| pMON142653 | EXP-ARUdo.Ubq2:1:9 | 30 |
| pMON140871 | EXP-BOUgr.Ubq1:1:6 | 38 |
| pMON140872 | EXP-BOUgr.Ubq1:1:7 | 41 |
| pMON140873 | EXP-BOUgr.Ubq2:1:14 | 52 |
| pMON140874 | EXP-BOUgr.Ubq2:1:15 | 55 |
| pMON142887 | EXP-MISsi.Ubq1:1:7 | 76 |
| pMON140875 | EXP-SORnu.Ubq1:1:6 | 92 |
| pMON140876 | EXP-SORnu.Ubq1:1:7 | 95 |
| pMON132037 | EXP-SETit.Ubq1:1:10 | 99 |
| pMON131958 | EXP-Sv.Ubq1:1:11 | 114 |
| pMON131959 | EXP-Sv.Ubq1:1:12 | 120 |
| pMON131961 | EXP-Zm.UbqM1:1:10 | 126 |
| pMON131963 | EXP-Zm.UbqM1:1:12 | 132 |
| pMON131962 | EXP-Zm.UbqM1:1:11 | 138 |
| pMON132932 | EXP-Sb.Ubq4:1:2 | 140 |
| pMON132931 | EXP-Sb.Ubq6:1:3 | 148 |
| pMON132974 | EXP-Sb.Ubq7:1:2 | 150 |
| pMON142738 | EXP-Cl.Ubq10 | 168 |

Plants were transformed using *Agrobacterium*-mediated transformations, for instance as described in U.S. Patent Application Publication 2009/0138985.

Histochemical GUS analysis was used for qualitative expression analysis of transformed plants. Whole tissue sections were incubated with GUS staining solution X-Gluc (5-bromo-4-chloro-3-indolyl-b-glucuronide) (1 mg/ml) for an appropriate length of time, rinsed, and visually inspected for blue coloration. GUS activity was qualitatively determined by direct visual inspection or inspection under a microscope using selected plant organs and tissues. The $R_0$ plants are inspected for expression in the roots and leaves, as well as the anther, silk, and developing seed and embryo, 21 days after pollination (21 DAP).

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 μl. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

The average $R_0$ GUS expression observed for each transformation is presented in Tables 19 and 20 below.

TABLE 19

Average $R_0$ GUS expression in root and leaf tissue.

| EXP sequence | SEQ ID NO: | V3 Root | V4 Root | V7 Root | VT Root | V3 Leaf | V4 Leaf | V7 Leaf | VT Leaf |
|---|---|---|---|---|---|---|---|---|---|
| EXP-AGRne.Ubq1:1:7 | 1 | 16 | | 25 | 14 | 49 | | 60 | 48 |
| EXP-AGRne.Ubq1:1:8 | 5 | 13 | | 20 | 22 | 38 | | 38 | 52 |
| EXP-ARUdo.Ubq1:1:8 | 13 | 18 | | 34 | 89 | 117 | | 48 | 106 |
| EXP-ARUdo.Ubq1:1:9 | 18 | 19 | | 20 | 68 | 105 | | 33 | 69 |
| EXP-ARUdo.Ubq2:1:8 | 27 | 14 | | 19 | 27 | 58 | | 57 | 47 |
| EXP-ARUdo.Ubq2:1:9 | 30 | 14 | | 15 | 25 | 40 | | 38 | 40 |
| EXP-BOUgr.Ubq1:1:6 | 38 | 12 | | 28 | 16 | 43 | | 46 | 27 |
| EXP-BOUgr.Ubq1:1:7 | 41 | 14 | | 24 | 114 | 51 | | 48 | 48 |
| EXP-BOUgr.Ubq2:1:14 | 52 | 17 | | 13 | 28 | 46 | | 33 | 41 |
| EXP-BOUgr.Ubq2:1:15 | 55 | 11 | | 67 | 36 | 86 | | 72 | 36 |
| EXP-MISsi.Ubq1:1:7 | 76 | 17 | | 28 | 13 | 18 | | 12 | 18 |
| EXP-SORnu.Ubq1:1:6 | 92 | 14 | | 45 | 33 | 44 | | 64 | 55 |
| EXP-SORnu.Ubq1:1:7 | 95 | 11 | | 18 | 20 | 31 | | 36 | 48 |
| EXP-SETit.Ubq1:1:10 | 99 | 0 | | 29 | 57 | 58 | | 37 | 46 |
| EXP-Sv.Ubq1:1:11 | 114 | nd | | nd | 9 | 20 | | 55 | 29 |
| EXP-Sv.Ubq1:1:12 | 120 | 63 | | 0 | 28 | 184 | | 27 | 16 |
| EXP-Zm.UbqM1:1:10 | 126 | 0 | | 237 | 18 | 221 | | 272 | 272 |
| EXP-Zm.UbqM1:1:12 | 132 | 0 | | 21 | 43 | 234 | | 231 | 196 |
| EXP-Zm.UbqM1:1:11 | 138 | 124 | | 103 | 112 | 311 | | 369 | 297 |
| EXP-Sb.Ubq4:1:2 | 140 | 125 | | 0 | 95 | 233 | | 150 | 88 |
| EXP-Sb.Ubq6:1:3 | 148 | 154 | | 13 | 128 | 53 | | 39 | 55 |
| EXP-Sb.Ubq7:1:2 | 150 | 37 | | 22 | 18 | 165 | | 89 | 177 |
| EXP-Cl.Ubq10 | 168 | | 61 | 67 | 32 | | 111 | 58 | 115 |

TABLE 20

Average $R_0$ GUS expression in corn reproductive organs (anther, silk) and developing seed (embryo and endosperm).

| EXP sequence | SEQ ID NO: | VT Anther | VT/R1 Silk | 21 DAP Embryo | 21 DAP Endosperm |
|---|---|---|---|---|---|
| EXP-AGRne.Ubq1:1:7 | 1 | 149 | 36 | 59 | 59 |
| EXP-AGRne.Ubq1:1:8 | 5 | 73 | 66 | 33 | 58 |
| EXP-ARUdo.Ubq1:1:8 | 13 | 321 | 253 | 177 | 355 |
| EXP-ARUdo.Ubq1:1:9 | 18 | 242 | 268 | 97 | 266 |
| EXP-ARUdo.Ubq2:1:8 | 27 | 104 | 99 | 79 | 157 |
| EXP-ARUdo.Ubq2:1:9 | 30 | 78 | 71 | 82 | 139 |
| EXP-BOUgr.Ubq1:1:6 | 38 | 58 | 250 | 43 | 63 |
| EXP-BOUgr.Ubq1:1:7 | 41 | 58 | 77 | 40 | 49 |
| EXP-BOUgr.Ubq2:1:14 | 52 | 236 | 377 | 48 | 137 |
| EXP-BOUgr.Ubq2:1:15 | 55 | 203 | 134 | 47 | 180 |
| EXP-MISsi.Ubq1:1:7 | 76 | 24 | 16 | 29 | 32 |
| EXP-SORnu.Ubq1:1:6 | 92 | 361 | 80 | 37 | 94 |
| EXP-SORnu.Ubq1:1:7 | 95 | 195 | 114 | 20 | 55 |
| EXP-SETit.Ubq1:1:10 | 99 | 132 | 85 | 50 | 63 |
| EXP-Sv.Ubq1:1:11 | 114 | 217 | 3 | 45 | 92 |
| EXP-Sv.Ubq1:1:12 | 120 | 120 | 21 | 49 | 112 |
| EXP-Zm.UbqM1:1:10 | 126 | 261 | 506 | 403 | 376 |
| EXP-Zm.UbqM1:1:12 | 132 | 775 | 362 | 253 | 247 |
| EXP-Zm.UbqM1:1:11 | 138 | 551 | 452 | 234 | 302 |
| EXP-Sb.Ubq4:1:2 | 140 | 213 | 0 | 25 | 79 |
| EXP-Sb.Ubq6:1:3 | 148 | 295 | 87 | 51 | 61 |
| EXP-Sb.Ubq7:1:2 | 150 | 423 | 229 | 274 | 90 |
| EXP-Cl.Ubq10 | 168 | 237 | 82 | 91 | 210 |

In $R_0$ corn plants, GUS expression levels in the leaf and root differed amongst the ubiquitin EXP sequences. While all of the EXP sequences demonstrated the ability to drive GUS transgene expression in stably transformed plants, each EXP sequence demonstrated a unique pattern of expression relative to the others. For example, the EXP sequences, EXP-AGRne.Ubq1:1:7 (SEQ ID NO: 1), EXP-AGRne.Ubq1:1:8 (SEQ ID NO: 5), EXP-ARUdo.Ubq1:1:8 (SEQ ID NO: 13), EXP-ARUdo.Ubq1:1:9 (SEQ ID NO: 18), EXP-ARUdo.Ubq2:1:8 (SEQ ID NO: 27), EXP-ARUdo.Ubq2:1:9 (SEQ ID NO: 30), EXP-BOUgr.Ubq1:1:6 (SEQ ID NO: 38), EXP-BOUgr.Ubq1:1:7 (SEQ ID NO: 41), EXP-BOUgr.Ubq2:1:14 (SEQ ID NO: 52), EXP-BOUgr.Ubq2:1:15 (SEQ ID NO: 55), EXP-MISsi.Ubq1:1:7 (SEQ ID NO: 76), EXP-SORnu.Ubq1:1:6 (SEQ ID NO: 92), EXP-SORnu.Ubq1:1:7 (SEQ ID NO: 95), EXP-SETit.Ubq1:1:10 (SEQ ID NO: 99), EXP-Sv.Ubq1:1:11 (SEQ ID NO: 114), EXP-Zm.UbqM1:1:12 (SEQ ID NO: 132), and EXP-Sb.Ubq7:1:2 (SEQ ID NO: 150) demonstrated lower levels of GUS expression in the root at V3 and V7 stages of development relative to EXP-Sv.Ubq1:1:12 (SEQ ID NO: 120), EXP-Zm.UbqM1:1:10 (SEQ ID NO: 126), EXP-Zm.UbqM1:1:11 (SEQ ID NO: 138), EXP-Sb.Ubq4:1:2 (SEQ ID NO: 140), and EXP-Sb.Ubq6:1:3 (SEQ ID NO: 148). Higher levels of GUS expression were observed in later stages of root development (VT) for EXP-ARUdo.Ubq1:1:8 (SEQ ID NO: 13), EXP-ARUdo.Ubq1:1:9 (SEQ ID NO: 18), EXP-BOUgr.Ubq1:1:7 (SEQ ID NO: 41), EXP-Zm.UbqM1:1:11 (SEQ ID NO: 138), and EXP-Sb.Ubq6:1:3 (SEQ ID NO: 148). Root expression driven by EXP-Zm.UbqM1:1:10 (SEQ ID NO: 140) demonstrated no expression at V3 but was high at V7 and then dropped by VT stage. Root expression driven by EXP-Zm.UbqM1:1:11 (SEQ ID NO: 150) was maintained to a similar level throughout development from stages V3, and V7 through VT. Expression of GUS driven by EXP-Cl.Ubq10 (SEQ ID NO: 168) was relatively steady from V4 to V7 stage but dropped to approximately half that of V4 and V7 at VT stage.

GUS expression levels showed dramatic differences in leaf tissue as well. The EXP sequences, EXP-Zm.UbqM1:1:10 (SEQ ID NO: 126), EXP-Zm.UbqM1:1:12 (SEQ ID NO: 132) and EXP-Zm.UbqM1:1:11 (SEQ ID NO: 138) demonstrated the highest level of GUS expression observed across all three stages of development (V3, V7 and VT). The EXP sequence, EXP-Sb.Ubq4:1:2 (SEQ ID NO: 140), showed a decline in expression from V3 to VT stages of development. The EXP sequences, EXP-ARUdo.Ubq1:1:8 (SEQ ID NO: 13) and EXP-Sb.Ubq7:1:2 (SEQ ID NO: 150) demonstrated higher levels of GUS expression in V3 and VT stage of development with a lower level of expression in the middle of growth at V7 stage. The EXP sequence, EXP-ARUdo.Ubq2:1:9 (SEQ ID NO: 30), EXP-BOUgr.Ubq1:1:7 (SEQ ID NO: 41), and EXP-MISsi.Ubq1:1:7 (SEQ ID NO: 76) maintained GUS expression over all three stages, while EXP-ARUdo.Ubq2:1:8 (SEQ ID NO: 27), EXP-BOUgr.Ubq1:1:6 (SEQ ID NO: 38), and EXP-BOUgr.Ubq2:1:15 (SEQ ID NO: 55) showed a slight decrease in expression at VT stage. Expression driven by EXP-Cl.Ubq10 (SEQ ID NO: 168) was similar at V4 and VT stage but dropped to about half the level of V4 and VT at V7 stage.

Likewise, with respect to reproductive tissue (anther and silk) different patterns of expression were observed unique to each EXP sequence. For example, high levels of expression were observed in anther and silk for the EXP sequences EXP-ARUdo.Ubq1:1:8 (SEQ ID NO: 13), EXP-ARUdo.Ubq1:1:9 (SEQ ID NO: 18), EXP-BOUgr.Ubq2:1:14 (SEQ ID NO: 52), EXP-BOUgr.Ubq2:1:15 (SEQ ID NO: 55), EXP-SORnu.Ubq1:1:7 (SEQ ID NO: 95), EXP-Zm.UbqM1:1:10 (SEQ ID NO: 126), EXP-Zm.UbqM1:1:12 (SEQ ID NO: 132), EXP-Zm.UbqM1:1:11 (SEQ ID NO: 138), and EXP-Sb.Ubq7:1:2 (SEQ ID NO: 150). Expression driven by the EXP sequences EXP-AGRne.Ubq1:1:7 (SEQ ID NO: 1), EXP-SORnu.Ubq1:1:6 (SEQ ID NO: 92), EXP-Sv.Ubq1:1:11 (SEQ ID NO: 114), EXP-Sv.Ubq1:1:12 (SEQ ID NO: 120), EXP-Sb.Ubq4:1:2 (SEQ ID NO: 140), EXP-Sb.Ubq6:1:3 (SEQ ID NO: 148), and EXP-Cl.Ubq10 (SEQ ID NO: 168) was high in the anther but lower in the silk relative to each EXP sequence, while expression driven by EXP-BOUgr.Ubq1:1:6 (SEQ ID NO: 38) was higher in the silk in comparison to expression in the anther.

Expression in the developing seed (21 DAP embryo and endosperm) was different among the EXP sequences. The EXP sequences, EXP-Zm.UbqM1:1:10 (SEQ ID NO: 126), EXP-Zm.UbqM1:1:12 (SEQ ID NO: 132), and EXP-Zm.UbqM1:1:11 (SEQ ID NO: 138) drove high expression of GUS in the developing seed embryo and endosperm tissue. Levels of expression in the endosperm were about two-fold or more higher than in the embryo when GUS was driven by the EXP sequences, EXP-ARUdo.Ubq1:1:8 (SEQ ID NO: 13), EXP-ARUdo.Ubq1:1:9 (SEQ ID NO: 18), EXP-ARUdo.Ubq2:1:8 (SEQ ID NO: 27), EXP-BOUgr.Ubq2:1:14 (SEQ ID NO: 52), EXP-BOUgr.Ubq2:1:15 (SEQ ID NO: 55), EXP-SORnu.Ubq1:1:6 (SEQ ID NO: 92), EXP-SORnu.Ubq1:1:7 (SEQ ID NO: 95), EXP-Sv.Ubq1:1:12 (SEQ ID NO: 120), EXP-Sb.Ubq4:1:2 (SEQ ID NO: 140), and EXP-Cl.Ubq10 (SEQ ID NO: 168). Expression of GUS was three-fold higher in the embryo than in the endosperm when driven by EXP-Sb.Ubq7:1:2 (SEQ ID NO: 150). GUS expression levels were relatively equivalent in the embryo and endosperm when driven by the EXP sequences EXP-AGRne.Ubq1:1:7 (SEQ ID NO: 1), EXP-AGRne.Ubq1:1:8 (SEQ ID NO: 5), EXP-BOUgr.Ubq1:1:6 (SEQ ID NO: 38), EXP-BOUgr.Ubq1:1:7 (SEQ ID NO: 41), EXP-MISsi.Ubq1:1:7 (SEQ ID NO: 76), EXP-SETit.Ubq1:1:10 (SEQ ID NO: 99), and EXP-Sb.Ubq6:1:3 (SEQ ID NO: 148).

Each EXP sequence demonstrated the ability to drive transgene expression in stably transformed corn plants. However, each EXP sequence had a pattern of expression for each tissue that was unique and offers an opportunity to select the EXP sequence which will best provide expression of a specific transgene depending upon the tissue expression strategy needed to achieve the desired results. This example demonstrates that EXP sequences isolated from homologous genes do not necessarily behave equivalently in the transformed plant and that expression can only be determined through empirical investigation of the properties for each EXP sequence and cannot be predicted based upon the gene homology from which the promoter was derived.

Example 6

Enhancers Derived from the Regulatory Elements

Enhancers are derived from the promoter elements provided herein, such as those presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169. The enhancer element may be comprised of one or more cis regulatory elements that, when operably linked 5' or 3' to a promoter element, or operably linked 5' or 3' to additional enhancer elements that are operably linked to a promoter, can enhance or modulate expression of a transgene, or provide expression of a transgene in a specific cell type or plant organ or at a particular time point in development or circadian rhythm. Enhancers are made by removing the TATA box or functionally similar elements and any downstream DNA sequence from the promoters that allow transcription to be initiated from the promoters provided herein as described above, including fragments thereof, in which the TATA box or functionally similar elements and DNA sequence downstream of the TATA box are removed.

Enhancer elements may be derived from the promoter elements provided herein and cloned using methods known in the art to be operably linked 5' or 3' to a promoter element, or operably linked 5' or 3' to additional enhancer elements that are operably linked to a promoter. Alternatively, enhancer elements are cloned, using methods known in the art, to be operably linked to one or more copies of the enhancer element which are operably linked 5' or 3' to a promoter element, or operably linked 5' or 3' to additional enhancer elements that are operably linked to a promoter. Enhancer elements can also be cloned to be operably linked 5' or 3' to a promoter element derived from a different genus organism, or operably linked 5' or 3' to additional enhancer elements derived from other genus organisms or the same genus organism that are operably linked to a promoter derived from either the same or different genus organism, resulting in a chimeric regulatory element. A GUS expression plant transformation vector is constructed using methods known in the art similar to the constructs described in the previous examples in which the resulting plant expression vectors contain a right border region from *A. tumefaciens*, a first expression cassette to test the regulatory or a chimeric regulatory element comprised of, a regulatory or chimeric regulatory element, operably linked to an intron derived from the HSP70 heat shock protein of *Z. mays* (I-Zm.DnaK-1:1:1 SEQ ID NO: 165) or any of the introns presented herein or any other intron, operably linked to a coding sequence for GUS that either possesses a processable intron (GUS-2, SEQ ID NO: 155) or no intron (GUS-1, SEQ ID NO: 154), operably linked to the Nopaline synthase 3' UTR from *A. tumefaciens* (T-AGRtu.nos-1:1:13, SEQ ID NO: 158) or the 3' UTR from the rice lipid transfer protein gene (T-Os.LTP-1:1:1, SEQ ID NO: 160); a second transgene selection cassette used for selection of transformed plant cells that confers resistance to the herbicide glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by other *Agrobacterium*-mediated or particle bombardment methods known in the art. Alternatively, protoplast cells derived from corn or other genus plants are transformed using methods known in the art to perform transient assays GUS expression driven by the regulatory element comprising one or more enhancers is evaluated in stable or transient plant assays to determine the effects of the enhancer element on expression of a transgene. Modifications to one or more enhancer elements or duplication of one or more enhancer elements is performed based upon empirical experimentation and the resulting gene expression regulation that is observed using each regulatory element composition. Altering the relative positions of one or more enhancers in the resulting regulatory or chimeric regulatory element may affect the transcriptional activity or specificity of the regulatory or chimeric regulatory element and is determined empirically to identify the best enhancers for the desired transgene expression profile within the corn plant or other genus plant.

Example 7

Analysis of Intron Enhancement of GUS Activity Using Plant Derived Protoplasts

An intron is selected based upon experimentation and comparison with an intronless expression vector control to empirically select an intron and configuration within the vector transfer DNA (T-DNA) element arrangement for optimal expression of a transgene. For example, in the expression of an herbicide resistance gene, such as CP4, which confers tolerance to glyphosate, it is desirable to have transgene expression within the reproductive tissues as well as the vegetative tissues, to prevent the loss of yield when applying the herbicide. An intron in this instance would be selected upon its ability, when operably linked to a constitutive promoter, to enhance expression of the herbicide resistance conferring transgene, particularly within the reproductive cells and tissues of the transgenic plant and thus providing both vegetative and reproductive tolerance to the transgenic plant when sprayed with the herbicide. In most ubiquitin genes, the 5' UTR is comprised of a leader, which has an intron sequence embedded within it. The regulatory elements derived from such genes are therefore assayed using the entire 5' UTR comprising the promoter, leader, and intron. To achieve different expression profiles or to modulate the level of transgene expression, the intron from such a regulatory element may be removed or substituted with a heterologous intron.

Introns presented herein as SEQ ID NOs: 4, 12, 15, 20, 26, 29, 37, 40, 48, 51, 54, 57, 59, 65, 69, 81, 91, 94 and 171 are identified using genomic DNA contigs in comparison to expressed sequence tag clusters or cDNA contigs to identify exon and intron sequences within the genomic DNA. In addition, 5' UTR or leader sequences are also used to define the intron/exon splice junction of one or more introns under conditions when the gene sequence encodes a leader sequence that is interrupted by one or more introns. Introns are cloned using methods known in the art into a plant transformation vector to be operably linked 3' to a regulatory element and leader fragment and operably linked 5' to either a second leader fragment or to coding sequences, for instance as depicted in the expression cassettes presented in FIG. 9.

Thus, for instance, a first possible expression cassette (Expression Cassette Configuration 1 in FIG. 9) is comprised of a promoter or chimeric promoter element [A], operably linked 5' to a leader element [B], operably linked 5' to a test intron element [C], operably linked to a coding region [D], which is operably linked to a 3' UTR element [E]. Alternatively, a second possible expression cassette (Expression Cassette Configuration 2 in FIG. 9) is comprised of a promoter or chimeric promoter element [F], operably linked 5' to a first leader element or first leader element fragment [G], operably linked 5' to a test intron element [H], operably linked 5' to a second leader element or first leader element second fragment [I], operably linked to a coding region [J], which is operably linked to a 3' UTR element [K]. Further, a third possible expression cassette (Expression Cassette Configuration 3 in FIG. 9) is comprised of a promoter or chimeric promoter element [L], operably linked 5' to a leader element [M], operably linked 5' to a first fragment of the coding sequence element [N], operably linked 5' to an intron element [O] element, operably linked 5' to a second fragment of the coding sequence element [P], which is operably linked to a 3' UTR element [Q]. Expression Cassette Configuration 3 is designed to allow splicing of the intron in such a manner as to produce a complete open reading frame without a frame shift between the first and second fragment of the coding sequence.

As discussed above, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The DNA sequence around the 5' or 3' end splice junction sites of the intron can thus be modified.

The introns are assayed for an enhancement effect through the ability to enhance expression in transient assay or stable plant assay. For transient assay of intron enhancement, a base plant vector is constructed using methods known in the art. The intron is cloned into a base plant vector which comprises an expression cassette comprised of a constitutive promoter such as the Cauliflower mosaic virus promoter, P-CaMV.35S-enh-1:1:9 (SEQ ID NO: 166), operably linked 5' to a leader element, L-CaMV.35S-1:1:15 (SEQ ID NO: 167), operably linked 5' to a test intron element (e.g. one of SEQ ID NOs: 4, 12, 15, 20, 26, 29, 37, 40, 48, 51, 54, 57, 59, 65, 69, 81, 91, 94 and 171), operably linked to a coding sequence for GUS that either possesses a processable intron (GUS-2, SEQ ID NO: 155) or no intron (GUS-1, SEQ ID NO: 154), operably linked to the Nopaline synthase 3' UTR from *A. tumefaciens* (T-AGRtu.nos-1:1:13, SEQ ID NO: 158). Protoplast cells derived from corn or other genus plant tissue are transformed with the base plant vector and Luciferase control vectors as described previously in Example 2 above, and assayed for activity. To compare the relative ability of the intron to enhance expression, GUS values are expressed as a ratio of GUS to Luciferase activity and compared with those levels imparted by a construct comprising the constitutive promoter operably linked to a known intron standard such as that as the intron derived from the HSP70 heat shock protein of *Zea mays*, I-Zm.DnaK-1:1:1 (SEQ ID NO: 165), as well as a construct comprising the constitutive promoter, but without an intron operably linked to the promoter.

For stable plant assay of the introns presented as SEQ ID NOs: 4, 12, 15, 20, 26, 29, 37, 40, 48, 51, 54, 57, 59, 65, 69, 81, 91, 94 and 171, a GUS expression plant transformation vector is constructed similar to the constructs described in the previous examples in which the resulting plant expression vectors contains a right border region from *A. tumefaciens*, a first expression cassette to test the intron comprised of a constitutive promoter such as the Cauliflower mosaic virus promoter, P-CaMV.35S-enh-1:1:9 (SEQ ID NO: 166), operably linked 5' to a leader element, L-CaMV.35S-1:1:15 (SEQ ID NO: 167), operably linked 5' to a test intron element provided herein, operably linked to a coding sequence for GUS that either possesses a processable intron (GUS-2, SEQ ID NO: 155) or no intron (GUS-1, SEQ ID NO: 154), operably linked to the Nopaline synthase 3' UTR from *A. tumefaciens* (T-AGRtu.nos-1:1:13, SEQ ID NO: 158); a second transgene selection cassette used for selection of transformed plant cells that confers resistance to glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by *Agrobacterium*-mediated methods known in the art. Single-copy or low copy number transformants are selected for comparison to single-copy or low copy number transformed plants, transformed with a plant transformation vector identical to the test vector but without the test intron to determine if the test intron provides an intron mediated enhancement effect.

Any of the introns presented as SEQ ID NOs: 4, 12, 15, 20, 26, 29, 37, 40, 48, 51, 54, 57, 59, 65, 69, 81, 91, 94 and 171 can be modified in a number of ways, such as deleting fragments within the intron sequence, which may reduce expression or duplication of fragments with the intron that may enhance expression. In addition, DNA sequences within the intron that may affect the specificity of expression to either particular cells types or tissues and organs can be duplicated or altered or deleted to affect expression and patterns of expression of the transgene. In addition, the introns provided herein can be modified to remove any potential start codons (ATG) that may cause unintentional transcripts from being expressed from improperly spliced introns as different, longer or truncated proteins. Once the intron has been empirically tested, or it has been altered based upon experimentation, the intron is used to enhance expression of a transgene in stably transformed plants that can be of any genus monocot or dicot plant, so long as the intron provides enhancement of the transgene. The intron can also be used to enhance expression in other organisms, such as algae, fungi, or animal cells, so long as the intron provides enhancement or attenuation or specificity of expression of the transgene to which it is operably linked.

Having illustrated and described the principles of the invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a DNA sequence selected from the group consisting of:

a) a DNA sequence comprising SEQ ID NO: 17 and b) a fragment comprising at least 50 contiguous nucleotides of SEQ ID NO: 17, wherein the fragment has gene-regulatory activity;

wherein said DNA sequence is operably linked to a heterologous transcribable DNA molecule.

2. The recombinant DNA molecule of claim 1, wherein said DNA sequence comprises said fragment and has at least 90 percent sequence identity to the DNA sequence of SEQ ID NO:16 or 18 and has gene-regulatory activity.

3. The recombinant DNA molecule of claim 1, wherein said DNA sequence comprises said fragment and has at least 95 percent sequence identity to the DNA sequence of SEQ ID NO:16 or 18 and has gene-regulatory activity.

4. The DNA molecule of claim 1, wherein the heterologous transcribable DNA molecule is a gene of agronomic interest.

5. The recombinant DNA molecule of claim 4, wherein the gene of agronomic interest confers herbicide tolerance in a plant.

6. The recombinant DNA molecule of claim 4, wherein the gene of agronomic interest confers pest resistance in a plant.

7. A construct comprising the recombinant DNA molecule of claim 1.

8. A transgenic plant cell comprising a recombinant DNA molecule comprising a DNA sequence selected from the group consisting of:

a) a DNA sequence comprising SEQ ID NO: 17; and b) a fragment comprising at least 50 contiguous nucleotides of SEQ ID NO: 17, wherein the fragment has gene-regulatory activity;

wherein said DNA sequence is operably linked to a heterologous transcribable DNA molecule.

9. The transgenic plant cell of claim 8, wherein said transgenic plant cell is a monocotyledonous plant cell.

10. The transgenic plant cell of claim 8, wherein said transgenic plant cell is a dicotyledonous plant cell.

11. A transgenic plant, or part thereof, comprising a recombinant DNA molecule comprising a DNA sequence selected from the group consisting of:

a) a DNA sequence comprising SEQ ID NO: 17; and b) a fragment comprising at least 50 contiguous nucleotides of SEQ ID NO: 17, wherein the fragment has gene-regulatory activity;

wherein said DNA sequence is operably linked to a heterologous transcribable DNA molecule.

12. A progeny plant of the transgenic plant of claim 11, wherein the progeny plant comprises said recombinant DNA molecule.

13. A transgenic seed of the transgenic plant of claim 11, wherein the seed comprises said recombinant DNA molecule.

14. A method of expressing a transcribable DNA molecule comprising obtaining a transgenic plant according to claim 11 and cultivating said plant, wherein the transcribable DNA molecule is expressed.

15. A method of producing a transgenic plant comprising:

a) transforming a plant cell with the recombinant DNA molecule of claim 1 to produce a transformed plant cell; and b) regenerating a transgenic plant from the transformed plant cell.

16. The recombinant DNA molecule of claim 1, wherein said DNA sequence is selected from the group consisting of SEQ ID NOs: 16 and 18.

17. The transgenic plant cell of claim 8, wherein said DNA sequence is selected from the group consisting of SEQ ID NOs: 16 and 18.

18. The transgenic plant, or part thereof, of claim 11, wherein said DNA sequence is selected from the group consisting of SEQ ID NOs: 16 and 18.

* * * * *

SEQUENCE LISTING

```
<160> NUMBER OF SEQ ID NOS: 171

<210> SEQ ID NO 1
<211> LENGTH: 3143
<212> TYPE: DNA
<213> ORGANISM: Agrostis nebulosa

<400> SEQUENCE: 1

ggcctcttta cgtttggcac aatttaattg aatcccggca tggcatgtta gaccggagtg     60

agccggccct tttactggta tgacactccc tctgtcttga gtgtcgctgt gccagcttgt    120

acctctgtct atgttcacag cccgtgctgt gtacctagac cctccgtttg tccacattca    180

ttttaatctc tattgtatct tgtcaaaacc taaaagccta aaacgactct gataaaggga    240

cagaaagatt atacaagagc aagtgtataa tgaaataatg taagcgagct atatgaattg    300

tcacgtgtca tatttatgtt gagacgaaga agagaaaata aacaccatgc aaatttatgg    360

cgagtgatag atggccagat gggcacaagg cctcctattt cttaaatcgg attttgtaag    420

aacgaaaaaa gggacttata agagaatagg atagaccata tatcaatgat gtagtatgca    480

tcaagatcta actattatat gagtgaattg ataaatttat tctaggtgac atggccttaa    540

cgatgaacag tacatggtta aatcaataga acaatagcca actctagcag ctctaaaaaa    600

agatatatat tcgtcgaggc actattatgc aaccacatag tcaacttcaa caccgcttga    660

gtgcgttctc atgttttttt tttcttgcaa attacgcttt tctaaaataa aataatttgg    720

atcgtgcaat tatttcactt taggtgtgcg tgactacgtg agtaacattt ttgaatctca    780

gaaaggaaat aaaagtataa tactgctgcc tactttgagg attcggcttg ttatttaaaa    840

ccgtctttaa ggtcaaatgc tcaagattca ttcaacaatt gaaacgtctc acatgattaa    900

atcatgtata aggatgctaa ggtcttgctt gacaatgttt ttctaggaat ttcatctaac    960

tttttgagtg aaactatcaa ataataattt taaaacaatt ttataagaga agctccggag   1020

ataaaaggcc atctaatcta tgttagaaga gtgaagttta ctccctctgt cccaaaaata   1080
```

-continued

```
gaattctaag tatgaaatga ttttttgtt atacaaaagg agtatatatc acaagattga   1140
tgtcagttat gcttagggca cgtacacgac gctggtgctt taggtagacg ttaatcgttg   1200
tttctgcatt ttattttatt ttgttgccac ggtgtacatt tgggtagacg tttgtcacag   1260
gcattgccac tcaaacaagc agccggcgct tggagctttt atagtttgaa aagtgacggt   1320
tttaaggatg ggtaagctga ttagtatatg taagtttagc tttttccatt gtaggttaag   1380
ccttaaggct cttacacaat tgtttcatta ttctcattct ttaagagccc atataagcgt   1440
tcatgaattg tacatatcct tagatttttt tttttgggta aagctcgagc ttctgtatct   1500
aaaagtagag aaatcagaaa aagattcatg ttttggtagt tttgatttct tgcctccata   1560
ataattttgg tttaccattt tttgtttgat tttagtttta gaagcgttta tagcaggatt   1620
taaaatccaa aactaccatt atcttcaagt gaccgtcagt gagccgttta acggcgtcga   1680
caagtccaac ggacaccaac cagtgaacca ccagcgtcga gccaagcgat gcaaacggaa   1740
cggccgagac gttgacacct ttggcgcggc acggcatgtc ggatctccct ctctggcccc   1800
ctctcgagag ttccagctcc acctccaccg gtggcggttt ccaagtccgt tccgttccgt   1860
tccgcctcct gcctgctcct ctcagacggc acgaaaccgt gacggcaccg gcagcacggg   1920
gggattcctt ttccactgct ccttcctttt cccttcctcg cccgccgcta taaatagcca   1980
gccccgtccc cagattcttt cccaacctca tctttgttcg gagcacccac acaacccgat   2040
ccccaattcc ctcgtctctc ctcgcgagcc tcgtcgaccc ccccttcaag gtacggcgat   2100
cgtcctccct ccctctctct ctctaccttc tcttctctag actagatcgg cgacccggtc   2160
catggttagg gcctgctagt tctgttcctg ttttttccat ggctgcgagg taaaatagat   2220
ctgatggcgt tatgatggtt aactcgtcat actcttgcga tctatggtcc ctttaggaca   2280
tcgatttaat ttcggatggt tcgagatcgg tgatccatgg ttagtaccct aggcagtggg   2340
gttagatccg tgctgttagg gttcgtagat ggattctgat tgctcagtaa ctgggaaacc   2400
tgggatggtt ctagctggga atcctgggat ggttctagct ggttcgcaga tgagatcgat   2460
ttcatggtct gctatatctt gtttcgttgc ctaggttccg tttaatctgt ccgtggtatg   2520
atgttagcct ttgataaggt tcgatcgtgc tagctacgtc ctgcgcagca tttaattgtc   2580
aggtcataat ttttagcatt cctgtttttg tttggtttgg ttttgtctgg ttgggctgta   2640
gatagtttca atctacctgt cggtttattt tattaaattt ggattggatc tgtatgtgtc   2700
acatatatct tcatgattaa tatggttgga attatctctt catcttttag atatatatgg   2760
ataggtatat atgttgctgt gggttttact ggtactttat tagatatatt catgcttaga   2820
tacatgaagc aacgtgctgt tacagtttaa taattcttgt ttatctaata aacaaataag   2880
gataggtata tatgttgctg atggttttac tgatacttta ttagatagta cttctttgac   2940
atgaaggaac atcctgcgac agcttaataa ttattcttca tctaataaaa agcttgcttt   3000
ttaattattt tgatatactt ggatgatgtc atgcagcagc tatgtgtgaa ttttcggccc   3060
tgtcttcata tgatgtttat ttgcttggga ctgtttcttt ggctgataac tcaccctgtt   3120
gtttggtgat ccttctgcag gtg                                            3143
```

```
<210> SEQ ID NO 2
<211> LENGTH: 2005
<212> TYPE: DNA
<213> ORGANISM: Agrostis nebulosa

<400> SEQUENCE: 2

ggcctcttta cgtttggcac aatttaattg aatcccggca tggcatgtta gaccggagtg     60
```

-continued

```
agccggccct tttactggta tgacactccc tctgtcttga gtgtcgctgt gccagcttgt    120
acctctgtct atgttcacag cccgtgctgt gtacctagac cctccgtttg tccacattca    180
ttttaatctc tattgtatct tgtcaaaacc taaaagccta aaacgactct gataaaggga    240
cagaaagatt atacaagagc aagtgtataa tgaaataatg taagcgagct atatgaattg    300
tcacgtgtca tatttatgtt gagacgaaga agagaaaata aacaccatgc aaatttatgg    360
cgagtgatag atggccagat gggcacaagg cctcctattt cttaaatcgg attttgtaag    420
aacgaaaaaa gggacttata agagaatagg atagaccata tatcaatgat gtagtatgca    480
tcaagatcta actattatat gagtgaattg ataaatttat tctaggtgac atggccttaa    540
cgatgaacag tacatggtta aatcaataga acaatagcca actctagcag ctctaaaaaa    600
agatatatat tcgtcgaggc actattatgc aaccacatag tcaacttcaa caccgcttga    660
gtgcgttctc atgttttttt tttcttgcaa attacgcttt tctaaaataa aataatttgg    720
atcgtgcaat tatttcactt taggtgtgcg tgactacgtg agtaacattt ttgaatctca    780
gaaaggaaat aaaagtataa tactgctgcc tactttgagg attcggcttg ttatttaaaa    840
ccgtctttaa ggtcaaatgc tcaagattca ttcaacaatt gaaacgtctc acatgattaa    900
atcatgtata aggatgctaa ggtcttgctt gacaatgttt ttctaggaat ttcatctaac    960
tttttgagtg aaactatcaa ataataattt taaaacaatt ttataagaga agctccggag   1020
ataaaaggcc atctaatcta tgttagaaga gtgaagttta ctccctctgt cccaaaaata   1080
gaattctaag tatgaaatga tttttttgtt atacaaaagg agtatatatc acaagattga   1140
tgtcagttat gcttagggca cgtacacgac gctggtgctt taggtagacg ttaatcgttg   1200
tttctgcatt ttattttatt ttgttgccac ggtgtacatt tgggtagacg tttgtcacag   1260
gcattgccac tcaaacaagc agccggcgct tggagctttt atagtttgaa aagtgacggt   1320
tttaaggatg ggtaagctga ttagtatatg taagtttagc tttttccatt gtaggttaag   1380
ccttaaggct cttacacaat tgtttcatta ttctcattct ttaagagccc atataagcgt   1440
tcatgaattg tacatatcct tagatttttt tttttgggta aagctcgagc ttctgtatct   1500
aaaagtagag aaatcagaaa aagattcatg ttttggtagt tttgatttct tgcctccata   1560
ataattttgg tttaccattt tttgtttgat tttagtttta gaagcgttta tagcaggatt   1620
taaaatccaa aactaccatt atcttcaagt gaccgtcagt gagccgttta acggcgtcga   1680
caagtccaac ggacaccaac cagtgaacca ccagcgtcga gccaagcgat gcaaacggaa   1740
cggccgagac gttgacacct ttggcgcggc acggcatgtc ggatctccct ctctggcccc   1800
ctctcgagag ttccagctcc acctccaccg gtggcggttt ccaagtccgt tccgttccgt   1860
tccgcctcct gcctgctcct ctcagacggc acgaaaccgt gacggcaccg gcagcacggg   1920
gggattcctt ttccactgct ccttcctttt cccttcctcg cccgccgcta taaatagcca   1980
gccccgtccc cagattcttt cccaa                                         2005
```

<210> SEQ ID NO 3
<211> LENGTH: 85
<212> TYPE: DNA
<213> ORGANISM: Agrostis nebulosa

<400> SEQUENCE: 3

```
cctcatcttt gttcggagca cccacacaac ccgatcccca attccctcgt ctctcctcgc     60
gagcctcgtc gacccccccct tcaag                                          85
```

<210> SEQ ID NO 4
<211> LENGTH: 1053
<212> TYPE: DNA
<213> ORGANISM: Agrostis nebulosa

<400> SEQUENCE: 4
gtacggcgat cgtcctccct ccctctctct ctctaccttc tcttctctag actagatcgg 60
cgacccggtc catggttagg gcctgctagt tctgttcctg ttttttccat ggctgcgagg 120
taaaatagat ctgatggcgt tatgatggtt aactcgtcat actcttgcga tctatggtcc 180
ctttaggaca tcgatttaat ttcggatggt tcgagatcgg tgatccatgg ttagtaccct 240
aggcagtggg gttagatccg tgctgttagg gttcgtagat ggattctgat tgctcagtaa 300
ctgggaaacc tgggatggtt ctagctggga atcctgggat ggttctagct ggttcgcaga 360
tgagatcgat ttcatggtct gctatatctt gtttcgttgc ctaggttccg tttaatctgt 420
ccgtggtatg atgttagcct ttgataaggt tcgatcgtgc tagctacgtc ctgcgcagca 480
tttaattgtc aggtcataat ttttagcatt cctgtttttg tttggtttgg ttttgtctgg 540
ttgggctgta gatagtttca atctacctgt cggtttattt tattaaattt ggattggatc 600
tgtatgtgtc acatatatct tcatgattaa tatggttgga attatctctt catcttttag 660
atatatatgg ataggtatat atgttgctgt gggttttact ggtactttat tagatatatt 720
catgcttaga tacatgaagc aacgtgctgt tacagtttaa taattcttgt ttatctaata 780
aacaaataag gataggtata tatgttgctg atggttttac tgatacttta ttagatagta 840
cttctttgac atgaaggaac atcctgcgac agcttaataa ttattcttca tctaataaaa 900
agcttgcttt ttaattattt tgatatactt ggatgatgtc atgcagcagc tatgtgtgaa 960
ttttcggccc tgtcttcata tgatgtttat ttgcttggga ctgtttcttt ggctgataac 1020
tcaccctgtt gtttggtgat ccttctgcag gtg 1053

<210> SEQ ID NO 5
<211> LENGTH: 2137
<212> TYPE: DNA
<213> ORGANISM: Agrostis nebulosa

<400> SEQUENCE: 5
gagaagctcc ggagataaaa ggccatctaa tctatgttag aagagtgaag tttactccct 60
ctgtcccaaa aatagaattc taagtatgaa atgatttttt tgttatacaa aaggagtata 120
tatcacaaga ttgatgtcag ttatgcttag ggcacgtaca cgacgctggt gctttaggta 180
gacgttaatc gttgtttctg cattttattt tattttgttg ccacggtgta catttgggta 240
gacgtttgtc acaggcattg ccactcaaac aagcagccgg cgcttggagc ttttatagtt 300
tgaaaagtga cggttttaag gatgggtaag ctgattagta tatgtaagtt tagctttttc 360
cattgtaggt taagccttaa ggctcttaca caattgtttc attattctca ttctttaaga 420
gcccatataa gcgttcatga attgtacata tccttagatt tttttttttg ggtaaagctc 480
gagcttctgt atctaaaagt agagaaatca gaaaaagatt catgttttgg tagttttgat 540
ttcttgcctc cataataatt ttggtttacc attttttgtt tgattttagt tttagaagcg 600
tttatagcag gatttaaaat ccaaaactac cattatcttc aagtgaccgt cagtgagccg 660
tttaacggcg tcgacaagtc caacggacac caaccagtga accaccagcg tcgagccaag 720
cgatgcaaac ggaacggccg agacgttgac acctttggcg cggcacggca tgtcggatct 780
ccctctctgg ccccctctcg agagttccag ctccacctcc accggtggcg gtttccaagt 840
ccgttccgtt ccgttccgcc tcctgcctgc tcctctcaga cggcacgaaa ccgtgacggc 900
accggcagca cggggggatt ccttttccac tgctccttcc ttttcccttc ctcgcccgcc 960
gctataaata gccagccccg tccccagatt ctttcccaac ctcatctttg ttcggagcac 1020
ccacacaacc cgatccccaa ttccctcgtc tctcctcgcg agcctcgtcg acccccccctt 1080 caaggtacgg cgatcgtcct ccctccctct ctctctctac cttctcttct ctagactaga 1140
tcggcgaccc ggtccatggt tagggcctgc tagttctgtt cctgtttttt ccatggctgc 1200
gaggtaaaat agatctgatg gcgttatgat ggttaactcg tcatactctt gcgatctatg 1260
gtccctttag gacatcgatt taatttcgga tggttcgaga tcggtgatcc atggttagta 1320
ccctaggcag tggggttaga tccgtgctgt tagggttcgt agatggattc tgattgctca 1380
gtaactggga aacctgggat ggttctagct gggaatcctg ggatggttct agctggttcg 1440
cagatgagat cgatttcatg gtctgctata tcttgtttcg ttgcctaggt tccgtttaat 1500
ctgtccgtgg tatgatgtta gcctttgata aggttcgatc gtgctagcta cgtcctgcgc 1560
agcatttaat tgtcaggtca taatttttag cattcctgtt tttgtttggt ttggttttgt 1620
ctggttgggc tgtagatagt ttcaatctac ctgtcggttt attttattaa atttggattg 1680
gatctgtatg tgtcacatat atcttcatga ttaatatggt tggaattatc tcttcatctt 1740
ttagatatat atggataggt atatatgttg ctgtgggttt tactggtact ttattagata 1800
tattcatgct tagatacatg aagcaacgtg ctgttacagt ttaataattc ttgtttatct 1860
aataaacaaa taaggatagg tatatatgtt gctgatggtt ttactgatac tttattagat 1920
agtacttctt tgacatgaag gaacatcctg cgacagctta ataattattc ttcatctaat 1980
aaaaagcttg ctttttaatt attttgatat acttggatga tgtcatgcag cagctatgtg 2040
tgaattttcg gccctgtctt catatgatgt ttatttgctt gggactgttt ctttggctga 2100
taactcaccc tgttgtttgg tgatccttct gcaggtg 2137

<210> SEQ ID NO 6
<211> LENGTH: 999
<212> TYPE: DNA
<213> ORGANISM: Agrostis nebulosa

<400> SEQUENCE: 6
gagaagctcc ggagataaaa ggccatctaa tctatgttag aagagtgaag tttactccct 60
ctgtcccaaa aatagaattc taagtatgaa atgatttttt tgttatacaa aaggagtata 120
tatcacaaga ttgatgtcag ttatgcttag ggcacgtaca cgacgctggt gctttaggta 180
gacgttaatc gttgtttctg cattttattt tattttgttg ccacggtgta catttgggta 240
gacgtttgtc acaggcattg ccactcaaac aagcagccgg cgcttggagc ttttatagtt 300
tgaaaagtga cggttttaag gatgggtaag ctgattagta tatgtaagtt tagcttttc 360 cattgtaggt taagccttaa ggctcttaca caattgtttc attattctca ttctttaaga 420
gcccatataa gcgttcatga attgtacata tccttagatt tttttttttg ggtaaagctc 480
gagcttctgt atctaaaagt agagaaatca gaaaaagatt catgttttgg tagttttgat 540
ttcttgcctc cataataatt ttggtttacc attttttgtt tgattttagt tttagaagcg 600
tttatagcag gatttaaaat ccaaaactac cattatcttc aagtgaccgt cagtgagccg 660
tttaacggcg tcgacaagtc caacggacac caaccagtga accaccagcg tcgagccaag 720
cgatgcaaac ggaacggccg agacgttgac acctttggcg cggcacggca tgtcggatct 780

```
ccctctctgg ccccctctcg agagttccag ctccacctcc accggtggcg gtttccaagt    840

ccgttccgtt ccgttccgcc tcctgcctgc tcctctcaga cggcacgaaa ccgtgacggc    900

accggcagca cggggggatt ccttttccac tgctccttcc ttttcccttc ctcgcccgcc    960

gctataaata gccagccccg tccccagatt ctttcccaa                           999
```

<210> SEQ ID NO 7
<211> LENGTH: 1900
<212> TYPE: DNA
<213> ORGANISM: Agrostis nebulosa

<400> SEQUENCE: 7

```
gtagacgttt gtcacaggca ttgccactca aacaagcagc cggcgcttgg agcttttata      60

gtttgaaaag tgacggtttt aaggatgggt aagctgatta gtatatgtaa gtttagcttt    120

ttccattgta ggttaagcct taaggctctt acacaattgt ttcattattc tcattcttta    180

agagcccata taagcgttca tgaattgtac atatccttag attttttttt ttgggtaaag    240

ctcgagcttc tgtatctaaa agtagagaaa tcagaaaaag attcatgttt tggtagtttt    300

gatttcttgc ctccataata attttggttt accatttttt gtttgatttt agttttagaa    360

gcgtttatag caggatttaa aatccaaaac taccattatc ttcaagtgac cgtcagtgag    420

ccgtttaacg gcgtcgacaa gtccaacgga caccaaccag tgaaccacca gcgtcgagcc    480

aagcgatgca aacggaacgg ccgagacgtt gacacctttg gcgcggcacg gcatgtcgga    540

tctccctctc tggccccctc tcgagagttc cagctccacc tccaccggtg gcggtttcca    600

agtccgttcc gttccgttcc gcctcctgcc tgctcctctc agacggcacg aaaccgtgac    660

ggcaccggca gcacgggggg attccttttc cactgctcct tccttttccc ttcctcgccc    720

gccgctataa atagccagcc ccgtccccag attctttccc aacctcatct ttgttcggag    780

cacccacaca acccgatccc caattccctc gtctctcctc gcgagcctcg tcgacccccc    840

cttcaaggta cggcgatcgt cctccctccc tctctctctc taccttctct tctctagact    900

agatcggcga cccggtccat ggttagggcc tgctagttct gttcctgttt tttccatggc    960

tgcgaggtaa aatagatctg atggcgttat gatggttaac tcgtcatact cttgcgatct   1020

atggtccctt taggacatcg atttaatttc ggatggttcg agatcggtga tccatggtta   1080

gtaccctagg cagtggggtt agatccgtgc tgttagggtt cgtagatgga ttctgattgc   1140

tcagtaactg ggaaacctgg gatggttcta gctgggaatc ctgggatggt tctagctggt   1200

tcgcagatga gatcgatttc atggtctgct atatcttgtt tcgttgccta ggttccgttt   1260

aatctgtccg tggtatgatg ttagcctttg ataaggttcg atcgtgctag ctacgtcctg   1320

cgcagcattt aattgtcagg tcataatttt tagcattcct gtttttgttt ggtttggttt   1380

tgtctggttg ggctgtagat agtttcaatc tacctgtcgg tttattttat taaatttgga   1440

ttggatctgt atgtgtcaca tatatcttca tgattaatat ggttggaatt atctcttcat   1500

cttttagata tatatggata ggtatatatg ttgctgtggg ttttactggt actttattag   1560

atatattcat gcttagatac atgaagcaac gtgctgttac agtttaataa ttcttgttta   1620

tctaataaac aaataaggat aggtatatat gttgctgatg gttttactga tactttatta   1680

gatagtactt ctttgacatg aaggaacatc ctgcgacagc ttaataatta ttcttcatct   1740

aataaaaagc ttgcttttta attattttga tatacttgga tgatgtcatg cagcagctat   1800

gtgtgaattt tcggccctgt cttcatatga tgtttatttg cttgggactg tttctttggc   1860

tgataactca ccctgttgtt tggtgatcct tctgcaggtg                          1900
```

<210> SEQ ID NO 8
<211> LENGTH: 762
<212> TYPE: DNA
<213> ORGANISM: Agrostis nebulosa

<400> SEQUENCE: 8
gtagacgttt gtcacaggca ttgccactca aacaagcagc cggcgcttgg agcttttata 60
gtttgaaaag tgacggtttt aaggatgggt aagctgatta gtatatgtaa gtttagcttt 120
ttccattgta ggttaagcct taaggctctt acacaattgt ttcattattc tcattcttta 180
agagcccata taagcgttca tgaattgtac atatccttag attttttttt ttgggtaaag 240
ctcgagcttc tgtatctaaa agtagagaaa tcagaaaaag attcatgttt tggtagtttt 300
gatttcttgc ctccataata attttggttt accatttttt gtttgatttt agttttagaa 360
gcgtttatag caggatttaa aatccaaaac taccattatc ttcaagtgac cgtcagtgag 420
ccgtttaacg gcgtcgacaa gtccaacgga caccaaccag tgaaccacca gcgtcgagcc 480
aagcgatgca aacggaacgg ccgagacgtt gacacctttg gcgcggcacg gcatgtcgga 540
tctccctctc tggcccctc tcgagagttc cagctccacc tccaccggtg gcggtttcca 600
agtccgttcc gttccgttcc gcctcctgcc tgctcctctc agacggcacg aaaccgtgac 660
ggcaccggca gcacgggggg attccttttc cactgctcct tccttttccc ttcctcgccc 720
gccgctataa atagccagcc ccgtccccag attctttccc aa 762

<210> SEQ ID NO 9
<211> LENGTH: 5068
<212> TYPE: DNA
<213> ORGANISM: Arundo donax

<400> SEQUENCE: 9
ggcctcttta cgtttggcac aatttgatcg aatccaacac ggcaagttaa catttgaaga 60
ttgaaccggg cactaatgca agtctacaac taagaactac aagaaagcat gttccttgag 120
gtacttggat gcaacctcac aattatcaaa ttaattaaca actacagtta gaattttaga 180
tcacaagaat atcacgaact gtggatacta cttcaagggc tattcttttc tgaatgttgc 240
agttggttgt tttaaacata ttacaaacta ggtgtttaaa tgccaaaaag ttcatggaaa 300
aagattaagc taatattcca tccgtccaca aaatttaaat gctaggaatc attatatttg 360
tggatagaag gagtagttag taagacctac acttaattac acattggtca ttcctggagg 420
aataatcccc catagcaagt tgttttgagt ttgactaccc aaacttgcat aaattttttc 480
ttaaaaaaag gggagcttc accattccat caagatggcg aggctaaatg aaacgcacga 540
tgggcaaaac ggactaacgt acaaacaaca aggcaatgaa agatagggtt ttgataaata 600
tcaaatatac aaagtcaacc aaagaaaaaa gagatcccaa tggctaacct ttggatccgt 660
gtcgcaattt gtgctttagg acatacaagg tggatttctt ctttggcaaa ctctataata 720
attgggtgac ggtggcctca cggcagcctc aaagagtcgg tagcaacttt tagatctttt 780
gagctgaaac tcaattatgt agtagaatga tatttagata gatagatcga aatttggggg 840
tgtgaaaaca aagaggttct caatattgat agcaactcca acgaatggat atggaaaata 900
catgattttt tattcgagta gaaaaaggag gggaacggaa caaatctagc aatagtagcc 960
accaaagatg aggaccctgg atttcggatc caatagtggt aaggaagaaa gggccggact 1020
atccagaata aggtgaattg gtcaaggaag cggaagtctc cataaagaaa ttgtgggctc 1080

-continued

```
acttgatgtg agaaagaaga ccgaccaaga agcgggtttt gggggacaga ggagattggt   1140
gccaggttgc agtggcatgt atgtggggga agaggcaatg acaacggccg agagaggaga   1200
agggaatgag gtaagtattt gaagtgaaga ggtgcccata taggttaaaa aatgagctgt   1260
ggatttaaat caaaggtgtc agcgacacag gcacggaagt accctaagtt acctatgtgg   1320
gtcgcatatc acgctaagtt ccttcaccgt acaaggtgaa agtaacactg gcaatgtgcc   1380
ccagctgcaa ggcttgtcta tcaatgtggc cctacaaggc tcctggctac cccaggagct   1440
caaaacacgt ggcacatggt ggtacttcgc ccgacctcta tgctcaccgt gcacccggcc   1500
ccgaggtcaa tggctcctga gcacccgact gcatgactgg acccctgagt acccgacccc   1560
cgggacaagc tcccgtggac cttccccggg gatcaggctc acgagtactc gacctcacgt   1620
caatggctct cccgagtacc caaccttgtg tcgatagctc actaaggatc atgtgctaat   1680
ccttagcatc tcggattttg agtactaggc cattatttgc atgccatcct cttggatcta   1740
tgcggatttt caaggacctt acctaagcat caacatgcac aaacacaaac ccttcgtgaa   1800
gccatcccca actactcggg tggcaggacc ctcgacacgt gcgatgcgag ctcggacaga   1860
gctgacaaga acctcccgac ggcgcattaa atgccctggc aagggcgccc cgcctcgtcg   1920
agctctggac ttcatcaagt cacatcaaca gcaggcaggc gctccttccg cagacttcat   1980
catgagggaa tccgttaccc tctatttaca tagtgcagcg gggaatgtgg agatcaaatc   2040
tctccaatga tgtcactgtg tagcatgtat tagcacgcca acaccctgtc gcttaccacg   2100
aggatcagcc atgcaagcaa gagatgttgg tcgggcctcg gtggcaactg aggctatagt   2160
gacctatgac gagcaggcca tagataggcc cactggcaag cccaagaatc gctagacggg   2220
ctagatctgg acacttgtcc gcaccaagca ctaccgttgc aactgcaacc tctatatgta   2280
actatagatt cacatgttgc gacatctttg cccaatacgt attgtaccct agacagctca   2340
ccctatcttt ttctttttt tcctctttct tcttcctcct ccttgcatgg agacgtagaa   2400
ggactcctcc cttgtgacta ttaaaggaag gacttagggc tgtgctaggg gagagaactt   2460
ttggacttgg gagagctctg cactgaacat cttcctctcc acgcttgtaa tattttccac   2520
aacaaagaat tccataaagc cggatgtagg gctattatcc ctctcgggag gcctgaacca   2580
gggtaaaaca ccactcttct caccagcgtt cgccgcatta gtctagacta gcatcttttg   2640
accctatatc gaaccatcta gggactttac gtcccctgcc tgcagtttcc cggtgacaga   2700
atgactatga tttttcgtcg attttataaa agtgaaaaca accggttgat atctatgcgc   2760
actattttcc tacatatatt tctaacttct tgcttagcca tgtcggttaa gagcaagtgg   2820
agagcactct catttcgtag aacaagtgat gaatgccgac ctgcatcatc ttacttagac   2880
ttgatcatca agtggaatcc ccattcatct taataatctc atattgagtg ccaatgcaac   2940
attgttataa tcctcttcat atgctaattc ttcaaagcta acgtagttaa atgaaggcaa   3000
aatatgcaac ttcgtcctct aagtttgctc aaaggctcat ttttaccctt taactatcaa   3060
accgattact ttcgtccctg aactttcatg tttggtccaa tttaatccct gggctgatgt   3120
atccgtccac ggtggtgtgt ccaatcagtg aataatctag ttagtgaagc cagaagtcca   3180
tagtgcccct tgctctgtca ccatatatcc agttcaaccg caccaatttg ccatctcgaa   3240
ctggttcatg ttttattcag gttggtaaat gaattttgcc aattcaatgt agttagatat   3300
ttccatgtca ttttagtaca tttaccaatt ttttatattc tggctagaaa aggagaatgg   3360
tgacgtcttt cggaagatca agatcaatta tcaagtatca gcaacagcac ctgaaggttg   3420
gagtgcatta gttgtcattg agaataatgc tagctattca ttgcactggc attagagaca   3480
```

-continued gagagggcga gccagtttga catggcaaat tagcacagtc aaactggata cgtggtgacg 3540
gagggagggg cactatgaat ttttggtgac ggagggaggg gcactatgaa tttttggctt 3600
tgctgacggg acacgccact atggatgaaa ttggacaaaa tacgaatatt caaggatgaa 3660
agtggtcggt ttgatagttc agggatgaaa tgtgtctttg ggcaaacttt gaggacgaag 3720
ttgcctattt tgcattaaac gaatatattt atatacccca aaaaaaagaa tacacatctc 3780
cactccgagc cggcatgtgg ggtccccact agtcagccac tgtatggcgc cgactagctc 3840
aacggccacg aaccagccaa ccaccagcgc aacctaaacg gcgtaaacgt tgacggcatc 3900
tctctctcgc cccgtctcga agcttccgca ccgctcgctg gtcgctgccc ggcgccgctc 3960
gtgctggact ctttccgtgg cggcttccgc gaaattgcgt ggtggagagg agagacggaa 4020
ccgtcacggc actggattcc ttccccaccc ggcttggccg gcccctcctc gcctccataa 4080
ataggcaccc cgtcctcgcc tcctctcccc acctcatctc ctcctttccc gtgaaccgtg 4140
aacacaaccc gacccagatc ccctcttgcg agcttcgtcg atccctcctc cgcgtcaagg 4200
tacggagctt ctcctccccc ttcttctcta gatcggcgtg ttatgttgtt tccgtggttg 4260
cttggttgga tgaatcgaat gattcttagg gcctaggagg ctggttagat ctgttgcgtt 4320
ctgtttcgta gatggatttt ggtgtaagat caggtcggtt ccgctgttta acttgtgatg 4380
ctagtgtgat ttttgggagg atttgagttg ttaatctggg agttgttggg aggttctcgt 4440
aggcggattg tagatgaagt cgcccgcacg atttgcgtgg cttgttgggt agctagggtt 4500
agatctgctc ggatttttca ttgttactta ttgagagata atgtagctaa cctttacttg 4560
ttcatctatg tatctcgtat tcgtattcat ctggttcgat ggtgctagat agatgcgcct 4620
gatttgtccg atcgaattgg gtagcatccg cggcttgttt ggtagtgttc tgattgattt 4680
gtcgctctag atctgagtgg aataatatta catctcaaca tgttactaga aacttggttt 4740
atagctccgg atttacatgt ttattcttat gtaaggtttt aaatgaaaga tttatgctac 4800
tgctgctcgt tgatccttta gcatccacct gaggaacatg catgcatctg ttacttcttt 4860
tgatatatgc ttagatagtt gttagtatat actgctgttg ttcgatgatc cttcaggatg 4920
aacatgcatg atcatgttac ttgtttttat atgcttctgc tgttcgttga ttctttagta 4980
ctacctacct gatcatcttg catgtttcct gcttgttaga gattaattga ttaggcttac 5040
cttgttgcct ggtgattctt ccttgcag 5068

<210> SEQ ID NO 10
<211> LENGTH: 4114
<212> TYPE: DNA
<213> ORGANISM: Arundo donax

<400> SEQUENCE: 10
ggcctcttta cgtttggcac aatttgatcg aatccaacac ggcaagttaa catttgaaga 60
ttgaaccggg cactaatgca agtctacaac taagaactac aagaaagcat gttccttgag 120
gtacttggat gcaacctcac aattatcaaa ttaattaaca actacagtta gaattttaga 180
tcacaagaat atcacgaact gtggatacta cttcaagggc tattcttttc tgaatgttgc 240
agttggttgt tttaaacata ttacaaacta ggtgtttaaa tgccaaaaag ttcatggaaa 300
aagattaagc taatattcca tccgtccaca aaatttaaat gctaggaatc attatatttg 360
tggatagaag gagtagttag taagacctac acttaattac acattggtca ttcctggagg 420
aataatcccc catagcaagt tgttttgagt ttgactaccc aaacttgcat aaattttttc 480

-continued

```
ttaaaaaaag ggggagcttc accattccat caagatggcg aggctaaatg aaacgcacga    540
tgggcaaaac ggactaacgt acaaacaaca aggcaatgaa agatagggtt ttgataaata    600
tcaaatatac aaagtcaacc aaagaaaaaa gagatcccaa tggctaacct ttggatccgt    660
gtcgcaattt gtgctttagg acatacaagg tggatttctt ctttggcaaa ctctataata    720
attgggtgac ggtggcctca cggcagcctc aaagagtcgg tagcaacttt tagatctttt    780
gagctgaaac tcaattatgt agtagaatga tatttagata gatagatcga aatttggggg    840
tgtgaaaaca aagaggttct caatattgat agcaactcca acgaatggat atggaaaata    900
catgattttt tattcgagta gaaaaaggag gggaacggaa caaatctagc aatagtagcc    960
accaaagatg aggaccctgg atttcggatc caatagtggt aaggaagaaa gggccggact   1020
atccagaata aggtgaattg gtcaaggaag cggaagtctc cataaagaaa ttgtgggctc   1080
acttgatgtg agaaagaaga ccgaccaaga agcgggtttt gggggacaga ggagattggt   1140
gccaggttgc agtggcatgt atgtggggga agaggcaatg acaacggccg agagaggaga   1200
agggaatgag gtaagtattt gaagtgaaga ggtgcccata taggttaaaa aatgagctgt   1260
ggatttaaat caaaggtgtc agcgacacag gcacggaagt accctaagtt acctatgtgg   1320
gtcgcatatc acgctaagtt ccttcaccgt acaaggtgaa agtaacactg gcaatgtgcc   1380
ccagctgcaa ggcttgtcta tcaatgtggc cctacaaggc tcctggctac cccaggagct   1440
caaaacacgt ggcacatggt ggtacttcgc ccgacctcta tgctcaccgt gcacccggcc   1500
ccgaggtcaa tggctcctga gcacccgact gcatgactgg acccctgagt acccgacccc   1560
cgggacaagc tcccgtggac cttccccggg gatcaggctc acgagtactc gacctcacgt   1620
caatggctct cccgagtacc caaccttgtg tcgatagctc actaaggatc atgtgctaat   1680
ccttagcatc tcggattttg agtactaggc cattatttgc atgccatcct cttggatcta   1740
tgcggatttt caaggacctt acctaagcat caacatgcac aaacacaaac ccttcgtgaa   1800
gccatcccca actactcggg tggcaggacc ctcgacacgt gcgatgcgag ctcggacaga   1860
gctgacaaga acctcccgac ggcgcattaa atgccctggc aagggcgccc cgcctcgtcg   1920
agctctggac ttcatcaagt cacatcaaca gcaggcaggc gctccttccg cagacttcat   1980
catgagggaa tccgttaccc tctatttaca tagtgcagcg gggaatgtgg agatcaaatc   2040
tctccaatga tgtcactgtg tagcatgtat tagcacgcca acaccctgtc gcttaccacg   2100
aggatcagcc atgcaagcaa gagatgttgg tcgggcctcg gtggcaactg aggctatagt   2160
gacctatgac gagcaggcca tagataggcc cactggcaag cccaagaatc gctagacggg   2220
ctagatctgg acacttgtcc gcaccaagca ctaccgttgc aactgcaacc tctatatgta   2280
actatagatt cacatgttgc gacatctttg cccaatacgt attgtaccct agacagctca   2340
ccctatcttt ttcttttttt tcctctttct tcttcctcct ccttgcatgg agacgtagaa   2400
ggactcctcc cttgtgacta ttaaaggaag gacttagggc tgtgctaggg gagagaactt   2460
ttggacttgg gagagctctg cactgaacat cttcctctcc acgcttgtaa tattttccac   2520
aacaaagaat tccataaagc cggatgtagg gctattatcc ctctcgggag gcctgaacca   2580
gggtaaaaca ccactcttct caccagcgtt cgccgcatta gtctagacta gcatcttttg   2640
accctatatc gaaccatcta gggactttac gtcccctgcc tgcagtttcc cggtgacaga   2700
atgactatga tttttcgtcg attttataaa agtgaaaaca accggttgat atctatgcgc   2760
actattttcc tacatatatt tctaacttct tgcttagcca tgtcggttaa gagcaagtgg   2820
agagcactct catttcgtag aacaagtgat gaatgccgac ctgcatcatc ttacttagac   2880
```

ttgatcatca agtggaatcc ccattcatct taataatctc atattgagtg ccaatgcaac 2940
attgttataa tcctcttcat atgctaattc ttcaaagcta acgtagttaa atgaaggcaa 3000
aatatgcaac ttcgtcctct aagtttgctc aaaggctcat ttttaccctt taactatcaa 3060
accgattact ttcgtccctg aactttcatg tttggtccaa tttaatccct gggctgatgt 3120
atccgtccac ggtggtgtgt ccaatcagtg aataatctag ttagtgaagc cagaagtcca 3180
tagtgcccct tgctctgtca ccatatatcc agttcaaccg caccaatttg ccatctcgaa 3240
ctggttcatg ttttattcag gttggtaaat gaattttgcc aattcaatgt agttagatat 3300
ttccatgtca ttttagtaca tttaccaatt ttttatattc tggctagaaa aggagaatgg 3360
tgacgtcttt cggaagatca agatcaatta tcaagtatca gcaacagcac ctgaaggttg 3420
gagtgcatta gttgtcattg agaataatgc tagctattca ttgcactggc attagagaca 3480
gagagggcga gccagtttga catggcaaat tagcacagtc aaactggata cgtggtgacg 3540
gagggagggg cactatgaat ttttggtgac ggagggaggg gcactatgaa tttttggctt 3600
tgctgacggg acacgccact atggatgaaa ttggacaaaa tacgaatatt caaggatgaa 3660
agtggtcggt ttgatagttc agggatgaaa tgtgtctttg ggcaaacttt gaggacgaag 3720
ttgcctattt tgcattaaac gaatatattt atataccccca aaaaaaagaa tacacatctc 3780
cactccgagc cggcatgtgg ggtccccact agtcagccac tgtatggcgc cgactagctc 3840
aacggccacg aaccagccaa ccaccagcgc aacctaaacg gcgtaaacgt tgacggcatc 3900
tctctctcgc cccgtctcga agcttccgca ccgctcgctg gtcgctgccc ggcgccgctc 3960
gtgctggact ctttccgtgg cggcttccgc gaaattgcgt ggtggagagg agagacggaa 4020
ccgtcacggc actggattcc ttccccaccc ggcttggccg gcccctcctc gcctccataa 4080
ataggcaccc cgtcctcgcc tcctctcccc acct 4114

<210> SEQ ID NO 11
<211> LENGTH: 85
<212> TYPE: DNA
<213> ORGANISM: Arundo donax

<400> SEQUENCE: 11
catctcctcc tttcccgtga accgtgaaca caacccgacc cagatcccct cttgcgagct 60
tcgtcgatcc ctcctccgcg tcaag 85

<210> SEQ ID NO 12
<211> LENGTH: 869
<212> TYPE: DNA
<213> ORGANISM: Arundo donax

<400> SEQUENCE: 12
gtacggagct tctcctcccc cttcttctct agatcggcgt gttatgttgt ttccgtggtt 60
gcttggttgg atgaatcgaa tgattcttag ggcctaggag gctggttaga tctgttgcgt 120
tctgtttcgt agatggattt tggtgtaaga tcaggtcggt tccgctgttt aacttgtgat 180
gctagtgtga tttttgggag gatttgagtt gttaatctgg gagttgttgg gaggttctcg 240
taggcggatt gtagatgaag tcgcccgcac gatttgcgtg gcttgttggg tagctagggt 300
tagatctgct cggatttttc attgttactt attgagagat aatgtagcta acctttactt 360
gttcatctat gtatctcgta ttcgtattca tctggttcga tggtgctaga tagatgcgcc 420
tgatttgtcc gatcgaattg ggtagcatcc gcggcttgtt tggtagtgtt ctgattgatt 480

-continued

```
tgtcgctcta gatctgagtg gaataatatt acatctcaac atgttactag aaacttggtt    540

tatagctccg gatttacatg tttattctta tgtaaggttt taaatgaaag atttatgcta    600

ctgctgctcg ttgatccttt agcatccacc tgaggaacat gcatgcatct gttacttctt    660

ttgatatatg cttagatagt tgttagtata tactgctgtt gttcgatgat ccttcaggat    720

gaacatgcat gatcatgtta cttgttttta tatgcttctg ctgttcgttg attctttagt    780

actacctacc tgatcatctt gcatgtttcc tgcttgttag agattaattg attaggctta    840

ccttgttgcc tggtgattct tccttgcag                                      869


<210> SEQ ID NO 13
<211> LENGTH: 2969
<212> TYPE: DNA
<213> ORGANISM: Arundo donax

<400> SEQUENCE: 13

gatcagccat gcaagcaaga gatgttggtc gggcctcggt ggcaactgag gctatagtga     60

cctatgacga gcaggccata gataggccca ctggcaagcc caagaatcgc tagacgggct    120

agatctggac acttgtccgc accaagcact accgttgcaa ctgcaacctc tatatgtaac    180

tatagattca catgttgcga catctttgcc caatacgtat tgtaccctag acagctcacc    240

ctatcttttt ctttttttc ctctttcttc ttcctcctcc ttgcatggag acgtagaagg    300

actcctccct tgtgactatt aaaggaagga cttagggctg tgctagggga gagaactttt    360

ggacttggga gagctctgca ctgaacatct tcctctccac gcttgtaata ttttccacaa    420

caaagaattc cataaagccg gatgtagggc tattatccct ctcgggaggc ctgaaccagg    480

gtaaaacacc actcttctca ccagcgttcg ccgcattagt ctagactagc atcttttgac    540

cctatatcga accatctagg gactttacgt cccctgcctg cagtttcccg gtgacagaat    600

gactatgatt tttcgtcgat tttataaaag tgaaaacaac cggttgatat ctatgcgcac    660

tattttccta catatatttc taacttcttg cttagccatg tcggttaaga gcaagtggag    720

agcactctca tttcgtagaa caagtgatga atgccgacct gcatcatctt acttagactt    780

gatcatcaag tggaatcccc attcatctta ataatctcat attgagtgcc aatgcaacat    840

tgttataatc ctcttcatat gctaattctt caaagctaac gtagttaaat gaaggcaaaa    900

tatgcaactt cgtcctctaa gtttgctcaa aggctcattt ttacccttta actatcaaac    960

cgattacttt cgtccctgaa ctttcatgtt tggtccaatt taatccctgg gctgatgtat   1020

ccgtccacgg tggtgtgtcc aatcagtgaa taatctagtt agtgaagcca gaagtccata   1080

gtgccccttg ctctgtcacc atatatccag ttcaaccgca ccaatttgcc atctcgaact   1140

ggttcatgtt ttattcaggt tggtaaatga attttgccaa ttcaatgtag ttagatattt   1200

ccatgtcatt ttagtacatt taccaatttt ttatattctg gctagaaaag gagaatggtg   1260

acgtctttcg gaagatcaag atcaattatc aagtatcagc aacagcacct gaaggttgga   1320

gtgcattagt tgtcattgag aataatgcta gctattcatt gcactggcat tagagacaga   1380

gagggcgagc cagtttgaca tggcaaatta gcacagtcaa actggatacg tggtgacgga   1440

gggaggggca ctatgaattt ttggtgacgg agggaggggc actatgaatt tttggctttg   1500

ctgacgggac acgccactat ggatgaaatt ggacaaaata cgaatattca aggatgaaag   1560

tggtcggttt gatagttcag ggatgaaatg tgtctttggg caaactttga ggacgaagtt   1620

gcctattttg cattaaacga atatatttat ataccccaaa aaaaagaata cacatctcca   1680

ctccgagccg gcatgtgggg tccccactag tcagccactg tatggcgccg actagctcaa   1740
```

cggccacgaa ccagccaacc accagcgcaa cctaaacggc gtaaacgttg acggcatctc 1800
tctctcgccc cgtctcgaag cttccgcacc gctcgctggt cgctgcccgg cgccgctcgt 1860
gctggactct ttccgtggcg gcttccgcga aattgcgtgg tggagaggag agacggaacc 1920
gtcacggcac tggattcctt ccccacccgg cttggccggc ccctcctcgc ctccataaat 1980
aggcaccccg tcctcgcctc ctctccccac ctcatctcct cctttcccgt gaaccgtgaa 2040
cacaacccga cccagatccc ctcttgcgag cttcgtcgat ccctcctccg cgtcaaggta 2100
cggagcttct cctccccctt cttctctaga tcggcgtgtt atgttgtttc cgtggttgct 2160
tggttggatg aatcgaatga ttcttagggc ctaggaggct ggttagatct gttgcgttct 2220
gtttcgtaga tggattttgg tgtaagatca ggtcggttcc gctgtttaac ttgtgatgct 2280
agtgtgattt ttgggaggat ttgagttgtt aatctgggag ttgttgggag gttctcgtag 2340
gcggattgta gatgaagtcg cccgcacgat ttgcgtggct tgttgggtag ctagggttag 2400
atctgctcgg atttttcatt gttacttatt gagagataat gtagctaacc tttacttgtt 2460
catctatgta tctcgtattc gtattcatct ggttcgatgg tgctagatag atgcgcctga 2520
tttgtccgat cgaattgggt agcatccgcg gcttgtttgg tagtgttctg attgatttgt 2580
cgctctagat ctgagtggaa taatattaca tctcaacatg ttactagaaa cttggtttat 2640
agctccggat ttacatgttt attcttatgt aaggttttaa atgaaagatt tatgctactg 2700
ctgctcgttg atcctttagc atccacctga ggaacatgca tgcatctgtt acttcttttg 2760
atatatgctt agatagttgt tagtatatac tgctgttgtt cgatgatcct tcaggatgaa 2820
catgcatgat catgttactt gtttttatat gcttctgctg ttcgttgatt ctttagtact 2880
acctacctga tcatcttgca tgtttcctgc ttgttagaga ttaattgatt aggcttacct 2940
tgttgcctgg tgattcttcc ttgcaggtg 2969

<210> SEQ ID NO 14
<211> LENGTH: 2012
<212> TYPE: DNA
<213> ORGANISM: Arundo donax

<400> SEQUENCE: 14
gatcagccat gcaagcaaga gatgttggtc gggcctcggt ggcaactgag gctatagtga 60
cctatgacga gcaggccata gataggccca ctggcaagcc caagaatcgc tagacgggct 120
agatctggac acttgtccgc accaagcact accgttgcaa ctgcaacctc tatatgtaac 180
tatagattca catgttgcga catctttgcc caatacgtat tgtaccctag acagctcacc 240
ctatcttttt cttttttttc ctctttcttc ttcctcctcc ttgcatggag acgtagaagg 300
actcctccct tgtgactatt aaaggaagga cttagggctg tgctagggga gagaactttt 360
ggacttggga gagctctgca ctgaacatct tcctctccac gcttgtaata ttttccacaa 420
caaagaattc cataaagccg gatgtagggc tattatccct ctcgggaggc ctgaaccagg 480
gtaaaacacc actcttctca ccagcgttcg ccgcattagt ctagactagc atcttttgac 540
cctatatcga accatctagg gactttacgt cccctgcctg cagtttcccg gtgacagaat 600
gactatgatt tttcgtcgat tttataaaag tgaaaacaac cggttgatat ctatgcgcac 660
tattttccta catatatttc taacttcttg cttagccatg tcggttaaga gcaagtggag 720
agcactctca tttcgtagaa caagtgatga atgccgacct gcatcatctt acttagactt 780
gatcatcaag tggaatcccc attcatctta ataatctcat attgagtgcc aatgcaacat 840

```
tgttataatc ctcttcatat gctaattctt caaagctaac gtagttaaat gaaggcaaaa    900
tatgcaactt cgtcctctaa gtttgctcaa aggctcattt ttacccttta actatcaaac    960
cgattacttt cgtccctgaa ctttcatgtt tggtccaatt taatccctgg gctgatgtat   1020
ccgtccacgg tggtgtgtcc aatcagtgaa taatctagtt agtgaagcca gaagtccata   1080
gtgccccttg ctctgtcacc atatatccag ttcaaccgca ccaatttgcc atctcgaact   1140
ggttcatgtt ttattcaggt tggtaaatga attttgccaa ttcaatgtag ttagatattt   1200
ccatgtcatt ttagtacatt taccaatttt ttatattctg gctagaaaag gagaatggtg   1260
acgtctttcg gaagatcaag atcaattatc aagtatcagc aacagcacct gaaggttgga   1320
gtgcattagt tgtcattgag aataatgcta gctattcatt gcactggcat tagagacaga   1380
gagggcgagc cagtttgaca tggcaaatta gcacagtcaa actggatacg tggtgacgga   1440
gggaggggca ctatgaattt ttggtgacgg agggaggggc actatgaatt tttggctttg   1500
ctgacgggac acgccactat ggatgaaatt ggacaaaata cgaatattca aggatgaaag   1560
tggtcggttt gatagttcag ggatgaaatg tgtctttggg caaactttga ggacgaagtt   1620
gcctattttg cattaaacga atatatttat ataccccaaa aaaaagaata cacatctcca   1680
ctccgagccg gcatgtgggg tccccactag tcagccactg tatggcgccg actagctcaa   1740
cggccacgaa ccagccaacc accagcgcaa cctaaacggc gtaaacgttg acggcatctc   1800
tctctcgccc cgtctcgaag cttccgcacc gctcgctggt cgctgcccgg cgccgctcgt   1860
gctggactct ttccgtggcg gcttccgcga aattgcgtgg tggagaggag agacggaacc   1920
gtcacggcac tggattcctt ccccacccgg cttggccggc ccctcctcgc ctccataaat   1980
aggcaccccg tcctcgcctc ctctccccac ct                                 2012
```

<210> SEQ ID NO 15
<211> LENGTH: 872
<212> TYPE: DNA
<213> ORGANISM: Arundo donax

<400> SEQUENCE: 15

```
gtacggagct tctcctcccc cttcttctct agatcggcgt gttatgttgt ttccgtggtt     60
gcttggttgg atgaatcgaa tgattcttag ggcctaggag gctggttaga tctgttgcgt    120
tctgtttcgt agatggattt tggtgtaaga tcaggtcggt tccgctgttt aacttgtgat    180
gctagtgtga tttttgggag gatttgagtt gttaatctgg gagttgttgg gaggttctcg    240
taggcggatt gtagatgaag tcgcccgcac gatttgcgtg gcttgttggg tagctagggt    300
tagatctgct cggatttttc attgttactt attgagagat aatgtagcta acctttactt    360
gttcatctat gtatctcgta ttcgtattca tctggttcga tggtgctaga tagatgcgcc    420
tgatttgtcc gatcgaattg ggtagcatcc gcggcttgtt tggtagtgtt ctgattgatt    480
tgtcgctcta gatctgagtg gaataatatt acatctcaac atgttactag aaacttggtt    540
tatagctccg gatttacatg tttattctta tgtaaggttt taaatgaaag atttatgcta    600
ctgctgctcg ttgatccttt agcatccacc tgaggaacat gcatgcatct gttacttctt    660
ttgatatatg cttagatagt tgttagtata tactgctgtt gttcgatgat ccttcaggat    720
gaacatgcat gatcatgtta cttgttttta tatgcttctg ctgttcgttg attctttagt    780
actacctacc tgatcatctt gcatgtttcc tgcttgttag agattaattg attaggctta    840
ccttgttgcc tggtgattct tccttgcagg tg                                  872
```

-continued

<210> SEQ ID NO 16
<211> LENGTH: 1954
<212> TYPE: DNA
<213> ORGANISM: Arundo donax

<400> SEQUENCE: 16

```
tgatgtatcc gtccacggtg gtgtgtccaa tcagtgaata atctagttag tgaagccaga     60
agtccatagt gccccttgct ctgtcaccat atatccagtt caaccgcacc aatttgccat    120
ctcgaactgg ttcatgtttt attcaggttg gtaaatgaat tttgccaatt caatgtagtt    180
agatatttcc atgtcatttt agtacattta ccaatttttt atattctggc tagaaaagga    240
gaatggtgac gtctttcgga agatcaagat caattatcaa gtatcagcaa cagcacctga    300
aggttggagt gcattagttg tcattgagaa taatgctagc tattcattgc actggcatta    360
gagacagaga gggcgagcca gtttgacatg gcaaattagc acagtcaaac tggatacgtg    420
gtgacggagg gaggggcact atgaattttt ggtgacggag ggaggggcac tatgaatttt    480
tggctttgct gacgggacac gccactatgg atgaaattgg acaaaatacg aatattcaag    540
gatgaaagtg gtcggtttga tagttcaggg atgaaatgtg tctttgggca aactttgagg    600
acgaagttgc ctattttgca ttaaacgaat atatttatat accccaaaaa aaagaataca    660
catctccact ccgagccggc atgtggggtc cccactagtc agccactgta tggcgccgac    720
tagctcaacg gccacgaacc agccaaccac cagcgcaacc taaacggcgt aaacgttgac    780
ggcatctctc tctcgccccg tctcgaagct tccgcaccgc tcgctggtcg ctgcccggcg    840
ccgctcgtgc tggactcttt ccgtggcggc ttccgcgaaa ttgcgtggtg gagaggagag    900
acggaaccgt cacggcactg gattccttcc ccacccggct tggccggccc ctcctcgcct    960
ccataaatag gcaccccgtc ctcgcctcct ctccccacct catctcctcc tttcccgtga   1020
accgtgaaca caacccgacc cagatcccct cttgcgagct tcgtcgatcc ctcctccgcg   1080
tcaaggtacg gagcttctcc tccccttct tctctagatc ggcgtgttat gttgtttccg    1140
tggttgcttg gttggatgaa tcgaatgatt cttagggcct aggaggctgg ttagatctgt   1200
tgcgttctgt ttcgtagatg gattttggtg taagatcagg tcggttccgc tgtttaactt   1260
gtgatgctag tgtgattttt gggaggattt gagttgttaa tctgggagtt gttgggaggt   1320
tctcgtaggc ggattgtaga tgaagtcgcc cgcacgattt gcgtggcttg ttgggtagct   1380
agggttagat ctgctcggat ttttcattgt tacttattga gagataatgt agctaacctt   1440
tacttgttca tctatgtatc tcgtattcgt attcatctgg ttcgatggtg ctagatagat   1500
gcgcctgatt tgtccgatcg aattgggtag catccgcggc ttgtttggta gtgttctgat   1560
tgatttgtcg ctctagatct gagtggaata atattacatc tcaacatgtt actagaaact   1620
tggtttatag ctccggattt acatgtttat tcttatgtaa ggttttaaat gaaagattta   1680
tgctactgct gctcgttgat cctttagcat ccacctgagg aacatgcatg catctgttac   1740
ttcttttgat atatgcttag atagttgtta gtatatactg ctgttgttcg atgatccttc   1800
aggatgaaca tgcatgatca tgttacttgt ttttatatgc ttctgctgtt cgttgattct   1860
ttagtactac ctacctgatc atcttgcatg tttcctgctt gttagagatt aattgattag   1920
gcttaccttg ttgcctggtg attcttcctt gcag                                1954
```

<210> SEQ ID NO 17
<211> LENGTH: 1000
<212> TYPE: DNA
<213> ORGANISM: Arundo donax -continued

<400> SEQUENCE: 17
tgatgtatcc gtccacggtg gtgtgtccaa tcagtgaata atctagttag tgaagccaga 60
agtccatagt gccccttgct ctgtcaccat atatccagtt caaccgcacc aatttgccat 120
ctcgaactgg ttcatgtttt attcaggttg gtaaatgaat tttgccaatt caatgtagtt 180
agatatttcc atgtcatttt agtacattta ccaatttttt atattctggc tagaaaagga 240
gaatggtgac gtctttcgga agatcaagat caattatcaa gtatcagcaa cagcacctga 300
aggttggagt gcattagttg tcattgagaa taatgctagc tattcattgc actggcatta 360
gagacagaga gggcgagcca gtttgacatg gcaaattagc acagtcaaac tggatacgtg 420
gtgacggagg gaggggcact atgaattttt ggtgacggag ggaggggcac tatgaatttt 480
tggctttgct gacgggacac gccactatgg atgaaattgg acaaaatacg aatattcaag 540
gatgaaagtg gtcggtttga tagttcaggg atgaaatgtg tctttgggca aactttgagg 600
acgaagttgc ctattttgca ttaaacgaat atatttatat accccaaaaa aaagaataca 660
catctccact ccgagccggc atgtggggtc cccactagtc agccactgta tggcgccgac 720
tagctcaacg gccacgaacc agccaaccac cagcgcaacc taaacggcgt aaacgttgac 780
ggcatctctc tctcgccccg tctcgaagct tccgcaccgc tcgctggtcg ctgcccggcg 840
ccgctcgtgc tggactcttt ccgtggcggc ttccgcgaaa ttgcgtggtg gagaggagag 900
acggaaccgt cacggcactg gattccttcc ccacccggct tggccggccc ctcctcgcct 960
ccataaatag gcaccccgtc ctcgcctcct ctccccacct 1000

<210> SEQ ID NO 18
<211> LENGTH: 1957
<212> TYPE: DNA
<213> ORGANISM: Arundo donax

<400> SEQUENCE: 18
tgatgtatcc gtccacggtg gtgtgtccaa tcagtgaata atctagttag tgaagccaga 60
agtccatagt gccccttgct ctgtcaccat atatccagtt caaccgcacc aatttgccat 120
ctcgaactgg ttcatgtttt attcaggttg gtaaatgaat tttgccaatt caatgtagtt 180
agatatttcc atgtcatttt agtacattta ccaatttttt atattctggc tagaaaagga 240
gaatggtgac gtctttcgga agatcaagat caattatcaa gtatcagcaa cagcacctga 300
aggttggagt gcattagttg tcattgagaa taatgctagc tattcattgc actggcatta 360
gagacagaga gggcgagcca gtttgacatg gcaaattagc acagtcaaac tggatacgtg 420
gtgacggagg gaggggcact atgaattttt ggtgacggag ggaggggcac tatgaatttt 480
tggctttgct gacgggacac gccactatgg atgaaattgg acaaaatacg aatattcaag 540
gatgaaagtg gtcggtttga tagttcaggg atgaaatgtg tctttgggca aactttgagg 600
acgaagttgc ctattttgca ttaaacgaat atatttatat accccaaaaa aaagaataca 660
catctccact ccgagccggc atgtggggtc cccactagtc agccactgta tggcgccgac 720
tagctcaacg gccacgaacc agccaaccac cagcgcaacc taaacggcgt aaacgttgac 780
ggcatctctc tctcgccccg tctcgaagct tccgcaccgc tcgctggtcg ctgcccggcg 840
ccgctcgtgc tggactcttt ccgtggcggc ttccgcgaaa ttgcgtggtg gagaggagag 900
acggaaccgt cacggcactg gattccttcc ccacccggct tggccggccc ctcctcgcct 960
ccataaatag gcaccccgtc ctcgcctcct ctccccacct catctcctcc tttcccgtga 1020
accgtgaaca caacccgacc cagatcccct cttgcgagct tcgtcgatcc ctcctccgcg 1080

```
tcaaggtacg gagcttctcc tccccccttct tctctagatc ggcgtgttat gttgtttccg   1140
tggttgcttg gttggatgaa tcgaatgatt cttagggcct aggaggctgg ttagatctgt   1200
tgcgttctgt ttcgtagatg gattttggtg taagatcagg tcggttccgc tgtttaactt   1260
gtgatgctag tgtgattttt gggaggattt gagttgttaa tctgggagtt gttgggaggt   1320
tctcgtaggc ggattgtaga tgaagtcgcc cgcacgattt gcgtggcttg ttgggtagct   1380
agggttagat ctgctcggat ttttcattgt tacttattga gagataatgt agctaacctt   1440
tacttgttca tctatgtatc tcgtattcgt attcatctgg ttcgatggtg ctagatagat   1500
gcgcctgatt tgtccgatcg aattgggtag catccgcggc ttgtttggta gtgttctgat   1560
tgatttgtcg ctctagatct gagtggaata atattacatc tcaacatgtt actagaaact   1620
tggtttatag ctccggattt acatgtttat tcttatgtaa ggttttaaat gaaagattta   1680
tgctactgct gctcgttgat cctttagcat ccacctgagg aacatgcatg catctgttac   1740
ttcttttgat atatgcttag atagttgtta gtatatactg ctgttgttcg atgatccttc   1800
aggatgaaca tgcatgatca tgttacttgt ttttatatgc ttctgctgtt cgttgattct   1860
ttagtactac ctacctgatc atcttgcatg tttcctgctt gttagagatt aattgattag   1920
gcttaccttg ttgcctggtg attcttcctt gcaggtg                             1957
```

<210> SEQ ID NO 19
<211> LENGTH: 1957
<212> TYPE: DNA
<213> ORGANISM: Arundo donax

<400> SEQUENCE: 19

```
tgatgtatcc gtccacggtg gtgtgtccaa tcagtgaata atctagttag tgaagccaga     60
agtccatagt gccccttgct ctgtcaccat atatccagtt caaccgcacc aatttgccat    120
ctcgaactgg ttcatgtttt attcaggttg gtaaatgaat tttgccaatt caatgtagtt    180
agatatttcc atgtcatttt agtacattta ccaatttttt atattctggc tagaaaagga    240
gaatggtgac gtctttcgga agatcaagat caattatcaa gtatcagcaa cagcacctga    300
aggttggagt gcattagttg tcattgagaa taatgctagc tattcattgc actggcatta    360
gagacagaga gggcgagcca gtttgacatg gcaaattagc acagtcaaac tggatacgtg    420
gtgacggagg gaggggcact atgaattttt ggtgacggag ggaggggcac tatgaatttt    480
tggctttgct gacgggacac gccactatgg atgaaattgg acaaaatacg aatattcaag    540
gatgaaagtg gtcggtttga tagttcaggg atgaaatgtg tctttgggca aactttgagg    600
acgaagttgc ctattttgca ttaaacgaat atatttatat accccaaaaa aaagaataca    660
catctccact ccgagccggc atgtggggtc cccactagtc agccactgta tggcgccgac    720
tagctcaacg gccacgaacc agccaaccac cagcgcaacc taaacggcgt aaacgttgac    780
ggcatctctc tctcgccccg tctcgaagct tccgcaccgc tcgctggtcg ctgcccggcg    840
ccgctcgtgc tggactcttt ccgtggcggc ttccgcgaaa ttgcgtggtg gagaggagag    900
acggaaccgt cacggcactg gattccttcc ccacccggct tggccggccc ctcctcgcct    960
ccataaatag gcaccccgtc ctcgcctcct ctccccacct catctcctcc tttcccgtga   1020
accgtgaaca caacccgacc cagatcccct cttgcgagct tcgtcgatcc ctcctccgcg   1080
tcaaggtacg gagcttctcc tccccccttct tctctagatc ggcgtgttat gttgtttccg   1140
tggttgcttg gttggatgaa tcgaatgatt cttagggcct aggaggctgg ttagatctgt   1200
```

-continued tgcgttctgt ttcgtagatg gattttggtg taagatcagg tcggttccgc tgtttaactt 1260
gtgatgctag tgtgattttt gggaggattt gagttgttaa tctgggagtt gttgggaggt 1320
tctcgtaggc ggattgtaga tgaagtcgcc cgcacgattt gcgtggcttg ttgggtagct 1380
agggttagat ctgctcggat ttttcattgt tacttattga gagataatgt agctaacctt 1440
tacttgttca tctatgtata tcgtattcgt attcatctgg ttcgatggtg ctagatagat 1500
gcgcctgatt tgtccgatcg aattgggtag catccgcggc ttgtttggta gtgttctgat 1560
tgatttgtcg ctctagatct gagtggaata atattacatc tcaacatgtt actagaaact 1620
tggtttatag ctccggattt acatgtttat tcttatgtaa ggttttaaat gaaagattta 1680
tgctactgct gctcgttgat cctttagcat ccacctgagg aacatgcatg catctgttac 1740
ttcttttgat atatgcttag atagttgtta gtatatactg ctgttgttcg atgatccttc 1800
aggatgaaca tgcatgatca tgttacttgt ttttatatgc ttctgctgtt cgttgattct 1860
ttagtactac ctacctgatc atcttgcatg tttcctgctt gttagagatt aattgattag 1920
gcttaccttg ttgcctggtg attcttcctt gcaggtg 1957

<210> SEQ ID NO 20
<211> LENGTH: 872
<212> TYPE: DNA
<213> ORGANISM: Arundo donax

<400> SEQUENCE: 20
gtacggagct tctcctcccc cttcttctct agatcggcgt gttatgttgt ttccgtggtt 60
gcttggttgg atgaatcgaa tgattcttag ggcctaggag gctggttaga tctgttgcgt 120
tctgtttcgt agatggattt tggtgtaaga tcaggtcggt tccgctgttt aacttgtgat 180
gctagtgtga tttttgggag gatttgagtt gttaatctgg gagttgttgg gaggttctcg 240
taggcggatt gtagatgaag tcgcccgcac gatttgcgtg gcttgttggg tagctagggt 300
tagatctgct cggatttttc attgttactt attgagagat aatgtagcta acctttactt 360
gttcatctat gtatatcgta ttcgtattca tctggttcga tggtgctaga tagatgcgcc 420
tgatttgtcc gatcgaattg ggtagcatcc gcggcttgtt tggtagtgtt ctgattgatt 480
tgtcgctcta gatctgagtg gaataatatt acatctcaac atgttactag aaacttggtt 540
tatagctccg gatttacatg tttattctta tgtaaggttt taaatgaaag atttatgcta 600
ctgctgctcg ttgatccttt agcatccacc tgaggaacat gcatgcatct gttacttctt 660
ttgatatatg cttagatagt tgttagtata tactgctgtt gttcgatgat ccttcaggat 720
gaacatgcat gatcatgtta cttgttttta tatgcttctg ctgttcgttg attctttagt 780
actacctacc tgatcatctt gcatgtttcc tgcttgttag agattaattg attaggctta 840
ccttgttgcc tggtgattct tccttgcagg tg 872

<210> SEQ ID NO 21
<211> LENGTH: 1712
<212> TYPE: DNA
<213> ORGANISM: Arundo donax

<400> SEQUENCE: 21
gtgacgtctt tcggaagatc aagatcaatt atcaagtatc agcaacagca cctgaaggtt 60
ggagtgcatt agttgtcatt gagaataatg ctagctattc attgcactgg cattagagac 120
agagagggcg agccagtttg acatggcaaa ttagcacagt caaactggat acgtggtgac 180
ggagggaggg gcactatgaa tttttggtga cggagggagg ggcactatga atttttggct 240
ttgctgacgg gacacgccac tatggatgaa attggacaaa atacgaatat tcaaggatga 300
aagtggtcgg tttgatagtt cagggatgaa atgtgtcttt gggcaaactt tgaggacgaa 360
gttgcctatt ttgcattaaa cgaatatatt tatataccc aaaaaaaaga atacacatct 420
ccactccgag ccggcatgtg gggtccccac tagtcagcca ctgtatggcg ccgactagct 480
caacggccac gaaccagcca accaccagcg caacctaaac ggcgtaaacg ttgacggcat 540
ctctctctcg ccccgtctcg aagcttccgc accgctcgct ggtcgctgcc cggcgccgct 600
cgtgctggac tctttccgtg gcggcttccg cgaaattgcg tggtggagag gagagacgga 660
accgtcacgg cactggattc cttccccacc cggcttggcc ggcccctcct cgcctccata 720
aataggcacc ccgtcctcgc ctcctctccc cacctcatct cctcctttcc cgtgaaccgt 780
gaacacaacc cgacccagat cccctcttgc gagcttcgtc gatccctcct ccgcgtcaag 840
gtacggagct tctcctcccc cttcttctct agatcggcgt gttatgttgt ttccgtggtt 900
gcttggttgg atgaatcgaa tgattcttag ggcctaggag gctggttaga tctgttgcgt 960
tctgtttcgt agatggattt tggtgtaaga tcaggtcggt tccgctgttt aacttgtgat 1020
gctagtgtga tttttgggag gatttgagtt gttaatctgg gagttgttgg gaggttctcg 1080
taggcggatt gtagatgaag tcgcccgcac gatttgcgtg gcttgttggg tagctagggt 1140
tagatctgct cggatttttc attgttactt attgagagat aatgtagcta acctttactt 1200
gttcatctat gtatctcgta ttcgtattca tctggttcga tggtgctaga tagatgcgcc 1260
tgatttgtcc gatcgaattg ggtagcatcc gcggcttgtt tggtagtgtt ctgattgatt 1320
tgtcgctcta gatctgagtg gaataatatt acatctcaac atgttactag aaacttggtt 1380
tatagctccg gatttacatg tttattctta tgtaaggttt taaatgaaag atttatgcta 1440
ctgctgctcg ttgatccttt agcatccacc tgaggaacat gcatgcatct gttacttctt 1500
ttgatatatg cttagatagt tgttagtata tactgctgtt gttcgatgat ccttcaggat 1560
gaacatgcat gatcatgtta cttgttttta tatgcttctg ctgttcgttg attctttagt 1620
actacctacc tgatcatctt gcatgtttcc tgcttgttag agattaattg attaggctta 1680
ccttgttgcc tggtgattct tccttgcagg tg 1712

<210> SEQ ID NO 22
<211> LENGTH: 755
<212> TYPE: DNA
<213> ORGANISM: Arundo donax

<400> SEQUENCE: 22
gtgacgtctt tcggaagatc aagatcaatt atcaagtatc agcaacagca cctgaaggtt 60
ggagtgcatt agttgtcatt gagaataatg ctagctattc attgcactgg cattagagac 120
agagagggcg agccagtttg acatggcaaa ttagcacagt caaactggat acgtggtgac 180
ggagggaggg gcactatgaa tttttggtga cggagggagg ggcactatga atttttggct 240
ttgctgacgg gacacgccac tatggatgaa attggacaaa atacgaatat tcaaggatga 300
aagtggtcgg tttgatagtt cagggatgaa atgtgtcttt gggcaaactt tgaggacgaa 360
gttgcctatt ttgcattaaa cgaatatatt tatataccc aaaaaaaaga atacacatct 420
ccactccgag ccggcatgtg gggtccccac tagtcagcca ctgtatggcg ccgactagct 480
caacggccac gaaccagcca accaccagcg caacctaaac ggcgtaaacg ttgacggcat 540
ctctctctcg ccccgtctcg aagcttccgc accgctcgct ggtcgctgcc cggcgccgct 600

-continued

```
cgtgctggac tctttccgtg gcggcttccg cgaaattgcg tggtggagag gagagacgga    660

accgtcacgg cactggattc cttccccacc cggcttggcc ggcccctcct cgcctccata    720

aataggcacc ccgtcctcgc ctcctctccc cacct                               755


<210> SEQ ID NO 23
<211> LENGTH: 3276
<212> TYPE: DNA
<213> ORGANISM: Arundo donax

<400> SEQUENCE: 23

ggcctcttta cgtttggcac aatttgatcg aatccaacac ggcaagttag cctttgaagc     60

ttgaaccggg cactaatgca agtatataat aactgagaac tacaagaaag catattcctt    120

gaggtactta tgcaacctta caattatcaa attaattaac aactagcagt tagaatttta    180

tatcacaaga atatcatgaa ccgtggatac tacttcttaa agggctattc tttttctgaa    240

tgtcgcagtt ggttatttta accatattac aaactagggg tttaaatccc aaaaagttca    300

cggaaaggga ttaagcaagt agttagcaag actcacactt atgaccgtta gccaaattac    360

acattggtca ttccaggagg agtaatcccc catagctagt tgttttgagt ttgactaccc    420

aaacttgcat aatcgttttc ctagaggggg gggggggtt caccattcca tcaagatgag    480

gcaaagctaa atgaaacaca cgagaggcaa aacggactga cgtgatagag tttttaataa    540

atatcaaata tgtagagtca accaaagaaa aaagatatcc caatggctaa actttggatc    600

tatgtcgtaa ttcgtgtttt aggacataca aggcgaattc cttctacggc aaactctaga    660

atagctgggc gacaatggcc tcacgatagc ctcaaagagt tggtagcaac tttgagatct    720

tttgatccga aactcaatta tgtagtacaa tgatatttag atagattgat tgaaagttgg    780

gggtgggggc gaaagcgaag gggatctcaa tattaataca tctatagtga atggatatag    840

aaaacacagg atttccaatt caagtagaaa taggaggaac ggaacagatc tagcaatagt    900

agccaccaaa gacgaggagg attctagatt gcaaatccaa ggtgaaagga agaaatgttg    960

aactatccag aataaggcgg attggccaag gaggcggaag tctctagaaa gaagtcattt   1020

ggctctgagg gctcacttga tgcgagaagg aagactgact gaggaatgga ttttggtgga   1080

ccgaggaaat tggtgctggg ttgcagaggc atgtatgtgg gaaaagaggc agtggcaacg   1140

atcgagagag gagaagggaa tgaggtaagt atttgaagtg aagaggagcc catataggtg   1200

aaaaataaaa ataatccatc gtggattcaa ataatcaaag ggctatgacc tttcatcaat   1260

tttagaaaag tgaaaacaac cggtttaaca cctatatgca ccattttcct acatagattt   1320

ttaacttctt acttaaccat gttgactaag agcaagtgga gagcactctc atttcataga   1380

acaagtgatg aatgccaacc tgcattatta tcttaattag actttgatca tcaagtggaa   1440

tcccatttat cttaataatc ttggcaacat tgttataatg ctacttcata tgctaattct   1500

tcaaagctaa catcgttaaa cgaatacata tctcctgtat tctaagaccc tatttagaat   1560

acagaaattt tacagaaatc agttcaattc tcgtagaatt gggaaagaaa tcctccgttc   1620

caaacgtgac ctaagccggc atggcacgac cccactcgtc aggcactgta tgtaaacgtc   1680

agcaactccg tggcaagtaa cgtcgagagg aggagcgggc ctaacggcgc cgactagctc   1740

aacggccacc aaccagccaa ccaccagcgc aaccgaaacg gcgcaaacgt tgacgtcatc   1800

tctctctctc tcgcgccccg cgtcccgaag cttccgcacc actcgctggt cgctgctagc   1860

tgggccccac cggccggccc cgttcgtgct ggactcttct tcctcgaaat tgcgtggtgg   1920

agagggagag ggggcacctc gagacggaac cgtcacggca cgggattcct tccccacccg   1980
```

```
gcccctcctc gtctccataa ataggcgccc cctcctcgcg tcctctcccc cgtctcatct   2040

cctcctgttc cgtgaaccgt gaacgcaacc cgacccccag atctctctcg cgagcatcgt   2100

cgatccctcc tccgcgtcaa ggtacggatc ttctccttcc tccccccttcc cctctgggtc   2160

ggcgtgtcgt gttgtttctc tagttgcttg gctggatgga tcgagtggtt cttagggctt   2220

agatggctgg ttagatctgt tgcgttctgt ttcgtagatg gatttttggt gtagatctgg   2280

taggttatgc tggttaactg gtgatgctcc tgcgattttt gggggatctg agttgttaat   2340

ctggtagttg tatggggttc tcgtagccgg attgtagatg aaatcgtccg cgcggtttgc   2400

gtggctcgtt ggttagctag ggttagatct gctcggattt ttcattgttc ctgattcaga   2460

gatgtagtta acctttactt gttcatcttt gtatctcgta ttcgtacctg catgtatgat   2520

ctgtttcgat ggtgctagat aggtgcgcct gatttgtccg atcgaatctg gtagcatgcg   2580

ctgtttgttt ggtagtgttc tgattgattt gtcgctctag atctgagtag aataggatta   2640

tttctcaaca tgatattaga agcttggttt atagctccgg attagcatgt atgttacatg   2700

tttattctta tgtaaggttt taaacggaag atatatgcta ctgctgctca ttgattcttt   2760

atcatccacc tgagtccatg catgcttctg ttacttcttt tgatatgtgc ttagatagct   2820

gttgatatgt actgctgctg ttagatgatc cttcaggatg aacatgcatg attctgttac   2880

ttgttttggt atgcttagat aaatcaagat acgcttctgc tgttcgttga ttctttagta   2940

ctacctacct gatcagctta gatagatcaa gatatgcttc tgctgttcgt tgattcttta   3000

gtaataccta cctgatcagc ttagatagat caagatacgc ttctgctgtt cgttgattct   3060

ctagtactac ctacctgata aacatgcatg ttttctgctt gttaaaggtt gattgcttag   3120

gctcatcttt ttcttttcgt tgattctcta gtactaccta cctgataaac atgcatgttt   3180

tctgcttgtt aaagattgat tgcttagtct catctttttc tttctctttt gtctaccgcc   3240

aggcctaacc ttgttgctgg tgactctttc ttgcag                               3276
```

<210> SEQ ID NO 24
<211> LENGTH: 2033
<212> TYPE: DNA
<213> ORGANISM: Arundo donax

<400> SEQUENCE: 24

```
ggcctcttta cgtttggcac aatttgatcg aatccaacac ggcaagttag cctttgaagc     60

ttgaaccggg cactaatgca agtatataat aactgagaac tacaagaaag catattcctt    120

gaggtactta tgcaacctta caattatcaa attaattaac aactagcagt tagaatttta    180

tatcacaaga atatcatgaa ccgtggatac tacttcttaa agggctattc tttttctgaa    240

tgtcgcagtt ggttatttta accatattac aaactagggg tttaaatccc aaaaagttca    300

cggaaaggga ttaagcaagt agttagcaag actcacactt atgaccgtta gccaaattac    360

acattggtca ttccaggagg agtaatcccc catagctagt tgttttgagt ttgactaccc    420

aaacttgcat aatcgttttc ctagaggggg gggggggtt caccattcca tcaagatgag    480

gcaaagctaa atgaaacaca cgagaggcaa aacggactga cgtgatagag tttttaataa    540

atatcaaata tgtagagtca accaaagaaa aaagatatcc caatggctaa actttggatc    600

tatgtcgtaa ttcgtgtttt aggacataca aggcgaattc cttctacggc aaactctaga    660

atagctgggc gacaatggcc tcacgatagc ctcaaagagt tggtagcaac tttgagatct    720

tttgatccga aactcaatta tgtagtacaa tgatatttag atagattgat tgaaagttgg    780
```

-continued

```
gggtgggggc gaaagcgaag gggatctcaa tattaataca tctatagtga atggatatag    840
aaaacacagg atttccaatt caagtagaaa taggaggaac ggaacagatc tagcaatagt    900
agccaccaaa gacgaggagg attctagatt gcaaatccaa ggtgaaagga agaaatgttg    960
aactatccag aataaggcgg attggccaag gaggcggaag tctctagaaa gaagtcattt   1020
ggctctgagg gctcacttga tgcgagaagg aagactgact gaggaatgga ttttggtgga   1080
ccgaggaaat tggtgctggg ttgcagaggc atgtatgtgg gaaaagaggc agtggcaacg   1140
atcgagagag gagaagggaa tgaggtaagt atttgaagtg aagaggagcc catataggtg   1200
aaaaataaaa ataatccatc gtggattcaa ataatcaaag ggctatgacc tttcatcaat   1260
tttagaaaag tgaaaacaac cggtttaaca cctatatgca ccattttcct acatagattt   1320
ttaacttctt acttaaccat gttgactaag agcaagtgga gagcactctc atttcataga   1380
acaagtgatg aatgccaacc tgcattatta tcttaattag actttgatca tcaagtggaa   1440
tcccatttat cttaataatc ttggcaacat tgttataatg ctacttcata tgctaattct   1500
tcaaagctaa catcgttaaa cgaatacata tctcctgtat tctaagaccc tatttagaat   1560
acagaaattt tacagaaatc agttcaattc tcgtagaatt gggaaagaaa tcctccgttc   1620
caaacgtgac ctaagccggc atggcacgac cccactcgtc aggcactgta tgtaaacgtc   1680
agcaactccg tggcaagtaa cgtcgagagg aggagcgggc ctaacggcgc cgactagctc   1740
aacggccacc aaccagccaa ccaccagcgc aaccgaaacg gcgcaaacgt tgacgtcatc   1800
tctctctctc tcgcgccccg cgtcccgaag cttccgcacc actcgctggt cgctgctagc   1860
tgggccccac cggccggccc cgttcgtgct ggactcttct tcctcgaaat tgcgtggtgg   1920
agagggagag ggggcacctc gagacggaac cgtcacggca cgggattcct tccccacccg   1980
gcccctcctc gtctccataa ataggcgccc cctcctcgcg tcctctcccc cgt          2033
```

```
<210> SEQ ID NO 25
<211> LENGTH: 88
<212> TYPE: DNA
<213> ORGANISM: Arundo donax

<400> SEQUENCE: 25

ctcatctcct cctgttccgt gaaccgtgaa cgcaacccga cccccagatc tctctcgcga      60
gcatcgtcga tccctcctcc gcgtcaag                                          88


<210> SEQ ID NO 26
<211> LENGTH: 1155
<212> TYPE: DNA
<213> ORGANISM: Arundo donax

<400> SEQUENCE: 26

gtacggatct tctccttcct ccccctccc ctctgggtcg gcgtgtcgtg ttgtttctct      60
agttgcttgg ctggatggat cgagtggttc ttagggctta gatggctggt tagatctgtt    120
gcgttctgtt tcgtagatgg atttttggtg tagatctggt aggttatgct ggttaactgg    180
tgatgctcct gcgatttttg gggatctga gttgttaatc tggtagttgt atggggttct      240
cgtagccgga ttgtagatga aatcgtccgc gcggtttgcg tggctcgttg gttagctagg    300
gttagatctg ctcggatttt tcattgttcc tgattcagag atgtagttaa cctttacttg    360
ttcatctttg tatctcgtat tcgtacctgc atgtatgatc tgtttcgatg gtgctagata    420
ggtgcgcctg atttgtccga tcgaatctgg tagcatgcgc tgtttgtttg gtagtgttct    480
gattgatttg tcgctctaga tctgagtaga ataggattat ttctcaacat gatattagaa    540
```

-continued gcttggttta tagctccgga ttagcatgta tgttacatgt ttattcttat gtaaggtttt 600
aaacggaaga tatatgctac tgctgctcat tgattcttta tcatccacct gagtccatgc 660
atgcttctgt tacttctttt gatatgtgct tagatagctg ttgatatgta ctgctgctgt 720
tagatgatcc ttcaggatga acatgcatga ttctgttact tgttttggta tgcttagata 780
aatcaagata cgcttctgct gttcgttgat tctttagtac tacctacctg atcagcttag 840
atagatcaag atatgcttct gctgttcgtt gattctttag taatacctac ctgatcagct 900
tagatagatc aagatacgct tctgctgttc gttgattctc tagtactacc tacctgataa 960
acatgcatgt tttctgcttg ttaaaggttg attgcttagg ctcatctttt tcttttcgtt 1020
gattctctag tactacctac ctgataaaca tgcatgtttt ctgcttgtta aagattgatt 1080
gcttagtctc atctttttct ttctcttttg tctaccgcca ggcctaacct tgttgctggt 1140
gactctttct tgcag 1155

<210> SEQ ID NO 27
<211> LENGTH: 3250
<212> TYPE: DNA
<213> ORGANISM: Arundo donax

<400> SEQUENCE: 27
gaatccaaca cggcaagtta gcctttgaag cttgaaccgg gcactaatgc aagtatataa 60
taactgagaa ctacaagaaa gcatattcct tgaggtactt atgcaacctt acaattatca 120
aattaattaa caactagcag ttagaatttt atatcacaag aatatcatga accgtggata 180
ctacttctta aagggctatt ctttttctga atgtcgcagt tggttatttt aaccatatta 240
caaactaggg gtttaaatcc caaaaagttc acggaaaggg attaagcaag tagttagcaa 300
gactcacact tatgaccgtt agccaaatta cacattggtc attccaggag gagtaatccc 360
ccatagctag ttgttttgag tttgactacc caaacttgca taatcgtttt cctagagggg 420
gggggggggt tcaccattcc atcaagatga ggcaaagcta aatgaaacac acgagaggca 480
aaacggactg acgtgataga gtttttaata aatatcaaat atgtagagtc aaccaaagaa 540
aaaagatatc ccaatggcta aactttggat ctatgtcgta attcgtgttt taggacatac 600
aaggcgaatt ccttctacgg caaactctag aatagctggg cgacaatggc ctcacgatag 660
cctcaaagag ttggtagcaa ctttgagatc ttttgatccg aaactcaatt atgtagtaca 720
atgatattta gatagattga ttgaaagttg ggggtggggg cgaaagcgaa ggggatctca 780
atattaatac atctatagtg aatggatata gaaaacacag gatttccaat tcaagtagaa 840
ataggaggaa cggaacagat ctagcaatag tagccaccaa agacgaggag gattctagat 900
tgcaaatcca aggtgaaagg aagaaatgtt gaactatcca gaataaggcg gattggccaa 960
ggaggcggaa gtctctagaa agaagtcatt tggctctgag ggctcacttg atgcgagaag 1020
gaagactgac tgaggaatgg attttggtgg accgaggaaa ttggtgctgg gttgcagagg 1080
catgtatgtg ggaaaagagg cagtggcaac gatcgagaga ggagaaggga atgaggtaag 1140
tatttgaagt gaagaggagc ccatataggt gaaaaataaa aataatccat cgtggattca 1200
aataatcaaa gggctatgac ctttcatcaa ttttagaaaa gtgaaaacaa ccggtttaac 1260
acctatatgc accattttcc tacatagatt tttaacttct tacttaacca tgttgactaa 1320
gagcaagtgg agagcactct catttcatag aacaagtgat gaatgccaac ctgcattatt 1380
atcttaatta gactttgatc atcaagtgga atcccattta tcttaataat cttggcaaca 1440

-continued

```
ttgttataat gctacttcat atgctaattc ttcaaagcta acatcgttaa acgaatacat   1500

atctcctgta ttctaagacc ctatttagaa tacagaaatt ttacagaaat cagttcaatt   1560

ctcgtagaat tgggaaagaa atcctccgtt ccaaacgtga cctaagccgg catggcacga   1620

ccccactcgt caggcactgt atgtaaacgt cagcaactcc gtggcaagta acgtcgagag   1680

gaggagcggg cctaacggcg ccgactagct caacggccac caaccagcca accaccagcg   1740

caaccgaaac ggcgcaaacg ttgacgtcat ctctctctct ctcgcgcccc gcgtcccgaa   1800

gcttccgcac cactcgctgg tcgctgctag ctgggcccca ccggccggcc ccgttcgtgc   1860

tggactcttc ttcctcgaaa ttgcgtggtg gagagggaga gggggcacct cgagacggaa   1920

ccgtcacggc acgggattcc ttccccaccc ggcccctcct cgtctccata aataggcgcc   1980

ccctcctcgc gtcctctccc ccgtctcatc tcctcctgtt ccgtgaaccg tgaacgcaac   2040

ccgacccccca gatctctctc gcgagcatcg tcgatccctc ctccgcgtca aggtacggat   2100

cttctccttc ctccccccttc ccctctgggt cggcgtgtcg tgttgtttct ctagttgctt   2160

ggctggatgg atcgagtggt tcttagggct tagatggctg gttagatctg ttgcgttctg   2220

tttcgtagat ggatttttgg tgtagatctg gtaggttatg ctggttaact ggtgatgctc   2280

ctgcgatttt tgggggatct gagttgttaa tctggtagtt gtatggggtt ctcgtagccg   2340

gattgtagat gaaatcgtcc gcgcggtttg cgtggctcgt tggttagcta gggttagatc   2400

tgctcggatt tttcattgtt cctgattcag agatgtagtt aacctttact tgttcatctt   2460

tgtatctcgt attcgtacct gcatgtatga tctgtttcga tggtgctaga taggtgcgcc   2520

tgatttgtcc gatcgaatct ggtagcatgc gctgtttgtt tggtagtgtt ctgattgatt   2580

tgtcgctcta gatctgagta gaataggatt atttctcaac atgatattag aagcttggtt   2640

tatagctccg gattagcatg tatgttacat gtttattctt atgtaaggtt ttaaacggaa   2700

gatatatgct actgctgctc attgattctt tatcatccac ctgagtccat gcatgcttct   2760

gttacttctt ttgatatgtg cttagatagc tgttgatatg tactgctgct gttagatgat   2820

ccttcaggat gaacatgcat gattctgtta cttgttttgg tatgcttaga taaatcaaga   2880

tacgcttctg ctgttcgttg attctttagt actacctacc tgatcagctt agatagatca   2940

agatatgctt ctgctgttcg ttgattcttt agtaatacct acctgatcag cttagataga   3000

tcaagatacg cttctgctgt tcgttgattc tctagtacta cctacctgat aaacatgcat   3060

gttttctgct tgttaaaggt tgattgctta ggctcatctt tttcttttcg ttgattctct   3120

agtactacct acctgataaa catgcatgtt ttctgcttgt taaagattga ttgcttagtc   3180

tcatcttttt ctttctcttt tgtctaccgc caggcctaac cttgttgctg gtgactcttt   3240

cttgcaggtg                                                          3250
```

<210> SEQ ID NO 28
<211> LENGTH: 2004
<212> TYPE: DNA
<213> ORGANISM: Arundo donax

<400> SEQUENCE: 28

```
gaatccaaca cggcaagtta gcctttgaag cttgaaccgg gcactaatgc aagtatataa     60

taactgagaa ctacaagaaa gcatattcct tgaggtactt atgcaacctt acaattatca    120

aattaattaa caactagcag ttagaatttt atatcacaag aatatcatga accgtggata    180

ctacttctta aagggctatt ctttttctga atgtcgcagt tggttatttt aaccatatta    240

caaactaggg gtttaaatcc caaaaagttc acggaaaggg attaagcaag tagttagcaa    300
```

gactcacact tatgaccgtt agccaaatta cacattggtc attccaggag gagtaatccc 360
ccatagctag ttgttttgag tttgactacc caaacttgca taatcgtttt cctagagggg 420
gggggggggt tcaccattcc atcaagatga ggcaaagcta aatgaaacac acgagaggca 480
aaacggactg acgtgataga gtttttaata aatatcaaat atgtagagtc aaccaaagaa 540
aaaagatatc ccaatggcta aactttggat ctatgtcgta attcgtgttt taggacatac 600
aaggcgaatt ccttctacgg caaactctag aatagctggg cgacaatggc ctcacgatag 660
cctcaaagag ttggtagcaa ctttgagatc ttttgatccg aaactcaatt atgtagtaca 720
atgatattta gatagattga ttgaaagttg ggggtggggg cgaaagcgaa ggggatctca 780
atattaatac atctatagtg aatggatata gaaaacacag gatttccaat tcaagtagaa 840
ataggaggaa cggaacagat ctagcaatag tagccaccaa agacgaggag gattctagat 900
tgcaaatcca aggtgaaagg aagaaatgtt gaactatcca gaataaggcg gattggccaa 960
ggaggcggaa gtctctagaa agaagtcatt tggctctgag ggctcacttg atgcgagaag 1020
gaagactgac tgaggaatgg attttggtgg accgaggaaa ttggtgctgg gttgcagagg 1080
catgtatgtg ggaaaagagg cagtggcaac gatcgagaga ggagaaggga atgaggtaag 1140
tatttgaagt gaagaggagc ccatataggt gaaaaataaa aataatccat cgtggattca 1200
aataatcaaa gggctatgac ctttcatcaa ttttagaaaa gtgaaaacaa ccggtttaac 1260
acctatatgc accatttcc tacatagatt tttaacttct tacttaacca tgttgactaa 1320
gagcaagtgg agagcactct catttcatag aacaagtgat gaatgccaac ctgcattatt 1380
atcttaatta gactttgatc atcaagtgga atcccattta tcttaataat cttggcaaca 1440
ttgttataat gctacttcat atgctaattc ttcaaagcta acatcgttaa acgaatacat 1500
atctcctgta ttctaagacc ctatttagaa tacagaaatt ttacagaaat cagttcaatt 1560
ctcgtagaat tgggaaagaa atcctccgtt ccaaacgtga cctaagccgg catggcacga 1620
ccccactcgt caggcactgt atgtaaacgt cagcaactcc gtggcaagta acgtcgagag 1680
gaggagcggg cctaacggcg ccgactagct caacggccac caaccagcca accaccagcg 1740
caaccgaaac ggcgcaaacg ttgacgtcat ctctctctct ctcgcgcccc gcgtcccgaa 1800
gcttccgcac cactcgctgg tcgctgctag ctgggcccca ccggccggcc ccgttcgtgc 1860
tggactcttc ttcctcgaaa ttgcgtggtg gagagggaga gggggcacct cgagacggaa 1920
ccgtcacggc acgggattcc ttccccaccc ggcccctcct cgtctccata aataggcgcc 1980
ccctcctcgc gtcctctccc ccgt 2004

<210> SEQ ID NO 29
<211> LENGTH: 1158
<212> TYPE: DNA
<213> ORGANISM: Arundo donax

<400> SEQUENCE: 29
gtacggatct tctccttcct ccccccttccc ctctgggtcg gcgtgtcgtg ttgtttctct 60
agttgcttgg ctggatggat cgagtggttc ttagggctta gatggctggt tagatctgtt 120
gcgttctgtt tcgtagatgg atttttggtg tagatctggt aggttatgct ggttaactgg 180
tgatgctcct gcgatttttg ggggatctga gttgttaatc tggtagttgt atggggttct 240
cgtagccgga ttgtagatga aatcgtccgc gcggtttgcg tggctcgttg gttagctagg 300
gttagatctg ctcggatttt tcattgttcc tgattcagag atgtagttaa cctttacttg 360

-continued

```
ttcatctttg tatctcgtat tcgtacctgc atgtatgatc tgtttcgatg gtgctagata    420
ggtgcgcctg atttgtccga tcgaatctgg tagcatgcgc tgtttgtttg gtagtgttct    480
gattgatttg tcgctctaga tctgagtaga ataggattat ttctcaacat gatattagaa    540
gcttggttta tagctccgga ttagcatgta tgttacatgt ttattcttat gtaaggtttt    600
aaacggaaga tatatgctac tgctgctcat tgattcttta tcatccacct gagtccatgc    660
atgcttctgt tacttctttt gatatgtgct tagatagctg ttgatatgta ctgctgctgt    720
tagatgatcc ttcaggatga acatgcatga ttctgttact tgttttggta tgcttagata    780
aatcaagata cgcttctgct gttcgttgat tctttagtac tacctacctg atcagcttag    840
atagatcaag atatgcttct gctgttcgtt gattctttag taatacctac ctgatcagct    900
tagatagatc aagatacgct tctgctgttc gttgattctc tagtactacc tacctgataa    960
acatgcatgt tttctgcttg ttaaaggttg attgcttagg ctcatctttt tcttttcgtt   1020
gattctctag tactacctac ctgataaaca tgcatgtttt ctgcttgtta aagattgatt   1080
gcttagtctc atctttttct ttctcttttg tctaccgcca ggcctaacct tgttgctggt   1140
gactctttct tgcaggtg                                                 1158
```

<210> SEQ ID NO 30
<211> LENGTH: 2247
<212> TYPE: DNA
<213> ORGANISM: Arundo donax

<400> SEQUENCE: 30

```
tcacttgatg cgagaaggaa gactgactga ggaatggatt ttggtggacc gaggaaattg     60
gtgctgggtt gcagaggcat gtatgtggga aaagaggcag tggcaacgat cgagagagga    120
gaagggaatg aggtaagtat ttgaagtgaa gaggagccca tataggtgaa aaataaaaat    180
aatccatcgt ggattcaaat aatcaaaggg ctatgacctt tcatcaattt tagaaaagtg    240
aaaacaaccg gtttaacacc tatatgcacc attttcctac atagattttt aacttcttac    300
ttaaccatgt tgactaagag caagtggaga gcactctcat ttcatagaac aagtgatgaa    360
tgccaacctg cattattatc ttaattagac tttgatcatc aagtggaatc ccatttatct    420
taataatctt ggcaacattg ttataatgct acttcatatg ctaattcttc aaagctaaca    480
tcgttaaacg aatacatatc tcctgtattc taagacccta tttagaatac agaaatttta    540
cagaaatcag ttcaattctc gtagaattgg gaaagaaatc ctccgttcca aacgtgacct    600
aagccggcat ggcacgaccc cactcgtcag gcactgtatg taaacgtcag caactccgtg    660
gcaagtaacg tcgagaggag gagcgggcct aacggcgccg actagctcaa cggccaccaa    720
ccagccaacc accagcgcaa ccgaaacggc gcaaacgttg acgtcatctc tctctctctc    780
gcgccccgcg tcccgaagct tccgcaccac tcgctggtcg ctgctagctg ggccccaccg    840
gccggccccg ttcgtgctgg actcttcttc ctcgaaattg cgtggtggag agggagaggg    900
ggcacctcga gacggaaccg tcacggcacg ggattccttc cccacccggc ccctcctcgt    960
ctccataaat aggcgccccc tcctcgcgtc ctctcccccg tctcatctcc tcctgttccg   1020
tgaaccgtga acgcaacccg acccccagat ctctctcgcg agcatcgtcg atccctcctc   1080
cgcgtcaagg tacggatctt ctccttcctc ccccttcccc tctgggtcgg cgtgtcgtgt   1140
tgtttctcta gttgcttggc tggatggatc gagtggttct tagggcttag atggctggtt   1200
agatctgttg cgttctgttt cgtagatgga tttttggtgt agatctggta ggttatgctg   1260
gttaactggt gatgctcctg cgatttttgg gggatctgag ttgttaatct ggtagttgta   1320
```

tggggttctc gtagccggat tgtagatgaa atcgtccgcg cggtttgcgt ggctcgttgg 1380
ttagctaggg ttagatctgc tcggattttt cattgttcct gattcagaga tgtagttaac 1440
ctttacttgt tcatctttgt atctcgtatt cgtacctgca tgtatgatct gtttcgatgg 1500
tgctagatag gtgcgcctga tttgtccgat cgaatctggt agcatgcgct gtttgtttgg 1560
tagtgttctg attgatttgt cgctctagat ctgagtagaa taggattatt tctcaacatg 1620
atattagaag cttggtttat agctccggat tagcatgtat gttacatgtt tattcttatg 1680
taaggtttta aacggaagat atatgctact gctgctcatt gattctttat catccacctg 1740
agtccatgca tgcttctgtt acttcttttg atatgtgctt agatagctgt tgatatgtac 1800
tgctgctgtt agatgatcct tcaggatgaa catgcatgat tctgttactt gttttggtat 1860
gcttagataa atcaagatac gcttctgctg ttcgttgatt ctttagtact acctacctga 1920
tcagcttaga tagatcaaga tatgcttctg ctgttcgttg attctttagt aatacctacc 1980
tgatcagctt agatagatca agatacgctt ctgctgttcg ttgattctct agtactacct 2040
acctgataaa catgcatgtt ttctgcttgt taaaggttga ttgcttaggc tcatcttttt 2100
cttttcgttg attctctagt actacctacc tgataaacat gcatgttttc tgcttgttaa 2160
agattgattg cttagtctca tctttttctt tctcttttgt ctaccgccag gcctaacctt 2220
gttgctggtg actctttctt gcaggtg 2247

<210> SEQ ID NO 31
<211> LENGTH: 1001
<212> TYPE: DNA
<213> ORGANISM: Arundo donax

<400> SEQUENCE: 31
tcacttgatg cgagaaggaa gactgactga ggaatggatt ttggtggacc gaggaaattg 60
gtgctgggtt gcagaggcat gtatgtggga aaagaggcag tggcaacgat cgagagagga 120
gaagggaatg aggtaagtat ttgaagtgaa gaggagccca tataggtgaa aaataaaaat 180
aatccatcgt ggattcaaat aatcaaaggg ctatgacctt tcatcaattt tagaaaagtg 240
aaaacaaccg gtttaacacc tatatgcacc attttcctac atagattttt aacttcttac 300
ttaaccatgt tgactaagag caagtggaga gcactctcat ttcatagaac aagtgatgaa 360
tgccaacctg cattattatc ttaattagac tttgatcatc aagtggaatc ccatttatct 420
taataatctt ggcaacattg ttataatgct acttcatatg ctaattcttc aaagctaaca 480
tcgttaaacg aatacatatc tcctgtattc taagacccta tttagaatac agaaatttta 540
cagaaatcag ttcaattctc gtagaattgg gaaagaaatc ctccgttcca aacgtgacct 600
aagccggcat ggcacgaccc cactcgtcag gcactgtatg taaacgtcag caactccgtg 660
gcaagtaacg tcgagaggag gagcgggcct aacggcgccg actagctcaa cggccaccaa 720
ccagccaacc accagcgcaa ccgaaacggc gcaaacgttg acgtcatctc tctctctctc 780
gcgccccgcg tcccgaagct tccgcaccac tcgctggtcg ctgctagctg ggccccaccg 840
gccggccccg ttcgtgctgg actcttcttc ctcgaaattg cgtggtggag agggagaggg 900
ggcacctcga gacggaaccg tcacggcacg ggattccttc cccacccggc ccctcctcgt 960
ctccataaat aggcgccccc tcctcgcgtc ctctcccccg t 1001

<210> SEQ ID NO 32
<211> LENGTH: 1942
<212> TYPE: DNA

<213> ORGANISM: Arundo donax

<400> SEQUENCE: 32
catgttgact aagagcaagt ggagagcact ctcatttcat agaacaagtg atgaatgcca 60
acctgcatta ttatcttaat tagactttga tcatcaagtg gaatcccatt tatcttaata 120
atcttggcaa cattgttata atgctacttc atatgctaat tcttcaaagc taacatcgtt 180
aaacgaatac atatctcctg tattctaaga ccctatttag aatacagaaa ttttacagaa 240
atcagttcaa ttctcgtaga attgggaaag aaatcctccg ttccaaacgt gacctaagcc 300
ggcatggcac gaccccactc gtcaggcact gtatgtaaac gtcagcaact ccgtggcaag 360
taacgtcgag aggaggagcg ggcctaacgg cgccgactag ctcaacggcc accaaccagc 420
caaccaccag cgcaaccgaa acggcgcaaa cgttgacgtc atctctctct ctctcgcgcc 480
ccgcgtcccg aagcttccgc accactcgct ggtcgctgct agctgggccc caccggccgg 540
ccccgttcgt gctggactct tcttcctcga aattgcgtgg tggagaggga gagggggcac 600
ctcgagacgg aaccgtcacg gcacgggatt ccttccccac ccggcccctc ctcgtctcca 660
taaataggcg cccccctcctc gcgtcctctc ccccgtctca tctcctcctg ttccgtgaac 720
cgtgaacgca acccgacccc cagatctctc tcgcgagcat cgtcgatccc tcctccgcgt 780
caaggtacgg atcttctcct tcctcccccct tcccctctgg gtcggcgtgt cgtgttgttt 840
ctctagttgc ttggctggat ggatcgagtg gttcttaggg cttagatggc tggttagatc 900
tgttgcgttc tgtttcgtag atggattttt ggtgtagatc tggtaggtta tgctggttaa 960
ctggtgatgc tcctgcgatt tttgggggat ctgagttgtt aatctggtag ttgtatgggg 1020
ttctcgtagc cggattgtag atgaaatcgt ccgcgcggtt tgcgtggctc gttggttagc 1080
tagggttaga tctgctcgga tttttcattg ttcctgattc agagatgtag ttaaccttta 1140
cttgttcatc tttgtatctc gtattcgtac ctgcatgtat gatctgtttc gatggtgcta 1200
gataggtgcg cctgatttgt ccgatcgaat ctggtagcat gcgctgtttg tttggtagtg 1260
ttctgattga tttgtcgctc tagatctgag tagaatagga ttatttctca acatgatatt 1320
agaagcttgg tttatagctc cggattagca tgtatgttac atgtttattc ttatgtaagg 1380
ttttaaacgg aagatatatg ctactgctgc tcattgattc tttatcatcc acctgagtcc 1440
atgcatgctt ctgttacttc ttttgatatg tgcttagata gctgttgata tgtactgctg 1500
ctgttagatg atccttcagg atgaacatgc atgattctgt tacttgtttt ggtatgctta 1560
gataaatcaa gatacgcttc tgctgttcgt tgattcttta gtactaccta cctgatcagc 1620
ttagatagat caagatatgc ttctgctgtt cgttgattct ttagtaatac ctacctgatc 1680
agcttagata gatcaagata cgcttctgct gttcgttgat tctctagtac tacctacctg 1740
ataaacatgc atgttttctg cttgttaaag gttgattgct taggctcatc tttttctttt 1800
cgttgattct ctagtactac ctacctgata aacatgcatg ttttctgctt gttaaagatt 1860
gattgcttag tctcatcttt ttctttctct tttgtctacc gccaggccta accttgttgc 1920
tggtgactct ttcttgcagg tg 1942

<210> SEQ ID NO 33
<211> LENGTH: 696
<212> TYPE: DNA
<213> ORGANISM: Arundo donax

<400> SEQUENCE: 33
catgttgact aagagcaagt ggagagcact ctcatttcat agaacaagtg atgaatgcca 60
acctgcatta ttatcttaat tagactttga tcatcaagtg gaatcccatt tatcttaata 120
atcttggcaa cattgttata atgctacttc atatgctaat tcttcaaagc taacatcgtt 180
aaacgaatac atatctcctg tattctaaga ccctatttag aatacagaaa ttttacagaa 240
atcagttcaa ttctcgtaga attgggaaag aaatcctccg ttccaaacgt gacctaagcc 300
ggcatggcac gaccccactc gtcaggcact gtatgtaaac gtcagcaact ccgtggcaag 360
taacgtcgag aggaggagcg ggcctaacgg cgccgactag ctcaacggcc accaaccagc 420
caaccaccag cgcaaccgaa acggcgcaaa cgttgacgtc atctctctct ctctcgcgcc 480
ccgcgtcccg aagcttccgc accactcgct ggtcgctgct agctgggccc caccggccgg 540
ccccgttcgt gctggactct tcttcctcga aattgcgtgg tggagaggga gagggggcac 600
ctcgagacgg aaccgtcacg gcacgggatt ccttccccac ccggcccctc ctcgtctcca 660
taaataggcg ccccctcctc gcgtcctctc ccccgt 696

<210> SEQ ID NO 34
<211> LENGTH: 3511
<212> TYPE: DNA
<213> ORGANISM: Bouteloua gracilis

<400> SEQUENCE: 34
gtggccagct tttgttctag ttcaacggtc ccggccttcc gtgcacctaa tactacactg 60
attaatctat tgcagctaac ctcaaaagaa atacacttgc agttgtctgt cccaatcaag 120
ccactagcag actctcatgt cattgatgga ggaaattaaa ttcagtcttt gacgtggatg 180
caacaactgc acagtatacc atgcatctta attagccgtt gtgtcaaagt ttgttttgct 240
gacgttttga gaaaaccaac tttgaccaac aggagatgag cgtcttgcgt ttggcacagt 300
gtaatggaat ccggcacggc aagttagact ctgtagtgtt agcggtctct ttacgtttgg 360
cacaatttaa ttgaatcccg gcatggcatg ttagaccgga gtgagccggc ccttttactg 420
gtatgacact ccctctgtct tgagtgtcgc tgtgccagct tgtacctctg tctatgttca 480
cagcccgtgc tgtgtaccta gaccctccgt ttgtccacat tcattttaat ctctattgta 540
tcttgtcaaa acctaaaagc ctaaaacgac tctgataaag ggacagaaag attatacaag 600
agcaagtgta taatgaaata atgtaagcga gctatatgaa ttgtcacgtg tcatatttat 660
gttgagacga agaagagaaa ataaacacca tgcaaattta tggcgagtga tagatggcca 720
gatgggcaca aggcctccta tttcttaaat cggattttgt aagaacgaaa aaagggactt 780
ataagagaat aggatagacc atatatcaat gatgtagtat gcatcaagat ctaactatta 840
tatgagtgaa ttgataaatt tattctaggt gacatggcct taacgatgaa cagtacgtgg 900
ttaaatcaat agaacaatag ccaactctag cggctctaaa aaaagatata tattcgtcga 960
ggcactatta tgcaaccaca tagtcaactt caacgccgct tgagtgcgtt ctcatgtttt 1020
ttttttcttg caaattacgc ttttctaaaa taaaataatt tggatcgtgc aattatttca 1080
ctttaggtgt gcgtgactac gtgagtaaca attttgaatc tcagaaagga aataaaagta 1140
taatactgct acctactttg aggattcagc ttgttactta aaaccgtctt taaggtcaaa 1200
tgctcaagat tcattcaaca attgaaacgt ctcacatgat taaaccatgt ataaggatgc 1260
taaggtcttg cttgacaatg tttttctagg aatttcatct aactttttga gtgaaactat 1320
caaataataa ttttaaaaca attttataag agaagctccg gagataaaag ggcatctaat 1380
ctatgttaga agagtgaagt ttactccctc tgtcccaaaa atagaattct aagtatgaaa 1440

-continued

```
tgattttttt gttatacgaa aggagtatat atcacaagat tgatgtcagt tatgcttagg   1500
gcacgtacac gacgctggtg ctttaggtag acgttaatcg ttgtttctgc attttatttt   1560
attttgttgc cacggtgtac atttgggtag acgtttgtca caggcattgc cactcaaaca   1620
agcagccggc gcttggagct tttatagttt gaaaagtgac ggttttaatg atgggtaagc   1680
tgattagtat atgtaagttt agctttttcc attgtaggtt aagccttaag gctcttacac   1740
aattgtttca ttattctcat tctttaagag cccatataag cgttcatgaa ttgtacatat   1800
ccttagatgt ttttttttt gggtaaagct cgagcttctc tatctaaaag tagagaaatc   1860
agaaaaagat tcatgttttg gtagttttga tttcttgcct ccataataat tttggtttac   1920
catttttgt ttgattttag ttttagaagc gtttatagca ggatttaaaa tccaaaacta   1980
ccattatctt caagtgaccg tcagtgagcc gtttaacggc gtcgacaagt ccaacggaca   2040
ccaaccagtg aaccaccagc gtcgagccaa gcgatgcaaa cggaacggcc gagacgttga   2100
cacctttggc gcggcacggc atgtcggatc tccctctctg gccagagagt tccagctcca   2160
cctccacctc cacctccacc ggtggcggtt tccaagtccg ttccgttccg ttccgttccg   2220
ttccgttccg cctcctgcct gctcctctca gacggcacga aaccgtgacg gcaccggcag   2280
cacgggggga ttcctttcc actgctcctt cctcttccct tcctcgcccg ccgctataaa   2340
tagccagccc cgtccccaga ttctttccca acctcatctt tgttcggagc acgcacacaa   2400
cccgatcccc aattccctcg tctctcctcg cgagcctcgt cgaccccccc cttcaaggta   2460
cggcgatcat cctccctccc tccctctctc taccttctct tctctagact agatcggcga   2520
cccggtccat ggttagggcc tgctagttct gttcctgttt tttccatggc tgcgaggtaa   2580
aatagatctg atggcgttat gatggttaac tcgtcatact cttgcgatct atggtccctt   2640
taggacatcg atttaatttc ggatggttcg agatcggtga tccatggtta gtaccctagg   2700
cagtggggtt agatccgtgc tgttagggtt cgtagatgga ttctgattgc tcagtaactg   2760
ggaaacctgg gatggttcta gctgggaatc ctgggatggt tctagctggt tcgcagatga   2820
gatcgatttc atggtctgct atatcttgtt tcgttgccta ggttccgttt aatctgtccg   2880
tggtatgatg ttagcctttg ataaggttcg atcgtgctag ctacgtcctg cgcagcattt   2940
aattgtcagg tcataatttt tagcattcct gtttttgttt ggtttggttt tgtctggttg   3000
ggctgtagat agtttcaatc tacctgtcgg tttattttat taaatttgga ttggatctgt   3060
atgtgtcaca tatatcttca tgattaagat ggttggaatt atctcttcat cttttagata   3120
tatatggata ggtatatatg ttgctgtggg ttttactggt actttattag atatattcat   3180
gcttagatac atgaagcaac gtgctgttac agtttaataa ttcttgttta tctaataaac   3240
aaataaggat aggtatatgt tgctgatggt tttactgata ctttattaga tagtactttg   3300
acatgaagga acatcctgcg acagcttaat aattattctt catctaataa aaagcttgct   3360
ttttaattat tttaattatt ttgatatact tggatgatgt catgcagcag ctatgtgtga   3420
attttcggcc ctgtcttcat atgatgttta tttgcttggg actgtttctt tggctgataa   3480
cttaccctgt tgtttggtga tccttctgca g                                  3511
```

```
<210> SEQ ID NO 35
<211> LENGTH: 2371
<212> TYPE: DNA
<213> ORGANISM: Bouteloua gracilis

<400> SEQUENCE: 35

gtggccagct tttgttctag ttcaacggtc ccggccttcc gtgcacctaa tactacactg     60
```

-continued

```
attaatctat tgcagctaac ctcaaaagaa atacacttgc agttgtctgt cccaatcaag    120
ccactagcag actctcatgt cattgatgga ggaaattaaa ttcagtcttt gacgtggatg    180
caacaactgc acagtatacc atgcatctta attagccgtt gtgtcaaagt ttgttttgct    240
gacgttttga gaaaaccaac tttgaccaac aggagatgag cgtcttgcgt ttggcacagt    300
gtaatggaat ccggcacggc aagttagact ctgtagtgtt agcggtctct ttacgtttgg    360
cacaatttaa ttgaatcccg gcatggcatg ttagaccgga gtgagccggc ccttttactg    420
gtatgacact ccctctgtct tgagtgtcgc tgtgccagct tgtacctctg tctatgttca    480
cagcccgtgc tgtgtaccta gaccctccgt ttgtccacat tcattttaat ctctattgta    540
tcttgtcaaa acctaaaagc ctaaaacgac tctgataaag ggacagaaag attatacaag    600
agcaagtgta taatgaaata atgtaagcga gctatatgaa ttgtcacgtg tcatatttat    660
gttgagacga agaagagaaa ataaacacca tgcaaattta tggcgagtga tagatggcca    720
gatgggcaca aggcctccta tttcttaaat cggattttgt aagaacgaaa aaagggactt    780
ataagagaat aggatagacc atatatcaat gatgtagtat gcatcaagat ctaactatta    840
tatgagtgaa ttgataaatt tattctaggt gacatggcct taacgatgaa cagtacgtgg    900
ttaaatcaat agaacaatag ccaactctag cggctctaaa aaaagatata tattcgtcga    960
ggcactatta tgcaaccaca tagtcaactt caacgccgct tgagtgcgtt ctcatgtttt   1020
ttttttcttg caaattacgc ttttctaaaa taaaataatt tggatcgtgc aattatttca   1080
ctttaggtgt gcgtgactac gtgagtaaca attttgaatc tcagaaagga aataaaagta   1140
taatactgct acctactttg aggattcagc ttgttactta aaaccgtctt taaggtcaaa   1200
tgctcaagat tcattcaaca attgaaacgt ctcacatgat taaaccatgt ataaggatgc   1260
taaggtcttg cttgacaatg tttttctagg aatttcatct aactttttga gtgaaactat   1320
caaataataa ttttaaaaca attttataag agaagctccg gagataaaag ggcatctaat   1380
ctatgttaga agagtgaagt ttactccctc tgtcccaaaa atagaattct aagtatgaaa   1440
tgattttttt gttatacgaa aggagtatat atcacaagat tgatgtcagt tatgcttagg   1500
gcacgtacac gacgctggtg ctttaggtag acgttaatcg ttgtttctgc attttatttt   1560
attttgttgc cacggtgtac atttgggtag acgtttgtca caggcattgc cactcaaaca   1620
agcagccggc gcttggagct tttatagttt gaaaagtgac ggttttaatg atgggtaagc   1680
tgattagtat atgtaagttt agctttttcc attgtaggtt aagccttaag gctcttacac   1740
aattgtttca ttattctcat tctttaagag cccatataag cgttcatgaa ttgtacatat   1800
ccttagatgt ttttttttt gggtaaagct cgagcttctc tatctaaaag tagagaaatc    1860
agaaaaagat tcatgttttg gtagttttga tttcttgcct ccataataat tttggtttac   1920
catttttgt ttgattttag ttttagaagc gtttatagca ggatttaaaa tccaaaacta    1980
ccattatctt caagtgaccg tcagtgagcc gtttaacggc gtcgacaagt ccaacggaca   2040
ccaaccagtg aaccaccagc gtcgagccaa gcgatgcaaa cggaacggcc gagacgttga   2100
cacctttggc gcggcacggc atgtcggatc tccctctctg gccagagagt tccagctcca   2160
cctccacctc cacctccacc ggtggcggtt tccaagtccg ttccgttccg ttccgttccg   2220
ttccgttccg cctcctgcct gctcctctca gacggcacga aaccgtgacg gcaccggcag   2280
cacgggggga ttccttttcc actgctcctt cctcttccct tcctcgcccg ccgctataaa   2340
tagccagccc cgtccccaga ttctttccca a                                  2371
```

<210> SEQ ID NO 36
<211> LENGTH: 86
<212> TYPE: DNA
<213> ORGANISM: Bouteloua gracilis

<400> SEQUENCE: 36
cctcatcttt gttcggagca cgcacacaac ccgatcccca attccctcgt ctctcctcgc 60
gagcctcgtc gaccccccccc ttcaag 86

<210> SEQ ID NO 37
<211> LENGTH: 1054
<212> TYPE: DNA
<213> ORGANISM: Bouteloua gracilis

<400> SEQUENCE: 37
gtacggcgat catcctccct ccctccctct ctctaccttc tcttctctag actagatcgg 60
cgacccggtc catggttagg gcctgctagt tctgttcctg ttttttccat ggctgcgagg 120
taaaatagat ctgatggcgt tatgatggtt aactcgtcat actcttgcga tctatggtcc 180
ctttaggaca tcgatttaat ttcggatggt tcgagatcgg tgatccatgg ttagtaccct 240
aggcagtggg gttagatccg tgctgttagg gttcgtagat ggattctgat tgctcagtaa 300
ctgggaaacc tgggatggtt ctagctggga atcctgggat ggttctagct ggttcgcaga 360
tgagatcgat ttcatggtct gctatatctt gtttcgttgc ctaggttccg tttaatctgt 420
ccgtggtatg atgttagcct ttgataaggt tcgatcgtgc tagctacgtc ctgcgcagca 480
tttaattgtc aggtcataat ttttagcatt cctgtttttg tttggtttgg ttttgtctgg 540
ttgggctgta gatagtttca atctacctgt cggtttattt tattaaattt ggattggatc 600
tgtatgtgtc acatatatct tcatgattaa gatggttgga attatctctt catcttttag 660
atatatatgg ataggtatat atgttgctgt gggttttact ggtactttat tagatatatt 720
catgcttaga tacatgaagc aacgtgctgt tacagtttaa taattcttgt ttatctaata 780
aacaaataag gataggtata tgttgctgat ggttttactg atactttatt agatagtact 840
ttgacatgaa ggaacatcct gcgacagctt aataattatt cttcatctaa taaaaagctt 900
gctttttaat tattttaatt attttgatat acttggatga tgtcatgcag cagctatgtg 960
tgaattttcg gccctgtctt catatgatgt ttatttgctt gggactgttt ctttggctga 1020
taacttaccc tgttgtttgg tgatccttct gcag 1054

<210> SEQ ID NO 38
<211> LENGTH: 3142
<212> TYPE: DNA
<213> ORGANISM: Bouteloua gracilis

<400> SEQUENCE: 38
gaatcccggc atggcatgtt agaccggagt gagccggccc ttttactggt atgacactcc 60
ctctgtcttg agtgtcgctg tgccagcttg tacctctgtc tatgttcaca gcccgtgctg 120
tgtacctaga ccctccgttt gtccacattc attttaatct ctattgtatc ttgtcaaaac 180
ctaaaagcct aaaacgactc tgataaaggg acagaaagat tatacaagag caagtgtata 240
atgaaataat gtaagcgagc tatatgaatt gtcacgtgtc atatttatgt tgagacgaag 300
aagagaaaat aaacaccatg caaatttatg gcgagtgata gatggccaga tgggcacaag 360
gcctcctatt tcttaaatcg gattttgtaa gaacgaaaaa agggacttat aagagaatag 420
gatagaccat atatcaatga tgtagtatgc atcaagatct aactattata tgagtgaatt 480
gataaattta ttctaggtga catggcctta acgatgaaca gtacgtggtt aaatcaatag 540
aacaatagcc aactctagcg gctctaaaaa aagatatata ttcgtcgagg cactattatg 600
caaccacata gtcaacttca acgccgcttg agtgcgttct catgtttttt ttttcttgca 660
aattacgctt ttctaaaata aaataatttg gatcgtgcaa ttatttcact ttaggtgtgc 720
gtgactacgt gagtaacaat tttgaatctc agaaaggaaa taaaagtata atactgctac 780
ctactttgag gattcagctt gttacttaaa accgtcttta aggtcaaatg ctcaagattc 840
attcaacaat tgaaacgtct cacatgatta aaccatgtat aaggatgcta aggtcttgct 900
tgacaatgtt tttctaggaa tttcatctaa ctttttgagt gaaactatca aataataatt 960
ttaaaacaat tttataagag aagctccgga gataaaaggg catctaatct atgttagaag 1020
agtgaagttt actccctctg tcccaaaaat agaattctaa gtatgaaatg atttttttgt 1080
tatacgaaag gagtatatat cacaagattg atgtcagtta tgcttagggc acgtacacga 1140
cgctggtgct ttaggtagac gttaatcgtt gtttctgcat tttattttat tttgttgcca 1200
cggtgtacat ttgggtagac gtttgtcaca ggcattgcca ctcaaacaag cagccggcgc 1260
ttggagcttt tatagtttga aaagtgacgg ttttaatgat gggtaagctg attagtatat 1320
gtaagtttag ctttttccat tgtaggttaa gccttaaggc tcttacacaa ttgtttcatt 1380
attctcattc tttaagagcc catataagcg ttcatgaatt gtacatatcc ttagatgttt 1440
tttttttggg gtaaagctcg agcttctcta tctaaaagta gagaaatcag aaaaagattc 1500
atgttttggt agttttgatt tcttgcctcc ataataattt tggtttacca tttttgttt 1560
gattttagtt ttagaagcgt ttatagcagg atttaaaatc caaaactacc attatcttca 1620
agtgaccgtc agtgagccgt ttaacggcgt cgacaagtcc aacggacacc aaccagtgaa 1680
ccaccagcgt cgagccaagc gatgcaaacg gaacggccga gacgttgaca cctttggcgc 1740
ggcacggcat gtcggatctc cctctctggc cagagagttc cagctccacc tccacctcca 1800
cctccaccgg tggcggtttc caagtccgtt ccgttccgtt ccgttccgtt ccgttccgcc 1860
tcctgcctgc tcctctcaga cggcacgaaa ccgtgacggc accggcagca cggggggatt 1920
ccttttccac tgctccttcc tcttcccttc ctcgcccgcc gctataaata gccagccccg 1980
tccccagatt ctttcccaac ctcatctttg ttcggagcac gcacacaacc cgatccccaa 2040
ttccctcgtc tctcctcgcg agcctcgtcg accccccct tcaaggtacg gcgatcatcc 2100
tccctccctc cctctctcta ccttctcttc tctagactag atcggcgacc cggtccatgg 2160
ttagggcctg ctagttctgt tcctgttttt tccatggctg cgaggtaaaa tagatctgat 2220
ggcgttatga tggttaactc gtcatactct tgcgatctat ggtcccttta ggacatcgat 2280
ttaatttcgg atggttcgag atcggtgatc catggttagt accctaggca gtggggttag 2340
atccgtgctg ttagggttcg tagatggatt ctgattgctc agtaactggg aaacctggga 2400
tggttctagc tgggaatcct gggatggttc tagctggttc gcagatgaga tcgatttcat 2460
ggtctgctat atcttgtttc gttgcctagg ttccgtttaa tctgtccgtg gtatgatgtt 2520
agcctttgat aaggttcgat cgtgctagct acgtcctgcg cagcatttaa ttgtcaggtc 2580
ataattttta gcattcctgt ttttgtttgg tttggttttg tctggttggg ctgtagatag 2640
tttcaatcta cctgtcggtt tattttatta aatttggatt ggatctgtat gtgtcacata 2700
tatcttcatg attaagatgg ttggaattat ctcttcatct tttagatata tatggatagg 2760
tatatatgtt gctgtgggtt ttactggtac tttattagat atattcatgc ttagatacat 2820

-continued

```
gaagcaacgt gctgttacag tttaataatt cttgtttatc taataaacaa ataaggatag   2880

gtatatgttg ctgatggttt tactgatact ttattagata gtactttgac atgaaggaac   2940

atcctgcgac agcttaataa ttattcttca tctaataaaa agcttgcttt ttaattattt   3000

taattatttt gatatacttg gatgatgtca tgcagcagct atgtgtgaat tttcggccct   3060

gtcttcatat gatgtttatt tgcttgggac tgtttctttg gctgataact taccctgttg   3120

tttggtgatc cttctgcagg tg                                            3142
```

<210> SEQ ID NO 39
<211> LENGTH: 1999
<212> TYPE: DNA
<213> ORGANISM: Bouteloua gracilis

<400> SEQUENCE: 39

```
gaatcccggc atggcatgtt agaccggagt gagccggccc ttttactggt atgacactcc     60

ctctgtcttg agtgtcgctg tgccagcttg tacctctgtc tatgttcaca gcccgtgctg    120

tgtacctaga ccctccgttt gtccacattc attttaatct ctattgtatc ttgtcaaaac    180

ctaaaagcct aaaacgactc tgataaaggg acagaaagat tatacaagag caagtgtata    240

atgaaataat gtaagcgagc tatatgaatt gtcacgtgtc atatttatgt tgagacgaag    300

aagagaaaat aaacaccatg caaatttatg gcgagtgata gatggccaga tgggcacaag    360

gcctcctatt tcttaaatcg gattttgtaa gaacgaaaaa agggacttat aagagaatag    420

gatagaccat atatcaatga tgtagtatgc atcaagatct aactattata tgagtgaatt    480

gataaattta ttctaggtga catggcctta acgatgaaca gtacgtggtt aaatcaatag    540

aacaatagcc aactctagcg gctctaaaaa aagatatata ttcgtcgagg cactattatg    600

caaccacata gtcaacttca acgccgcttg agtgcgttct catgtttttt ttttcttgca    660

aattacgctt ttctaaaata aaataatttg gatcgtgcaa ttatttcact ttaggtgtgc    720

gtgactacgt gagtaacaat tttgaatctc agaaaggaaa taaaagtata atactgctac    780

ctactttgag gattcagctt gttacttaaa accgtcttta aggtcaaatg ctcaagattc    840

attcaacaat tgaaacgtct cacatgatta aaccatgtat aaggatgcta aggtcttgct    900

tgacaatgtt tttctaggaa tttcatctaa ctttttgagt gaaactatca aataataatt    960

ttaaaacaat tttataagag aagctccgga gataaaaggg catctaatct atgttagaag   1020

agtgaagttt actccctctg tcccaaaaat agaattctaa gtatgaaatg atttttttgt   1080

tatacgaaag gagtatatat cacaagattg atgtcagtta tgcttagggc acgtacacga   1140

cgctggtgct ttaggtagac gttaatcgtt gtttctgcat tttattttat tttgttgcca   1200

cggtgtacat ttgggtagac gtttgtcaca ggcattgcca ctcaaacaag cagccggcgc   1260

ttggagcttt tatagtttga aaagtgacgg ttttaatgat gggtaagctg attagtatat   1320

gtaagtttag ctttttccat tgtaggttaa gccttaaggc tcttacacaa ttgtttcatt   1380

attctcattc tttaagagcc catataagcg ttcatgaatt gtacatatcc ttagatgttt   1440

tttttttggg gtaaagctcg agcttctcta tctaaaagta gagaaatcag aaaaagattc   1500

atgttttggt agttttgatt tcttgcctcc ataataattt tggtttacca ttttttgttt   1560

gattttagtt ttagaagcgt ttatagcagg atttaaaatc caaaactacc attatcttca   1620

agtgaccgtc agtgagccgt ttaacggcgt cgacaagtcc aacggacacc aaccagtgaa   1680

ccaccagcgt cgagccaagc gatgcaaacg gaacggccga gacgttgaca cctttggcgc   1740

ggcacggcat gtcggatctc cctctctggc cagagagttc cagctccacc tccacctcca   1800
```

-continued

```
cctccaccgg tggcggtttc caagtccgtt ccgttccgtt ccgttccgtt ccgttccgcc   1860

tcctgcctgc tcctctcaga cggcacgaaa ccgtgacggc accggcagca cggggggatt   1920

ccttttccac tgctccttcc tcttcccttc ctcgcccgcc gctataaata gccagccccg   1980

tccccagatt ctttcccaa                                                1999


<210> SEQ ID NO 40
<211> LENGTH: 1057
<212> TYPE: DNA
<213> ORGANISM: Bouteloua gracilis

<400> SEQUENCE: 40

gtacggcgat catcctccct ccctccctct ctctaccttc tcttctctag actagatcgg     60

cgacccggtc catggttagg gcctgctagt tctgttcctg ttttttccat ggctgcgagg    120

taaaatagat ctgatggcgt tatgatggtt aactcgtcat actcttgcga tctatggtcc    180

ctttaggaca tcgatttaat ttcggatggt tcgagatcgg tgatccatgg ttagtaccct    240

aggcagtggg gttagatccg tgctgttagg gttcgtagat ggattctgat tgctcagtaa    300

ctgggaaacc tgggatggtt ctagctggga atcctgggat ggttctagct ggttcgcaga    360

tgagatcgat ttcatggtct gctatatctt gtttcgttgc ctaggttccg tttaatctgt    420

ccgtggtatg atgttagcct ttgataaggt tcgatcgtgc tagctacgtc ctgcgcagca    480

tttaattgtc aggtcataat ttttagcatt cctgtttttg tttggtttgg ttttgtctgg    540

ttgggctgta gatagtttca atctacctgt cggtttattt tattaaattt ggattggatc    600

tgtatgtgtc acatatatct tcatgattaa gatggttgga attatctctt catcttttag    660

atatatatgg ataggtatat atgttgctgt gggttttact ggtactttat tagatatatt    720

catgcttaga tacatgaagc aacgtgctgt tacagtttaa taattcttgt ttatctaata    780

aacaaataag gataggtata tgttgctgat ggttttactg atactttatt agatagtact    840

ttgacatgaa ggaacatcct gcgacagctt aataattatt cttcatctaa taaaaagctt    900

gctttttaat tattttaatt attttgatat acttggatga tgtcatgcag cagctatgtg    960

tgaattttcg gccctgtctt catatgatgt ttatttgctt gggactgttt ctttggctga   1020

taacttaccc tgttgtttgg tgatccttct gcaggtg                            1057


<210> SEQ ID NO 41
<211> LENGTH: 2165
<212> TYPE: DNA
<213> ORGANISM: Bouteloua gracilis

<400> SEQUENCE: 41

gagaagctcc ggagataaaa gggcatctaa tctatgttag aagagtgaag tttactccct     60

ctgtcccaaa aatagaattc taagtatgaa atgatttttt tgttatacga aaggagtata    120

tatcacaaga ttgatgtcag ttatgcttag ggcacgtaca cgacgctggt gctttaggta    180

gacgttaatc gttgtttctg cattttattt tattttgttg ccacggtgta catttgggta    240

gacgtttgtc acaggcattg ccactcaaac aagcagccgg cgcttggagc ttttatagtt    300

tgaaaagtga cggttttaat gatgggtaag ctgattagta tatgtaagtt tagctttttc    360

cattgtaggt taagccttaa ggctcttaca caattgtttc attattctca ttctttaaga    420

gcccatataa gcgttcatga attgtacata tccttagatg tttttttttt tgggtaaagc    480

tcgagcttct ctatctaaaa gtagagaaat cagaaaaaga ttcatgtttt ggtagttttg    540
```

-continued

```
atttcttgcc tccataataa ttttggttta ccattttttg tttgatttta gttttagaag    600

cgtttatagc aggatttaaa atccaaaact accattatct tcaagtgacc gtcagtgagc    660

cgtttaacgg cgtcgacaag tccaacggac accaaccagt gaaccaccag cgtcgagcca    720

agcgatgcaa acggaacggc cgagacgttg acacctttgg cgcggcacgg catgtcggat    780

ctccctctct ggccagagag ttccagctcc acctccacct ccacctccac cggtggcggt    840

ttccaagtcc gttccgttcc gttccgttcc gttccgttcc gcctcctgcc tgctcctctc    900

agacggcacg aaaccgtgac ggcaccggca gcacgggggg attccttttc cactgctcct    960

tcctcttccc ttcctcgccc gccgctataa atagccagcc ccgtccccag attctttccc   1020

aacctcatct ttgttcggag cacgcacaca acccgatccc caattccctc gtctctcctc   1080

gcgagcctcg tcgacccccc ccttcaaggt acggcgatca tcctccctcc ctccctctct   1140

ctaccttctc ttctctagac tagatcggcg acccggtcca tggttagggc ctgctagttc   1200

tgttcctgtt ttttccatgg ctgcgaggta aaatagatct gatggcgtta tgatggttaa   1260

ctcgtcatac tcttgcgatc tatggtccct ttaggacatc gatttaattt cggatggttc   1320

gagatcggtg atccatggtt agtaccctag gcagtggggt tagatccgtg ctgttagggt   1380

tcgtagatgg attctgattg ctcagtaact gggaaacctg ggatggttct agctgggaat   1440

cctgggatgg ttctagctgg ttcgcagatg agatcgattt catggtctgc tatatcttgt   1500

ttcgttgcct aggttccgtt taatctgtcc gtggtatgat gttagccttt gataaggttc   1560

gatcgtgcta gctacgtcct gcgcagcatt taattgtcag gtcataattt ttagcattcc   1620

tgtttttgtt tggtttggtt ttgtctggtt gggctgtaga tagtttcaat ctacctgtcg   1680

gtttatttta ttaaatttgg attggatctg tatgtgtcac atatatcttc atgattaaga   1740

tggttggaat tatctcttca tcttttagat atatatggat aggtatatat gttgctgtgg   1800

gttttactgg tactttatta gatatattca tgcttagata catgaagcaa cgtgctgtta   1860

cagtttaata attcttgttt atctaataaa caaataagga taggtatatg ttgctgatgg   1920

ttttactgat actttattag atagtacttt gacatgaagg aacatcctgc gacagcttaa   1980

taattattct tcatctaata aaaagcttgc tttttaatta ttttaattat tttgatatac   2040

ttggatgatg tcatgcagca gctatgtgtg aattttcggc cctgtcttca tatgatgttt   2100

atttgcttgg gactgtttct ttggctgata acttaccctg ttgtttggtg atccttctgc   2160

aggtg                                                               2165
```

<210> SEQ ID NO 42
<211> LENGTH: 1022
<212> TYPE: DNA
<213> ORGANISM: Bouteloua gracilis

<400> SEQUENCE: 42

```
gagaagctcc ggagataaaa gggcatctaa tctatgttag aagagtgaag tttactccct     60

ctgtcccaaa aatagaattc taagtatgaa atgatttttt tgttatacga aaggagtata    120

tatcacaaga ttgatgtcag ttatgcttag ggcacgtaca cgacgctggt gctttaggta    180

gacgttaatc gttgtttctg cattttattt tattttgttg ccacggtgta catttgggta    240

gacgtttgtc acaggcattg ccactcaaac aagcagccgg cgcttggagc ttttatagtt    300

tgaaaagtga cggttttaat gatgggtaag ctgattagta tatgtaagtt tagctttttc    360

cattgtaggt taagccttaa ggctcttaca caattgtttc attattctca ttctttaaga    420

gcccatataa gcgttcatga attgtacata tccttagatg tttttttttt tgggtaaagc    480
```

-continued

```
tcgagcttct ctatctaaaa gtagagaaat cagaaaaaga ttcatgtttt ggtagttttg     540

atttcttgcc tccataataa ttttggttta ccattttttg tttgatttta gttttagaag     600

cgtttatagc aggatttaaa atccaaaact accattatct tcaagtgacc gtcagtgagc     660

cgtttaacgg cgtcgacaag tccaacggac accaaccagt gaaccaccag cgtcgagcca     720

agcgatgcaa acggaacggc cgagacgttg acacctttgg cgcggcacgg catgtcggat     780

ctccctctct ggccagagag ttccagctcc acctccacct ccacctccac cggtggcggt     840

ttccaagtcc gttccgttcc gttccgttcc gttccgttcc gcctcctgcc tgctcctctc     900

agacggcacg aaaccgtgac ggcaccggca gcacgggggg attccttttc cactgctcct     960

tcctcttccc ttcctcgccc gccgctataa atagccagcc ccgtccccag attctttccc    1020

aa                                                                   1022
```

<210> SEQ ID NO 43
<211> LENGTH: 1903
<212> TYPE: DNA
<213> ORGANISM: Bouteloua gracilis

<400> SEQUENCE: 43

```
actcaaacaa gcagccggcg cttggagctt ttatagtttg aaaagtgacg gttttaatga      60

tgggtaagct gattagtata tgtaagttta gctttttcca ttgtaggtta agccttaagg     120

ctcttacaca attgtttcat tattctcatt ctttaagagc ccatataagc gttcatgaat     180

tgtacatatc cttagatgtt tttttttttg ggtaaagctc gagcttctct atctaaaagt     240

agagaaatca gaaaaagatt catgttttgg tagttttgat ttcttgcctc cataataatt     300

ttggtttacc atttttgtt tgattttagt tttagaagcg tttatagcag gatttaaaat     360

ccaaaactac cattatcttc aagtgaccgt cagtgagccg tttaacggcg tcgacaagtc     420

caacggacac caaccagtga accaccagcg tcgagccaag cgatgcaaac ggaacggccg     480

agacgttgac acctttggcg cggcacggca tgtcggatct ccctctctgg ccagagagtt     540

ccagctccac ctccacctcc acctccaccg gtggcggttt ccaagtccgt tccgttccgt     600

tccgttccgt tccgttccgc ctcctgcctg ctcctctcag acggcacgaa accgtgacgg     660

caccggcagc acgggggat tccttttcca ctgctccttc ctcttccctt cctcgcccgc     720

cgctataaat agccagcccc gtccccagat tctttcccaa cctcatcttt gttcggagca     780

cgcacacaac ccgatcccca attccctcgt ctctcctcgc gagcctcgtc gacccccccc     840

ttcaaggtac ggcgatcatc ctccctccct ccctctctct accttctctt ctctagacta     900

gatcggcgac ccggtccatg gttagggcct gctagttctg ttcctgtttt ttccatggct     960

gcgaggtaaa atagatctga tggcgttatg atggttaact cgtcatactc ttgcgatcta    1020

tggtcccttt aggacatcga tttaatttcg gatggttcga gatcggtgat ccatggttag    1080

taccctaggc agtggggtta gatccgtgct gttagggttc gtagatggat tctgattgct    1140

cagtaactgg gaaacctggg atggttctag ctgggaatcc tgggatggtt ctagctggtt    1200

cgcagatgag atcgatttca tggtctgcta tatcttgttt cgttgcctag gttccgttta    1260

atctgtccgt ggtatgatgt tagcctttga taaggttcga tcgtgctagc tacgtcctgc    1320

gcagcattta attgtcaggt cataattttt agcattcctg tttttgtttg gtttggtttt    1380

gtctggttgg gctgtagata gtttcaatct acctgtcggt ttattttatt aaatttggat    1440

tggatctgta tgtgtcacat atatcttcat gattaagatg gttggaatta tctcttcatc    1500
```

-continued

```
ttttagatat atatggatag gtatatatgt tgctgtgggt tttactggta ctttattaga   1560
tatattcatg cttagataca tgaagcaacg tgctgttaca gtttaataat tcttgtttat   1620
ctaataaaca aataaggata ggtatatgtt gctgatggtt ttactgatac tttattagat   1680
agtactttga catgaaggaa catcctgcga cagcttaata attattcttc atctaataaa   1740
aagcttgctt tttaattatt ttaattattt tgatatactt ggatgatgtc atgcagcagc   1800
tatgtgtgaa ttttcggccc tgtcttcata tgatgtttat ttgcttggga ctgtttcttt   1860
ggctgataac ttaccctgtt gtttggtgat ccttctgcag gtg                     1903
```

<210> SEQ ID NO 44
<211> LENGTH: 760
<212> TYPE: DNA
<213> ORGANISM: Bouteloua gracilis

<400> SEQUENCE: 44

```
actcaaacaa gcagccggcg cttggagctt ttatagtttg aaaagtgacg gttttaatga     60
tgggtaagct gattagtata tgtaagttta gctttttcca ttgtaggtta agccttaagg    120
ctcttacaca attgtttcat tattctcatt ctttaagagc ccatataagc gttcatgaat    180
tgtacatatc cttagatgtt tttttttttg ggtaaagctc gagcttctct atctaaaagt    240
agagaaatca gaaaaagatt catgttttgg tagttttgat ttcttgcctc cataataatt    300
ttggtttacc attttttgtt tgattttagt tttagaagcg tttatagcag gatttaaaat    360
ccaaaactac cattatcttc aagtgaccgt cagtgagccg tttaacggcg tcgacaagtc    420
caacggacac caaccagtga accaccagcg tcgagccaag cgatgcaaac ggaacggccg    480
agacgttgac acctttggcg cggcacggca tgtcggatct ccctctctgg ccagagagtt    540
ccagctccac ctccacctcc acctccaccg gtggcggttt ccaagtccgt tccgttccgt    600
tccgttccgt tccgttccgc ctcctgcctg ctcctctcag acggcacgaa accgtgacgg    660
caccggcagc acggggggat tccttttcca ctgctccttc ctcttccctt cctcgcccgc    720
cgctataaat agccagcccc gtccccagat tctttcccaa                         760
```

<210> SEQ ID NO 45
<211> LENGTH: 3234
<212> TYPE: DNA
<213> ORGANISM: Bouteloua gracilis

<400> SEQUENCE: 45

```
ggcctcttta cgtttggcac aacttagttg aatccggctt ccggcaaact atatggcaag     60
ttagacccaa gtgtgagccg gccaccgcaa gttattgtga cattatacgt aggaagcaag    120
tgtataataa gaatatgaga taatgtaagc agctatatga attatcacgt catatttatg    180
ttaagatgaa gaggagagaa taaacggtac gtaaatttat agcgagtgat agacgggcac    240
gaggcctcct agctatttcc ataaatcgga ttttgtaaga acaaaaaaga ggacttatta    300
taagagaatg tggtaagtaa gcatactccc tccgtttcaa attataagtt gttttaactt    360 ttttttttata tctattttac tatacattag atataataat gtgtctagat acataataaa    420
atggatgaac aaaaaagtca aagtgactta caatttggaa cggagggagt aagttcaagc    480
catcaaggca cttctatgca accacatagt caacttgaat gccgcttgag tgccttctca    540
agtttttttt ttcttgcaaa aattgtttct ttttttttaa aaaagtataa tttggatcgt    600
gcaaatttct ctctaggtgt gtgtgtgact gtgtgagtaa caatttctct agttgtgcgt    660
gactgctgct tactttggag attacaatat atttctaaaa tgcttcgatt acttatttat    720
```

-continued

```
aaaccgtctc taaggccaat tgctcaagat tcattcaaca attgaaacgt ctcacatgat    780
taaatcatat aaagtttcta agtcttgttt gacaagattt ttttagattt tcatctaaat    840
tggatgaaac tatcaaacac taattttaaa aaatataaga gaagctccgg agataaaagg    900
tcgtctatgt tattataaga gtaaagtcgt ctattctctt cgtcccaaca tatataattc    960
taagcatgaa ttgctttctt tttggacaaa aggagtatgc cacaacacaa gaatgatgtc   1020
accgtcatgc ttagatcctt ttatggtaaa gcttcacctt ctataatcta acaatagaga   1080
aatcggggaa aaatcatgtt ttggttgttt ttatttctaa cctccacaat aactttggtt   1140
taccattttt tgtttgattt tagttttaga gaagcgttta taacaggacc taaaatcttt   1200
ttttgagtac acagtacaac gcagacgctc atacacgcac gcacaatgtc ctctatgaac   1260
acacgtaagg aaaccctaca ccttgagcac cttcgaagga ctgagccggc aaatctagag   1320
attctcgaag tcactattgg cacctcgtta tcaacgagaa cgtcgcttac cacttaaagc   1380
ataacaccga gaaatcccgt aacaaatcca gtaaaatacg agcacccgta ccaagttgaa   1440
tatttgaacc cgagtgggta gattccaccg caaaggacct aaccagatca tttcgcaaac   1500
aggaactaaa atcggtagag agcccagaca aaaacctttt ctaagagcaa ctccagtgaa   1560
agcccctact ttaggtataa aatgcaacac tagtggagct tctaaataaa cttctatttt   1620
tcatgccctc ctaaaattta ctcctaaaac cctagctata ggagcctcct atccatcctc   1680
tattttattc cactagaatt gattataaat ttagcctctt aaattttata agttgggagt   1740
cgagggtaac tagagttgct ctaaacggac cttatcttca agtgacctca gtgagcccgt   1800
ttaacggcgt cgacaagtct aatctaacgg acaccaacca gagaaccacc gccagcgccg   1860
agccaagcga cgttgacatc ttggcgcggc acggcatctc cctggcgtct ggtcccctcc   1920
cgagacttcc gctccacctc ccaccggtgg cggtttccga gtccgttccg cctcctctca   1980
cacggcacga aaccttgacg gcaccggcag cacgggggat tccgttccca cggctccttc   2040
cctttccctt cctcgcccgc tgctataaat agccagcccc atccccagct tcttccccaa   2100
cctcatcttc tcgtgttgtt cggcccaacc cgatcgatcc ccaattccct cgtcgtctct   2160
cgtcgcgagc ctcgtcgatc cccgcttcaa ggtacagcga tcgatcgatc atcctcgctc   2220
tctctacctt ctctctctta gggcgtgctg gttctgttcc tgtttttcca tggctgcgag   2280
gtacaataga ttggcgattc atggttaggg cctgctagtt ctgttcctgt ttttttttt    2340
tccatggctg cgaggcacaa tagatctgat ggcgttatga tggttaactt gtcatactct   2400
tgcgatctat ggtcccttta ggagtttagg acatcgattt aatttcggat agttcgagat   2460
ctgtgatcca tggttagtac cctaggcagt ggggttagat ccgtgctgtt atggttcgta   2520
gatggattct gattgctcag taactgggaa tcctgggatg gttctagctg gttcgcagat   2580
aagatcgatt tcatgatatg ctatatcttg tttggttgcc gtggttccgt taaatctgtc   2640
tgttatgatc ttagtctttg ataaggttcg gtcgtgctag ctacgtcctg tgcagcactt   2700
aattgtcagg tcataatttt tagcatgcct tttttttatt ggtttggttt tgtctgactg   2760
ggctgtagat agtttcaatc tttgtctgac tgggctgtag atagtttcaa tcttcctgtc   2820
tgtttatttt attaaatttg gatctgtatg tgtgtcatat atcttcatct tttagatata   2880
tcgataggta tatatgttgc tgtcgttttt tactgttcct ttatgagata tattcatgct   2940
tagatacatg aaacaacgtg ctgttacagt ttaatagttc ttgtttatct aataaacaaa   3000
taaggatagg tgctgcagtt agttttactg gtactttttt tgacatgaac ctacggctta   3060
```

-continued

```
ataattagtc ttcatcaaat aaaaagcata ttttttaatt atttcgatat acttgaatga   3120
tgtcatatgc agcatctgtg tgaatttttg gccctgtctt catatgatgt ttatttgctt   3180
gggactgttt ctttggctga taactcaccc tgttgtttgg tgatccttct gcag         3234

<210> SEQ ID NO 46
<211> LENGTH: 2100
<212> TYPE: DNA
<213> ORGANISM: Bouteloua gracilis

<400> SEQUENCE: 46
ggcctcttta cgtttggcac aacttagttg aatccggctt ccggcaaact atatggcaag     60
ttagacccaa gtgtgagccg gccaccgcaa gttattgtga cattatacgt aggaagcaag    120
tgtataataa gaatatgaga taatgtaagc agctatatga attatcacgt catatttatg    180
ttaagatgaa gaggagagaa taaacggtac gtaaatttat agcgagtgat agacgggcac    240
gaggcctcct agctatttcc ataaatcgga ttttgtaaga acaaaaaaga ggacttatta    300
taagagaatg tggtaagtaa gcatactccc tccgtttcaa attataagtt gttttaactt    360
tttttttata tctattttac tatacattag atataataat gtgtctagat acataataaa    420
atggatgaac aaaaaagtca aagtgactta caatttggaa cggagggagt aagttcaagc    480
catcaaggca cttctatgca accacatagt caacttgaat gccgcttgag tgccttctca    540
agtttttttt ttcttgcaaa aattgtttct tttttttaa aaaagtataa tttggatcgt    600
gcaaatttct ctctaggtgt gtgtgtgact gtgtgagtaa caatttctct agttgtgcgt    660
gactgctgct tactttggag attacaatat atttctaaaa tgcttcgatt acttatttat    720
aaaccgtctc taaggccaat tgctcaagat tcattcaaca attgaaacgt ctcacatgat    780
taaatcatat aaagtttcta agtcttgttt gacaagattt ttttagattt tcatctaaat    840
tggatgaaac tatcaaacac taattttaaa aaatataaga gaagctccgg agataaaagg    900
tcgtctatgt tattataaga gtaaagtcgt ctattctctt cgtcccaaca tatataattc    960
taagcatgaa ttgctttctt tttggacaaa aggagtatgc cacaacacaa gaatgatgtc   1020
accgtcatgc ttagatcctt ttatggtaaa gcttcacctt ctataatcta acaatagaga   1080
aatcggggaa aaatcatgtt ttggttgttt ttatttctaa cctccacaat aactttggtt   1140
taccattttt tgtttgattt tagttttaga gaagcgttta taacaggacc taaaatcttt   1200
ttttgagtac acagtacaac gcagacgctc atacacgcac gcacaatgtc ctctatgaac   1260
acacgtaagg aaaccctaca ccttgagcac cttcgaagga ctgagccggc aaatctagag   1320
attctcgaag tcactattgg cacctcgtta tcaacgagaa cgtcgcttac cacttaaagc   1380
ataacaccga gaaatcccgt aacaaatcca gtaaaatacg agcacccgta ccaagttgaa   1440
tatttgaacc cgagtgggta gattccaccg caaaggacct aaccagatca tttcgcaaac   1500
aggaactaaa atcggtagag agcccagaca aaaacctttt ctaagagcaa ctccagtgaa   1560
agcccctact ttaggtataa aatgcaacac tagtggagct tctaaataaa cttctatttt   1620
tcatgccctc ctaaaattta ctcctaaaac cctagctata ggagcctcct atccatcctc   1680
tattttattc cactagaatt gattataaat ttagcctctt aaattttata agttgggagt   1740
cgagggtaac tagagttgct ctaaacggac cttatcttca agtgacctca gtgagcccgt   1800
ttaacggcgt cgacaagtct aatctaacgg acaccaacca gagaaccacc gccagcgccg   1860
agccaagcga cgttgacatc ttggcgcggc acggcatctc cctggcgtct ggtcccctcc   1920
cgagacttcc gctccacctc ccaccggtgg cggtttccga gtccgttccg cctcctctca   1980
```

cacggcacga aaccttgacg gcaccggcag cacgggggat tccgttccca cggctccttc 2040
cctttccctt cctcgcccgc tgctataaat agccagcccc atccccagct tcttccccaa 2100

<210> SEQ ID NO 47
<211> LENGTH: 91
<212> TYPE: DNA
<213> ORGANISM: Bouteloua gracilis

<400> SEQUENCE: 47
cctcatcttc tcgtgttgtt cggcccaacc cgatcgatcc ccaattccct cgtcgtctct 60
cgtcgcgagc ctcgtcgatc cccgcttcaa g 91

<210> SEQ ID NO 48
<211> LENGTH: 1043
<212> TYPE: DNA
<213> ORGANISM: Bouteloua gracilis

<400> SEQUENCE: 48
gtacagcgat cgatcgatca tcctcgctct ctctaccttc tctctcttag ggcgtgctgg 60
ttctgttcct gtttttccat ggctgcgagg tacaatagat tggcgattca tggttagggc 120
ctgctagttc tgttcctgtt ttttttttt ccatggctgc gaggcacaat agatctgatg 180
gcgttatgat ggttaacttg tcatactctt gcgatctatg gtccctttag gagtttagga 240
catcgattta atttcggata gttcgagatc tgtgatccat ggttagtacc ctaggcagtg 300
gggttagatc cgtgctgtta tggttcgtag atggattctg attgctcagt aactgggaat 360
cctgggatgg ttctagctgg ttcgcagata agatcgattt catgatatgc tatatcttgt 420
ttggttgccg tggttccgtt aaatctgtct gttatgatct tagtctttga taaggttcgg 480
tcgtgctagc tacgtcctgt gcagcactta attgtcaggt cataattttt agcatgcctt 540
ttttttattg gtttggtttt gtctgactgg gctgtagata gtttcaatct ttgtctgact 600
gggctgtaga tagtttcaat cttcctgtct gtttatttta ttaaatttgg atctgtatgt 660
gtgtcatata tcttcatctt ttagatatat cgataggtat atatgttgct gtcgtttttt 720
actgttcctt tatgagatat attcatgctt agatacatga aacaacgtgc tgttacagtt 780
taatagttct tgtttatcta ataaacaaat aaggataggt gctgcagtta gttttactgg 840
tacttttttt gacatgaacc tacggcttaa taattagtct tcatcaaata aaaagcatat 900
tttttaatta tttcgatata cttgaatgat gtcatatgca gcatctgtgt gaatttttgg 960
ccctgtcttc atatgatgtt tatttgcttg ggactgtttc tttggctgat aactcaccct 1020
gttgtttggt gatccttctg cag 1043

<210> SEQ ID NO 49
<211> LENGTH: 3176
<212> TYPE: DNA
<213> ORGANISM: Bouteloua gracilis

<400> SEQUENCE: 49
aagttagacc caagtgtgag ccggccaccg caagttattg tgacattata cgtaggaagc 60
aagtgtataa taagaatatg agataatgta agcagctata tgaattatca cgtcatattt 120
atgttaagat gaagaggaga gaataaacgg tacgtaaatt tatagcgagt gatagacggg 180
cacgaggcct cctagctatt tccataaatc ggattttgta agaacaaaaa agaggactta 240
ttataagaga atgtggtaag taagcatact ccctccgttt caaattataa gttgttttaa 300

-continued

```
cttttttttt atatctattt tactatacat tagatataat aatgtgtcta gatacataat    360
aaaatggatg aacaaaaaag tcaaagtgac ttacaatttg gaacggaggg agtaagttca    420
agccatcaag gcacttctat gcaaccacat agtcaacttg aatgccgctt gagtgccttc    480
tcaagttttt tttttcttgc aaaaattgtt tctttttttt taaaaaagta taatttggat    540
cgtgcaaatt tctctctagg tgtgtgtgtg actgtgtgag taacaatttc tctagttgtg    600
cgtgactgct gcttactttg gagattacaa tatatttcta aaatgcttcg attacttatt    660
tataaaccgt ctctaaggcc aattgctcaa gattcattca acaattgaaa cgtctcacat    720
gattaaatca tataaagttt ctaagtcttg tttgacaaga tttttttaga ttttcatcta    780
aattggatga aactatcaaa cactaatttt aaaaaatata agagaagctc cggagataaa    840
aggtcgtcta tgttattata agagtaaagt cgtctattct cttcgtccca acatatataa    900
ttctaagcat gaattgcttt ctttttggac aaaaggagta tgccacaaca caagaatgat    960
gtcaccgtca tgcttagatc cttttatggt aaagcttcac cttctataat ctaacaatag   1020
agaaatcggg gaaaaatcat gttttggttg tttttatttc taacctccac aataactttg   1080
gtttaccatt ttttgtttga ttttagtttt agagaagcgt ttataacagg acctaaaatc   1140
ttttttgag tacacagtac aacgcagacg ctcatacacg cacgcacaat gtcctctatg   1200
aacacacgta aggaaaccct acaccttgag caccttcgaa ggactgagcc ggcaaatcta   1260
gagattctcg aagtcactat tggcacctcg ttatcaacga gaacgtcgct taccacttaa   1320
agcataacac cgagaaatcc cgtaacaaat ccagtaaaat acgagcaccc gtaccaagtt   1380
gaatatttga acccgagtgg gtagattcca ccgcaaagga cctaaccaga tcatttcgca   1440
aacaggaact aaaatcggta gagagcccag acaaaaacct tttctaagag caactccagt   1500
gaaagcccct actttaggta taaaatgcaa cactagtgga gcttctaaat aaacttctat   1560
ttttcatgcc ctcctaaaat ttactcctaa aaccctagct ataggagcct cctatccatc   1620
ctctatttta ttccactaga attgattata aatttagcct cttaaatttt ataagttggg   1680
agtcgagggt aactagagtt gctctaaacg gaccttatct tcaagtgacc tcagtgagcc   1740
cgtttaacgg cgtcgacaag tctaatctaa cggacaccaa ccagagaacc accgccagcg   1800
ccgagccaag cgacgttgac atcttggcgc ggcacggcat ctccctggcg tctggtcccc   1860
tcccgagact tccgctccac ctcccaccgg tggcggtttc cgagtccgtt ccgcctcctc   1920
tcacacggca cgaaaccttg acggcaccgg cagcacgggg gattccgttc ccacggctcc   1980
ttccctttcc cttcctcgcc cgctgctata aatagccagc cccatcccca gcttcttccc   2040
caacctcatc ttctcgtgtt gttcggccca acccgatcga tccccaattc cctcgtcgtc   2100
tctcgtcgcg agcctcgtcg atccccgctt caaggtacag cgatcgatcg atcatcctcg   2160
ctctctctac cttctctctc ttagggcgtg ctggttctgt tcctgttttt ccatggctgc   2220
gaggtacaat agattggcga ttcatggtta gggcctgcta gttctgttcc tgtttttttt   2280
ttttccatgg ctgcgaggca caatagatct gatggcgtta tgatggttaa cttgtcatac   2340
tcttgcgatc tatggtccct ttaggagttt aggacatcga tttaatttcg gatagttcga   2400
gatctgtgat ccatggttag taccctaggc agtggggtta gatccgtgct gttatggttc   2460
gtagatggat tctgattgct cagtaactgg gaatcctggg atggttctag ctggttcgca   2520
gataagatcg atttcatgat atgctatatc ttgtttggtt gccgtggttc cgttaaatct   2580
gtctgttatg atcttagtct tgataaggtt cggtcgtgct agctacgtcc tgtgcagcac   2640
ttaattgtca ggtcataatt tttagcatgc cttttttta ttggtttggt tttgtctgac   2700
```

-continued

```
tgggctgtag atagtttcaa tctttgtctg actgggctgt agatagtttc aatcttcctg   2760
tctgtttatt ttattaaatt tggatctgta tgtgtgtcat atatcttcat cttttagata   2820
tatcgatagg tatatatgtt gctgtcgttt tttactgttc ctttatgaga tatattcatg   2880
cttagataca tgaaacaacg tgctgttaca gtttaatagt tcttgtttat ctaataaaca   2940
aataaggata ggtgctgcag ttagttttac tggtactttt tttgacatga acctacggct   3000
taataattag tcttcatcaa ataaaaagca tattttttaa ttatttcgat atacttgaat   3060
gatgtcatat gcagcatctg tgtgaatttt tggccctgtc ttcatatgat gtttatttgc   3120
ttgggactgt ttctttggct gataactcac cctgttgttt ggtgatcctt ctgcag       3176
```

<210> SEQ ID NO 50
<211> LENGTH: 2043
<212> TYPE: DNA
<213> ORGANISM: Bouteloua gracilis

<400> SEQUENCE: 50

```
aagttagacc caagtgtgag ccggccaccg caagttattg tgacattata cgtaggaagc     60
aagtgtataa taagaatatg agataatgta agcagctata tgaattatca cgtcatattt    120
atgttaagat gaagaggaga gaataaacgg tacgtaaatt tatagcgagt gatagacggg    180
cacgaggcct cctagctatt tccataaatc ggattttgta agaacaaaaa agaggactta    240
ttataagaga atgtggtaag taagcatact ccctccgttt caaattataa gttgttttaa    300
cttttttttt atatctattt tactatacat tagatataat aatgtgtcta gatacataat    360
aaaatggatg aacaaaaaag tcaaagtgac ttacaatttg gaacggaggg agtaagttca    420
agccatcaag gcacttctat gcaaccacat agtcaacttg aatgccgctt gagtgccttc    480
tcaagttttt tttttcttgc aaaaattgtt tctttttttt taaaaaagta taatttggat    540
cgtgcaaatt tctctctagg tgtgtgtgtg actgtgtgag taacaatttc tctagttgtg    600
cgtgactgct gcttactttg gagattacaa tatatttcta aaatgcttcg attacttatt    660
tataaaccgt ctctaaggcc aattgctcaa gattcattca acaattgaaa cgtctcacat    720
gattaaatca tataaagttt ctaagtcttg tttgacaaga ttttttttaga ttttcatcta    780
aattggatga aactatcaaa cactaatttt aaaaaaatata agagaagctc cggagataaa    840
aggtcgtcta tgttattata agagtaaagt cgtctattct cttcgtccca acatatataa    900
ttctaagcat gaattgcttt ctttttggac aaaaggagta tgccacaaca caagaatgat    960
gtcaccgtca tgcttagatc cttttatggt aaagcttcac cttctataat ctaacaatag   1020
agaaatcggg gaaaaatcat gttttggttg tttttatttc taacctccac aataactttg   1080
gtttaccatt ttttgtttga ttttagtttt agagaagcgt ttataacagg acctaaaatc   1140
tttttttgag tacacagtac aacgcagacg ctcatacacg cacgcacaat gtcctctatg   1200
aacacacgta aggaaaccct acacccttgag caccttcgaa ggactgagcc ggcaaatcta   1260
gagattctcg aagtcactat tggcacctcg ttatcaacga gaacgtcgct taccacttaa   1320
agcataacac cgagaaatcc cgtaacaaat ccagtaaaat acgagcaccc gtaccaagtt   1380
gaatatttga acccgagtgg gtagattcca ccgcaaagga cctaaccaga tcatttcgca   1440
aacaggaact aaaatcggta gagagcccag acaaaaacct tttctaagag caactccagt   1500
gaaagcccct actttaggta taaaatgcaa cactagtgga gcttctaaat aaacttctat   1560
ttttcatgcc ctcctaaaat ttactcctaa aaccctagct ataggagcct cctatccatc   1620
```

ctctatttta ttccactaga attgattata aatttagcct cttaaatttt ataagttggg 1680
agtcgagggt aactagagtt gctctaaacg gaccttatct tcaagtgacc tcagtgagcc 1740
cgtttaacgg cgtcgacaag tctaatctaa cggacaccaa ccagagaacc accgccagcg 1800
ccgagccaag cgacgttgac atcttggcgc ggcacggcat ctccctggcg tctggtcccc 1860
tcccgagact tccgctccac ctcccaccgg tggcggtttc cgagtccgtt ccgcctcctc 1920
tcacacggca cgaaaccttg acggcaccgg cagcacgggg gattccgttc ccacggctcc 1980
ttccctttcc cttcctcgcc cgctgctata aatagccagc cccatcccca gcttcttccc 2040
caa 2043

<210> SEQ ID NO 51
<211> LENGTH: 1042
<212> TYPE: DNA
<213> ORGANISM: Bouteloua gracilis

<400> SEQUENCE: 51
gtacagcgat cgatcgatca tcctcgctct ctctaccttc tctctcttag ggcgtgctgg 60
ttctgttcct gtttttccat ggctgcgagg tacaatagat tggcgattca tggttagggc 120
ctgctagttc tgttcctgtt ttttttttt ccatggctgc gaggcacaat agatctgatg 180
gcgttatgat ggttaacttg tcatactctt gcgatctatg gtccctttag gagtttagga 240
catcgattta atttcggata gttcgagatc tgtgatccat ggttagtacc ctaggcagtg 300
gggttagatc cgtgctgtta tggttcgtag atggattctg attgctcagt aactgggaat 360
cctgggatgg ttctagctgg ttcgcagata agatcgattt catgatatgc tatatcttgt 420
ttggttgccg tggttccgtt aaatctgtct gttatgatct tagtcttgat aaggttcggt 480
cgtgctagct acgtcctgtg cagcacttaa ttgtcaggtc ataattttta gcatgccttt 540
tttttattgg tttggttttg tctgactggg ctgtagatag tttcaatctt tgtctgactg 600
ggctgtagat agtttcaatc ttcctgtctg tttattttat taaatttgga tctgtatgtg 660
tgtcatatat cttcatcttt tagatatatc gataggtata tatgttgctg tcgtttttta 720
ctgttccttt atgagatata ttcatgctta gatacatgaa acaacgtgct gttacagttt 780
aatagttctt gtttatctaa taaacaaata aggataggtg ctgcagttag ttttactggt 840
actttttttg acatgaacct acggcttaat aattagtctt catcaaataa aaagcatatt 900
ttttaattat ttcgatatac ttgaatgatg tcatatgcag catctgtgtg aatttttggc 960
cctgtcttca tatgatgttt atttgcttgg gactgtttct ttggctgata actcaccctg 1020
ttgtttggtg atccttctgc ag 1042

<210> SEQ ID NO 52
<211> LENGTH: 3139
<212> TYPE: DNA
<213> ORGANISM: Bouteloua gracilis

<400> SEQUENCE: 52
gacattatac gtaggaagca agtgtataat aagaatatga gataatgtaa gcagctatat 60
gaattatcac gtcatattta tgttaagatg aagaggagag aataaacggt acgtaaattt 120
atagcgagtg atagacgggc acgaggcctc ctagctattt ccataaatcg gattttgtaa 180
gaacaaaaaa gaggacttat tataagagaa tgtggtaagt aagcatactc cctccgtttc 240
aaattataag ttgttttaac ttttttttta tatctatttt actatacatt agatataata 300
atgtgtctag atacataata aaatggatga acaaaaaagt caaagtgact tacaatttgg 360

-continued

```
aacggaggga gtaagttcaa gccatcaagg cacttctatg caaccacata gtcaacttga    420
atgccgcttg agtgccttct caagtttttt ttttcttgca aaaattgttt cttttttttt    480
aaaaaagtat aatttggatc gtgcaaattt ctctctaggt gtgtgtgtga ctgtgtgagt    540
aacaatttct ctagttgtgc gtgactgctg cttactttgg agattacaat atatttctaa    600
aatgcttcga ttacttattt ataaaccgtc tctaaggcca attgctcaag attcattcaa    660
caattgaaac gtctcacatg attaaatcat ataaagtttc taagtcttgt ttgacaagat    720
ttttttagat tttcatctaa attggatgaa actatcaaac actaatttta aaaaatataa    780
gagaagctcc ggagataaaa ggtcgtctat gttattataa gagtaaagtc gtctattctc    840
ttcgtcccaa catatataat tctaagcatg aattgctttc tttttggaca aaaggagtat    900
gccacaacac aagaatgatg tcaccgtcat gcttagatcc ttttatggta aagcttcacc    960
ttctataatc taacaataga gaaatcgggg aaaaatcatg ttttggttgt ttttatttct   1020
aacctccaca ataactttgg tttaccattt tttgtttgat tttagtttta gagaagcgtt   1080
tataacagga cctaaaatct ttttttgagt acacagtaca acgcagacgc tcatacacgc   1140
acgcacaatg tcctctatga acacacgtaa ggaaacccta caccttgagc accttcgaag   1200
gactgagccg gcaaatctag agattctcga agtcactatt ggcacctcgt tatcaacgag   1260
aacgtcgctt accacttaaa gcataacacc gagaaatccc gtaacaaatc cagtaaaata   1320
cgagcacccg taccaagttg aatatttgaa cccgagtggg tagattccac cgcaaaggac   1380
ctaaccagat catttcgcaa acaggaacta aaatcggtag agagcccaga caaaaaacct   1440
ttctaagagc aactccagtg aaagccccta ctttaggtat aaaatgcaac actagtggag   1500
cttctaaata aacttctatt tttcatgccc tcctaaaatt tactcctaaa accctagcta   1560
taggagcctc ctatccatcc tctattttat tccactagaa ttgattataa atttagcctc   1620
ttaaatttta taagttggga gtcgagggta actagagttg ctctaaacgg accttatctt   1680
caagtgacct cagtgagccc gtttaacggc gtcgacaagt ctaatctaac ggacaccaac   1740
cagagaacca ccgccagcgc cgagccaagc gacgttgaca tcttggcgcg gcacggcatc   1800
tccctggcgt ctggtcccct cccgagactt ccgctccacc tcccaccggt ggcggtttcc   1860
gagtccgttc cgcctcctct cacacggcac gaaaccttga cggcaccggc agcacggggg   1920
attccgttcc cacggctcct tccctttccc ttcctcgccc gctgctataa atagccagcc   1980
ccatccccag cttcttcccc aacctcatct tctcgtgttg ttcggcccaa cccgatcgat   2040
ccccaattcc ctcgtcgtct ctcgtcgcga gcctcgtcga tccccgcttc aaggtacagc   2100
gatcgatcga tcatcctcgc tctctctacc ttctctctct tagggcgtgc tggttctgtt   2160
cctgttttc catggctgcg aggtacaata gattggcgat tcatggttag ggcctgctag    2220
ttctgttcct gttttttttt tttccatggc tgcgaggcac aatagatctg atggcgttat   2280
gatggttaac ttgtcatact cttgcgatct atggtccctt taggagttta ggacatcgat   2340
ttaatttcgg atagttcgag atctgtgatc catggttagt accctaggca gtggggttag   2400
atccgtgctg ttatggttcg tagatggatt ctgattgctc agtaactggg aatcctggga   2460
tggttctagc tggttcgcag ataagatcga tttcatgata tgctatatct tgtttggttg   2520
ccgtggttcc gttaaatctg tctgttatga tcttagtctt tgataaggtt cggtcgtgct   2580
agctacgtcc tgtgcagcac ttaattgtca ggtcataatt tttagcatgc cttttttta    2640
ttggtttggt tttgtctgac tgggctgtag atagtttcaa tctttgtctg actgggctgt   2700
```

-continued agatagtttc aatcttcctg tctgtttatt ttattaaatt tggatctgta tgtgtgtcat 2760
atatcttcat cttttagata tatcgatagg tatatatgtt gctgtcgttt tttactgttc 2820
ctttatgaga tatattcatg cttagataca tgaaacaacg tgctgttaca gtttaatagt 2880
tcttgtttat ctaataaaca aataaggata ggtgctgcag ttagttttac tggtactttt 2940
tttgacatga acctacggct taataattag tcttcatcaa ataaaaagca tattttttaa 3000
ttatttcgat atacttgaat gatgtcatat gcagcatctg tgtgaatttt tggccctgtc 3060
ttcatatgat gtttatttgc ttgggactgt ttctttggct gataactcac cctgttgttt 3120
ggtgatcctt ctgcaggtg 3139

<210> SEQ ID NO 53
<211> LENGTH: 2002
<212> TYPE: DNA
<213> ORGANISM: Bouteloua gracilis

<400> SEQUENCE: 53
gacattatac gtaggaagca agtgtataat aagaatatga gataatgtaa gcagctatat 60
gaattatcac gtcatattta tgttaagatg aagaggagag aataaacggt acgtaaattt 120
atagcgagtg atagacgggc acgaggcctc ctagctattt ccataaatcg gattttgtaa 180
gaacaaaaaa gaggacttat tataagagaa tgtggtaagt aagcatactc cctccgtttc 240
aaattataag ttgttttaac ttttttttta tatctatttt actatacatt agatataata 300
atgtgtctag atacataata aaatggatga acaaaaaagt caaagtgact tacaatttgg 360
aacggaggga gtaagttcaa gccatcaagg cacttctatg caaccacata gtcaacttga 420
atgccgcttg agtgccttct caagtttttt ttttcttgca aaaattgttt cttttttttt 480
aaaaaagtat aatttggatc gtgcaaattt ctctctaggt gtgtgtgtga ctgtgtgagt 540
aacaatttct ctagttgtgc gtgactgctg cttactttgg agattacaat atatttctaa 600
aatgcttcga ttacttattt ataaaccgtc tctaaggcca attgctcaag attcattcaa 660
caattgaaac gtctcacatg attaaatcat ataaagtttc taagtcttgt ttgacaagat 720
ttttttagat tttcatctaa attggatgaa actatcaaac actaatttta aaaaatataa 780
gagaagctcc ggagataaaa ggtcgtctat gttattataa gagtaaagtc gtctattctc 840
ttcgtcccaa catatataat tctaagcatg aattgctttc tttttggaca aaaggagtat 900
gccacaacac aagaatgatg tcaccgtcat gcttagatcc ttttatggta aagcttcacc 960
ttctataatc taacaataga gaaatcgggg aaaaatcatg ttttggttgt ttttatttct 1020
aacctccaca ataactttgg tttaccattt tttgtttgat tttagtttta gagaagcgtt 1080
tataacagga cctaaaatct ttttttgagt acacagtaca acgcagacgc tcatacacgc 1140
acgcacaatg tcctctatga acacacgtaa ggaaacccta caccttgagc accttcgaag 1200
gactgagccg gcaaatctag agattctcga agtcactatt ggcacctcgt tatcaacgag 1260
aacgtcgctt accacttaaa gcataacacc gagaaatccc gtaacaaatc cagtaaaata 1320
cgagcacccg taccaagttg aatatttgaa cccgagtggg tagattccac cgcaaaggac 1380
ctaaccagat catttcgcaa acaggaacta aaatcggtag agagcccaga caaaaacctt 1440
ttctaagagc aactccagtg aaagccccta ctttaggtat aaaatgcaac actagtggag 1500
cttctaaata aacttctatt tttcatgccc tcctaaaatt tactcctaaa accctagcta 1560
taggagcctc ctatccatcc tctattttat tccactagaa ttgattataa atttagcctc 1620
ttaaatttta taagttggga gtcgagggta actagagttg ctctaaacgg accttatctt 1680
caagtgacct cagtgagccc gtttaacggc gtcgacaagt ctaatctaac ggacaccaac 1740
cagagaacca ccgccagcgc cgagccaagc gacgttgaca tcttggcgcg gcacggcatc 1800
tccctggcgt ctggtcccct cccgagactt ccgctccacc tcccaccggt ggcggtttcc 1860
gagtccgttc cgcctcctct cacacggcac gaaaccttga cggcaccggc agcacggggg 1920
attccgttcc cacggctcct tccctttccc ttcctcgccc gctgctataa atagccagcc 1980
ccatccccag cttcttcccc aa 2002

<210> SEQ ID NO 54
<211> LENGTH: 1046
<212> TYPE: DNA
<213> ORGANISM: Bouteloua gracilis

<400> SEQUENCE: 54
gtacagcgat cgatcgatca tcctcgctct ctctaccttc tctctcttag ggcgtgctgg 60
ttctgttcct gtttttccat ggctgcgagg tacaatagat tggcgattca tggttagggc 120
ctgctagttc tgttcctgtt ttttttttt ccatggctgc gaggcacaat agatctgatg 180
gcgttatgat ggttaacttg tcatactctt gcgatctatg gtccctttag gagtttagga 240
catcgattta atttcggata gttcgagatc tgtgatccat ggttagtacc ctaggcagtg 300
gggttagatc cgtgctgtta tggttcgtag atggattctg attgctcagt aactgggaat 360
cctgggatgg ttctagctgg ttcgcagata agatcgattt catgatatgc tatatcttgt 420
ttggttgccg tggttccgtt aaatctgtct gttatgatct tagtctttga taaggttcgg 480
tcgtgctagc tacgtcctgt gcagcactta attgtcaggt cataattttt agcatgcctt 540 tttttattg gtttggtttt gtctgactgg gctgtagata gtttcaatct ttgtctgact 600
gggctgtaga tagtttcaat cttcctgtct gtttatttta ttaaatttgg atctgtatgt 660
gtgtcatata tcttcatctt ttagatatat cgataggtat atatgttgct gtcgtttttt 720
actgttcctt tatgagatat attcatgctt agatacatga aacaacgtgc tgttacagtt 780
taatagttct tgtttatcta ataaacaaat aaggataggt gctgcagtta gttttactgg 840 tactttttt gacatgaacc tacggcttaa taattagtct tcatcaaata aaaagcatat 900
tttttaatta tttcgatata cttgaatgat gtcatatgca gcatctgtgt gaatttttgg 960
ccctgtcttc atatgatgtt tatttgcttg ggactgtttc tttggctgat aactcaccct 1020
gttgtttggt gatccttctg caggtg 1046

<210> SEQ ID NO 55
<211> LENGTH: 2160
<212> TYPE: DNA
<213> ORGANISM: Bouteloua gracilis

<400> SEQUENCE: 55
gagaaatcgg ggaaaaatca tgttttggtt gtttttattt ctaacctcca caataacttt 60
ggtttaccat tttttgtttg attttagttt tagagaagcg tttataacag gacctaaaat 120
ctttttttga gtacacagta caacgcagac gctcatacac gcacgcacaa tgtcctctat 180
gaacacacgt aaggaaaccc tacaccttga gcaccttcga aggactgagc cggcaaatct 240
agagattctc gaagtcacta ttggcacctc gttatcaacg agaacgtcgc ttaccactta 300
aagcataaca ccgagaaatc ccgtaacaaa tccagtaaaa tacgagcacc cgtaccaagt 360
tgaatatttg aacccgagtg ggtagattcc accgcaaagg acctaaccag atcatttcgc 420

-continued

```
aaacaggaac taaaatcggt agagagccca gacaaaaacc ttttctaaga gcaactccag     480
tgaaagcccc tactttaggt ataaaatgca acactagtgg agcttctaaa taaacttcta     540
tttttcatgc cctcctaaaa tttactccta aaaccctagc tataggagcc tcctatccat     600
cctctatttt attccactag aattgattat aaatttagcc tcttaaattt tataagttgg     660
gagtcgaggg taactagagt tgctctaaac ggaccttatc ttcaagtgac ctcagtgagc     720
ccgtttaacg gcgtcgacaa gtctaatcta acggacacca accagagaac caccgccagc     780
gccgagccaa gcgacgttga catcttggcg cggcacggca tctccctggc gtctggtccc     840
ctcccgagac ttccgctcca cctcccaccg gtggcggttt ccgagtccgt tccgcctcct     900
ctcacacggc acgaaacctt gacggcaccg gcagcacggg ggattccgtt cccacggctc     960
cttccctttc ccttcctcgc ccgctgctat aaatagccag ccccatcccc agcttcttcc    1020
ccaacctcat cttctcgtgt tgttcggccc aacccgatcg atccccaatt ccctcgtcgt    1080
ctctcgtcgc gagcctcgtc gatccccgct tcaaggtaca gcgatcgatc gatcatcctc    1140
gctctctcta ccttctctct cttagggcgt gctggttctg ttcctgtttt tccatggctg    1200
cgaggtacaa tagattggcg attcatggtt agggcctgct agttctgttc ctgttttttt    1260
ttttccatgg ctgcgaggca caatagatct gatggcgtta tgatggttaa cttgtcatac    1320
tcttgcgatc tatggtccct ttaggagttt aggacatcga tttaatttcg gatagttcga    1380
gatctgtgat ccatggttag taccctaggc agtggggtta gatccgtgct gttatggttc    1440
gtagatggat tctgattgct cagtaactgg gaatcctggg atggttctag ctggttcgca    1500
gataagatcg atttcatgat atgctatatc ttgtttggtt gccgtggttc cgttaaatct    1560
gtctgttatg atcttagtct ttgataaggt tcggtcgtgc tagctacgtc ctgtgcagca    1620
cttaattgtc aggtcataat ttttagcatg cctttttttt attggtttgg ttttgtctga    1680
ctgggctgta gatagtttca atctttgtct gactgggctg tagatagttt caatcttcct    1740
gtctgtttat tttattaaat ttggatctgt atgtgtgtca tatatcttca tcttttagat    1800
atatcgatag gtatatatgt tgctgtcgtt ttttactgtt cctttatgag atatattcat    1860
gcttagatac atgaaacaac gtgctgttac agtttaatag ttcttgttta tctaataaac    1920
aaataaggat aggtgctgca gttagtttta ctggtacttt ttttgacatg aacctacggc    1980
ttaataatta gtcttcatca aataaaaagc atattttttta attatttcga tatacttgaa    2040
tgatgtcata tgcagcatct gtgtgaattt ttggccctgt cttcatatga tgtttatttg    2100
cttgggactg tttctttggc tgataactca ccctgttgtt tggtgatcct tctgcaggtg    2160
```

<210> SEQ ID NO 56
<211> LENGTH: 1024
<212> TYPE: DNA
<213> ORGANISM: Bouteloua gracilis

<400> SEQUENCE: 56

```
gagaaatcgg ggaaaaatca tgttttggtt gtttttattt ctaacctcca caataacttt      60
ggtttaccat tttttgtttg attttagttt tagagaagcg tttataacag gacctaaaat     120 cttttttga gtacacagta caacgcagac gctcatacac gcacgcacaa tgtcctctat     180
gaacacacgt aaggaaaccc tacaccttga gcaccttcga aggactgagc cggcaaatct     240
agagattctc gaagtcacta ttggcacctc gttatcaacg agaacgtcgc ttaccactta     300
aagcataaca ccgagaaatc ccgtaacaaa tccagtaaaa tacgagcacc cgtaccaagt     360
tgaatatttg aacccgagtg ggtagattcc accgcaaagg acctaaccag atcatttcgc     420
```

-continued

```
aaacaggaac taaaatcggt agagagccca gacaaaaacc ttttctaaga gcaactccag    480

tgaaagcccc tactttaggt ataaaatgca acactagtgg agcttctaaa taaacttcta    540

tttttcatgc cctcctaaaa tttactccta aaaccctagc tataggagcc tcctatccat    600

cctctatttt attccactag aattgattat aaatttagcc tcttaaattt tataagttgg    660

gagtcgaggg taactagagt tgctctaaac ggaccttatc ttcaagtgac ctcagtgagc    720

ccgtttaacg gcgtcgacaa gtctaatcta acggacacca accagagaac caccgccagc    780

gccgagccaa gcgacgttga catcttggcg cggcacggca tctccctggc gtctggtccc    840

ctcccgagac ttccgctcca cctcccaccg gtggcggttt ccgagtccgt tccgcctcct    900

ctcacacggc acgaaacctt gacggcaccg gcagcacggg ggattccgtt cccacggctc    960

cttccctttc ccttcctcgc ccgctgctat aaatagccag ccccatcccc agcttcttcc   1020

ccaa                                                                1024
```

<210> SEQ ID NO 57
<211> LENGTH: 1045
<212> TYPE: DNA
<213> ORGANISM: Bouteloua gracilis

<400> SEQUENCE: 57

```
gtacagcgat cgatcgatca tcctcgctct ctctaccttc tctctcttag ggcgtgctgg     60

ttctgttcct gtttttccat ggctgcgagg tacaatagat tggcgattca tggttagggc    120

ctgctagttc tgttcctgtt ttttttttc catggctgcg aggcacaata gatctgatgg    180

cgttatgatg gttaacttgt catactcttg cgatctatgg tccctttagg agtttaggac    240

atcgatttaa tttcggatag ttcgagatct gtgatccatg gttagtaccc taggcagtgg    300

ggttagatcc gtgctgttat ggttcgtaga tggattctga ttgctcagta actgggaatc    360

ctgggatggt tctagctggt tcgcagataa gatcgatttc atgatatgct atatcttgtt    420

tggttgccgt ggttccgtta aatctgtctg ttatgatctt agtctttgat aaggttcggt    480

cgtgctagct acgtcctgtg cagcacttaa ttgtcaggtc ataattttta gcatgccttt    540

tttttattgg tttggttttg tctgactggg ctgtagatag tttcaatctt tgtctgactg    600

ggctgtagat agtttcaatc ttcctgtctg tttattttat taaatttgga tctgtatgtg    660

tgtcatatat cttcatcttt tagatatatc gataggtata tatgttgctg tcgtttttta    720

ctgttccttt atgagatata ttcatgctta gatacatgaa acaacgtgct gttacagttt    780

aatagttctt gtttatctaa taaacaaata aggataggtg ctgcagttag ttttactggt    840

acttttttg acatgaacct acggcttaat aattagtctt catcaaataa aaagcatatt    900

ttttaattat ttcgatatac ttgaatgatg tcatatgcag catctgtgtg aatttttggc    960

cctgtcttca tatgatgttt atttgcttgg gactgtttct ttggctgata actcaccctg   1020

ttgtttggtg atccttctgc aggtg                                         1045
```

<210> SEQ ID NO 58
<211> LENGTH: 2160
<212> TYPE: DNA
<213> ORGANISM: Bouteloua gracilis

<400> SEQUENCE: 58

```
gagaaatcgg ggaaaaatca tgttttggtt gtttttattt ctaacctcca caataacttt     60

ggtttaccat tttttgtttg attttagttt tagagaagcg tttataacag gacctaaaat    120
```

-continued

```
cttttttga gtacacagta caacgcagac gctcatacac gcacgcacaa tgtcctctat    180
gaacacacgt aaggaaaccc tacaccttga gcaccttcga aggactgagc cggcaaatct    240
agagattctc gaagtcacta ttggcacctc gttatcaacg agaacgtcgc ttaccactta    300
aagcataaca ccgagaaatc ccgtaacaaa tccagtaaaa tacgagcacc cgtaccaagt    360
tgaatatttg aacccgagtg ggtagattcc accgcaaagg acctaaccag atcatttcgc    420
aaacaggaac taaaatcggt agagagccca gacaaaaacc ttttctaaga gcaactccag    480
tgaaagcccc tactttaggt ataaaatgca acactagtgg agcttctaaa taaacttcta    540
tttttcatgc cctcctaaaa tttactccta aaaccctagc tataggagcc tcctatccat    600
cctctatttt attccactag aattgattat aaatttagcc tcttaaattt tataagttgg    660
gagtcgaggg taactagagt tgctctaaac ggaccttatc ttcaagtgac ctcagtgagc    720
ccgtttaacg gcgtcgacaa gtctaatcta acggacacca accagagaac caccgccagc    780
gccgagccaa gcgacgttga catcttggcg cggcacggca tctccctggc gtctggtccc    840
ctcccgagac ttccgctcca cctcccaccg gtggcggttt ccgagtccgt tccgcctcct    900
ctcacacggc acgaaacctt gacggcaccg gcagcacggg ggattccgtt cccacggctc    960
cttccctttc ccttcctcgc ccgctgctat aaatagccag ccccatcccc agcttcttcc   1020
ccaacctcat cttctcgtgt tgttcggccc aacccgatcg atccccaatt ccctcgtcgt   1080
ctctcgtcgc gagcctcgtc gatccccgct tcaaggtaca gcgatcgatc gatcatcctc   1140
gctctctcta ccttctctct cttagggcgt gctggttctg ttcctgtttt tccatggctg   1200
cgaggtacaa tagattggcg attcatggtt agggcctgct agttctgttc ctgttttttt   1260
tttttccatg gctgcgaggc acaatagatc tgatggcgtt atgatggtta acttgtcata   1320
ctcttgcgat ctatggtccc tttaggagtt taggacatcg atttaatttc ggatagttcg   1380
agatctgtga tccatggtta gtaccctagg cagtggggtt agatccgtgc tgttatggtt   1440
cgtagatgga ttctgattgc tcagtaactg ggaatcctgg gatggttcta gctggttcgc   1500
agataagatc gatttcatga tatgctatat cttgtttggt tgccgtggtt ccgttaaatc   1560
tgtctgttat gatcttagtc ttgataaggt tcggtcgtgc tagctacgtc ctgtgcagca   1620
cttaattgtc aggtcataat ttttagcatg ccttttttt attggtttgg ttttgtctga   1680
ctgggctgta gatagtttca atctttgtct gactgggctg tagatagttt caatcttcct   1740
gtctgtttat tttattaaat ttggatctgt atgtgtgtca tatatcttca tcttttagat   1800
atatcgatag gtatatatgt tgctgtcgtt ttttactgtt cctttatgag atatattcat   1860
gcttagatac atgaaacaac gtgctgttac agtttaatag ttcttgttta tctaataaac   1920
aaataaggat aggtgctgca gttagtttta ctggtacttt ttttgacatg aacctacggc   1980
ttaataatta gtcttcatca aataaaaagc atatttttta attatttcga tatacttgaa   2040
tgatgtcata tgcagcatct gtgtgaattt ttggccctgt cttcatatga tgtttatttg   2100
cttgggactg tttctttggc tgataactca ccctgttgtt tggtgatcct tctgcaggtg   2160
```

<210> SEQ ID NO 59
<211> LENGTH: 1045
<212> TYPE: DNA
<213> ORGANISM: Bouteloua gracilis

<400> SEQUENCE: 59

```
gtacagcgat cgatcgatca tcctcgctct ctctaccttc tctctcttag ggcgtgctgg     60
ttctgttcct gtttttccat ggctgcgagg tacaatagat tggcgattca tggttagggc    120
```

-continued

```
ctgctagttc tgttcctgtt tttttttttt ccatggctgc gaggcacaat agatctgatg    180

gcgttatgat ggttaacttg tcatactctt gcgatctatg gtccctttag gagtttagga    240

catcgattta atttcggata gttcgagatc tgtgatccat ggttagtacc ctaggcagtg    300

gggttagatc cgtgctgtta tggttcgtag atggattctg attgctcagt aactgggaat    360

cctgggatgg ttctagctgg ttcgcagata agatcgattt catgatatgc tatatcttgt    420

ttggttgccg tggttccgtt aaatctgtct gttatgatct tagtcttgat aaggttcggt    480

cgtgctagct acgtcctgtg cagcacttaa ttgtcaggtc ataattttta gcatgccttt    540

tttttattgg tttggttttg tctgactggg ctgtagatag tttcaatctt tgtctgactg    600

ggctgtagat agtttcaatc ttcctgtctg tttattttat taaatttgga tctgtatgtg    660

tgtcatatat cttcatcttt tagatatatc gataggtata tatgttgctg tcgtttttta    720

ctgttccttt atgagatata ttcatgctta gatacatgaa acaacgtgct gttacagttt    780

aatagttctt gtttatctaa taaacaaata aggataggtg ctgcagttag ttttactggt    840

actttttttg acatgaacct acggcttaat aattagtctt catcaaataa aaagcatatt    900

ttttaattat ttcgatatac ttgaatgatg tcatatgcag catctgtgtg aatttttggc    960

cctgtcttca tatgatgttt atttgcttgg gactgtttct ttggctgata actcaccctg   1020

ttgtttggtg atccttctgc aggtg                                         1045
```

<210> SEQ ID NO 60
<211> LENGTH: 1885
<212> TYPE: DNA
<213> ORGANISM: Bouteloua gracilis

<400> SEQUENCE: 60

```
caacgagaac gtcgcttacc acttaaagca taacaccgag aaatcccgta acaaatccag     60

taaaatacga gcacccgtac caagttgaat atttgaaccc gagtgggtag attccaccgc    120

aaaggaccta accagatcat ttcgcaaaca ggaactaaaa tcggtagaga gcccagacaa    180

aaaccttttc taagagcaac tccagtgaaa gcccctactt taggtataaa atgcaacact    240

agtggagctt ctaaataaac ttctattttt catgccctcc taaaatttac tcctaaaacc    300

ctagctatag gagcctccta tccatcctct attttattcc actagaattg attataaatt    360

tagcctctta aattttataa gttgggagtc gagggtaact agagttgctc taaacggacc    420

ttatcttcaa gtgacctcag tgagcccgtt taacggcgtc gacaagtcta atctaacgga    480

caccaaccag agaaccaccg ccagcgccga gccaagcgac gttgacatct tggcgcggca    540

cggcatctcc ctggcgtctg gtcccctccc gagacttccg ctccacctcc caccggtggc    600

ggtttccgag tccgttccgc ctcctctcac acggcacgaa accttgacgg caccggcagc    660

acgggggatt ccgttcccac ggctccttcc ctttcccttc ctcgcccgct gctataaata    720

gccagcccca tccccagctt cttccccaac ctcatcttct cgtgttgttc ggcccaaccc    780

gatcgatccc caattccctc gtcgtctctc gtcgcgagcc tcgtcgatcc ccgcttcaag    840

gtacagcgat cgatcgatca tcctcgctct ctctaccttc tctctcttag ggcgtgctgg    900

ttctgttcct gtttttccat ggctgcgagg tacaatagat tggcgattca tggttagggc    960

ctgctagttc tgttcctgtt tttttttttt ccatggctgc gaggcacaat agatctgatg   1020

gcgttatgat ggttaacttg tcatactctt gcgatctatg gtccctttag gagtttagga   1080

catcgattta atttcggata gttcgagatc tgtgatccat ggttagtacc ctaggcagtg   1140
```

```
gggttagatc cgtgctgtta tggttcgtag atggattctg attgctcagt aactgggaat   1200
cctgggatgg ttctagctgg ttcgcagata agatcgattt catgatatgc tatatcttgt   1260
ttggttgccg tggttccgtt aaatctgtct gttatgatct tagtcttgat aaggttcggt   1320
cgtgctagct acgtcctgtg cagcacttaa ttgtcaggtc ataattttta gcatgccttt   1380
tttttattgg tttggttttg tctgactggg ctgtagatag tttcaatctt tgtctgactg   1440
ggctgtagat agtttcaatc ttcctgtctg tttattttat taaatttgga tctgtatgtg   1500
tgtcatatat cttcatcttt tagatatatc gataggtata tatgttgctg tcgtttttta   1560
ctgttccttt atgagatata ttcatgctta gatacatgaa acaacgtgct gttacagttt   1620
aatagttctt gtttatctaa taaacaaata aggataggtg ctgcagttag ttttactggt   1680
actttttttg acatgaacct acggcttaat aattagtctt catcaaataa aaagcatatt   1740
ttttaattat ttcgatatac ttgaatgatg tcatatgcag catctgtgtg aatttttggc   1800
cctgtcttca tatgatgttt atttgcttgg gactgtttct ttggctgata actcaccctg   1860
ttgtttggtg atccttctgc aggtg                                          1885
```

<210> SEQ ID NO 61
<211> LENGTH: 749
<212> TYPE: DNA
<213> ORGANISM: Bouteloua gracilis

<400> SEQUENCE: 61

```
caacgagaac gtcgcttacc acttaaagca taacaccgag aaatcccgta acaaatccag     60
taaaatacga gcacccgtac caagttgaat atttgaaccc gagtgggtag attccaccgc    120
aaaggaccta accagatcat ttcgcaaaca ggaactaaaa tcggtagaga gcccagacaa    180
aaaccttttc taagagcaac tccagtgaaa gcccctactt taggtataaa atgcaacact    240
agtggagctt ctaaataaac ttctattttt catgccctcc taaaatttac tcctaaaacc    300
ctagctatag gagcctccta tccatcctct attttattcc actagaattg attataaatt    360
tagcctctta aattttataa gttgggagtc gagggtaact agagttgctc taaacggacc    420
ttatcttcaa gtgacctcag tgagcccgtt taacggcgtc gacaagtcta atctaacgga    480
caccaaccag agaaccaccg ccagcgccga gccaagcgac gttgacatct tggcgcggca    540
cggcatctcc ctggcgtctg gtcccctccc gagacttccg ctccacctcc caccggtggc    600
ggtttccgag tccgttccgc ctcctctcac acggcacgaa accttgacgg caccggcagc    660
acgggggatt ccgttcccac ggctccttcc ctttcccttc ctcgcccgct gctataaata    720
gccagcccca tccccagctt cttccccaa                                      749
```

<210> SEQ ID NO 62
<211> LENGTH: 6813
<212> TYPE: DNA
<213> ORGANISM: Miscanthus sinesis

<400> SEQUENCE: 62

```
agcagactcg cattatcgat gggggaaatg aaattcagcg tttgacgtgg atgcaacaac     60
tgcactgcac aggatatctt agccgttgtg tcgaagtttg ctttgctaac gttttgagaa    120
aaccagcttt gaccaacacg agacgagcgc cttacgtttg gcacaatgta atgtagcccg    180
gcacggcaag ttagactagt atattgtgtt agccggcctc tttacgtttg gcacagttta    240
attgaatccg gcatggcaag ttagactgga gtgtgagccg gtcattgcaa agttattatg    300
acatatatat aagagcacaa gtgtataata agataatgta agcaaggcag caagctatat    360
```

-continued

```
gaattgtcac gttatattta tgttgagatg ttgagatgaa gaagagaaaa taaacagcct    420
ataaattcat agcgagtgat agacgggcac aaggcctcct atttcttaaa ccgaattttg    480
taagaacaaa aaaaaggact tataggagaa tgggatagac catatatcaa cgggaaaggt    540
acacgttgct cgagtgtttt aggcgttctg ctcactcgat cctgtagctg tccgatctgc    600
ggcgtcaaca cggcgcgcaa caagcggtgg cgggcccctc ggtagccgcg gtcggaccgg    660
acgatggcct atggcgaccc gcggcctggg cgtggcctgt gcgtgcatgc gccataggtc    720
ccggtgcatg gtgcaggcgg caggtgcatg tgcatggagt aggctttggt gctggtgcag    780
gctttggtca ggtgcaggag gggtaggttg cgcaggtgag aggtgaggtg catgctgacc    840
cgtcacatca ccttactcct agcccctaag tcttgcatgt atgcagattt attcttttag    900
cagcgacaga ttcagcagcg agagaccggc taccgtagca ttttcatttt tatttgataa    960
ttagtattta attatggact aattaggttc aaaatattcg tctcgcgatt tccaaccaaa   1020
ctgtgcaatt agttttttc gtctacattt aatgctctat acacgtatca caagattcaa   1080
cgtgatggct actgtagcac tttttgaaaa aactttttgc aactaaacaa ggcctgaggt   1140
atcgtttaaa tttaggtaca aaaaatataa gggtgtcaca tcgaatgtta cacgagatat   1200
catatgtgag tgttcggata gtaataataa aataaattac acaagtcctt agtaatccac   1260
gagacgaatt tattgagtct aattaatcag tcattagcac atggtgcatt catgcatctg   1320
catattattt tgtgttgctt ggttgaaagt tggatttcaa attgagttga atttgcattt   1380
tgaaattgct ttggaaaaat tagaaaaaaa gaaaaaaaat gaatttccct ccctcctttc   1440
tcatttccct gctttcggcc cctctgtgta gaactattcg agttctcagg tcgagtgctc   1500
gaatcatcta gcttctcttt tttgaggaga gccagagagc cagattcaga atagccagcc   1560
tcctttttag gagagagctc atcccctttt atagttgaag gcagcgacga agccagcggg   1620
gggctacccg tgctccagcc tccctacggc catgatttac atggaacccg ggcttagctc   1680
gggctaccgc catgaggagg aagaagaaga taaggagggg ctagaggaag aagaagagga   1740
agctagccct ggcttcgtcg attcctggct tcgtcgctgg ttgaagggga tgggctctta   1800
caagtcagag aaagagagag aatgtatacg tgtgctatct agtcttgttg cccacgctgt   1860
caggtacgag acggttgtcg gcgcccacaa tactgtttat gtccagatgc atgtggcagg   1920
ctctaccgtg ttcgcctgtt atggcaaatg tcggcgcata caatactatt tgggttctga   1980
cacgcctgaa aggttgcata gtgcctatct ggcatggcct ggtggcaccg tccggcatgt   2040
gcgcaggata tgccagggta cggtccttgg tattacggtt tgacttgagc gccttacctt   2100
atctgctccg cctgatcccc gggctcttac cgagcgggcg tccccggtcg gtcgttccca   2160
gtcggccccg actgtgtcgg tcggggaaga gctgcaagca gaggtccggc gtatccccga   2220
tcgaaaaagg aagtcggagt cagactatgt ctccacctta gccaggcctt ccggtcgggg   2280
atcggatcat tctcccggcc tgtcattagg tatctgggtc ggcccgagag gtgtgcgttg   2340
tcgctacgct gtctgctggg ccgagtttct gttgggaagc gggtccattg gggaccccgg   2400
gtttatgaac ccgacacgtg gtcactatgc tgcatactcc ctatacagcc gctgaccagt   2460
acgctggttc accgcgtcgc ccgcgcggga cggaatggga tgtcacgacc cgctgaacgc   2520
cggggcatgg catcagcggc gaacaggcac ccggcgtgga gctgtccgtg tcaccatcta   2580
cagtgttgac gggacccgca taaaaggaga aaaaaggccc gacggtcctg gaagccttcc   2640
tctccttagc tcttctccct ctttctctct gtgtaacctg ctcttcccct tcgtctataa   2700
```

-continued

```
aaagggaagt aggacgtccc aggaagagaa gggcggttca ccactctaca tggctataga 2760
cataaaaaca cacgccttgg gagcacactc acatcagaga cttgggacct atccctctct 2820
cgctcgtttg taacccctac tacaaacttt tagtgctagt aacacgagca gcagcgacga 2880
actagacgta aggactttct gcccgaacca gtataaacat cgtgtcatct aagcacacca 2940
tacgagccag acgcgcaata ctagaaattt actagtcggt aactcgaaac accgacatct 3000
agctaatctt tttgttttat ttggtttccc tttgaaatct tctaatttag ctttcataga 3060
aataatctag gtattttttta ttttatatgt tctatctgtt tgcattaatt ttgatcattt 3120
gatctgaatg ctgtggtcac gagaatcgag tgtttcatgg ccttaaaaca ctcgattatg 3180
ccatctgacc cgttttcaac cattctagtg tttctgagct atatcaatgg tgcagcatgt 3240
tagtatacat atctaactat tactccgtat atgagtgagt tgttaaattt attccaggtg 3300
aaatggcatt aacgatagcc aataggcggc taaattaata gccatactct aacagctcta 3360
aaaaacatat attcatcgag gcacctttat gcaaccacat agtcaacttc aacgtcgctt 3420
gcgtgcgttc tcaagttttc tttcttgcaa attacatttt ttttaaaaaa aagtataatt 3480
tgtatcgtgc gatttttttct ctctaggtgt gcgtgactgt gggagtaaca attttgaatc 3540
tcaagaagga aataaaagaa taatactgct gcctactttg aggatttcag tatttttctc 3600
taaaatgttt tggtgtgata tctaaaccgt ctttaaagcc aattgctcaa gattcattca 3660
acaattgaaa cgtctcacat gactaaatga tataaggttg ctaaggtctt tcttgataag 3720
ctttttttatg aatttcatct aaattttcga gtgaaactat taaatactaa ggttgctaag 3780
tgtcattctc gctcgagaag tctaacgctt taaactttaa ccaaatatat acaagaaaat 3840
attaatattt atagtacata attagtatca ttagatagat cgttgaatct attttcataa 3900
caaacttatt tgaagaaaca aatgttgttc atatatttct atatacgaat accatagcga 3960
cacttatttt agaatgtagg gagtactccc tttgtgccgc tttgagtgtc gctttggcag 4020
ctagtaccta tgtccacctt cacagcttgt gcctagtacc tagactcttt ctctgtccac 4080
attcatttaa tctctgttgt accttgttcg gagataaaac gactctgata aagggacgag 4140
gaagtagtat gttagaggag tgaagtctac tccctttgcc gcaaaaaggt aatcctaagt 4200
gtgaattgta ttctttttttg accaaaggaa tatacaacaa gaatgatgtc atcatcatgc 4260
ttcgatcctt ttttttggta aagcttgagc ttctgtaaaa atagagaaat catgggaaaa 4320
atcacgtttt ggtggttttg atttctagcc tccacaataa ctttggtttt actatttttt 4380
gtttgatttt agtttcagaa gtccactttt gtacgtgctc gtagagccta aacaaaaggc 4440
tttccaaaac gaccttatct tcgagtgttg taaaaaaaat gagcccgttt aacggcgtcg 4500
acaagtctaa cggacaccaa ccagcgaacc accagcgccg agccaagcga agcagactgc 4560
agacggcacg gccgagacgt tgacaccttg gcgcggcaac ggcatctctc tggccccctc 4620
tcgagagttc cgctccacct ccgcatccac ctccacctcc acctccaccg gtggcggttt 4680
ccaagtccgt cccgttccgc cacctgctcc tctcacacgg cacgaaaccg tcacggcacc 4740
ggcagcacag cacgggggat tcctttccca ccgctccgtc cctttctctt cctcgcccgc 4800
ccgttataaa tagccagccc catccctcgt ctctcgtgtt gttcggagcg cacacacaac 4860
ccgatcccca atcaatcgat ccccgcttca aggtacggcg atcctcctcc ctctctctct 4920
accttctctt ctctacacta gatcggcggt ccatggttag ggcctgctag ttccgttcct 4980
gtttttccat ggctgcgagg tacaatagat ctgatggcgt tatgatggtt aacttgtcat 5040
gcttttgcga tttatagtcc ctttagatag ttcgagatcg gtgatccatg gttagtaccc 5100
```

taggctgtgg agtcgggtta gatccgcgct gttagggttc gtatatggag gcgagctgtt 5160
ctgattgtta acttgctggg aatcctggga tggttctagc tgttccgcag atgagatcga 5220
tttcatgatc tgctgtatct atccgtggta tgatgttagc ctttgatatg gttcgatcgt 5280
gctagctacg tcctgtgcac ttaattgtca ggtcataatt tttactatac ttttttttg 5340
gtttggtttg gtttcgtctg atttggctgt cgttctagat cagagtagaa actgtttcaa 5400
actacctgtt ggatttatta aggtagcgtt tggttcctgg tatcgaatca tacacgcacc 5460
agtgcatctt ggatagccag ctggggccca cctgtccaac cgtttggttg ccggatcgaa 5520
cgagtccatt caagaccgaa ccatgcagag caatcgaata ttctcttgtg acgctgtatc 5580
atccagttcg gcaaaaaaca ccgaatgccg ccatacagga caccgtactg agcgtctgca 5640
actctgcatc ccgctcactg ctcacatctc cgcttgccgc ctcacccatc cgactcagac 5700
cagagccaca cggattactg ctgctggtgt gtgtattaac aaaagatcca tttgaccgga 5760
gcacatgcag cttggatgga aaaaatttat tatattcgtc agtgctgcat atgtactcat 5820
acttgcatga tggttttatt tattcgacct catcagtcct ggcactatgg aaagtcattg 5880
tagtatagat tttttaatat aatataaatc attggtgact tatcttgctt aattttattt 5940
tcttattatg aaatatcgtt gcattcataa tagcaaattt gtgcaaatat atagaatcta 6000
cgtgaaattc ttggttggac caatacaaca aacccctcaa acattctctt gtactgaacc 6060
ataccattcc gtacaaccat ccaaacaaaa atcatgtatc atcatgtaca tgtaaccaaa 6120
caattaacac gcaccatcct attcagactt gtctcatcca taatctatcc atccaggatg 6180
atccatccca ttcatctata tacacccaat caaacgctac ctaaaatttg gatctgtatg 6240
tgtcacatat atcttaataa gatggatgga aatatctctt tatcttttag atatggatag 6300
gtatatatgt tgctgtgggt ttgttagtta tatatatacg tgcttacata cgtgaagaaa 6360
cctgctgcta cagtttaata attcttgttc atctcaacaa ataacgatag gcgtatatgt 6420
tgctgtgttt tttactggta ctttgttaga tatatacatg cttacataca tgaagaacac 6480
atgctacagt tcaaaaattc ttgttcatct cataaacaaa aaggaggtgt atatgttgct 6540
gtgggtttta ctggtacttt attagatata tacatgctta catagatgaa gcaacatgct 6600
gctatggtgt ttaataatta ttgtttatct aataaacaaa catgcttttt aattatcttg 6660
atatgtttgg atgatggcat atgcagcagc tatgtgtgga ttttaaatac ccagcatcat 6720
gagcatgcat gaccctgcct tagtatgcag ttatttgctt gagactgttt cttttgttga 6780
tactcatcct ttagttcggt cactcttctg cag 6813

<210> SEQ ID NO 63
<211> LENGTH: 5359
<212> TYPE: DNA
<213> ORGANISM: Miscanthus sinesis

<400> SEQUENCE: 63
agcagactcg cattatcgat gggggaaatg aaattcagcg tttgacgtgg atgcaacaac 60
tgcactgcac aggatatctt agccgttgtg tcgaagtttg ctttgctaac gttttgagaa 120
aaccagcttt gaccaacacg agacgagcgc cttacgtttg gcacaatgta atgtagcccg 180
gcacggcaag ttagactagt atattgtgtt agccggcctc tttacgtttg gcacagttta 240
attgaatccg gcatggcaag ttagactgga gtgtgagccg gtcattgcaa agttattatg 300
acatatatat aagagcacaa gtgtataata agataatgta agcaaggcag caagctatat 360

-continued

```
gaattgtcac gttatattta tgttgagatg ttgagatgaa gaagagaaaa taaacagcct    420
ataaattcat agcgagtgat agacgggcac aaggcctcct atttcttaaa ccgaattttg    480
taagaacaaa aaaaaggact tataggagaa tgggatagac catatatcaa cgggaaaggt    540
acacgttgct cgagtgtttt aggcgttctg ctcactcgat cctgtagctg tccgatctgc    600
ggcgtcaaca cggcgcgcaa caagcggtgg cgggcccctc ggtagccgcg gtcggaccgg    660
acgatggcct atggcgaccc gcggcctggg cgtggcctgt gcgtgcatgc gccataggtc    720
ccggtgcatg gtgcaggcgg caggtgcatg tgcatggagt aggctttggt gctggtgcag    780
gctttggtca ggtgcaggag gggtaggttg cgcaggtgag aggtgaggtg catgctgacc    840
cgtcacatca ccttactcct agcccctaag tcttgcatgt atgcagattt attcttttag    900
cagcgacaga ttcagcagcg agagaccggc taccgtagca ttttcatttt tatttgataa    960
ttagtattta attatggact aattaggttc aaaatattcg tctcgcgatt tccaaccaaa   1020
ctgtgcaatt agttttttc gtctacattt aatgctctat acacgtatca caagattcaa    1080
cgtgatggct actgtagcac tttttgaaaa aactttttgc aactaaacaa ggcctgaggt   1140
atcgtttaaa tttaggtaca aaaaatataa gggtgtcaca tcgaatgtta cacgagatat   1200
catatgtgag tgttcggata gtaataataa aataaattac acaagtcctt agtaatccac   1260
gagacgaatt tattgagtct aattaatcag tcattagcac atggtgcatt catgcatctg   1320
catattattt tgtgttgctt ggttgaaagt tggatttcaa attgagttga atttgcattt   1380
tgaaattgct ttggaaaaat tagaaaaaaa gaaaaaaaat gaatttccct ccctcctttc   1440
tcatttccct gctttcggcc cctctgtgta gaactattcg agttctcagg tcgagtgctc   1500
gaatcatcta gcttctcttt tttgaggaga gccagagagc cagattcaga atagccagcc   1560
tcctttttag gagagagctc atcccctttt atagttgaag gcagcgacga agccagcggg   1620
gggctacccg tgctccagcc tccctacggc catgatttac atggaacccg ggcttagctc   1680
gggctaccgc catgaggagg aagaagaaga taaggagggg ctagaggaag aagaagagga   1740
agctagccct ggcttcgtcg attcctggct tcgtcgctgg ttgaagggga tgggctctta   1800
caagtcagag aaagagagag aatgtatacg tgtgctatct agtcttgttg cccacgctgt   1860
caggtacgag acggttgtcg gcgcccacaa tactgtttat gtccagatgc atgtggcagg   1920
ctctaccgtg ttcgcctgtt atggcaaatg tcggcgcata caatactatt tgggttctga   1980
cacgcctgaa aggttgcata gtgcctatct ggcatggcct ggtggcaccg tccggcatgt   2040
gcgcaggata tgccagggta cggtccttgg tattacggtt tgacttgagc gccttacctt   2100
atctgctccg cctgatcccc gggctcttac cgagcgggcg tccccggtcg gtcgttccca   2160
gtcggccccg actgtgtcgg tcggggaaga gctgcaagca gaggtccggc gtatccccga   2220
tcgaaaaagg aagtcggagt cagactatgt ctccacctta gccaggcctt ccggtcgggg   2280
atcggatcat tctcccggcc tgtcattagg tatctgggtc ggcccgagag gtgtgcgttg   2340
tcgctacgct gtctgctggg ccgagtttct gttgggaagc gggtccattg gggaccccgg   2400
gtttatgaac ccgacacgtg gtcactatgc tgcatactcc ctatacagcc gctgaccagt   2460
acgctggttc accgcgtcgc ccgcgcggga cggaatggga tgtcacgacc cgctgaacgc   2520
cggggcatgg catcagcggc gaacaggcac ccggcgtgga gctgtccgtg tcaccatcta   2580
cagtgttgac gggacccgca taaaaggaga aaaaaggccc gacggtcctg gaagccttcc   2640
tctccttagc tcttctccct ctttctctct gtgtaacctg ctcttcccct tcgtctataa   2700
aaagggaagt aggacgtccc aggaagagaa gggcggttca ccactctaca tggctataga   2760
```

-continued

```
cataaaaaca cacgccttgg gagcacactc acatcagaga cttgggacct atccctctct   2820
cgctcgtttg taacccctac tacaaacttt tagtgctagt aacacgagca gcagcgacga   2880
actagacgta aggactttct gcccgaacca gtataaacat cgtgtcatct aagcacacca   2940
tacgagccag acgcgcaata ctagaaattt actagtcggt aactcgaaac accgacatct   3000
agctaatctt tttgttttat ttggtttccc tttgaaatct tctaatttag ctttcataga   3060
aataatctag gtattttta ttttatatgt tctatctgtt tgcattaatt ttgatcattt   3120
gatctgaatg ctgtggtcac gagaatcgag tgtttcatgg ccttaaaaca ctcgattatg   3180
ccatctgacc cgttttcaac cattctagtg tttctgagct atatcaatgg tgcagcatgt   3240
tagtatacat atctaactat tactccgtat atgagtgagt tgttaaattt attccaggtg   3300
aaatggcatt aacgatagcc aataggcggc taaattaata gccatactct aacagctcta   3360
aaaaacatat attcatcgag gcacctttat gcaaccacat agtcaacttc aacgtcgctt   3420
gcgtgcgttc tcaagttttc tttcttgcaa attacatttt ttttaaaaaa aagtataatt   3480
tgtatcgtgc gatttttct ctctaggtgt gcgtgactgt gggagtaaca attttgaatc   3540
tcaagaagga aataaaagaa taatactgct gcctactttg aggatttcag tatttttctc   3600
taaaatgttt tggtgtgata tctaaaccgt ctttaaagcc aattgctcaa gattcattca   3660
acaattgaaa cgtctcacat gactaaatga tataaggttg ctaaggtctt tcttgataag   3720
cttttttatg aatttcatct aaattttcga gtgaaactat taaatactaa ggttgctaag   3780
tgtcattctc gctcgagaag tctaacgctt taaactttaa ccaaatatat acaagaaaat   3840
attaatattt atagtacata attagtatca ttagatagat cgttgaatct attttcataa   3900
caaacttatt tgaagaaaca aatgttgttc atatatttct atatacgaat accatagcga   3960
cacttatttt agaatgtagg gagtactccc tttgtgccgc tttgagtgtc gctttggcag   4020
ctagtaccta tgtccacctt cacagcttgt gcctagtacc tagactcttt ctctgtccac   4080
attcatttaa tctctgttgt accttgttcg gagataaaac gactctgata aagggacgag   4140
gaagtagtat gttagaggag tgaagtctac tccctttgcc gcaaaaaggt aatcctaagt   4200
gtgaattgta ttcttttttg accaaaggaa tatacaacaa gaatgatgtc atcatcatgc   4260
ttcgatcctt tttttggta aagcttgagc ttctgtaaaa atagagaaat catgggaaaa   4320
atcacgtttt ggtggttttg atttctagcc tccacaataa ctttggtttt actatttttt   4380
gtttgatttt agtttcagaa gtccactttt gtacgtgctc gtagagccta aacaaaaggc   4440
tttccaaaac gaccttatct tcgagtgttg taaaaaaaat gagcccgttt aacggcgtcg   4500
acaagtctaa cggacaccaa ccagcgaacc accagcgccg agccaagcga agcagactgc   4560
agacggcacg gccgagacgt tgacaccttg gcgcggcaac ggcatctctc tggccccctc   4620
tcgagagttc cgctccacct ccgcatccac ctccacctcc acctccaccg gtggcggttt   4680
ccaagtccgt cccgttccgc cacctgctcc tctcacacgg cacgaaaccg tcacggcacc   4740
ggcagcacag cacgggggat tcctttccca ccgctccgtc cctttctctt cctcgcccgc   4800
ccgttataaa tagccagccc catccctcgt ctctcgtgtt gttcggagcg cacacacaac   4860
ccgatcccca atcaatcgat ccccgcttca aggtacggcg atcctcctcc ctctctctct   4920
accttctctt ctctacacta gatcggcggt ccatggttag ggcctgctag ttccgttcct   4980
gtttttccat ggctgcgagg tacaatagat ctgatggcgt tatgatggtt aacttgtcat   5040
gcttttgcga tttatagtcc ctttagatag ttcgagatcg gtgatccatg gttagtaccc   5100
```

-continued taggctgtgg agtcgggtta gatccgcgct gttagggttc gtatatggag gcgagctgtt 5160
ctgattgtta acttgctggg aatcctggga tggttctagc tgttccgcag atgagatcga 5220
tttcatgatc tgctgtatct atccgtggta tgatgttagc ctttgatatg gttcgatcgt 5280
gctagctacg tcctgtgcac ttaattgtca ggtcataatt tttactatac tttttttttg 5340
gtttggtttg gtttcgtct 5359

<210> SEQ ID NO 64
<211> LENGTH: 63
<212> TYPE: DNA
<213> ORGANISM: Miscanthus sinesis

<400> SEQUENCE: 64
gatttggctg tcgttctaga tcagagtaga aactgtttca aactacctgt tggatttatt 60
aag 63

<210> SEQ ID NO 65
<211> LENGTH: 1391
<212> TYPE: DNA
<213> ORGANISM: Miscanthus sinesis

<400> SEQUENCE: 65
gtagcgtttg gttcctggta tcgaatcata cacgcaccag tgcatcttgg atagccagct 60
ggggcccacc tgtccaaccg tttggttgcc ggatcgaacg agtccattca agaccgaacc 120
atgcagagca atcgaatatt ctcttgtgac gctgtatcat ccagttcggc aaaaaacacc 180
gaatgccgcc atacaggaca ccgtactgag cgtctgcaac tctgcatccc gctcactgct 240
cacatctccg cttgccgcct cacccatccg actcagacca gagccacacg gattactgct 300
gctggtgtgt gtattaacaa aagatccatt tgaccggagc acatgcagct tggatggaaa 360
aaatttatta tattcgtcag tgctgcatat gtactcatac ttgcatgatg gttttattta 420
ttcgacctca tcagtcctgg cactatggaa agtcattgta gtatagattt tttaatataa 480
tataaatcat tggtgactta tcttgcttaa ttttattttc ttattatgaa atatcgttgc 540
attcataata gcaaatttgt gcaaatatat agaatctacg tgaaattctt ggttggacca 600
atacaacaaa cccctcaaac attctcttgt actgaaccat accattccgt acaaccatcc 660
aaacaaaaat catgtatcat catgtacatg taaccaaaca attaacacgc accatcctat 720
tcagacttgt ctcatccata atctatccat ccaggatgat ccatcccatt catctatata 780
cacccaatca aacgctacct aaaatttgga tctgtatgtg tcacatatat cttaataaga 840
tggatggaaa tatctcttta tcttttagat atggataggt atatatgttg ctgtgggttt 900
gttagttata tatatacgtg cttacatacg tgaagaaacc tgctgctaca gtttaataat 960
tcttgttcat ctcaacaaat aacgataggc gtatatgttg ctgtgttttt tactggtact 1020
ttgttagata tatacatgct tacatacatg aagaacacat gctacagttc aaaaattctt 1080
gttcatctca taaacaaaaa ggaggtgtat atgttgctgt gggttttact ggtactttat 1140
tagatatata catgcttaca tagatgaagc aacatgctgc tatggtgttt aataattatt 1200
gtttatctaa taaacaaaca tgctttttaa ttatcttgat atgtttggat gatggcatat 1260
gcagcagcta tgtgtggatt ttaaataccc agcatcatga gcatgcatga ccctgcctta 1320
gtatgcagtt atttgcttga gactgtttct tttgttgata ctcatccttt agttcggtca 1380
ctcttctgca g 1391

<210> SEQ ID NO 66
<211> LENGTH: 4402
<212> TYPE: DNA
<213> ORGANISM: Miscanthus sinesis

<400> SEQUENCE: 66
cacgtggtca ctatgctgca tactccctat acagccgctg accagtacgc tggttcaccg 60
cgtcgcccgc gcgggacgga atgggatgtc acgacccgct gaacgccggg gcatggcatc 120
agcggcgaac aggcacccgg cgtggagctg tccgtgtcac catctacagt gttgacggga 180
cccgcataaa aggagaaaaa aggcccgacg gtcctggaag ccttcctctc cttagctctt 240
ctccctcttt ctctctgtgt aacctgctct tccccttcgt ctataaaaag ggaagtagga 300
cgtcccagga agagaagggc ggttcaccac tctacatggc tatagacata aaaacacacg 360
ccttgggagc acactcacat cagagacttg ggacctatcc ctctctcgct cgtttgtaac 420
ccctactaca aacttttagt gctagtaaca cgagcagcag cgacgaacta gacgtaagga 480
ctttctgccc gaaccagtat aaacatcgtg tcatctaagc acaccatacg agccagacgc 540
gcaatactag aaatttacta gtcggtaact cgaaacaccg acatctagct aatctttttg 600
ttttatttgg tttccctttg aaatcttcta atttagcttt catagaaata atctaggtat 660
tttttatttt atatgttcta tctgtttgca ttaattttga tcatttgatc tgaatgctgt 720
ggtcacgaga atcgagtgtt tcatggcctt aaaacactcg attatgccat ctgacccgtt 780
ttcaaccatt ctagtgtttc tgagctatat caatggtgca gcatgttagt atacatatct 840
aactattact ccgtatatga gtgagttgtt aaatttattc caggtgaaat ggcattaacg 900
atagccaata ggcggctaaa ttaatagcca tactctaaca gctctaaaaa acatatattc 960
atcgaggcac ctttatgcaa ccacatagtc aacttcaacg tcgcttgcgt gcgttctcaa 1020
gttttctttc ttgcaaatta catttttttt aaaaaaaagt ataatttgta tcgtgcgatt 1080
ttttctctct aggtgtgcgt gactgtggga gtaacaattt tgaatctcaa gaaggaaata 1140
aaagaataat actgctgcct actttgagga tttcagtatt tttctctaaa atgttttggt 1200
gtgatatcta aaccgtcttt aaagccaatt gctcaagatt cattcaacaa ttgaaacgtc 1260
tcacatgact aaatgatata aggttgctaa ggtctttctt gataagcttt tttatgaatt 1320
tcatctaaat tttcgagtga aactattaaa tactaaggtt gctaagtgtc attctcgctc 1380
gagaagtcta acgctttaaa ctttaaccaa atatatacaa gaaaatatta atatttatag 1440
tacataatta gtatcattag atagatcgtt gaatctattt tcataacaaa cttatttgaa 1500
gaaacaaatg ttgttcatat atttctatat acgaatacca tagcgacact tattttagaa 1560
tgtagggagt actccctttg tgccgctttg agtgtcgctt tggcagctag tacctatgtc 1620
caccttcaca gcttgtgcct agtacctaga ctctttctct gtccacattc atttaatctc 1680
tgttgtacct tgttcggaga taaaacgact ctgataaagg gacgaggaag tagtatgtta 1740
gaggagtgaa gtctactccc tttgccgcaa aaaggtaatc ctaagtgtga attgtattct 1800
tttttgacca aaggaatata caacaagaat gatgtcatca tcatgcttcg atcctttttt 1860
ttggtaaagc ttgagcttct gtaaaaatag agaaatcatg ggaaaaatca cgttttggtg 1920
gttttgattt ctagcctcca caataacttt ggttttacta ttttttgttt gattttagtt 1980
tcagaagtcc acttttgtac gtgctcgtag agcctaaaca aaaggctttc caaaacgacc 2040
ttatcttcga gtgttgtaaa aaaaatgagc ccgtttaacg gcgtcgacaa gtctaacgga 2100
caccaaccag cgaaccacca gcgccgagcc aagcgaagca gactgcagac ggcacggccg 2160

-continued

```
agacgttgac accttggcgc ggcaacggca tctctctggc cccctctcga gagttccgct   2220
ccacctccgc atccacctcc acctccacct ccaccggtgg cggtttccaa gtccgtcccg   2280
ttccgccacc tgctcctctc acacggcacg aaaccgtcac ggcaccggca gcacagcacg   2340
ggggattcct ttcccaccgc tccgtccctt tctcttcctc gcccgcccgt tataaatagc   2400
cagccccatc cctcgtctct cgtgttgttc ggagcgcaca cacaacccga tccccaatca   2460
atcgatcccc gcttcaaggt acggcgatcc tcctccctct ctctctacct tctcttctct   2520
acactagatc ggcggtccat ggttagggcc tgctagttcc gttcctgttt ttccatggct   2580
gcgaggtaca atagatctga tggcgttatg atggttaact tgtcatgctt ttgcgattta   2640
tagtcccttt agatagttcg agatcggtga tccatggtta gtaccctagg ctgtggagtc   2700
gggttagatc cgcgctgtta gggttcgtat atggaggcga gctgttctga ttgttaactt   2760
gctgggaatc ctgggatggt tctagctgtt ccgcagatga gatcgatttc atgatctgct   2820
gtatctatcc gtggtatgat gttagccttt gatatggttc gatcgtgcta gctacgtcct   2880
gtgcacttaa ttgtcaggtc ataattttta ctatactttt tttttggttt ggtttggttt   2940
cgtctgattt ggctgtcgtt ctagatcaga gtagaaactg tttcaaacta cctgttggat   3000
ttattaaggt agcgtttggt tcctggtatc gaatcataca cgcaccagtg catcttggat   3060
agccagctgg ggcccacctg tccaaccgtt tggttgccgg atcgaacgag tccattcaag   3120
accgaaccat gcagagcaat cgaatattct cttgtgacgc tgtatcatcc agttcggcaa   3180
aaaacaccga atgccgccat acaggacacc gtactgagcg tctgcaactc tgcatcccgc   3240
tcactgctca catctccgct tgccgcctca cccatccgac tcagaccaga gccacacgga   3300
ttactgctgc tggtgtgtgt attaacaaaa gatccattgg accggagcac atgcagcttg   3360
gatggaaaaa atttattata ttcgtcagtg ctgcatatgt actcatactt gcatgatggt   3420
tttatttatt cgacctcatc agtcctggca ctatggaaag tcattgtagt atagattttt   3480
taatataata taaatcattg gtgacttatc ttgcttaatt ttattttctt attatgaaat   3540
atcgttgcat tcataatagc aaatttgtgc aaatatatag aatctacgtg aaattcttgg   3600
ttggaccaat acaacaaacc cctcaaacat tctcttgtac tgaaccatac cattccgtac   3660
aaccatccaa acaaaaatca tgtatcatca tgtacatgta accaaacaat taacacgcac   3720
catcctattc agacttgtct catccataat ctatccatcc aggatgatcc atcccattca   3780
tctatataca cccaatcaaa cgctacctaa aatttggatc tgtatgtgtc acatatatct   3840
taataagatg gatggaaata tctctttatc ttttagatat ggataggtat atatgttgct   3900
gtgggtttgt tagttatata tatacgtgct tacatacgtg aagaaacctg ctgctacagt   3960
ttaataattc ttgttcatct caacaaataa cgataggcgt atatgttgct gtgtttttta   4020
ctggtacttt gttagatata tacatgctta catacatgaa gaacacatgc tacagttcaa   4080
aaattcttgt tcatctcata aacaaaaagg aggtgtatat gttgctgtgg gttttactgg   4140
tactttatta gatatataca tgcttacata gatgaagcaa catgctgcta tggtgtttaa   4200
taattattgt ttatctaata aacaaacatg ctttttaatt atcttgatat gtttggatga   4260
tggcatatgc agcagctatg tgtggatttt aaatacccag catcatgagc atgcatgacc   4320
ctgccttagt atgcagttat ttgcttgaga ctgtttcttt tgttgatact catcctttag   4380
ttcggtcact cttctgcagg tg                                            4402
```

<210> SEQ ID NO 67
<211> LENGTH: 2423

<212> TYPE: DNA
<213> ORGANISM: Miscanthus sinesis

<400> SEQUENCE: 67

```
cacgtggtca ctatgctgca tactccctat acagccgctg accagtacgc tggttcaccg      60
cgtcgcccgc gcgggacgga atgggatgtc acgacccgct gaacgccggg gcatggcatc     120
agcggcgaac aggcacccgg cgtggagctg tccgtgtcac catctacagt gttgacggga     180
cccgcataaa aggagaaaaa aggcccgacg gtcctggaag ccttcctctc cttagctctt     240
ctccctcttt ctctctgtgt aacctgctct tccccttcgt ctataaaaag ggaagtagga     300
cgtcccagga agagaagggc ggttcaccac tctacatggc tatagacata aaaacacacg     360
ccttgggagc acactcacat cagagacttg ggacctatcc ctctctcgct cgtttgtaac     420
ccctactaca aacttttagt gctagtaaca cgagcagcag cgacgaacta gacgtaagga     480
ctttctgccc gaaccagtat aaacatcgtg tcatctaagc acaccatacg agccagacgc     540
gcaatactag aaatttacta gtcggtaact cgaaacaccg acatctagct aatctttttg     600
ttttatttgg tttccctttg aaatcttcta atttagcttt catagaaata atctaggtat     660
tttttatttt atatgttcta tctgtttgca ttaattttga tcatttgatc tgaatgctgt     720
ggtcacgaga atcgagtgtt tcatggcctt aaaacactcg attatgccat ctgacccgtt     780
ttcaaccatt ctagtgtttc tgagctatat caatggtgca gcatgttagt atacatatct     840
aactattact ccgtatatga gtgagttgtt aaatttattc caggtgaaat ggcattaacg     900
atagccaata ggcggctaaa ttaatagcca tactctaaca gctctaaaaa acatatattc     960
atcgaggcac ctttatgcaa ccacatagtc aacttcaacg tcgcttgcgt gcgttctcaa    1020
gttttctttc ttgcaaatta catttttttt aaaaaaaagt ataatttgta tcgtgcgatt    1080
ttttctctct aggtgtgcgt gactgtggga gtaacaattt tgaatctcaa gaaggaaata    1140
aaagaataat actgctgcct actttgagga tttcagtatt tttctctaaa atgttttggt    1200
gtgatatcta aaccgtcttt aaagccaatt gctcaagatt cattcaacaa ttgaaacgtc    1260
tcacatgact aaatgatata aggttgctaa ggtctttctt gataagcttt tttatgaatt    1320
tcatctaaat tttcgagtga aactattaaa tactaaggtt gctaagtgtc attctcgctc    1380
gagaagtcta acgctttaaa ctttaaccaa atatatacaa gaaaatatta atatttatag    1440
tacataatta gtatcattag atagatcgtt gaatctattt tcataacaaa cttatttgaa    1500
gaaacaaatg ttgttcatat atttctatat acgaatacca tagcgacact tattttagaa    1560
tgtagggagt actccctttg tgccgctttg agtgtcgctt tggcagctag tacctatgtc    1620
caccttcaca gcttgtgcct agtacctaga ctctttctct gtccacattc atttaatctc    1680
tgttgtacct tgttcggaga taaaacgact ctgataaagg gacgaggaag tagtatgtta    1740
gaggagtgaa gtctactccc tttgccgcaa aaaggtaatc ctaagtgtga attgtattct    1800
tttttgacca aaggaatata caacaagaat gatgtcatca tcatgcttcg atcctttttt    1860
ttggtaaagc ttgagcttct gtaaaaatag agaaatcatg ggaaaaatca cgttttggtg    1920
gttttgattt ctagcctcca caataacttt ggttttacta ttttttgttt gattttagtt    1980
tcagaagtcc acttttgtac gtgctcgtag agcctaaaca aaaggctttc caaaacgacc    2040
ttatcttcga gtgttgtaaa aaaaatgagc ccgtttaacg gcgtcgacaa gtctaacgga    2100
caccaaccag cgaaccacca gcgccgagcc aagcgaagca gactgcagac ggcacggccg    2160
agacgttgac accttggcgc ggcaacggca tctctctggc cccctctcga gagttccgct    2220
```

-continued

```
ccacctccgc atccacctcc acctccacct ccaccggtgg cggtttccaa gtccgtcccg   2280

ttccgccacc tgctcctctc acacggcacg aaaccgtcac ggcaccggca gcacagcacg   2340

ggggattcct ttcccaccgc tccgtccctt tctcttcctc gcccgcccgt tataaatagc   2400

cagccccatc cctcgtctct cgt                                             2423
```

<210> SEQ ID NO 68
<211> LENGTH: 55
<212> TYPE: DNA
<213> ORGANISM: Miscanthus sinesis

<400> SEQUENCE: 68

```
gttgttcgga gcgcacacac aacccgatcc ccaatcaatc gatccccgct tcaag           55
```

<210> SEQ ID NO 69
<211> LENGTH: 1924
<212> TYPE: DNA
<213> ORGANISM: Miscanthus sinesis

<400> SEQUENCE: 69

```
gtacggcgat cctcctccct ctctctctac cttctcttct ctacactaga tcggcggtcc     60

atggttaggg cctgctagtt ccgttcctgt ttttccatgg ctgcgaggta caatagatct    120

gatggcgtta tgatggttaa cttgtcatgc ttttgcgatt tatagtccct ttagatagtt    180

cgagatcggt gatccatggt tagtacccta ggctgtggag tcgggttaga tccgcgctgt    240

tagggttcgt atatggaggc gagctgttct gattgttaac ttgctgggaa tcctgggatg    300

gttctagctg ttccgcagat gagatcgatt tcatgatctg ctgtatctat ccgtggtatg    360

atgttagcct ttgatatggt tcgatcgtgc tagctacgtc ctgtgcactt aattgtcagg    420

tcataatttt tactatactt ttttttggt ttggtttggt ttcgtctgat ttggctgtcg    480

ttctagatca gagtagaaac tgtttcaaac tacctgttgg atttattaag gtagcgtttg    540

gttcctggta tcgaatcata cacgcaccag tgcatcttgg atagccagct ggggcccacc    600

tgtccaaccg tttggttgcc ggatcgaacg agtccattca agaccgaacc atgcagagca    660

atcgaatatt ctcttgtgac gctgtatcat ccagttcggc aaaaaacacc gaatgccgcc    720

atacaggaca ccgtactgag cgtctgcaac tctgcatccc gctcactgct cacatctccg    780

cttgccgcct cacccatccg actcagacca gagccacacg gattactgct gctggtgtgt    840

gtattaacaa aagatccatt tgaccggagc acatgcagct tggatggaaa aaatttatta    900

tattcgtcag tgctgcatat gtactcatac ttgcatgatg gttttattta ttcgacctca    960

tcagtcctgg cactatggaa agtcattgta gtatagattt tttaatataa tataaatcat   1020

tggtgactta tcttgcttaa ttttattttc ttattatgaa atatcgttgc attcataata   1080

gcaaatttgt gcaaatatat agaatctacg tgaaattctt ggttggacca atacaacaaa   1140

cccctcaaac attctcttgt actgaaccat accattccgt acaaccatcc aaacaaaaat   1200

catgtatcat catgtacatg taaccaaaca attaacacgc accatcctat tcagacttgt   1260

ctcatccata atctatccat ccaggatgat ccatcccatt catctatata cacccaatca   1320

aacgctacct aaaatttgga tctgtatgtg tcacatatat cttaataaga tggatggaaa   1380

tatctcttta tcttttagat atggataggt atatatgttg ctgtgggttt gttagttata   1440

tatatacgtg cttacatacg tgaagaaacc tgctgctaca gtttaataat tcttgttcat   1500

ctcaacaaat aacgataggc gtatatgttg ctgtgttttt tactggtact ttgttagata   1560

tatacatgct tacatacatg aagaacacat gctacagttc aaaaattctt gttcatctca   1620
```

-continued taaacaaaaa ggaggtgtat atgttgctgt gggttttact ggtactttat tagatatata 1680
catgcttaca tagatgaagc aacatgctgc tatggtgttt aataattatt gtttatctaa 1740
taaacaaaca tgctttttaa ttatcttgat atgtttggat gatggcatat gcagcagcta 1800
tgtgtggatt ttaaataccc agcatcatga gcatgcatga ccctgcctta gtatgcagtt 1860
atttgcttga gactgtttct tttgttgata ctcatccttt agttcggtca ctcttctgca 1920
ggtg 1924

<210> SEQ ID NO 70
<211> LENGTH: 3426
<212> TYPE: DNA
<213> ORGANISM: Miscanthus sinesis

<400> SEQUENCE: 70
gcaaccacat agtcaacttc aacgtcgctt gcgtgcgttc tcaagttttc tttcttgcaa 60
attacatttt ttttaaaaaa aagtataatt tgtatcgtgc gatttttttct ctctaggtgt 120 gcgtgactgt gggagtaaca attttgaatc tcaagaagga aataaaagaa taatactgct 180
gcctactttg aggatttcag tatttttctc taaaatgttt tggtgtgata tctaaaccgt 240
ctttaaagcc aattgctcaa gattcattca acaattgaaa cgtctcacat gactaaatga 300
tataaggttg ctaaggtctt tcttgataag ctttttatg aatttcatct aaattttcga 360
gtgaaactat taaatactaa ggttgctaag tgtcattctc gctcgagaag tctaacgctt 420
taaactttaa ccaaatatat acaagaaaat attaatattt atagtacata attagtatca 480
ttagatagat cgttgaatct attttcataa caaacttatt tgaagaaaca aatgttgttc 540
atatatttct atatacgaat accatagcga cacttatttt agaatgtagg gagtactccc 600
tttgtgccgc tttgagtgtc gctttggcag ctagtaccta tgtccacctt cacagcttgt 660
gcctagtacc tagactcttt ctctgtccac attcatttaa tctctgttgt accttgttcg 720
gagataaaac gactctgata aagggacgag gaagtagtat gttagaggag tgaagtctac 780
tccctttgcc gcaaaaaggt aatcctaagt gtgaattgta ttctttttttg accaaaggaa 840 tatacaacaa gaatgatgtc atcatcatgc ttcgatcctt ttttttggta aagcttgagc 900
ttctgtaaaa atagagaaat catgggaaaa atcacgtttt ggtggttttg atttctagcc 960
tccacaataa ctttggtttt actatttttt gtttgatttt agtttcagaa gtccactttt 1020
gtacgtgctc gtagagccta aacaaaaggc tttccaaaac gaccttatct tcgagtgttg 1080
taaaaaaaat gagcccgttt aacggcgtcg acaagtctaa cggacaccaa ccagcgaacc 1140
accagcgccg agccaagcga agcagactgc agacggcacg gccgagacgt tgacaccttg 1200
gcgcggcaac ggcatctctc tggccccctc tcgagagttc cgctccacct ccgcatccac 1260
ctccacctcc acctccaccg gtggcggttt ccaagtccgt cccgttccgc cacctgctcc 1320
tctcacacgg cacgaaaccg tcacggcacc ggcagcacag cacgggggat tcctttccca 1380
ccgctccgtc cctttctctt cctcgcccgc ccgttataaa tagccagccc catccctcgt 1440
ctctcgtgtt gttcggagcg cacacacaac ccgatcccca atcaatcgat ccccgcttca 1500
aggtacggcg atcctcctcc ctctctctct accttctctt ctctacacta gatcggcggt 1560
ccatggttag ggcctgctag ttccgttcct gtttttccat ggctgcgagg tacaatagat 1620
ctgatggcgt tatgatggtt aacttgtcat gcttttgcga tttatagtcc ctttagatag 1680
ttcgagatcg gtgatccatg gttagtaccc taggctgtgg agtcgggtta gatccgcgct 1740

-continued

```
gttagggttc gtatatggag gcgagctgtt ctgattgtta acttgctggg aatcctggga   1800

tggttctagc tgttccgcag atgagatcga tttcatgatc tgctgtatct atccgtggta   1860

tgatgttagc ctttgatatg gttcgatcgt gctagctacg tcctgtgcac ttaattgtca   1920

ggtcataatt tttactatac tttttttttg gtttggtttg gtttcgtctg atttggctgt   1980

cgttctagat cagagtagaa actgtttcaa actacctgtt ggatttatta aggtagcgtt   2040

tggttcctgg tatcgaatca tacacgcacc agtgcatctt ggatagccag ctggggccca   2100

cctgtccaac cgtttggttg ccggatcgaa cgagtccatt caagaccgaa ccatgcagag   2160

caatcgaata ttctcttgtg acgctgtatc atccagttcg gcaaaaaaca ccgaatgccg   2220

ccatacagga caccgtactg agcgtctgca actctgcatc ccgctcactg ctcacatctc   2280

cgcttgccgc ctcacccatc cgactcagac cagagccaca cggattactg ctgctggtgt   2340

gtgtattaac aaaagatcca tttgaccgga gcacatgcag cttggatgga aaaaatttat   2400

tatattcgtc agtgctgcat atgtactcat acttgcatga tggttttatt tattcgacct   2460

catcagtcct ggcactatgg aaagtcattg tagtatagat tttttaatat aatataaatc   2520

attggtgact tatcttgctt aattttattt tcttattatg aaatatcgtt gcattcataa   2580

tagcaaattt gtgcaaatat atagaatcta cgtgaaattc ttggttggac caatacaaca   2640

aacccctcaa acattctctt gtactgaacc ataccattcc gtacaaccat ccaaacaaaa   2700

atcatgtatc atcatgtaca tgtaaccaaa caattaacac gcaccatcct attcagactt   2760

gtctcatcca taatctatcc atccaggatg atccatccca ttcatctata tacacccaat   2820

caaacgctac ctaaaatttg gatctgtatg tgtcacatat atcttaataa gatggatgga   2880

aatatctctt tatcttttag atatggatag gtatatatgt tgctgtgggt ttgttagtta   2940

tatatatacg tgcttacata cgtgaagaaa cctgctgcta cagtttaata attcttgttc   3000

atctcaacaa ataacgatag gcgtatatgt tgctgtgttt tttactggta ctttgttaga   3060

tatatacatg cttacataca tgaagaacac atgctacagt tcaaaaattc ttgttcatct   3120

cataaacaaa aaggaggtgt atatgttgct gtgggtttta ctggtacttt attagatata   3180

tacatgctta catagatgaa gcaacatgct gctatggtgt ttaataatta ttgtttatct   3240

aataaacaaa catgcttttt aattatcttg atatgtttgg atgatggcat atgcagcagc   3300

tatgtgtgga ttttaaatac ccagcatcat gagcatgcat gaccctgcct tagtatgcag   3360

ttatttgctt gagactgttt cttttgttga tactcatcct ttagttcggt cactcttctg   3420

caggtg                                                              3426
```

<210> SEQ ID NO 71
<211> LENGTH: 1447
<212> TYPE: DNA
<213> ORGANISM: Miscanthus sinesis

<400> SEQUENCE: 71

```
gcaaccacat agtcaacttc aacgtcgctt gcgtgcgttc tcaagttttc tttcttgcaa     60

attacatttt ttttaaaaaa aagtataatt tgtatcgtgc gatttttttct ctctaggtgt    120

gcgtgactgt gggagtaaca attttgaatc tcaagaagga aataaaagaa taatactgct    180

gcctactttg aggatttcag tatttttctc taaaatgttt tggtgtgata tctaaaccgt    240

ctttaaagcc aattgctcaa gattcattca acaattgaaa cgtctcacat gactaaatga    300

tataaggttg ctaaggtctt tcttgataag cttttttatg aatttcatct aaattttcga    360

gtgaaactat taaatactaa ggttgctaag tgtcattctc gctcgagaag tctaacgctt    420
```

taaactttaa ccaaatatat acaagaaaat attaatattt atagtacata attagtatca 480
ttagatagat cgttgaatct attttcataa caaacttatt tgaagaaaca aatgttgttc 540
atatatttct atatacgaat accatagcga cacttatttt agaatgtagg gagtactccc 600
tttgtgccgc tttgagtgtc gctttggcag ctagtaccta tgtccacctt cacagcttgt 660
gcctagtacc tagactcttt ctctgtccac attcatttaa tctctgttgt accttgttcg 720
gagataaaac gactctgata aagggacgag gaagtagtat gttagaggag tgaagtctac 780
tccctttgcc gcaaaaaggt aatcctaagt gtgaattgta ttcttttttg accaaaggaa 840
tatacaacaa gaatgatgtc atcatcatgc ttcgatcctt tttttggta aagcttgagc 900 ttctgtaaaa atagagaaat catgggaaaa atcacgtttt ggtggttttg atttctagcc 960
tccacaataa ctttggtttt actatttttt gtttgatttt agtttcagaa gtccactttt 1020
gtacgtgctc gtagagccta aacaaaaggc tttccaaaac gaccttatct tcgagtgttg 1080
taaaaaaaat gagcccgttt aacggcgtcg acaagtctaa cggacaccaa ccagcgaacc 1140
accagcgccg agccaagcga agcagactgc agacggcacg gccgagacgt tgacaccttg 1200
gcgcggcaac ggcatctctc tggccccctc tcgagagttc cgctccacct ccgcatccac 1260
ctccacctcc acctccaccg gtggcggttt ccaagtccgt cccgttccgc cacctgctcc 1320
tctcacacgg cacgaaaccg tcacggcacc ggcagcacag cacgggggat tcctttccca 1380
ccgctccgtc cctttctctt cctcgcccgc ccgttataaa tagccagccc catccctcgt 1440
ctctcgt 1447

<210> SEQ ID NO 72
<211> LENGTH: 2878
<212> TYPE: DNA
<213> ORGANISM: Miscanthus sinesis

<400> SEQUENCE: 72
ctatatacga ataccatagc gacacttatt ttagaatgta gggagtactc cctttgtgcc 60
gctttgagtg tcgctttggc agctagtacc tatgtccacc ttcacagctt gtgcctagta 120
cctagactct ttctctgtcc acattcattt aatctctgtt gtaccttgtt cggagataaa 180
acgactctga taaagggacg aggaagtagt atgttagagg agtgaagtct actccctttg 240
ccgcaaaaag gtaatcctaa gtgtgaattg tattcttttt tgaccaaagg aatatacaac 300
aagaatgatg tcatcatcat gcttcgatcc tttttttgg taaagcttga gcttctgtaa 360
aaatagagaa atcatgggaa aaatcacgtt ttggtggttt tgatttctag cctccacaat 420
aactttggtt ttactatttt ttgtttgatt ttagtttcag aagtccactt ttgtacgtgc 480
tcgtagagcc taaacaaaag gctttccaaa acgaccttat cttcgagtgt tgtaaaaaaa 540
atgagcccgt ttaacggcgt cgacaagtct aacggacacc aaccagcgaa ccaccagcgc 600
cgagccaagc gaagcagact gcagacggca cggccgagac gttgacacct tggcgcggca 660
acggcatctc tctggccccc tctcgagagt tccgctccac ctccgcatcc acctccacct 720
ccacctccac cggtggcggt ttccaagtcc gtcccgttcc gccacctgct cctctcacac 780
ggcacgaaac cgtcacggca ccggcagcac agcacggggg attcctttcc caccgctccg 840
tccctttctc ttcctcgccc gcccgttata aatagccagc cccatccctc gtctctcgtg 900
ttgttcggag cgcacacaca acccgatccc caatcaatcg atccccgctt caaggtacgg 960
cgatcctcct ccctctctct ctaccttctc ttctctacac tagatcggcg gtccatggtt 1020

-continued

```
agggcctgct agttccgttc ctgtttttcc atggctgcga ggtacaatag atctgatggc   1080
gttatgatgg ttaacttgtc atgcttttgc gatttatagt ccctttagat agttcgagat   1140
cggtgatcca tggttagtac cctaggctgt ggagtcgggt tagatccgcg ctgttagggt   1200
tcgtatatgg aggcgagctg ttctgattgt taacttgctg ggaatcctgg gatggttcta   1260
gctgttccgc agatgagatc gatttcatga tctgctgtat ctatccgtgg tatgatgtta   1320
gcctttgata tggttcgatc gtgctagcta cgtcctgtgc acttaattgt caggtcataa   1380
tttttactat actttttttt tggtttggtt tggtttcgtc tgatttggct gtcgttctag   1440
atcagagtag aaactgtttc aaactacctg ttggatttat taaggtagcg tttggttcct   1500
ggtatcgaat catacacgca ccagtgcatc ttggatagcc agctggggcc cacctgtcca   1560
accgtttggt tgccggatcg aacgagtcca ttcaagaccg aaccatgcag agcaatcgaa   1620
tattctcttg tgacgctgta tcatccagtt cggcaaaaaa caccgaatgc cgccatacag   1680
gacaccgtac tgagcgtctg caactctgca tcccgctcac tgctcacatc tccgcttgcc   1740
gcctcaccca tccgactcag accagagcca cacggattac tgctgctggt gtgtgtatta   1800
acaaaagatc catttgaccg gagcacatgc agcttggatg gaaaaaattt attatattcg   1860
tcagtgctgc atatgtactc atacttgcat gatggtttta tttattcgac ctcatcagtc   1920
ctggcactat ggaaagtcat tgtagtatag attttttaat ataatataaa tcattggtga   1980
cttatcttgc ttaattttat tttcttatta tgaaatatcg ttgcattcat aatagcaaat   2040
ttgtgcaaat atatagaatc tacgtgaaat tcttggttgg accaatacaa caaacccctc   2100
aaacattctc ttgtactgaa ccataccatt ccgtacaacc atccaaacaa aaatcatgta   2160
tcatcatgta catgtaacca aacaattaac acgcaccatc ctattcagac ttgtctcatc   2220
cataatctat ccatccagga tgatccatcc cattcatcta tatacaccca atcaaacgct   2280
acctaaaatt tggatctgta tgtgtcacat atatcttaat aagatggatg gaaatatctc   2340
tttatctttt agatatggat aggtatatat gttgctgtgg gtttgttagt tatatatata   2400
cgtgcttaca tacgtgaaga aacctgctgc tacagtttaa taattcttgt tcatctcaac   2460
aaataacgat aggcgtatat gttgctgtgt tttttactgg tactttgtta gatatataca   2520
tgcttacata catgaagaac acatgctaca gttcaaaaat tcttgttcat ctcataaaca   2580
aaaaggaggt gtatatgttg ctgtgggttt tactggtact ttattagata tatacatgct   2640
tacatagatg aagcaacatg ctgctatggt gtttaataat tattgtttat ctaataaaca   2700
aacatgcttt ttaattatct tgatatgttt ggatgatggc atatgcagca gctatgtgtg   2760
gattttaaat acccagcatc atgagcatgc atgaccctgc cttagtatgc agttatttgc   2820
ttgagactgt ttcttttgtt gatactcatc ctttagttcg gtcactcttc tgcaggtg     2878
```

<210> SEQ ID NO 73
<211> LENGTH: 899
<212> TYPE: DNA
<213> ORGANISM: Miscanthus sinesis

<400> SEQUENCE: 73

```
ctatatacga ataccatagc gacacttatt ttagaatgta gggagtactc cctttgtgcc     60
gctttgagtg tcgctttggc agctagtacc tatgtccacc ttcacagctt gtgcctagta    120
cctagactct ttctctgtcc acattcattt aatctctgtt gtaccttgtt cggagataaa    180
acgactctga taaagggacg aggaagtagt atgttagagg agtgaagtct actccctttg    240
ccgcaaaaag gtaatcctaa gtgtgaattg tattcttttt tgaccaaagg aatatacaac    300
```

```
aagaatgatg tcatcatcat gcttcgatcc tttttttttgg taaagcttga gcttctgtaa    360

aaatagagaa atcatgggaa aaatcacgtt ttggtggttt tgatttctag cctccacaat    420

aactttggtt ttactatttt ttgtttgatt ttagtttcag aagtccactt ttgtacgtgc    480

tcgtagagcc taaacaaaag gctttccaaa acgaccttat cttcgagtgt tgtaaaaaaa    540

atgagcccgt ttaacggcgt cgacaagtct aacggacacc aaccagcgaa ccaccagcgc    600

cgagccaagc gaagcagact gcagacggca cggccgagac gttgacacct tggcgcggca    660

acggcatctc tctggccccc tctcgagagt tccgctccac ctccgcatcc acctccacct    720

ccacctccac cggtggcggt ttccaagtcc gtcccgttcc gccacctgct cctctcacac    780

ggcacgaaac cgtcacggca ccggcagcac agcacggggg attcctttcc caccgctccg    840

tccctttctc ttcctcgccc gcccgttata aatagccagc cccatccctc gtctctcgt     899
```

<210> SEQ ID NO 74
<211> LENGTH: 2670
<212> TYPE: DNA
<213> ORGANISM: Miscanthus sinesis

<400> SEQUENCE: 74

```
gtatgttaga ggagtgaagt ctactccctt tgccgcaaaa aggtaatcct aagtgtgaat     60

tgtattcttt tttgaccaaa ggaatataca acaagaatga tgtcatcatc atgcttcgat    120

cctttttttt ggtaaagctt gagcttctgt aaaaatagag aaatcatggg aaaaatcacg    180

ttttggtggt tttgatttct agcctccaca ataactttgg ttttactatt ttttgtttga    240

ttttagtttc agaagtccac ttttgtacgt gctcgtagag cctaaacaaa aggctttcca    300

aaacgacctt atcttcgagt gttgtaaaaa aaatgagccc gtttaacggc gtcgacaagt    360

ctaacggaca ccaaccagcg aaccaccagc gccgagccaa gcgaagcaga ctgcagacgg    420

cacggccgag acgttgacac cttggcgcgg caacggcatc tctctggccc cctctcgaga    480

gttccgctcc acctccgcat ccacctccac ctccacctcc accggtggcg gtttccaagt    540

ccgtcccgtt ccgccacctg ctcctctcac acggcacgaa accgtcacgg caccggcagc    600

acagcacggg ggattccttt cccaccgctc cgtccctttc tcttcctcgc ccgcccgtta    660

taaatagcca gccccatccc tcgtctctcg tgttgttcgg agcgcacaca caacccgatc    720

cccaatcaat cgatccccgc ttcaaggtac ggcgatcctc ctccctctct ctctaccttc    780

tcttctctac actagatcgg cggtccatgg ttagggcctg ctagttccgt tcctgttttt    840

ccatggctgc gaggtacaat agatctgatg gcgttatgat ggttaacttg tcatgctttt    900

gcgatttata gtccctttag atagttcgag atcggtgatc catggttagt accctaggct    960

gtggagtcgg gttagatccg cgctgttagg gttcgtatat ggaggcgagc tgttctgatt   1020

gttaacttgc tgggaatcct gggatggttc tagctgttcc gcagatgaga tcgatttcat   1080

gatctgctgt atctatccgt ggtatgatgt tagcctttga tatggttcga tcgtgctagc   1140

tacgtcctgt gcacttaatt gtcaggtcat aatttttact atactttttt tttggtttgg   1200

tttggtttcg tctgatttgg ctgtcgttct agatcagagt agaaactgtt tcaaactacc   1260

tgttggattt attaaggtag cgtttggttc ctggtatcga atcatacacg caccagtgca   1320

tcttggatag ccagctgggg cccacctgtc caaccgtttg gttgccggat cgaacgagtc   1380

cattcaagac cgaaccatgc agagcaatcg aatattctct tgtgacgctg tatcatccag   1440

ttcggcaaaa aacaccgaat gccgccatac aggacaccgt actgagcgtc tgcaactctg   1500
```

```
catcccgctc actgctcaca tctccgcttg ccgcctcacc catccgactc agaccagagc   1560
cacacggatt actgctgctg gtgtgtgtat taacaaaaga tccatttgac cggagcacat   1620
gcagcttgga tggaaaaaat ttattatatt cgtcagtgct gcatatgtac tcatacttgc   1680
atgatggttt tatttattcg acctcatcag tcctggcact atggaaagtc attgtagtat   1740
agatttttta atataatata aatcattggt gacttatctt gcttaatttt attttcttat   1800
tatgaaatat cgttgcattc ataatagcaa atttgtgcaa atatatagaa tctacgtgaa   1860
attcttggtt ggaccaatac aacaaacccc tcaaacattc tcttgtactg aaccatacca   1920
ttccgtacaa ccatccaaac aaaaatcatg tatcatcatg tacatgtaac caaacaatta   1980
acacgcacca tcctattcag acttgtctca tccataatct atccatccag gatgatccat   2040
cccattcatc tatatacacc caatcaaacg ctacctaaaa tttggatctg tatgtgtcac   2100
atatatctta ataagatgga tggaaatatc tctttatctt ttagatatgg ataggtatat   2160
atgttgctgt gggtttgtta gttatatata tacgtgctta catacgtgaa gaaacctgct   2220
gctacagttt aataattctt gttcatctca acaaataacg ataggcgtat atgttgctgt   2280
gttttttact ggtactttgt tagatatata catgcttaca tacatgaaga acacatgcta   2340
cagttcaaaa attcttgttc atctcataaa caaaaaggag gtgtatatgt tgctgtgggt   2400
tttactggta ctttattaga tatatacatg cttacataga tgaagcaaca tgctgctatg   2460
gtgtttaata attattgttt atctaataaa caaacatgct ttttaattat cttgatatgt   2520
ttggatgatg gcatatgcag cagctatgtg tggattttaa atacccagca tcatgagcat   2580
gcatgaccct gccttagtat gcagttattt gcttgagact gtttcttttg ttgatactca   2640
tcctttagtt cggtcactct tctgcaggtg                                    2670
```

<210> SEQ ID NO 75
<211> LENGTH: 691
<212> TYPE: DNA
<213> ORGANISM: Miscanthus sinesis

<400> SEQUENCE: 75

```
gtatgttaga ggagtgaagt ctactccctt tgccgcaaaa aggtaatcct aagtgtgaat     60
tgtattcttt tttgaccaaa ggaatataca acaagaatga tgtcatcatc atgcttcgat    120
ccttttttt ggtaaagctt gagcttctgt aaaaatagag aaatcatggg aaaaatcacg    180
ttttggtggt tttgatttct agcctccaca ataactttgg ttttactatt ttttgtttga    240
ttttagtttc agaagtccac ttttgtacgt gctcgtagag cctaaacaaa aggctttcca    300
aaacgacctt atcttcgagt gttgtaaaaa aaatgagccc gtttaacggc gtcgacaagt    360
ctaacggaca ccaaccagcg aaccaccagc gccgagccaa gcgaagcaga ctgcagacgg    420
cacggccgag acgttgacac cttggcgcgg caacggcatc tctctggccc cctctcgaga    480
gttccgctcc acctccgcat ccacctccac ctccacctcc accggtggcg gtttccaagt    540
ccgtcccgtt ccgccacctg ctcctctcac acggcacgaa accgtcacgg caccggcagc    600
acagcacggg ggattccttt cccaccgctc cgtccctttc tcttcctcgc ccgcccgtta    660
taaatagcca gccccatccc tcgtctctcg t                                   691
```

<210> SEQ ID NO 76
<211> LENGTH: 2485
<212> TYPE: DNA
<213> ORGANISM: Miscanthus sinesis

<400> SEQUENCE: 76

-continued

```
gtggttttga tttctagcct ccacaataac tttggtttta ctatttttttg tttgatttta     60
gtttcagaag tccacttttg tacgtgctcg tagagcctaa acaaaaggct ttccaaaacg    120
accttatctt cgagtgttgt aaaaaaaatg agcccgttta acggcgtcga caagtctaac    180
ggacaccaac cagcgaacca ccagcgccga gccaagcgaa gcagactgca gacggcacgg    240
ccgagacgtt gacaccttgg cgcggcaacg gcatctctct ggccccctct cgagagttcc    300
gctccacctc cgcatccacc tccacctcca cctccaccgg tggcggtttc caagtccgtc    360
ccgttccgcc acctgctcct ctcacacggc acgaaaccgt cacggcaccg gcagcacagc    420
acgggggatt cctttcccac cgctccgtcc ctttctcttc ctcgcccgcc cgttataaat    480
agccagcccc atccctcgtc tctcgtgttg ttcggagcgc acacacaacc cgatccccaa    540
tcaatcgatc cccgcttcaa ggtacggcga tcctcctccc tctctctcta ccttctcttc    600
tctacactag atcggcggtc catggttagg gcctgctagt tccgttcctg tttttccatg    660
gctgcgaggt acaatagatc tgatggcgtt atgatggtta acttgtcatg cttttgcgat    720
ttatagtccc tttagatagt tcgagatcgg tgatccatgg ttagtaccct aggctgtgga    780
gtcgggttag atccgcgctg ttagggttcg tatatggagg cgagctgttc tgattgttaa    840
cttgctggga atcctgggat ggttctagct gttccgcaga tgagatcgat ttcatgatct    900
gctgtatcta tccgtggtat gatgttagcc tttgatatgg ttcgatcgtg ctagctacgt    960
cctgtgcact taattgtcag gtcataattt ttactatact ttttttttgg tttggtttgg   1020
tttcgtctga tttggctgtc gttctagatc agagtagaaa ctgtttcaaa ctacctgttg   1080
gatttattaa ggtagcgttt ggttcctggt atcgaatcat acacgcacca gtgcatcttg   1140
gatagccagc tggggcccac ctgtccaacc gtttggttgc cggatcgaac gagtccattc   1200
aagaccgaac catgcagagc aatcgaatat tctcttgtga cgctgtatca tccagttcgg   1260
caaaaaacac cgaatgccgc catacaggac accgtactga gcgtctgcaa ctctgcatcc   1320
cgctcactgc tcacatctcc gcttgccgcc tcacccatcc gactcagacc agagccacac   1380
ggattactgc tgctggtgtg tgtattaaca aaagatccat ttgaccggag cacatgcagc   1440
ttggatggaa aaaatttatt atattcgtca gtgctgcata tgtactcata cttgcatgat   1500
ggttttattt attcgacctc atcagtcctg gcactatgga aagtcattgt agtatagatt   1560
ttttaatata atataaatca ttggtgactt atcttgctta attttatttt cttattatga   1620
aatatcgttg cattcataat agcaaatttg tgcaaatata tagaatctac gtgaaattct   1680
tggttggacc aatacaacaa acccctcaaa cattctcttg tactgaacca taccattccg   1740
tacaaccatc caaacaaaaa tcatgtatca tcatgtacat gtaaccaaac aattaacacg   1800
caccatccta ttcagacttg tctcatccat aatctatcca tccaggatga tccatcccat   1860
tcatctatat acacccaatc aaacgctacc taaaatttgg atctgtatgt gtcacatata   1920
tcttaataag atggatggaa atatctcttt atcttttaga tatggatagg tatatatgtt   1980
gctgtgggtt tgttagttat atatatacgt gcttacatac gtgaagaaac ctgctgctac   2040
agtttaataa ttcttgttca tctcaacaaa taacgatagg cgtatatgtt gctgtgtttt   2100
ttactggtac tttgttagat atatacatgc ttacatacat gaagaacaca tgctacagtt   2160
caaaaattct tgttcatctc ataaacaaaa aggaggtgta tatgttgctg tgggttttac   2220
tggtacttta ttagatatat acatgcttac atagatgaag caacatgctg ctatggtgtt   2280
taataattat tgtttatcta ataaacaaac atgcttttta attatcttga tatgtttgga   2340
```

-continued tgatggcata tgcagcagct atgtgtggat tttaaatacc cagcatcatg agcatgcatg 2400
accctgcctt agtatgcagt tatttgcttg agactgtttc ttttgttgat actcatcctt 2460
tagttcggtc actcttctgc aggtg 2485

<210> SEQ ID NO 77
<211> LENGTH: 506
<212> TYPE: DNA
<213> ORGANISM: Miscanthus sinesis

<400> SEQUENCE: 77
gtggttttga tttctagcct ccacaataac tttggtttta ctattttttg tttgatttta 60
gtttcagaag tccacttttg tacgtgctcg tagagcctaa acaaaaggct ttccaaaacg 120
accttatctt cgagtgttgt aaaaaaaatg agcccgttta acggcgtcga caagtctaac 180
ggacaccaac cagcgaacca ccagcgccga gccaagcgaa gcagactgca gacggcacgg 240
ccgagacgtt gacaccttgg cgcggcaacg gcatctctct ggccccctct cgagagttcc 300
gctccacctc cgcatccacc tccacctcca cctccaccgg tggcggtttc caagtccgtc 360
ccgttccgcc acctgctcct ctcacacggc acgaaaccgt cacggcaccg gcagcacagc 420
acgggggatt cctttcccac cgctccgtcc ctttctcttc ctcgcccgcc cgttataaat 480
agccagcccc atccctcgtc tctcgt 506

<210> SEQ ID NO 78
<211> LENGTH: 4079
<212> TYPE: DNA
<213> ORGANISM: Schizachyium scoparium

<400> SEQUENCE: 78
ctctatgcct gtgtcattgt gccagcccct acctctgtca atgttcaaga tccaaataag 60
agaatgggat agaccatata ttaatggtgt agtatgcatc aagatctgaa tattatatga 120
gtgaattgat aaatttattc taggtgacat ggccttaacg atggccagta cgtggttaaa 180
tcaatgaatc aatagccata ctctaatagc tctaaaaaag gatatatatt tgtcgaggca 240
ctattatgca accacatagt caacttcaaa gccgcttgag tgcgttctaa aaaaaaaatt 300
tcttgtaaat tacgcttttc tcaaaaaaat tggatcatgc atttatttca ctctaggtgt 360
gcgtgactac gtgaataaca attttgaatc tcagcaagga aataaaagta taataccgct 420
gtctactttg aagatcacaa tatctttctc ttagaatgtt tctgtttgtt atttaaaacc 480
atcgttatta aggtcaaatg atcaagattc attcaacaat tgaaacttct cacatgatta 540
catcatatat aaggttgcta aggtcttgct tgacaaggta tctctagtaa catctagttt 600
ttttgagtga aataataaaa ttttaaagca atgttacaag agaagctctg gagataaaag 660
ttagaagggt gaagtttact ccctctatcc caaagatgta attctaagaa tgacttaaat 720
tttttataca aaaggagtat atatcacaag attgatgtca tcgttatgct taggccacgt 780
acacgacgct ggcgcttatg tggacgttaa tcggtaattc ttcattttat tttattttgt 840
tgtcaccgcg tacatttggg ttaggcgttt gttaaaggca ttgccactca aacaagcagc 900
cgcgtttgga gcttttatag tttgaaaagt gacggttgta aagatgagta agctgattat 960
tagtagagta aattataatt atcatacaac aactctcaaa gtgggtgcac gttagtccaa 1020
catcttataa tttatccaac tcaatacaac aactatatag gtgggtgcat gttggtccaa 1080
catcttctaa tttgtttaat ttgatacgag aacttgtctt attggtacat atatgatcca 1140
aagcattgta acaacgtgtt tatgtatact cttaatcatg gtcatcagaa gctaacacac 1200

-continued

```
acgctcatgc catccatatc attcaacttt tgaatcgttt actatacaat attatttcta   1260
aatttggctg taaagatggc attgatttca taaatatgaa aaataccaaa ttgcacattt   1320
tctttctata ttataatatt gttttcatct attttcaccc cgtaaccttt aatttggtca   1380
tttagggctc actaaaactg atatgtgggt tgtgcatcgc ataagaatca agaacccaga   1440
agtaattttc aatactaaga aacaacaaaa tttggttttt ttttgtttgg tttcgattat   1500
agccgaacta accaaattta agaaagcttt ttatatttgg ccacataaga aatgatatca   1560
tttaatattg taactgattc aagctgagta atagatgaga tgagtgtgtt aggatgtgta   1620
gcttccgatg atagagaatt agagtgtaca aagacgcatc gttacaatat ttggacctta   1680
tatgcaccaa tgtgtcaagt ctcgcttcaa attaactata ttaaaagatg ttggatcaac   1740
atgcactcac ttagatatca gtcgtattaa attgaacaaa ttacaagata ttggactatg   1800
cacccactca aatagttgtt atatagtgaa tacagtttac tcttagtagt atatgtaagt   1860
tcagcctttt ctattgtagg ttaagcctta attaaggctc ttacacaatt gtttcattat   1920
tcgcgttcga agcagcttct tcgtagattt tgcgagggaa ggctgcctcg gttttgcctt   1980
ccctagcact catgtgagag cctctggcaa taggtcttct catttttatt cacattcttt   2040
aagagcccat ataagcgttc atgacttgta tatactctta gatctttttt tgtgggtaaa   2100
gctcaagcta atctaaaaat agagaaatca ggaacaaaga atcatgtttt ggtggttttg   2160
atttctagcc tccacaataa ttttagttta cctttttttg tttgatttta attttagaag   2220
ggtttatagc aggacttaaa atccaaaatg accattatct tcgagtaata acccgtttaa   2280
cggcgtcgac aagtctaacg gacaccaacc catgaaccac cagcgccgag ccaagaactg   2340
aaggtcgaga cgttgacacc tttggcgcga cacggcatgt tggcatctcc ctctctggcc   2400
ccctctcgag aattccgctc caccgcctca accggagacg gtttccaaag ttgtgcttag   2460
atgctcaaaa gttggtgaaa tcatttttat ttggcaattt gtgtccaact atagactaat   2520
taggctcaaa agatttgtct cgtaaagtac attcaaactg tgtaattagt tattttattt   2580
atctacattt aatactctat gaatgcgtca agagatttga tgtgacttta atgtgacgga   2640
caatctgaaa cttttacgca acttgcatat aaacagagcc caagtccgtt ccgttccgtt   2700
ccgcttcctc ctcccagacg gcacgaaacc gtgacggcac cggcagcacg gggattcctt   2760
tcccaccgct ccttcctttt cccttcatcg cccgcagcta taaatagcca cccccgtccg   2820
caacttcttt ccccaacctc atcttttgtt cggagcacgc acacaatccg atcgatcccc   2880
aatcccctcg tctctcctcg cgagcctcgt cgatccgcca ttcaaggtac ggcgatcatc   2940
ctccctccct ctctacctgc tcttctgtag atcggcgacc ccatccatgg ttagggcctg   3000
ctagttctgt tcctgttttt tttccatggc tgcgaggtag aatagatctg atggcgttat   3060
gatggttaat ttgtcatact cttgcggtct atgggtccct ttaggtcatc aatttaattt   3120
tgggtggttg agatcggtga tccatggtta gtaccctagt cagtggggtt ggatccgtgc   3180
tattagggtt cgtagatgga ttctgatggc tcagtaactg ggaatcctag gatggttcca   3240
tctggtttgc agatgagaac gatttcatca tctgctatat cttgtttcgt tgcgtaggtt   3300
ctgtttaaac taatccgtgg tatgatgtta gcctttgata aggttgattt catcatctgc   3360
tatatcttgt ttcgttgcgt aggttctgtt taaactaatc cgtggtatga tgttagcctt   3420
tgataaggtt tgattgtgct agctacgtcc tgtgcagcag ttaattgtca ggtcatacgt   3480
cataattttt agcatgtctg tttttgtttg atttcgttgt ctgattaggc tgtagatagt   3540
```

-continued ttcgatctac ctgtcggttt attttattaa aatttggatc cgtatgtgtg tcacatatat 3600
cttcatgatt aagatggagt tatatgggta ggttatacat gtggctgtgg atcatgatta 3660
agatggattg aagtatctct ttatctttta gttaggatag attattatat atgttgctgt 3720
tgattttatt ggttctttat tatatatatt catgcttata tacataaaag caatgtgcta 3780
ttacagttta atagttcttg attatctaat aaacaaataa ggataggtat atttgttgct 3840
gttggtttta ctggtactct attagatagt actttgacat gaagcaacat cctgctatgg 3900
attaataatt attcttcgtc taataaaaag catggttttt aattattttg atttgatata 3960
cttggatgat gtcatatgca gcagctattt gtgaattttt cggccgtatc ttcatattgc 4020
ttgggactgt ttctttggtt gataactcac cctgttgttt ggtgatcctt ctgcaggtg 4079

<210> SEQ ID NO 79
<211> LENGTH: 2831
<212> TYPE: DNA
<213> ORGANISM: Schizachyium scoparium

<400> SEQUENCE: 79
ctctatgcct gtgtcattgt gccagcccct acctctgtca atgttcaaga tccaaataag 60
agaatgggat agaccatata ttaatggtgt agtatgcatc aagatctgaa tattatatga 120
gtgaattgat aaatttattc taggtgacat ggccttaacg atggccagta cgtggttaaa 180
tcaatgaatc aatagccata ctctaatagc tctaaaaaag gatatatatt tgtcgaggca 240
ctattatgca accacatagt caacttcaaa gccgcttgag tgcgttctaa aaaaaaaatt 300
tcttgtaaat tacgcttttc tcaaaaaaat tggatcatgc atttatttca ctctaggtgt 360
gcgtgactac gtgaataaca attttgaatc tcagcaagga aataaaagta taataccgct 420
gtctactttg aagatcacaa tatctttctc ttagaatgtt tctgtttgtt atttaaaacc 480
atcgttatta aggtcaaatg atcaagattc attcaacaat tgaaacttct cacatgatta 540
catcatatat aaggttgcta aggtcttgct tgacaaggta tctctagtaa catctagttt 600
ttttgagtga aataataaaa ttttaaagca atgttacaag agaagctctg gagataaaag 660
ttagaagggt gaagtttact ccctctatcc caaagatgta attctaagaa tgacttaaat 720
tttttataca aaaggagtat atatcacaag attgatgtca tcgttatgct taggccacgt 780
acacgacgct ggcgcttatg tggacgttaa tcggtaattc ttcattttat tttattttgt 840
tgtcaccgcg tacatttggg ttaggcgttt gttaaaggca ttgccactca aacaagcagc 900
cgcgtttgga gcttttatag tttgaaaagt gacggttgta aagatgagta agctgattat 960
tagtagagta aattataatt atcatacaac aactctcaaa gtgggtgcac gttagtccaa 1020
catcttataa tttatccaac tcaatacaac aactatatag gtgggtgcat gttggtccaa 1080
catcttctaa tttgtttaat ttgatacgag aacttgtctt attggtacat atatgatcca 1140
aagcattgta acaacgtgtt tatgtatact cttaatcatg gtcatcagaa gctaacacac 1200
acgctcatgc catccatatc attcaacttt tgaatcgttt actatacaat attatttcta 1260
aatttggctg taaagatggc attgatttca taaatatgaa aaataccaaa ttgcacattt 1320
tctttctata ttataatatt gttttcatct attttcaccc cgtaaccttt aatttggtca 1380
tttagggctc actaaaactg atatgtgggt tgtgcatcgc ataagaatca agaacccaga 1440
agtaattttc aatactaaga aacaacaaaa tttggttttt ttttgtttgg tttcgattat 1500
agccgaacta accaaattta agaaagcttt ttatatttgg ccacataaga aatgatatca 1560
tttaatattg taactgattc aagctgagta atagatgaga tgagtgtgtt aggatgtgta 1620
gcttccgatg atagagaatt agagtgtaca aagacgcatc gttacaatat ttggacctta 1680
tatgcaccaa tgtgtcaagt ctcgcttcaa attaactata ttaaaagatg ttggatcaac 1740
atgcactcac ttagatatca gtcgtattaa attgaacaaa ttacaagata ttggactatg 1800
cacccactca aatagttgtt atatagtgaa tacagtttac tcttagtagt atatgtaagt 1860
tcagcctttt ctattgtagg ttaagcctta attaaggctc ttacacaatt gtttcattat 1920
tcgcgttcga agcagcttct tcgtagattt tgcgagggaa ggctgcctcg gttttgcctt 1980
ccctagcact catgtgagag cctctggcaa taggtcttct catttttatt cacattcttt 2040
aagagcccat ataagcgttc atgacttgta tatactctta gatctttttt tgtgggtaaa 2100
gctcaagcta atctaaaaat agagaaatca ggaacaaaga atcatgtttt ggtggttttg 2160
atttctagcc tccacaataa ttttagttta cctttttttg tttgatttta attttagaag 2220
ggtttatagc aggacttaaa atccaaaatg accattatct tcgagtaata acccgtttaa 2280
cggcgtcgac aagtctaacg gacaccaacc catgaaccac cagcgccgag ccaagaactg 2340
aaggtcgaga cgttgacacc tttggcgcga cacggcatgt tggcatctcc ctctctggcc 2400
ccctctcgag aattccgctc caccgcctca accggagacg gtttccaaag ttgtgcttag 2460
atgctcaaaa gttggtgaaa tcatttttat ttggcaattt gtgtccaact atagactaat 2520
taggctcaaa agatttgtct cgtaaagtac attcaaactg tgtaattagt tattttattt 2580
atctacattt aatactctat gaatgcgtca agagatttga tgtgacttta atgtgacgga 2640
caatctgaaa cttttacgca acttgcatat aaacagagcc caagtccgtt ccgttccgtt 2700
ccgcttcctc ctcccagacg gcacgaaacc gtgacggcac cggcagcacg gggattcctt 2760
tcccaccgct ccttcctttt cccttcatcg cccgcagcta taaatagcca cccccgtccg 2820
caacttcttt c 2831

<210> SEQ ID NO 80
<211> LENGTH: 95
<212> TYPE: DNA
<213> ORGANISM: Schizachyium scoparium

<400> SEQUENCE: 80
cccaacctca tcttttgttc ggagcacgca cacaatccga tcgatcccca atcccctcgt 60
ctctcctcgc gagcctcgtc gatccgccat tcaag 95

<210> SEQ ID NO 81
<211> LENGTH: 1153
<212> TYPE: DNA
<213> ORGANISM: Schizachyium scoparium

<400> SEQUENCE: 81
gtacggcgat catcctccct ccctctctac ctgctcttct gtagatcggc gaccccatcc 60
atggttaggg cctgctagtt ctgttcctgt ttttttcca tggctgcgag gtagaataga 120
tctgatggcg ttatgatggt taatttgtca tactcttgcg gtctatgggt ccctttaggt 180
catcaattta attttgggtg gttgagatcg gtgatccatg gttagtaccc tagtcagtgg 240
ggttggatcc gtgctattag ggttcgtaga tggattctga tggctcagta actgggaatc 300
ctaggatggt tccatctggt ttgcagatga gaacgatttc atcatctgct atatcttgtt 360
tcgttgcgta ggttctgttt aaactaatcc gtggtatgat gttagccttt gataaggttg 420
atttcatcat ctgctatatc ttgtttcgtt gcgtaggttc tgtttaaact aatccgtggt 480

-continued

```
atgatgttag cctttgataa ggtttgattg tgctagctac gtcctgtgca gcagttaatt    540

gtcaggtcat acgtcataat ttttagcatg tctgtttttg tttgatttcg ttgtctgatt    600

aggctgtaga tagtttcgat ctacctgtcg gtttatttta ttaaaatttg gatccgtatg    660

tgtgtcacat atatcttcat gattaagatg gagttatatg ggtaggttat acatgtggct    720

gtggatcatg attaagatgg attgaagtat ctctttatct tttagttagg atagattatt    780

atatatgttg ctgttgattt tattggttct ttattatata tattcatgct tatatacata    840

aaagcaatgt gctattacag tttaatagtt cttgattatc taataaacaa ataaggatag    900

gtatatttgt tgctgttggt tttactggta ctctattaga tagtactttg acatgaagca    960

acatcctgct atggattaat aattattctt cgtctaataa aaagcatggt ttttaattat   1020

tttgatttga tatacttgga tgatgtcata tgcagcagct atttgtgaat ttttcggccg   1080

tatcttcata ttgcttggga ctgtttcttt ggttgataac tcaccctgtt gtttggtgat   1140

ccttctgcag gtg                                                     1153
```

<210> SEQ ID NO 82
<211> LENGTH: 3281
<212> TYPE: DNA
<213> ORGANISM: Schizachyium scoparium

<400> SEQUENCE: 82

```
gtggacgtta atcggtaatt cttcatttta ttttattttg ttgtcaccgc gtacatttgg     60

gttaggcgtt tgttaaaggc attgccactc aaacaagcag ccgcgtttgg agcttttata    120

gtttgaaaag tgacggttgt aaagatgagt aagctgatta ttagtagagt aaattataat    180

tatcatacaa caactctcaa agtgggtgca cgttagtcca acatcttata atttatccaa    240

ctcaatacaa caactatata ggtgggtgca tgttggtcca acatcttcta atttgtttaa    300

tttgatacga gaacttgtct tattggtaca tatatgatcc aaagcattgt aacaacgtgt    360

ttatgtatac tcttaatcat ggtcatcaga agctaacaca cacgctcatg ccatccatat    420

cattcaactt ttgaatcgtt tactatacaa tattatttct aaatttggct gtaaagatgg    480

cattgatttc ataaatatga aaaataccaa attgcacatt ttctttctat attataatat    540

tgttttcatc tattttcacc ccgtaacctt taatttggtc atttagggct cactaaaact    600

gatatgtggg ttgtgcatcg cataagaatc aagaacccag aagtaatttt caatactaag    660

aaacaacaaa atttggtttt tttttgtttg gtttcgatta tagccgaact aaccaaattt    720

aagaaagctt tttatatttg gccacataag aaatgatatc atttaatatt gtaactgatt    780

caagctgagt aatagatgag atgagtgtgt taggatgtgt agcttccgat gatagagaat    840

tagagtgtac aaagacgcat cgttacaata tttggacctt atatgcacca atgtgtcaag    900

tctcgcttca aattaactat attaaaagat gttggatcaa catgcactca cttagatatc    960

agtcgtatta aattgaacaa attacaagat attggactat gcacccactc aaatagttgt   1020

tatatagtga atacagttta ctcttagtag tatatgtaag ttcagccttt tctattgtag   1080

gttaagcctt aattaaggct cttacacaat tgtttcatta ttcgcgttcg aagcagcttc   1140

ttcgtagatt ttgcgaggga aggctgcctc ggttttgcct tccctagcac tcatgtgaga   1200

gcctctggca ataggtcttc tcatttttat tcacattctt taagagccca tataagcgtt   1260

catgacttgt atatactctt agatcttttt tttgtgggta aagctcaagc taatctaaaa   1320

atagagaaat caggaacaaa gaatcatgtt ttggtggttt tgatttctag cctccacaat   1380

aattttagtt tacctttttt tgtttgattt taattttaga agggtttata gcaggactta   1440
```

```
aaatccaaaa tgaccattat cttcgagtaa taacccgttt aacggcgtcg acaagtctaa   1500

cggacaccaa cccatgaacc accagcgccg agccaagaac tgaaggtcga gacgttgaca   1560

cctttggcgc gacacggcat gttggcatct ccctctctgg ccccctctcg agaattccgc   1620

tccaccgcct caaccggaga cggtttccaa agttgtgctt agatgctcaa aagttggtga   1680

aatcattttt atttggcaat ttgtgtccaa ctatagacta attaggctca aaagatttgt   1740

ctcgtaaagt acattcaaac tgtgtaatta gttattttat ttatctacat ttaatactct   1800

atgaatgcgt caagagattt gatgtgactt taatgtgacg gacaatctga aacttttacg   1860

caacttgcat ataaacagag cccaagtccg ttccgttccg ttccgcttcc tcctcccaga   1920

cggcacgaaa ccgtgacggc accggcagca cggggattcc tttcccaccg ctccttcctt   1980

ttcccttcat cgcccgcagc tataaatagc cacccccgtc cgcaacttct ttccccaacc   2040

tcatcttttg ttcggagcac gcacacaatc cgatcgatcc ccaatcccct cgtctctcct   2100

cgcgagcctc gtcgatccgc cattcaaggt acggcgatca tcctccctcc ctctctacct   2160

gctcttctgt agatcggcga ccccatccat ggttagggcc tgctagttct gttcctgttt   2220

tttttccatg gctgcgaggt agaatagatc tgatggcgtt atgatggtta atttgtcata   2280

ctcttgcggt ctatgggtcc ctttaggtca tcaatttaat tttgggtggt tgagatcggt   2340

gatccatggt tagtacccta gtcagtgggg ttggatccgt gctattaggg ttcgtagatg   2400

gattctgatg gctcagtaac tgggaatcct aggatggttc catctggttt gcagatgaga   2460

acgatttcat catctgctat atcttgtttc gttgcgtagg ttctgtttaa actaatccgt   2520

ggtatgatgt tagcctttga taaggttgat ttcatcatct gctatatctt gtttcgttgc   2580

gtaggttctg tttaaactaa tccgtggtat gatgttagcc tttgataagg tttgattgtg   2640

ctagctacgt cctgtgcagc agttaattgt caggtcatac gtcataattt ttagcatgtc   2700

tgtttttgtt tgatttcgtt gtctgattag gctgtagata gtttcgatct acctgtcggt   2760

ttattttatt aaaatttgga tccgtatgtg tgtcacatat atcttcatga ttaagatgga   2820

gttatatggg taggttatac atgtggctgt ggatcatgat taagatggat tgaagtatct   2880

ctttatcttt tagttaggat agattattat atatgttgct gttgatttta ttggttcttt   2940

attatatata ttcatgctta tatacataaa agcaatgtgc tattacagtt taatagttct   3000

tgattatcta ataaacaaat aaggataggt atatttgttg ctgttggttt tactggtact   3060

ctattagata gtactttgac atgaagcaac atcctgctat ggattaataa ttattcttcg   3120

tctaataaaa agcatggttt ttaattattt tgatttgata tacttggatg atgtcatatg   3180

cagcagctat ttgtgaattt ttcggccgta tcttcatatt gcttgggact gtttctttgg   3240

ttgataactc accctgttgt ttggtgatcc ttctgcaggt g                       3281
```

<210> SEQ ID NO 83
<211> LENGTH: 2033
<212> TYPE: DNA
<213> ORGANISM: Schizachyium scoparium

<400> SEQUENCE: 83

```
gtggacgtta atcggtaatt cttcatttta ttttattttg ttgtcaccgc gtacatttgg     60

gttaggcgtt tgttaaaggc attgccactc aaacaagcag ccgcgtttgg agcttttata    120

gtttgaaaag tgacggttgt aaagatgagt aagctgatta ttagtagagt aaattataat    180

tatcatacaa caactctcaa agtgggtgca cgttagtcca acatcttata atttatccaa    240
```

```
ctcaatacaa caactatata ggtgggtgca tgttggtcca acatcttcta atttgtttaa    300
tttgatacga gaacttgtct tattggtaca tatatgatcc aaagcattgt aacaacgtgt    360
ttatgtatac tcttaatcat ggtcatcaga agctaacaca cacgctcatg ccatccatat    420
cattcaactt ttgaatcgtt tactatacaa tattatttct aaatttggct gtaaagatgg    480
cattgatttc ataaatatga aaaataccaa attgcacatt ttctttctat attataatat    540
tgttttcatc tattttcacc ccgtaacctt taatttggtc atttagggct cactaaaact    600
gatatgtggg ttgtgcatcg cataagaatc aagaacccag aagtaatttt caatactaag    660
aaacaacaaa atttggtttt tttttgtttg gtttcgatta tagccgaact aaccaaattt    720
aagaaagctt tttatatttg gccacataag aaatgatatc atttaatatt gtaactgatt    780
caagctgagt aatagatgag atgagtgtgt taggatgtgt agcttccgat gatagagaat    840
tagagtgtac aaagacgcat cgttacaata tttggacctt atatgcacca atgtgtcaag    900
tctcgcttca aattaactat attaaaagat gttggatcaa catgcactca cttagatatc    960
agtcgtatta aattgaacaa attacaagat attggactat gcacccactc aaatagttgt   1020
tatatagtga atacagttta ctcttagtag tatatgtaag ttcagccttt tctattgtag   1080
gttaagcctt aattaaggct cttacacaat tgtttcatta ttcgcgttcg aagcagcttc   1140
ttcgtagatt ttgcgaggga aggctgcctc ggttttgcct tccctagcac tcatgtgaga   1200
gcctctggca ataggtcttc tcatttttat tcacattctt taagagccca tataagcgtt   1260
catgacttgt atatactctt agatcttttt tttgtgggta aagctcaagc taatctaaaa   1320
atagagaaat caggaacaaa gaatcatgtt ttggtggttt tgatttctag cctccacaat   1380
aattttagtt tacctttttt tgtttgattt taattttaga agggtttata gcaggactta   1440
aaatccaaaa tgaccattat cttcgagtaa taacccgttt aacggcgtcg acaagtctaa   1500
cggacaccaa cccatgaacc accagcgccg agccaagaac tgaaggtcga gacgttgaca   1560
cctttggcgc gacacggcat gttggcatct ccctctctgg ccccctctcg agaattccgc   1620
tccaccgcct caaccggaga cggtttccaa agttgtgctt agatgctcaa aagttggtga   1680
aatcattttt atttggcaat ttgtgtccaa ctatagacta attaggctca aaagatttgt   1740
ctcgtaaagt acattcaaac tgtgtaatta gttattttat ttatctacat ttaatactct   1800
atgaatgcgt caagagattt gatgtgactt taatgtgacg gacaatctga aacttttacg   1860
caacttgcat ataaacagag cccaagtccg ttccgttccg ttccgcttcc tcctcccaga   1920
cggcacgaaa ccgtgacggc accggcagca cggggattcc tttcccaccg ctccttcctt   1980
ttcccttcat cgcccgcagc tataaatagc cacccccgtc cgcaacttct ttc          2033
```

<210> SEQ ID NO 84
<211> LENGTH: 2294
<212> TYPE: DNA
<213> ORGANISM: Schizachyium scoparium

<400> SEQUENCE: 84

```
gatattggac tatgcaccca ctcaaatagt tgttatatag tgaatacagt ttactcttag     60
tagtatatgt aagttcagcc ttttctattg taggttaagc cttaattaag gctcttacac    120
aattgtttca ttattcgcgt tcgaagcagc ttcttcgtag attttgcgag ggaaggctgc    180
ctcggttttg ccttccctag cactcatgtg agagcctctg gcaataggtc ttctcatttt    240
tattcacatt ctttaagagc ccatataagc gttcatgact tgtatatact cttagatctt    300
tttttgtgg gtaaagctca agctaatcta aaaatagaga aatcaggaac aaagaatcat    360
```

-continued

```
gttttggtgg ttttgatttc tagcctccac aataatttta gtttaccttt ttttgtttga    420
ttttaatttt agaagggttt atagcaggac ttaaaatcca aaatgaccat tatcttcgag    480
taataacccg tttaacggcg tcgacaagtc taacggacac caacccatga accaccagcg    540
ccgagccaag aactgaaggt cgagacgttg acacctttgg cgcgacacgg catgttggca    600
tctccctctc tggccccctc tcgagaattc cgctccaccg cctcaaccgg agacggtttc    660
caaagttgtg cttagatgct caaaagttgg tgaaatcatt tttatttggc aatttgtgtc    720
caactataga ctaattaggc tcaaaagatt tgtctcgtaa agtacattca aactgtgtaa    780
ttagttattt tatttatcta catttaatac tctatgaatg cgtcaagaga tttgatgtga    840
ctttaatgtg acggacaatc tgaaactttt acgcaacttg catataaaca gagcccaagt    900
ccgttccgtt ccgttccgct tcctcctccc agacggcacg aaaccgtgac ggcaccggca    960
gcacggggat tcctttccca ccgctccttc cttttccctt catcgcccgc agctataaat   1020
agccaccccc gtccgcaact tctttcccca acctcatctt ttgttcggag cacgcacaca   1080
atccgatcga tccccaatcc cctcgtctct cctcgcgagc ctcgtcgatc cgccattcaa   1140
ggtacggcga tcatcctccc tccctctcta cctgctcttc tgtagatcgg cgaccccatc   1200
catggttagg gcctgctagt tctgttcctg tttttttcc atggctgcga ggtagaatag   1260
atctgatggc gttatgatgg ttaatttgtc atactcttgc ggtctatggg tccctttagg   1320
tcatcaattt aattttgggt ggttgagatc ggtgatccat ggttagtacc ctagtcagtg   1380
gggttggatc cgtgctatta gggttcgtag atggattctg atggctcagt aactgggaat   1440
cctaggatgg ttccatctgg tttgcagatg agaacgattt catcatctgc tatatcttgt   1500
ttcgttgcgt aggttctgtt taaactaatc cgtggtatga tgttagcctt tgataaggtt   1560
gatttcatca tctgctatat cttgtttcgt tgcgtaggtt ctgtttaaac taatccgtgg   1620
tatgatgtta gcctttgata aggtttgatt gtgctagcta cgtcctgtgc agcagttaat   1680
tgtcaggtca tacgtcataa tttttagcat gtctgttttt gtttgatttc gttgtctgat   1740
taggctgtag atagtttcga tctacctgtc ggtttatttt attaaaattt ggatccgtat   1800
gtgtgtcaca tatatcttca tgattaagat ggagttatat gggtaggtta tacatgtggc   1860
tgtggatcat gattaagatg gattgaagta tctctttatc ttttagttag gatagattat   1920
tatatatgtt gctgttgatt ttattggttc tttattatat atattcatgc ttatatacat   1980
aaaagcaatg tgctattaca gtttaatagt tcttgattat ctaataaaca aataaggata   2040
ggtatatttg ttgctgttgg ttttactggt actctattag atagtacttt gacatgaagc   2100
aacatcctgc tatggattaa taattattct tcgtctaata aaaagcatgg tttttaatta   2160
ttttgatttg atatacttgg atgatgtcat atgcagcagc tatttgtgaa tttttcggcc   2220
gtatcttcat attgcttggg actgtttctt tggttgataa ctcaccctgt tgtttggtga   2280
tccttctgca ggtg                                                      2294
```

<210> SEQ ID NO 85
<211> LENGTH: 1046
<212> TYPE: DNA
<213> ORGANISM: Schizachyium scoparium

<400> SEQUENCE: 85

```
gatattggac tatgcaccca ctcaaatagt tgttatatag tgaatacagt ttactcttag     60
tagtatatgt aagttcagcc ttttctattg taggttaagc cttaattaag gctcttacac    120
```

-continued

```
aattgtttca ttattcgcgt tcgaagcagc ttcttcgtag attttgcgag ggaaggctgc    180

ctcggttttg ccttccctag cactcatgtg agagcctctg gcaataggtc ttctcatttt    240

tattcacatt ctttaagagc ccatataagc gttcatgact tgtatatact cttagatctt    300

ttttttgtgg gtaaagctca agctaatcta aaaatagaga aatcaggaac aaagaatcat    360

gttttggtgg ttttgatttc tagcctccac aataatttta gtttaccttt ttttgtttga    420

ttttaatttt agaagggttt atagcaggac ttaaaatcca aaatgaccat tatcttcgag    480

taataacccg tttaacggcg tcgacaagtc taacggacac caacccatga accaccagcg    540

ccgagccaag aactgaaggt cgagacgttg acacctttgg cgcgacacgg catgttggca    600

tctccctctc tggccccctc tcgagaattc cgctccaccg cctcaaccgg agacggtttc    660

caaagttgtg cttagatgct caaaagttgg tgaaatcatt tttatttggc aatttgtgtc    720

caactataga ctaattaggc tcaaaagatt tgtctcgtaa agtacattca aactgtgtaa    780

ttagttattt tatttatcta catttaatac tctatgaatg cgtcaagaga tttgatgtga    840

ctttaatgtg acggacaatc tgaaactttt acgcaacttg catataaaca gagcccaagt    900

ccgttccgtt ccgttccgct tcctcctccc agacggcacg aaaccgtgac ggcaccggca    960

gcacggggat tcctttccca ccgctccttc cttttccctt catcgcccgc agctataaat   1020

agccaccccc gtccgcaact tctttc                                        1046
```

<210> SEQ ID NO 86
<211> LENGTH: 1795
<212> TYPE: DNA
<213> ORGANISM: Schizachyium scoparium

<400> SEQUENCE: 86

```
gtcgacaagt ctaacggaca ccaacccatg aaccaccagc gccgagccaa gaactgaagg     60

tcgagacgtt gacacctttg gcgcgacacg gcatgttggc atctccctct ctggccccct    120

ctcgagaatt ccgctccacc gcctcaaccg gagacggttt ccaaagttgt gcttagatgc    180

tcaaaagttg gtgaaatcat ttttatttgg caatttgtgt ccaactatag actaattagg    240

ctcaaaagat ttgtctcgta aagtacattc aaactgtgta attagttatt ttatttatct    300

acatttaata ctctatgaat gcgtcaagag atttgatgtg actttaatgt gacggacaat    360

ctgaaacttt tacgcaactt gcatataaac agagcccaag tccgttccgt tccgttccgc    420

ttcctcctcc cagacggcac gaaaccgtga cggcaccggc agcacgggga ttcctttccc    480

accgctcctt ccttttccct tcatcgcccg cagctataaa tagccacccc cgtccgcaac    540

ttctttcccc aacctcatct tttgttcgga gcacgcacac aatccgatcg atccccaatc    600

ccctcgtctc tcctcgcgag cctcgtcgat ccgccattca aggtacggcg atcatcctcc    660

ctccctctct acctgctctt ctgtagatcg gcgaccccat ccatggttag ggcctgctag    720

ttctgttcct gtttttttc catggctgcg aggtagaata gatctgatgg cgttatgatg    780

gttaatttgt catactcttg cggtctatgg gtccctttag gtcatcaatt taattttggg    840

tggttgagat cggtgatcca tggttagtac cctagtcagt ggggttggat ccgtgctatt    900

agggttcgta gatggattct gatggctcag taactgggaa tcctaggatg gttccatctg    960

gtttgcagat gagaacgatt tcatcatctg ctatatcttg tttcgttgcg taggttctgt   1020

ttaaactaat ccgtggtatg atgttagcct ttgataaggt tgatttcatc atctgctata   1080

tcttgtttcg ttgcgtaggt tctgtttaaa ctaatccgtg gtatgatgtt agcctttgat   1140

aaggtttgat tgtgctagct acgtcctgtg cagcagttaa ttgtcaggtc atacgtcata   1200
```

-continued

```
atttttagca tgtctgtttt tgtttgattt cgttgtctga ttaggctgta gatagtttcg   1260

atctacctgt cggtttattt tattaaaatt tggatccgta tgtgtgtcac atatatcttc   1320

atgattaaga tggagttata tgggtaggtt atacatgtgg ctgtggatca tgattaagat   1380

ggattgaagt atctctttat cttttagtta ggatagatta ttatatatgt tgctgttgat   1440

tttattggtt ctttattata tatattcatg cttatataca taaaagcaat gtgctattac   1500

agtttaatag ttcttgatta tctaataaac aaataaggat aggtatattt gttgctgttg   1560

gttttactgg tactctatta gatagtactt tgacatgaag caacatcctg ctatggatta   1620

ataattattc ttcgtctaat aaaaagcatg gtttttaatt attttgattt gatatacttg   1680

gatgatgtca tatgcagcag ctatttgtga atttttcggc cgtatcttca tattgcttgg   1740

gactgtttct ttggttgata actcaccctg ttgtttggtg atccttctgc aggtg         1795
```

<210> SEQ ID NO 87
<211> LENGTH: 547
<212> TYPE: DNA
<213> ORGANISM: Schizachyium scoparium

<400> SEQUENCE: 87

```
gtcgacaagt ctaacggaca ccaacccatg aaccaccagc gccgagccaa gaactgaagg     60

tcgagacgtt gacacctttg gcgcgacacg gcatgttggc atctccctct ctggccccct    120

ctcgagaatt ccgctccacc gcctcaaccg gagacggttt ccaaagttgt gcttagatgc    180

tcaaaagttg gtgaaatcat ttttatttgg caatttgtgt ccaactatag actaattagg    240

ctcaaaagat ttgtctcgta aagtacattc aaactgtgta attagttatt ttatttatct    300

acatttaata ctctatgaat gcgtcaagag atttgatgtg actttaatgt gacggacaat    360

ctgaaacttt tacgcaactt gcatataaac agagcccaag tccgttccgt tccgttccgc    420

ttcctcctcc cagacggcac gaaaccgtga cggcaccggc agcacgggga ttcctttccc    480

accgctcctt ccttttccct tcatcgcccg cagctataaa tagccacccc cgtccgcaac    540

ttctttc                                                              547
```

<210> SEQ ID NO 88
<211> LENGTH: 3357
<212> TYPE: DNA
<213> ORGANISM: Sorghastrum nutans

<400> SEQUENCE: 88

```
gtggccagct tttgttctag ttcaacggtc cgggccttcc gggaacctaa tgcactaatt     60

gattattatt aatctactat tgcagctaac ctcaaaagaa atgctctgca gttagttgtc    120

cgtcccaatc aatccaccag cagactcaca ttattgatgg aggaaattaa attcagcctt    180

tgacgtggat gcaacaactg cacaagatac catctacttt gcttaatttg ctgatgtttt    240

gagaaaatta aaccagcttt gaccaacaca tgagatgggc gccttacgtt tggcacaatg    300

taatgtagtc cggcacggca agttagactc tgtgtgtagt gttatattag ccggcctctt    360

taggtttggc acaatttaat tgaatccggc atggcaagtt agactgcagt gtgagccggt    420

caccgcaagt taggatataa tatacaagag caagtataca ataaagtgac attagcgtaa    480

agttatatga catatggaat ataagagaaa atacggagta tataataagg tgaactgtat    540

agcgatcaaa tttatgctaa gcgaagaaaa gagaagataa ataggttgaa aacttatagt    600

gagctttggc tcataatcta aataattatg agagagtggg atcgaccaca tattcatttt    660
```

-continued

```
gtagtacgta ctctctccgt tttttataag ttgctttgat ttttttttat atcaattttg    720
ctatacatct aaacataata ggaatatcaa gttcatgaag gtcgtgattt gcactaaata    780
tgttccctta ttagatagac gagttgttta gttttattgt agatgatata gcgcttgcat    840
atagcatgtg aaccggctaa attattagcc atacacgact ataaaaaatg acattccttt    900
gaggaacttt tatgcaacca aatagtcaac ttcaatgttg ctagagcggg ctttaagcca    960
aaagcagctg ctgctttgtt tccgagagaa gggacattct agttgatagc aaaacaaata   1020
cgtagcagtt gtagcgagtg tgtgagtaat aatttttctc tagtgtgtac gagtatgcga   1080
gtaataattt taaatctcta gaaggaagaa aaataatatt gctacctact ttgaggatat   1140
caatacettt ctctaaaatg ttttggtgaa gccatcttta aagctaattg ttcaagattc   1200
aaccattggg acgtctcaaa tgattagatc ctataatact cctacgtact aaattataag   1260
tcgttttgat tttattggta catacatttt gctatgtgtt tagatataat aatatgtcta   1320
gatacattgg atgaaccgaa aaaatcgaaa cgacttataa tttggatcga aaggagtatt   1380
tgctaaagtc cttttcgaag ttccggctct aaatttttgg ataaaatttt atgaaatact   1440
atcttaagaa gtaatttgac tagagaagct tgaagagtat aatctcttaa ttttgtgcta   1500
caggagtgaa gccaacgtcg tatttagatc tagatgctgt caggtagtga ggacggaggg   1560
agtattggat aaagtcattc caagatctta gaaaattaaa gtatattaag tttgattaaa   1620
tttatatgac aagtaataac attcatgatg ccaattaagt atcattagat tcttcatcaa   1680
ctatattttc atagtatact tatttaatgt tataaatttt tataattttt tttataattt   1740
tagctaaact cgagatcgat tcttataatt aaaaataaac tgaaaaaaaa tcacatgttc   1800
aagtgacagg aggagccagt ttaacggcgt cgacaagtct aacggacacc aaccagcgaa   1860
ccaccagcgc cgagccaatc ccaagcgaag ccgactgcag acggccgaga cgttgacacc   1920
tttggcgcgg catccatctc tccggccccc tcttgagagt tccgccccac cggcggcggt   1980
ttccaagtcc gttccgcccg ccttcgcggt tggacttgtt ccggtggcgc ctggcggatc   2040
gcgtggcgga gcggagacga cgaggtgagc cgtgggcgtt cctcctcctg ctcctctcac   2100
acggcacgga acggaaccgt gacggcaccg ggcagcacgg gcgggattcc ttccccacct   2160
ctccttcggt cctccctcca tcataaatag ccaccccccct cccaccttct ttccccacct   2220
cgtctcccct cgtgttattc ggagcacaga cacaccccga tccccaatcc tctcctcgcg   2280
agcctcgtcg atccccgctt caaggtacgg cgatcatcct ccctccctaa ctccaatccg   2340
tggttagggc ctgctagatc gtcctccctc cctacctgcg atccgtggtt cgcgcctgct   2400
agttctgttt cctgtttgtc gatggctgcg aggtataata gatctgatgg cgtgcggtgt   2460
gacggttaaa ttcacatgct cttgcgattt atacgcgaat cgatctggga ttgctcgaga   2520
tcggtgatcc atggttagaa ccctaggcgg tggagtcggg ttaaatccgt gctgttaggg   2580
ttcgtaggtg gatgcgacct gttctggttg tttacttgtc agtatttagg aatcctacta   2640
ggatggttct agctggttcg cagatgagat cgatttcatg atctgctata tctttcgttg   2700
cctaagtttc gtttaatctg tccgtggtat gatgttagcc tttgatatgc ttcgatcgtg   2760
ctagctacct cctgtgcact aaattatcag ctcgtaattt ttagcatgcc cttttttttt   2820
tgggtattgt tcgattgagg tgtcgttcta gatcagagta ggaagactgt ttcaaactac   2880
ctgctggatt tattaaattt ggatctgtat gagtatcaca tatatctcca taatttagat   2940
ggatggaaat atcccttttt cttttagata ctgtttggta tagattttgc tgtgggtttt   3000
actggtactt agatactctt cgtttagata tggatatgtt tacatgcaga tacatgaagc   3060
```

-continued aacatgctgc tacagtttaa tatggatagg tgtatatgtt gttgtgggtc ctttacttac 3120
atgcttagat acatgaagca acatgctgct acgtttaata attattgttt atctgatctg 3180
atttaaacaa acatgctttt taattgtcct gaaatgcttg gatgatggca tatgcagcag 3240
ctatgtgtgg attttaaata cccagcatga gcatgcatga ccctaactta gtatgctgtt 3300
tatttgcttg acttttcttt tgttgatact caccctttttg tttgttgact cttgcag 3357

<210> SEQ ID NO 89
<211> LENGTH: 2218
<212> TYPE: DNA
<213> ORGANISM: Sorghastrum nutans

<400> SEQUENCE: 89
gtggccagct tttgttctag ttcaacggtc cgggccttcc gggaacctaa tgcactaatt 60
gattattatt aatctactat tgcagctaac ctcaaaagaa atgctctgca gttagttgtc 120
cgtcccaatc aatccaccag cagactcaca ttattgatgg aggaaattaa attcagcctt 180
tgacgtggat gcaacaactg cacaagatac catctacttt gcttaatttg ctgatgtttt 240
gagaaaatta aaccagcttt gaccaacaca tgagatgggc gccttacgtt tggcacaatg 300
taatgtagtc cggcacggca agttagactc tgtgtgtagt gttatattag ccggcctctt 360
taggtttggc acaatttaat tgaatccggc atggcaagtt agactgcagt gtgagccggt 420
caccgcaagt taggatataa tatacaagag caagtataca ataaagtgac attagcgtaa 480
agttatatga catatggaat ataagagaaa atacggagta tataataagg tgaactgtat 540
agcgatcaaa tttatgctaa gcgaagaaaa gagaagataa ataggttgaa aacttatagt 600
gagctttggc tcataatcta aataattatg agagagtggg atcgaccaca tattcatttt 660
gtagtacgta ctctctccgt tttttataag ttgctttgat tttttttat atcaattttg 720 ctatacatct aaacataata ggaatatcaa gttcatgaag gtcgtgattt gcactaaata 780
tgttccctta ttagatagac gagttgttta gttttattgt agatgatata gcgcttgcat 840
atagcatgtg aaccggctaa attattagcc atacacgact ataaaaaatg acattccttt 900
gaggaacttt tatgcaacca aatagtcaac ttcaatgttg ctagagcggg ctttaagcca 960
aaagcagctg ctgctttgtt tccgagagaa gggacattct agttgatagc aaaacaaata 1020
cgtagcagtt gtagcgagtg tgtgagtaat aatttttctc tagtgtgtac gagtatgcga 1080
gtaataattt taaatctcta gaaggaagaa aaataatatt gctacctact ttgaggatat 1140 caatacccttt ctctaaaatg ttttggtgaa gccatcttta aagctaattg ttcaagattc 1200
aaccattggg acgtctcaaa tgattagatc ctataatact cctacgtact aaattataag 1260
tcgttttgat tttattggta catacatttt gctatgtgtt tagatataat aatatgtcta 1320
gatacattgg atgaaccgaa aaaatcgaaa cgacttataa tttggatcga aaggagtatt 1380
tgctaaagtc cttttcgaag ttccggctct aaatttttgg ataaaatttt atgaaatact 1440
atcttaagaa gtaatttgac tagagaagct tgaagagtat aatctcttaa ttttgtgcta 1500
caggagtgaa gccaacgtcg tatttagatc tagatgctgt caggtagtga ggacggaggg 1560
agtattggat aaagtcattc caagatctta gaaaattaaa gtatattaag tttgattaaa 1620
tttatatgac aagtaataac attcatgatg ccaattaagt atcattagat tcttcatcaa 1680
ctatattttc atagtatact tatttaatgt tataaatttt tataattttt tttataattt 1740
tagctaaact cgagatcgat tcttataatt aaaaataaac tgaaaaaaaa tcacatgttc 1800

-continued

```
aagtgacagg aggagccagt ttaacggcgt cgacaagtct aacggacacc aaccagcgaa   1860

ccaccagcgc cgagccaatc ccaagcgaag ccgactgcag acggccgaga cgttgacacc   1920

tttggcgcgg catccatctc tccggccccc tcttgagagt tccgccccac cggcggcggt   1980

ttccaagtcc gttccgcccg ccttcgcggt tggacttgtt ccggtggcgc ctggcggatc   2040

gcgtggcgga gcggagacga cgaggtgagc cgtgggcgtt cctcctcctg ctcctctcac   2100

acggcacgga acggaaccgt gacggcaccg ggcagcacgg gcgggattcc ttccccacct   2160

ctccttcggt cctccctcca tcataaatag ccaccccccct cccaccttct ttccccac    2218
```

<210> SEQ ID NO 90
<211> LENGTH: 86
<212> TYPE: DNA
<213> ORGANISM: Sorghastrum nutans

<400> SEQUENCE: 90

```
ctcgtctccc ctcgtgttat tcggagcaca gacacacccc gatccccaat cctctcctcg     60

cgagcctcgt cgatccccgc ttcaag                                          86
```

<210> SEQ ID NO 91
<211> LENGTH: 1053
<212> TYPE: DNA
<213> ORGANISM: Sorghastrum nutans

<400> SEQUENCE: 91

```
gtacggcgat catcctccct ccctaactcc aatccgtggt tagggcctgc tagatcgtcc     60

tccctcccta cctgcgatcc gtggttcgcg cctgctagtt ctgtttcctg tttgtcgatg    120

gctgcgaggt ataatagatc tgatggcgtg cggtgtgacg gttaaattca catgctcttg    180

cgatttatac gcgaatcgat ctgggattgc tcgagatcgg tgatccatgg ttagaaccct    240

aggcggtgga gtcgggttaa atccgtgctg ttagggttcg taggtggatg cgacctgttc    300

tggttgttta cttgtcagta tttaggaatc ctactaggat ggttctagct ggttcgcaga    360

tgagatcgat ttcatgatct gctatatctt tcgttgccta agtttcgttt aatctgtccg    420

tggtatgatg ttagcctttg atatgcttcg atcgtgctag ctacctcctg tgcactaaat    480

tatcagctcg taatttttag catgcccttt tttttttggg tattgttcga ttgaggtgtc    540

gttctagatc agagtaggaa gactgtttca aactacctgc tggatttatt aaatttggat    600

ctgtatgagt atcacatata tctccataat ttagatggat ggaaatatcc ctttttcttt    660

tagatactgt ttggtataga ttttgctgtg ggttttactg gtacttagat actcttcgtt    720

tagatatgga tatgtttaca tgcagataca tgaagcaaca tgctgctaca gtttaatatg    780

gataggtgta tatgttgttg tgggtccttt acttacatgc ttagatacat gaagcaacat    840

gctgctacgt ttaataatta ttgtttatct gatctgattt aaacaaacat gctttttaat    900

tgtcctgaaa tgcttggatg atggcatatg cagcagctat gtgtggattt taaataccca    960

gcatgagcat gcatgaccct aacttagtat gctgtttatt tgcttgactt ttcttttgtt   1020

gatactcacc cttttgtttg ttgactcttg cag                                1053
```

<210> SEQ ID NO 92
<211> LENGTH: 3106
<212> TYPE: DNA
<213> ORGANISM: Sorghastrum nutans

<400> SEQUENCE: 92

```
agctttgacc aacacatgag atgggcgcct tacgtttggc acaatgtaat gtagtccggc     60
```

-continued

```
acggcaagtt agactctgtg tgtagtgtta tattagccgg cctctttagg tttggcacaa    120
tttaattgaa tccggcatgg caagttagac tgcagtgtga gccggtcacc gcaagttagg    180
atataatata caagagcaag tatacaataa agtgacatta gcgtaaagtt atatgacata    240
tggaatataa gagaaaatac ggagtatata ataaggtgaa ctgtatagcg atcaaattta    300
tgctaagcga agaaaagaga agataaatag gttgaaaact tatagtgagc tttggctcat    360
aatctaaata attatgagag agtgggatcg accacatatt cattttgtag tacgtactct    420
ctccgttttt tataagttgc tttgattttt ttttatatca attttgctat acatctaaac    480
ataataggaa tatcaagttc atgaaggtcg tgatttgcac taaatatgtt cccttattag    540
atagacgagt tgtttagttt tattgtagat gatatagcgc ttgcatatag catgtgaacc    600
ggctaaatta ttagccatac acgactataa aaaatgacat tcctttgagg aacttttatg    660
caaccaaata gtcaacttca atgttgctag agcgggcttt aagccaaaag cagctgctgc    720
tttgtttccg agagaaggga cattctagtt gatagcaaaa caaatacgta gcagttgtag    780
cgagtgtgtg agtaataatt tttctctagt gtgtacgagt atgcgagtaa taattttaaa    840
tctctagaag gaagaaaaat aatattgcta cctactttga ggatatcaat acctttctct    900
aaaatgtttt ggtgaagcca tctttaaagc taattgttca agattcaacc attgggacgt    960
ctcaaatgat tagatcctat aatactccta cgtactaaat tataagtcgt tttgatttta   1020
ttggtacata cattttgcta tgtgtttaga tataataata tgtctagata cattggatga   1080
accgaaaaaa tcgaaacgac ttataatttg gatcgaaagg agtatttgct aaagtccttt   1140
tcgaagttcc ggctctaaat ttttggataa aattttatga aatactatct taagaagtaa   1200
tttgactaga gaagcttgaa gagtataatc tcttaatttt gtgctacagg agtgaagcca   1260
acgtcgtatt tagatctaga tgctgtcagg tagtgaggac ggagggagta ttggataaag   1320
tcattccaag atcttagaaa attaaagtat attaagtttg attaaattta tatgacaagt   1380
aataacattc atgatgccaa ttaagtatca ttagattctt catcaactat attttcatag   1440
tatacttatt taatgttata aatttttata atttttttta taattttagc taaactcgag   1500
atcgattctt ataattaaaa ataaactgaa aaaaaatcac atgttcaagt gacaggagga   1560
gccagtttaa cggcgtcgac aagtctaacg gacaccaacc agcgaaccac cagcgccgag   1620
ccaatcccaa gcgaagccga ctgcagacgg ccgagacgtt gacacctttg gcgcggcatc   1680
catctctccg gccccctctt gagagttccg ccccaccggc ggcggtttcc aagtccgttc   1740
cgcccgcctt cgcggttgga cttgttccgg tggcgcctgg cggatcgcgt ggcggagcgg   1800
agacgacgag gtgagccgtg ggcgttcctc ctcctgctcc tctcacacgg cacggaacgg   1860
aaccgtgacg gcaccgggca gcacgggcgg gattccttcc ccacctctcc ttcggtcctc   1920
cctccatcat aaatagccac ccccctccca ccttctttcc ccacctcgtc tcccctcgtg   1980
ttattcggag cacagacaca ccccgatccc caatcctctc ctcgcgagcc tcgtcgatcc   2040
ccgcttcaag gtacggcgat catcctccct ccctaactcc aatccgtggt tagggcctgc   2100
tagatcgtcc tccctcccta cctgcgatcc gtggttcgcg cctgctagtt ctgtttcctg   2160
tttgtcgatg gctgcgaggt ataatagatc tgatggcgtg cggtgtgacg gttaaattca   2220
catgctcttg cgatttatac gcgaatcgat ctgggattgc tcgagatcgg tgatccatgg   2280
ttagaaccct aggcggtgga gtcgggttaa atccgtgctg ttagggttcg taggtggatg   2340
cgacctgttc tggttgttta cttgtcagta tttaggaatc ctactaggat ggttctagct   2400
```

-continued

```
ggttcgcaga tgagatcgat ttcatgatct gctatatctt tcgttgccta agtttcgttt   2460

aatctgtccg tggtatgatg ttagcctttg atatgcttcg atcgtgctag ctacctcctg   2520

tgcactaaat tatcagctcg taatttttag catgcccttt tttttttggg tattgttcga   2580

ttgaggtgtc gttctagatc agagtaggaa gactgtttca aactacctgc tggatttatt   2640

aaatttggat ctgtatgagt atcacatata tctccataat ttagatggat ggaaatatcc   2700

ctttttcttt tagatactgt ttggtataga ttttgctgtg ggttttactg gtacttagat   2760

actcttcgtt tagatatgga tatgtttaca tgcagataca tgaagcaaca tgctgctaca   2820

gtttaatatg gataggtgta tatgttgttg tgggtccttt acttacatgc ttagatacat   2880

gaagcaacat gctgctacgt ttaataatta ttgtttatct gatctgattt aaacaaacat   2940

gctttttaat tgtcctgaaa tgcttggatg atggcatatg cagcagctat gtgtggattt   3000

taaataccca gcatgagcat gcatgaccct aacttagtat gctgtttatt tgcttgactt   3060

ttcttttgtt gatactcacc cttttgtttg ttgactcttg caggtg                  3106
```

<210> SEQ ID NO 93
<211> LENGTH: 1964
<212> TYPE: DNA
<213> ORGANISM: Sorghastrum nutans

<400> SEQUENCE: 93

```
agctttgacc aacacatgag atgggcgcct tacgtttggc acaatgtaat gtagtccggc     60

acggcaagtt agactctgtg tgtagtgtta tattagccgg cctctttagg tttggcacaa    120

tttaattgaa tccggcatgg caagttagac tgcagtgtga gccggtcacc gcaagttagg    180

atataatata caagagcaag tatacaataa agtgacatta gcgtaaagtt atatgacata    240

tggaatataa gagaaaatac ggagtatata ataaggtgaa ctgtatagcg atcaaattta    300

tgctaagcga agaaaagaga agataaatag gttgaaaact tatagtgagc tttggctcat    360

aatctaaata attatgagag agtgggatcg accacatatt cattttgtag tacgtactct    420

ctccgttttt tataagttgc tttgattttt ttttatatca atttgctat acatctaaac     480

ataataggaa tatcaagttc atgaaggtcg tgatttgcac taaatatgtt cccttattag    540

atagacgagt tgtttagttt tattgtagat gatatagcgc ttgcatatag catgtgaacc    600

ggctaaatta ttagccatac acgactataa aaaatgacat tcctttgagg aacttttatg    660

caaccaaata gtcaacttca atgttgctag agcgggcttt aagccaaaag cagctgctgc    720

tttgtttccg agagaaggga cattctagtt gatagcaaaa caaatacgta gcagttgtag    780

cgagtgtgtg agtaataatt tttctctagt gtgtacgagt atgcgagtaa taattttaaa    840

tctctagaag gaagaaaaat aatattgcta cctactttga ggatatcaat acctttctct    900

aaaatgtttt ggtgaagcca tctttaaagc taattgttca agattcaacc attgggacgt    960

ctcaaatgat tagatcctat aatactccta cgtactaaat tataagtcgt tttgatttta   1020

ttggtacata catttgcta tgtgtttaga tataataata tgtctagata cattggatga    1080

accgaaaaaa tcgaaacgac ttataatttg gatcgaaagg agtatttgct aaagtccttt   1140

tcgaagttcc ggctctaaat ttttggataa aattttatga aatactatct taagaagtaa   1200

tttgactaga gaagcttgaa gagtataatc tcttaatttt gtgctacagg agtgaagcca   1260

acgtcgtatt tagatctaga tgctgtcagg tagtgaggac ggagggagta ttggataaag   1320

tcattccaag atcttagaaa attaaagtat attaagtttg attaaattta tatgacaagt   1380

aataacattc atgatgccaa ttaagtatca ttagattctt catcaactat attttcatag   1440
```

-continued tatacttatt taatgttata aatttttata attttttttta taattttagc taaactcgag 1500
atcgattctt ataattaaaa ataaactgaa aaaaaatcac atgttcaagt gacaggagga 1560
gccagtttaa cggcgtcgac aagtctaacg gacaccaacc agcgaaccac cagcgccgag 1620
ccaatcccaa gcgaagccga ctgcagacgg ccgagacgtt gacacctttg gcgcggcatc 1680
catctctccg gccccctctt gagagttccg ccccaccggc ggcggtttcc aagtccgttc 1740
cgcccgcctt cgcggttgga cttgttccgg tggcgcctgg cggatcgcgt ggcggagcgg 1800
agacgacgag gtgagccgtg ggcgttcctc ctcctgctcc tctcacacgg cacggaacgg 1860
aaccgtgacg gcaccgggca gcacgggcgg gattccttcc ccacctctcc ttcggtcctc 1920
cctccatcat aaatagccac ccccctccca ccttctttcc ccac 1964

<210> SEQ ID NO 94
<211> LENGTH: 1056
<212> TYPE: DNA
<213> ORGANISM: Sorghastrum nutans

<400> SEQUENCE: 94
gtacggcgat catcctccct ccctaactcc aatccgtggt tagggcctgc tagatcgtcc 60
tccctcccta cctgcgatcc gtggttcgcg cctgctagtt ctgtttcctg tttgtcgatg 120
gctgcgaggt ataatagatc tgatggcgtg cggtgtgacg gttaaattca catgctcttg 180
cgatttatac gcgaatcgat ctgggattgc tcgagatcgg tgatccatgg ttagaaccct 240
aggcggtgga gtcgggttaa atccgtgctg ttagggttcg taggtggatg cgacctgttc 300
tggttgttta cttgtcagta tttaggaatc ctactaggat ggttctagct ggttcgcaga 360
tgagatcgat ttcatgatct gctatatctt tcgttgccta agtttcgttt aatctgtccg 420
tggtatgatg ttagcctttg atatgcttcg atcgtgctag ctacctcctg tgcactaaat 480
tatcagctcg taatttttag catgcccttt tttttttggg tattgttcga ttgaggtgtc 540
gttctagatc agagtaggaa gactgtttca aactacctgc tggatttatt aaatttggat 600
ctgtatgagt atcacatata tctccataat ttagatggat ggaaatatcc ctttttcttt 660
tagatactgt ttggtataga ttttgctgtg ggttttactg gtacttagat actcttcgtt 720
tagatatgga tatgtttaca tgcagataca tgaagcaaca tgctgctaca gtttaatatg 780
gataggtgta tatgttgttg tgggtccttt acttacatgc ttagatacat gaagcaacat 840
gctgctacgt ttaataatta ttgtttatct gatctgattt aaacaaacat gctttttaat 900
tgtcctgaaa tgcttggatg atggcatatg cagcagctat gtgtggattt taaataccca 960
gcatgagcat gcatgaccct aacttagtat gctgtttatt tgcttgactt ttcttttgtt 1020
gatactcacc cttttgtttg ttgactcttg caggtg 1056

<210> SEQ ID NO 95
<211> LENGTH: 2165
<212> TYPE: DNA
<213> ORGANISM: Sorghastrum nutans

<400> SEQUENCE: 95
gattcaacca ttgggacgtc tcaaatgatt agatcctata atactcctac gtactaaatt 60
ataagtcgtt ttgattttat tggtacatac attttgctat gtgtttagat ataataatat 120
gtctagatac attggatgaa ccgaaaaaat cgaaacgact tataatttgg atcgaaagga 180
gtatttgcta aagtcctttt cgaagttccg gctctaaatt tttggataaa attttatgaa 240

-continued

```
atactatctt aagaagtaat ttgactagag aagcttgaag agtataatct cttaattttg    300

tgctacagga gtgaagccaa cgtcgtattt agatctagat gctgtcaggt agtgaggacg    360

gagggagtat tggataaagt cattccaaga tcttagaaaa ttaaagtata ttaagtttga    420

ttaaatttat atgacaagta ataacattca tgatgccaat taagtatcat tagattcttc    480

atcaactata ttttcatagt atacttattt aatgttataa atttttataa ttttttttat    540

aattttagct aaactcgaga tcgattctta taattaaaaa taaactgaaa aaaaatcaca    600

tgttcaagtg acaggaggag ccagtttaac ggcgtcgaca agtctaacgg acaccaacca    660

gcgaaccacc agcgccgagc caatcccaag cgaagccgac tgcagacggc cgagacgttg    720

acacctttgg cgcggcatcc atctctccgg ccccctcttg agagttccgc cccaccggcg    780

gcggtttcca agtccgttcc gcccgccttc gcggttggac ttgttccggt ggcgcctggc    840

ggatcgcgtg gcggagcgga gacgacgagg tgagccgtgg gcgttcctcc tcctgctcct    900

ctcacacggc acggaacgga accgtgacgg caccgggcag cacgggcggg attccttccc    960

cacctctcct tcggtcctcc ctccatcata aatagccacc cccctcccac cttctttccc   1020

cacctcgtct cccctcgtgt tattcggagc acagacacac cccgatcccc aatcctctcc   1080

tcgcgagcct cgtcgatccc cgcttcaagg tacggcgatc atcctccctc cctaactcca   1140

atccgtggtt agggcctgct agatcgtcct ccctccctac ctgcgatccg tggttcgcgc   1200

ctgctagttc tgtttcctgt ttgtcgatgg ctgcgaggta taatagatct gatggcgtgc   1260

ggtgtgacgg ttaaattcac atgctcttgc gatttatacg cgaatcgatc tgggattgct   1320

cgagatcggt gatccatggt tagaacccta ggcggtggag tcgggttaaa tccgtgctgt   1380

tagggttcgt aggtggatgc gacctgttct ggttgtttac ttgtcagtat ttaggaatcc   1440

tactaggatg gttctagctg gttcgcagat gagatcgatt tcatgatctg ctatatcttt   1500

cgttgcctaa gtttcgttta atctgtccgt ggtatgatgt tagcctttga tatgcttcga   1560

tcgtgctagc tacctcctgt gcactaaatt atcagctcgt aatttttagc atgccctttt   1620

ttttttgggt attgttcgat tgaggtgtcg ttctagatca gagtaggaag actgtttcaa   1680

actacctgct ggatttatta aatttggatc tgtatgagta tcacatatat ctccataatt   1740

tagatggatg gaaatatccc tttttctttt agatactgtt tggtatagat tttgctgtgg   1800

gttttactgg tacttagata ctcttcgttt agatatggat atgtttacat gcagatacat   1860

gaagcaacat gctgctacag tttaatatgg ataggtgtat atgttgttgt gggtccttta   1920

cttacatgct tagatacatg aagcaacatg ctgctacgtt taataattat tgtttatctg   1980

atctgattta aacaaacatg ctttttaatt gtcctgaaat gcttggatga tggcatatgc   2040

agcagctatg tgtggatttt aaatacccag catgagcatg catgacccta acttagtatg   2100

ctgtttattt gcttgacttt tcttttgttg atactcaccc ttttgtttgt tgactcttgc   2160

aggtg                                                                2165
```

<210> SEQ ID NO 96
<211> LENGTH: 1023
<212> TYPE: DNA
<213> ORGANISM: Sorghastrum nutans

<400> SEQUENCE: 96

```
gattcaacca ttgggacgtc tcaaatgatt agatcctata atactcctac gtactaaatt     60

ataagtcgtt ttgattttat tggtacatac attttgctat gtgtttagat ataataatat    120

gtctagatac attggatgaa ccgaaaaaat cgaaacgact tataatttgg atcgaaagga    180
```

-continued

```
gtatttgcta aagtcctttt cgaagttccg gctctaaatt tttggataaa attttatgaa    240

atactatctt aagaagtaat ttgactagag aagcttgaag agtataatct cttaattttg    300

tgctacagga gtgaagccaa cgtcgtattt agatctagat gctgtcaggt agtgaggacg    360

gagggagtat tggataaagt cattccaaga tcttagaaaa ttaaagtata ttaagtttga    420

ttaaatttat atgacaagta ataacattca tgatgccaat taagtatcat tagattcttc    480

atcaactata ttttcatagt atacttattt aatgttataa atttttataa ttttttttat    540

aattttagct aaactcgaga tcgattctta taattaaaaa taaactgaaa aaaaatcaca    600

tgttcaagtg acaggaggag ccagtttaac ggcgtcgaca agtctaacgg acaccaacca    660

gcgaaccacc agcgccgagc caatcccaag cgaagccgac tgcagacggc cgagacgttg    720

acacctttgg cgcggcatcc atctctccgg ccccctcttg agagttccgc cccaccggcg    780

gcggtttcca agtccgttcc gcccgccttc gcggttggac ttgttccggt ggcgcctggc    840

ggatcgcgtg gcggagcgga gacgacgagg tgagccgtgg gcgttcctcc tcctgctcct    900

ctcacacggc acggaacgga accgtgacgg caccgggcag cacgggcggg attccttccc    960

cacctctcct tcggtcctcc ctccatcata aatagccacc cccctcccac cttctttccc   1020

cac                                                                 1023
```

<210> SEQ ID NO 97
<211> LENGTH: 1866
<212> TYPE: DNA
<213> ORGANISM: Sorghastrum nutans

<400> SEQUENCE: 97

```
gtgctacagg agtgaagcca acgtcgtatt tagatctaga tgctgtcagg tagtgaggac     60

ggagggagta ttggataaag tcattccaag atcttagaaa attaaagtat attaagtttg    120

attaaattta tatgacaagt aataacattc atgatgccaa ttaagtatca ttagattctt    180

catcaactat attttcatag tatacttatt taatgttata aatttttata atttttttta    240

taattttagc taaactcgag atcgattctt ataattaaaa ataaactgaa aaaaaatcac    300

atgttcaagt gacaggagga gccagtttaa cggcgtcgac aagtctaacg gacaccaacc    360

agcgaaccac cagcgccgag ccaatcccaa gcgaagccga ctgcagacgg ccgagacgtt    420

gacacctttg gcgcggcatc catctctccg gccccctctt gagagttccg ccccaccggc    480

ggcggtttcc aagtccgttc cgcccgcctt cgcggttgga cttgttccgg tggcgcctgg    540

cggatcgcgt ggcggagcgg agacgacgag gtgagccgtg ggcgttcctc ctcctgctcc    600

tctcacacgg cacggaacgg aaccgtgacg gcaccgggca gcacgggcgg gattccttcc    660

ccacctctcc ttcggtcctc cctccatcat aaatagccac ccccctccca ccttctttcc    720

ccacctcgtc tcccctcgtg ttattcggag cacagacaca ccccgatccc caatcctctc    780

ctcgcgagcc tcgtcgatcc ccgcttcaag gtacggcgat catcctccct ccctaactcc    840

aatccgtggt tagggcctgc tagatcgtcc tccctcccta cctgcgatcc gtggttcgcg    900

cctgctagtt ctgtttcctg tttgtcgatg gctgcgaggt ataatagatc tgatggcgtg    960

cggtgtgacg gttaaattca catgctcttg cgatttatac gcgaatcgat ctgggattgc   1020

tcgagatcgg tgatccatgg ttagaaccct aggcggtgga gtcgggttaa atccgtgctg   1080

ttagggttcg taggtggatg cgacctgttc tggttgttta cttgtcagta tttaggaatc   1140

ctactaggat ggttctagct ggttcgcaga tgagatcgat ttcatgatct gctatatctt   1200
```

tcgttgccta agtttcgttt aatctgtccg tggtatgatg ttagcctttg atatgcttcg 1260
atcgtgctag ctacctcctg tgcactaaat tatcagctcg taatttttag catgcccttt 1320
tttttttggg tattgttcga ttgaggtgtc gttctagatc agagtaggaa gactgtttca 1380
aactacctgc tggatttatt aaatttggat ctgtatgagt atcacatata tctccataat 1440
ttagatggat ggaaatatcc ctttttcttt tagatactgt ttggtataga ttttgctgtg 1500
ggttttactg gtacttagat actcttcgtt tagatatgga tatgtttaca tgcagataca 1560
tgaagcaaca tgctgctaca gtttaatatg gataggtgta tatgttgttg tgggtccttt 1620
acttacatgc ttagatacat gaagcaacat gctgctacgt ttaataatta ttgtttatct 1680
gatctgattt aaacaaacat gctttttaat tgtcctgaaa tgcttggatg atggcatatg 1740
cagcagctat gtgtggattt taaataccca gcatgagcat gcatgaccct aacttagtat 1800
gctgtttatt tgcttgactt ttcttttgtt gatactcacc cttttgtttg ttgactcttg 1860
caggtg 1866

<210> SEQ ID NO 98
<211> LENGTH: 724
<212> TYPE: DNA
<213> ORGANISM: Sorghastrum nutans

<400> SEQUENCE: 98
gtgctacagg agtgaagcca acgtcgtatt tagatctaga tgctgtcagg tagtgaggac 60
ggagggagta ttggataaag tcattccaag atcttagaaa attaaagtat attaagtttg 120
attaaattta tatgacaagt aataacattc atgatgccaa ttaagtatca ttagattctt 180
catcaactat attttcatag tatacttatt taatgttata aatttttata attttttta 240 taattttagc taaactcgag atcgattctt ataattaaaa ataaactgaa aaaaaatcac 300
atgttcaagt gacaggagga gccagtttaa cggcgtcgac aagtctaacg gacaccaacc 360
agcgaaccac cagcgccgag ccaatcccaa gcgaagccga ctgcagacgg ccgagacgtt 420
gacacctttg gcgcggcatc catctctccg gccccctctt gagagttccg ccccaccggc 480
ggcggtttcc aagtccgttc cgcccgcctt cgcggttgga cttgttccgg tggcgcctgg 540
cggatcgcgt ggcggagcgg agacgacgag gtgagccgtg ggcgttcctc ctcctgctcc 600
tctcacacgg cacggaacgg aaccgtgacg gcaccgggca gcacgggcgg gattccttcc 660
ccacctctcc ttcggtcctc cctccatcat aaatagccac cccccctccca ccttctttcc 720 ccac 724

<210> SEQ ID NO 99
<211> LENGTH: 2625
<212> TYPE: DNA
<213> ORGANISM: Setaria italica

<400> SEQUENCE: 99
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420

```
aaaaaggctt atactaccag tatactatca accagcatgc cgtttttgaa gtatccagga    480
ttagaagctt ctactgcgct tttatattat agctgtggac ccgtggtaac ctttctcttt    540
tggcgcttgc ttaatctcgg ccgtgctggt ccatgcttag gcactaggca gagatagagc    600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacac gtaactggcc ctgtaactac tcgttcggcc    780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag catcggaaca ctggtgattg   1080
gtggagccgg cagtatgcgc cccagcacgg ccgaggtggt ggtggcccgt ggccctgctg   1140
tctgcgcggc tcgggacaac ttgaaactgg gccaccgcct cgtcgcaact cgcaacccgt   1200
tggcggaaga aaggaatggc tcgtaggggc ccgggtagaa tcgaagaatg ttgcgctggg   1260
cttcgattca cataacatgg gcctgaagct ctaaaacgac ggcccggtcg ccgcgcgatg   1320
gaaagagacc ggatcctcct cgtgaattct ggaaggccac acgagagcga cccaccaccg   1380
acgcggagga gtcgtgcgtg gtccaacacg gccggcgggc tgggctgcga ccttaaccag   1440
caaggcacgc cacgacccgc cccgccctcg aggcataaat accctcccat cccgttgccg   1500
caagactcag atcagattcc gatccccagt tcttccccaa tcaccttgtg gtctctcgtg   1560
tcgcggttcc cagggacgcc tccggctcgt cgctcgacag cgatctccgc cccagcaagg   1620
tatagattca gttccttgct ccgatcccaa tctggttgag atgttgctcc gatgcgactt   1680
gattatgtca tatatctgcg gtttgcaccg atctgaagcc tagggtttct cgagcgaccc   1740
agttatttgc aatttgcgat ttgctcgttt gttgcgcagc gtagtttatg tttggagtaa   1800
tcgaggattt gtatgcggcg tcggcgctac ctgcttaatc acgccatgtg acgcggttac   1860
ttgcagaggc tgggttctgt tatgtcgtga tctaagaatc tagattaggc tcagtcgttc   1920
ttgctgtcga ctagtttgtt ttgatatcca tgtagtacaa gttacttaaa atttaggtcc   1980
aatatatttt gcatgctttt ggcctgttat tcttgccaac aagttgtcct ggtaaaaagt   2040
agatgtgaaa gtcacgtatt gggacaaatt gatggtttag tgctatagtt ctatagttct   2100
gtgatacatc tatctgattt tttttggtct attggtgcct aacttatctg aaaatcatgg   2160
aacatgaggc tagtttgatc atggtttagt tcattgtgat taataatgta tgatttagta   2220
gctattttgg tgatcgtgtc attttatttg tgaatggaat cattgtatgt aaatgaagct   2280
agttcagggg ttacgatgta gctggctttg tattctaaag gctgctatta ttcatccatc   2340
gatttcacct atatgtaatc cagagctttt gatgtgaaat ttgtctgatc cttcactagg   2400
aaggacagaa cattgttaat attttggcac atctgtctta ttctcatcct ttgtttgaac   2460
atgttagcct gttcaaacag atactgttgt aatgtcctag ttatataggt acatatgtgt   2520
tctctattga gtttatggac ttttgtgtgt gaagttatat ttcattttgc tcaaaactca   2580
tgtttgcaag ctttctgaca ttattctatt gttctgaaac agggt                   2625
```

<210> SEQ ID NO 100
<211> LENGTH: 1492
<212> TYPE: DNA

<213> ORGANISM: Setaria italica

<400> SEQUENCE: 100
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ccgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cc 1492

<210> SEQ ID NO 101
<211> LENGTH: 127
<212> TYPE: DNA
<213> ORGANISM: Setaria italica

<400> SEQUENCE: 101
cgttgccgca agactcagat cagattccga tccccagttc ttccccaatc accttgtggt 60
ctctcgtgtc gcggttccca gggacgcctc cggctcgtcg ctcgacagcg atctccgccc 120
cagcaag 127

<210> SEQ ID NO 102
<211> LENGTH: 1006
<212> TYPE: DNA
<213> ORGANISM: Setaria italica

<400> SEQUENCE: 102
gtatagattc agttccttgc tccgatccca atctggttga gatgttgctc cgatgcgact 60
tgattatgtc atatatctgc ggtttgcacc gatctgaagc ctagggtttc tcgagcgacc 120

-continued cagttatttg caatttgcga tttgctcgtt tgttgcgcag cgtagtttat gtttggagta 180
atcgaggatt tgtatgcggc gtcggcgcta cctgcttaat cacgccatgt gacgcggtta 240
cttgcagagg ctgggttctg ttatgtcgtg atctaagaat ctagattagg ctcagtcgtt 300
cttgctgtcg actagtttgt tttgatatcc atgtagtaca agttacttaa aatttaggtc 360
caatatattt tgcatgcttt tggcctgtta ttcttgccaa caagttgtcc tggtaaaaag 420
tagatgtgaa agtcacgtat tgggacaaat tgatggttta gtgctatagt tctatagttc 480
tgtgatacat ctatctgatt ttttttggtc tattggtgcc taacttatct gaaaatcatg 540
gaacatgagg ctagtttgat catggtttag ttcattgtga ttaataatgt atgatttagt 600
agctattttg gtgatcgtgt cattttattt gtgaatggaa tcattgtatg taaatgaagc 660
tagttcaggg gttacgatgt agctggcttt gtattctaaa ggctgctatt attcatccat 720
cgatttcacc tatatgtaat ccagagcttt tgatgtgaaa tttgtctgat ccttcactag 780
gaaggacaga acattgttaa tattttggca catctgtctt attctcatcc tttgtttgaa 840
catgttagcc tgttcaaaca gatactgttg taatgtccta gttatatagg tacatatgtg 900
ttctctattg agtttatgga cttttgtgtg tgaagttata tttcattttg ctcaaaactc 960
atgtttgcaa gctttctgac attattctat tgttctgaaa cagggt 1006

<210> SEQ ID NO 103
<211> LENGTH: 2625
<212> TYPE: DNA
<213> ORGANISM: Setaria italica

<400> SEQUENCE: 103
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200

-continued

```
tggcggaaga aaggaatggc tcgtaggggc ccgggtagaa tcgaagaatg ttgcgctggg   1260

cttcgattca cataacatgg gcctgaagct ctaaaacgac ggcccggtcg ccgcgcgatg   1320

gaaagagacc ggatcctcct cgtgaattct ggaaggccac acgagagcga cccaccaccg   1380

acgcggagga gtcgtgcgtg gtccaacacg gccggcgggc tgggctgcga ccttaaccag   1440

caaggcacgc cacgacccgc cccgccctcg aggcataaat accctcccat cccgttgccg   1500

caagactcag atcagattcc gatccccagt tcttccccaa tcaccttgtg gtctctcgtg   1560

tcgcggttcc cagggacgcc tccggctcgt cgctcgacag cgatctccgc cccagcaagg   1620

tatagattca gttccttgct ccgatcccaa tctggttgag atgttgctcc gatgcgactt   1680

gattatgtca tatatctgcg gtttgcaccg atctgaagcc tagggtttct cgagcgaccc   1740

agttatttgc aatttgcgat ttgctcgttt gttgcgcagc gtagtttatg tttggagtaa   1800

tcgaggattt gtatgcggcg tcggcgctac ctgcttaatc acgccatgtg acgcggttac   1860

ttgcagaggc tgggttctgt tatgtcgtga tctaagaatc tagattaggc tcagtcgttc   1920

ttgctgtcga ctagtttgtt ttgatatcca tgtagtacaa gttacttaaa atttaggtcc   1980

aatatatttt gcatgctttt ggcctgttat tcttgccaac aagttgtcct ggtaaaaagt   2040

agatgtgaaa gtcacgtatt gggacaaatt gatggtttag tgctatagtt ctatagttct   2100

gtgatacatc tatctgattt tttttggtct attggtgcct aacttatctg aaaatcatgg   2160

aacatgaggc tagtttgatc atggtttagt tcattgtgat taataatgta tgatttagta   2220

gctattttgg tgatcgtgtc attttatttg tgaatggaat cattgtatgt aaatgaagct   2280

agttcagggg ttacgatgta gctggctttg tattctaaag gctgctatta ttcatccatc   2340

gatttcacct atatgtaatc cagagctttt gatgtgaaat ttgtctgatc cttcactagg   2400

aaggacagaa cattgttaat attttggcac atctgtctta ttctcatcct ttgtttgaac   2460

atgttagcct gttcaaacag atactgttgt aatgtcctag ttatataggt acatatgtgt   2520

tctctattga gtttatggac ttttgtgtgt gaagttatat ttcattttgc tcaaaactca   2580

tgtttgcaag ctttctgaca ttattctatt gttctgaaac aggtg                  2625
```

<210> SEQ ID NO 104
<211> LENGTH: 1492
<212> TYPE: DNA
<213> ORGANISM: Setaria italica

<400> SEQUENCE: 104

```
actgccgcga cacgcctcac tggcgggagg gctccgagcg ctctctcccc ggcggccggc     60

ggagcagcga tctggattgg agagaataga ggaaagagag ggaaaaggag agagatagcg    120

caaagagctg aaaagataag gttgtgcggg ctgtggtgat tagaggacca ctaatccctc    180

catctcctaa tgacgcggtg cccaagacca gtgccgcggc acaccagcgt ctaagtgaac    240

ttccgctaac cttccggtca ttgcgcctga aagatgtcat gtggcgaggc ccccctctca    300

gtagattgcc aactgcctac cgtgccactc ttccatgcat gattgctccc gtctatcccg    360

tttctcacaa cagatagaca acagtaagca tcactaaagc aagcatgtgt agaaccttaa    420

aaaaaggctt atactaccag tatactatca accagcatgc cgtttttgaa gtatccagga    480

ttagaagctt ctactgcgct tttatattat agctgtggac ctgtggtaac ctttctcttt    540

tggcgcttgc ttaatctcgg ccgtgctggt ccatgcttag gcactaggca gagatagagc    600

cgggggtgaa tggggctaaa gctcagctgc tcgaggggcc gtgggctggt ttccactagc    660

ctacagctgt gccacgtgcg gccgcgcaag ccgaagcaag cacgctgagc cgttggacag    720
```

cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cc 1492

<210> SEQ ID NO 105
<211> LENGTH: 1006
<212> TYPE: DNA
<213> ORGANISM: Setaria italica

<400> SEQUENCE: 105
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttatttg caatttgcga tttgctcgtt tgttgcgcag cgtagtttat gtttggagta 180
atcgaggatt tgtatgcggc gtcggcgcta cctgcttaat cacgccatgt gacgcggtta 240
cttgcagagg ctgggttctg ttatgtcgtg atctaagaat ctagattagg ctcagtcgtt 300
cttgctgtcg actagtttgt tttgatatcc atgtagtaca agttacttaa aatttaggtc 360
caatatattt tgcatgcttt tggcctgtta ttcttgccaa caagttgtcc tggtaaaaag 420
tagatgtgaa agtcacgtat tgggacaaat tgatggttta gtgctatagt tctatagttc 480
tgtgatacat ctatctgatt ttttttggtc tattggtgcc taacttatct gaaaatcatg 540
gaacatgagg ctagtttgat catggtttag ttcattgtga ttaataatgt atgatttagt 600
agctattttg gtgatcgtgt cattttattt gtgaatggaa tcattgtatg taaatgaagc 660
tagttcaggg gttacgatgt agctggcttt gtattctaaa ggctgctatt attcatccat 720
cgatttcacc tatatgtaat ccagagcttt tgatgtgaaa tttgtctgat ccttcactag 780
gaaggacaga acattgttaa tattttggca catctgtctt attctcatcc tttgtttgaa 840
catgttagcc tgttcaaaca gatactgttg taatgtccta gttatatagg tacatatgtg 900
ttctctattg agtttatgga cttttgtgtg tgaagttata tttcattttg ctcaaaactc 960
atgtttgcaa gctttctgac attattctat tgttctgaaa caggtg 1006

<210> SEQ ID NO 106
<211> LENGTH: 2167
<212> TYPE: DNA
<213> ORGANISM: Setaria italica

<400> SEQUENCE: 106
gccgtttttg aagtatccag gattagaagc ttctactgcg cttttatatt atagctgtgg 60

```
acctgtggta acctttctct tttggcgctt gcttaatctc ggccgtgctg gtccatgctt    120

aggcactagg cagagataga gccgggggtg aatggggcta aagctcagct gctcgagggg    180

ccgtgggctg gtttccacta gcctacagct gtgccacgtg cggccgcgca agccgaagca    240

agcacgctga gccgttggac agcttgtcat aatgccatta cgtggattac acgtaactgg    300

ccctgtaact actcgttcgg ccatcatcaa acgacgacgt ccgctaggcg acgacacggg    360

taatgcacgc agccacccag gcgcgcgcgc tagcggagca cggtcaggtg acacgggcgt    420

cgtgacgctt ccgagttgaa ggggttaacg ccagaaacag tgtttggcca gggtatgaac    480

ataacaaaaa atattcacac gaaagaatgg aagtatggag ctgctactgt gtaaatgcca    540

agcaggaaac tcacgcccgc taacatccaa cggccaacag ctcgacgtgc cggtcagcag    600

agcatcggaa cactggtgat tggtggagcc ggcagtatgc gccccagcac ggccgaggtg    660

gtggtggccc gtggccctgc tgtctgcgcg gctcgggaca acttgaaact gggccaccgc    720

ctcgtcgcaa ctcgcaaccc gttggcggaa gaaaggaatg gctcgtaggg gcccgggtag    780

aatcgaagaa tgttgcgctg ggcttcgatt cacataacat gggcctgaag ctctaaaacg    840

acggcccggt cgccgcgcga tggaaagaga ccggatcctc ctcgtgaatt ctggaaggcc    900

acacgagagc gacccaccac cgacgcggag gagtcgtgcg tggtccaaca cggccggcgg    960

gctgggctgc gaccttaacc agcaaggcac gccacgaccc gccccgccct cgaggcataa   1020

ataccctccc atcccgttgc cgcaagactc agatcagatt ccgatcccca gttcttcccc   1080

aatcaccttg tggtctctcg tgtcgcggtt cccagggacg cctccggctc gtcgctcgac   1140

agcgatctcc gccccagcaa ggtatagatt cagttccttg ctccgatccc aatctggttg   1200

agatgttgct ccgatgcgac ttgattatgt catatatctg cggtttgcac cgatctgaag   1260

cctagggttt ctcgagcgac ccagttattt gcaatttgcg atttgctcgt ttgttgcgca   1320

gcgtagttta tgtttggagt aatcgaggat ttgtatgcgg cgtcggcgct acctgcttaa   1380

tcacgccatg tgacgcggtt acttgcagag gctgggttct gttatgtcgt gatctaagaa   1440

tctagattag gctcagtcgt tcttgctgtc gactagtttg ttttgatatc catgtagtac   1500

aagttactta aaatttaggt ccaatatatt ttgcatgctt ttggcctgtt attcttgcca   1560

acaagttgtc ctggtaaaaa gtagatgtga aagtcacgta ttgggacaaa ttgatggttt   1620

agtgctatag ttctatagtt ctgtgataca tctatctgat ttttttggt ctattggtgc   1680

ctaacttatc tgaaaatcat ggaacatgag gctagtttga tcatggttta gttcattgtg   1740

attaataatg tatgatttag tagctatttt ggtgatcgtg tcattttatt tgtgaatgga   1800

atcattgtat gtaaatgaag ctagttcagg ggttacgatg tagctggctt tgtattctaa   1860

aggctgctat tattcatcca tcgatttcac ctatatgtaa tccagagctt ttgatgtgaa   1920

atttgtctga tccttcacta ggaaggacag aacattgtta atattttggc acatctgtct   1980

tattctcatc ctttgtttga acatgttagc ctgttcaaac agatactgtt gtaatgtcct   2040

agttatatag gtacatatgt gttctctatt gagtttatgg acttttgtgt gtgaagttat   2100

atttcatttt gctcaaaact catgtttgca agctttctga cattattcta ttgttctgaa   2160

acaggtg                                                             2167
```

<210> SEQ ID NO 107
<211> LENGTH: 1034
<212> TYPE: DNA
<213> ORGANISM: Setaria italica

<400> SEQUENCE: 107

```
gccgtttttg aagtatccag gattagaagc ttctactgcg cttttatatt atagctgtgg     60

acctgtggta acctttctct tttggcgctt gcttaatctc ggccgtgctg gtccatgctt    120

aggcactagg cagagataga gccgggggtg aatggggcta aagctcagct gctcgagggg    180

ccgtgggctg gtttccacta gcctacagct gtgccacgtg cggccgcgca agccgaagca    240

agcacgctga gccgttggac agcttgtcat aatgccatta cgtggattac acgtaactgg    300

ccctgtaact actcgttcgg ccatcatcaa acgacgacgt ccgctaggcg acgacacggg    360

taatgcacgc agccacccag gcgcgcgcgc tagcggagca cggtcaggtg acacgggcgt    420

cgtgacgctt ccgagttgaa ggggttaacg ccagaaacag tgtttggcca gggtatgaac    480

ataacaaaaa atattcacac gaaagaatgg aagtatggag ctgctactgt gtaaatgcca    540

agcaggaaac tcacgcccgc taacatccaa cggccaacag ctcgacgtgc cggtcagcag    600

agcatcggaa cactggtgat tggtggagcc ggcagtatgc gccccagcac ggccgaggtg    660

gtggtggccc gtggccctgc tgtctgcgcg gctcgggaca acttgaaact gggccaccgc    720

ctcgtcgcaa ctcgcaaccc gttggcggaa gaaaggaatg gctcgtaggg gcccgggtag    780

aatcgaagaa tgttgcgctg ggcttcgatt cacataacat gggcctgaag ctctaaaacg    840

acggcccggt cgccgcgcga tggaaagaga ccggatcctc ctcgtgaatt ctggaaggcc    900

acacgagagc gacccaccac cgacgcggag gagtcgtgcg tggtccaaca cggccggcgg    960

gctgggctgc gaccttaacc agcaaggcac gccacgaccc gccccgccct cgaggcataa   1020

ataccctccc atcc                                                     1034
```

<210> SEQ ID NO 108
<211> LENGTH: 1813
<212> TYPE: DNA
<213> ORGANISM: Setaria italica

<400> SEQUENCE: 108

```
cacgggtaat gcacgcagcc acccaggcgc gcgcgctagc ggagcacggt caggtgacac     60

gggcgtcgtg acgcttccga gttgaagggg ttaacgccag aaacagtgtt tggccagggt    120

atgaacataa caaaaaatat tcacacgaaa gaatggaagt atggagctgc tactgtgtaa    180

atgccaagca ggaaactcac gcccgctaac atccaacggc caacagctcg acgtgccggt    240

cagcagagca tcggaacact ggtgattggt ggagccggca gtatgcgccc cagcacggcc    300

gaggtggtgg tggcccgtgg ccctgctgtc tgcgcggctc gggacaactt gaaactgggc    360

caccgcctcg tcgcaactcg caacccgttg gcggaagaaa ggaatggctc gtagggggccc    420

gggtagaatc gaagaatgtt gcgctgggct tcgattcaca taacatgggc ctgaagctct    480

aaaacgacgg cccggtcgcc gcgcgatgga aagagaccgg atcctcctcg tgaattctgg    540

aaggccacac gagagcgacc caccaccgac gcggaggagt cgtgcgtggt ccaacacggc    600

cggcgggctg ggctgcgacc ttaaccagca aggcacgcca cgacccgccc cgccctcgag    660

gcataaatac cctcccatcc cgttgccgca agactcagat cagattccga tccccagttc    720

ttccccaatc accttgtggt ctctcgtgtc gcggttccca gggacgcctc cggctcgtcg    780

ctcgacagcg atctccgccc cagcaaggta tagattcagt tccttgctcc gatcccaatc    840

tggttgagat gttgctccga tgcgacttga ttatgtcata tatctgcggt ttgcaccgat    900

ctgaagccta gggtttctcg agcgacccag ttatttgcaa tttgcgattt gctcgtttgt    960

tgcgcagcgt agtttatgtt tggagtaatc gaggatttgt atgcggcgtc ggcgctacct   1020
```

gcttaatcac gccatgtgac gcggttactt gcagaggctg ggttctgtta tgtcgtgatc 1080
taagaatcta gattaggctc agtcgttctt gctgtcgact agtttgtttt gatatccatg 1140
tagtacaagt tacttaaaat ttaggtccaa tatattttgc atgcttttgg cctgttattc 1200
ttgccaacaa gttgtcctgg taaaaagtag atgtgaaagt cacgtattgg gacaaattga 1260
tggtttagtg ctatagttct atagttctgt gatacatcta tctgattttt tttggtctat 1320
tggtgcctaa cttatctgaa aatcatggaa catgaggcta gtttgatcat ggtttagttc 1380
attgtgatta ataatgtatg atttagtagc tattttggtg atcgtgtcat tttatttgtg 1440
aatggaatca ttgtatgtaa atgaagctag ttcaggggtt acgatgtagc tggctttgta 1500
ttctaaaggc tgctattatt catccatcga tttcacctat atgtaatcca gagcttttga 1560
tgtgaaattt gtctgatcct tcactaggaa ggacagaaca ttgttaatat tttggcacat 1620
ctgtcttatt ctcatccttt gtttgaacat gttagcctgt tcaaacagat actgttgtaa 1680
tgtcctagtt atataggtac atatgtgttc tctattgagt ttatggactt ttgtgtgtga 1740
agttatattt cattttgctc aaaactcatg tttgcaagct ttctgacatt attctattgt 1800
tctgaaacag gtg 1813

<210> SEQ ID NO 109
<211> LENGTH: 680
<212> TYPE: DNA
<213> ORGANISM: Setaria italica

<400> SEQUENCE: 109
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc 680

<210> SEQ ID NO 110
<211> LENGTH: 2634
<212> TYPE: DNA
<213> ORGANISM: Setaria viridis

<400> SEQUENCE: 110
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360

-continued

```
tttctcacaa cagatagaca acagtaagca tcactaaagc aagcatgtgt agaaccttaa    420
aaaaaggctt atactaccag tatactatca accagcatgc cgtttttgaa gtatccagga    480
ttagaagctt ctactgcgct tttatattat agctgtggac ctgtggtaac ctttctcttt    540
tggcgcttgc ttaatctcgg ccgtgctggt ccatgcttag gcactaggca gagatagagc    600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacag gtaactggcc ctgtaactac tcgttcggcc    780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag acatcggaac actggtgatt   1080
ggtggagccg gcagtatgcg ccccagcacg gccgaggtgg tggtggcccg tggccctgct   1140
gtctgcgcgg ctcgggacaa cttgaaactg ggccaccgcc tcgtcgcaac tcgcaacccg   1200
ttggcggaag aaaggaatgg ctcgtagggg cccgggtaga atccaagaat gttgcgctgg   1260
gcttcgattc acataacatg ggcctgaagc tctaaaacga cggcccggtc accgggcgat   1320
ggaaagagac cggatcctcc tcgtgaattc tggaaggcca cacgagagcg acccaccacc   1380
gacgcggagg agtcgtgcgt ggtccaacac ggccggcggg ctgggctgcg accttaacca   1440
gcaaggcacg ccacgacccg cctcgccctc gaggcataaa taccctccca tcccgttgcc   1500
gcaagactca gatcagattc cgatccccag ttcttcccca atcaccttgt ggtctctcgt   1560
gtcgcggttc ccagggacgc ctccggctcg tcgctcgaca gcgatctccg ccccagcaag   1620
gtatagattc agttccttgc tccgatccca atctggttga gatgttgctc cgatgcgact   1680
tgattatgtc atatatctgc ggtttgcacc gatctgaagc ctagggtttc tcgagcgacc   1740
cagttgtttg caatttgcga tttgctcgtt tgttgcgcat cgtagtttat gtttggagta   1800
atcgaggatt tgtatgcggc gtcggcgcta cctgcttaat cacgccatgt gacgcggtta   1860
cttgcagagg ctgggttagt gggttctgtt atgtcgtgat ctaagaatct agattaggct   1920
cagtcgttct tgctgtcgac tagtttgttt tgatatccat gtagtacaag ttacttaaaa   1980
tttaggtcca atatattttg catgcttttg gcctgttatt cttgccaaca agttgtcctg   2040
gtaaaaagta gatgtgaaag tcacgtattg ggacaaattg atggttaagt gctatagttc   2100
tatagttctg tgatacatct atctgatttt ttttggtcta ttggtgccta acttatctga   2160
aaatcatgga acatgaggct agtttgatca tggtttagtt cattgtgatt aataatgtat   2220
gatttagtag ctattttggt gatcgtgtca ttttatttgt gaatggaatc attgtatgta   2280
aatgaagcta gttcaggggt tatgatgtag ctggctttgt attctaaagg ctgctattat   2340
tcatccatcg atttcaccta tatgtaatcc agagctttcg atgtgaaatt tgtctgatcc   2400
ttcactagga aggacagaac attgttaata ttttggcaca tctgtcttat tctcatcctt   2460
tgtttgaaca tgttagcctg ttcaaacaga tactgttgta atgtcctagt tatataggta   2520
catatgtgtt ctctattgag tttatggact tttgtgtgtg aagttatatt tcattttgct   2580
caaaactcat gtttgcaagc tttctgacat tattctattg ttctgaaaca ggtg          2634
```

<210> SEQ ID NO 111

<211> LENGTH: 1493
<212> TYPE: DNA
<213> ORGANISM: Setaria viridis

<400> SEQUENCE: 111
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacag gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag acatcggaac actggtgatt 1080
ggtggagccg gcagtatgcg ccccagcacg gccgaggtgg tggtggcccg tggccctgct 1140
gtctgcgcgg ctcgggacaa cttgaaactg ggccaccgcc tcgtcgcaac tcgcaacccg 1200
ttggcggaag aaaggaatgg ctcgtagggg cccgggtaga atccaagaat gttgcgctgg 1260
gcttcgattc acataacatg ggcctgaagc tctaaaacga cggcccggtc accgggcgat 1320
ggaaagagac cggatcctcc tcgtgaattc tggaaggcca cacgagagcg acccaccacc 1380
gacgcggagg agtcgtgcgt ggtccaacac ggccggcggg ctgggctgcg accttaacca 1440
gcaaggcacg ccacgacccg cctcgccctc gaggcataaa taccctccca tcc 1493

<210> SEQ ID NO 112
<211> LENGTH: 127
<212> TYPE: DNA
<213> ORGANISM: Setaria viridis

<400> SEQUENCE: 112
cgttgccgca agactcagat cagattccga tccccagttc ttccccaatc accttgtggt 60
ctctcgtgtc gcggttccca gggacgcctc cggctcgtcg ctcgacagcg atctccgccc 120
cagcaag 127

<210> SEQ ID NO 113
<211> LENGTH: 1014
<212> TYPE: DNA
<213> ORGANISM: Setaria viridis

<400> SEQUENCE: 113
gtatagattc agttccttgc tccgatccca atctggttga gatgttgctc cgatgcgact 60

```
tgattatgtc atatatctgc ggtttgcacc gatctgaagc ctagggtttc tcgagcgacc    120
cagttgtttg caatttgcga tttgctcgtt tgttgcgcat cgtagtttat gtttggagta    180
atcgaggatt tgtatgcggc gtcggcgcta cctgcttaat cacgccatgt gacgcggtta    240
cttgcagagg ctgggttagt gggttctgtt atgtcgtgat ctaagaatct agattaggct    300
cagtcgttct tgctgtcgac tagtttgttt tgatatccat gtagtacaag ttacttaaaa    360
tttaggtcca atatatttg catgcttttg gcctgttatt cttgccaaca agttgtcctg    420
gtaaaaagta gatgtgaaag tcacgtattg ggacaaattg atggttaagt gctatagttc    480
tatagttctg tgatacatct atctgatttt ttttggtcta ttggtgccta acttatctga    540
aaatcatgga acatgaggct agtttgatca tggtttagtt cattgtgatt aataatgtat    600
gatttagtag ctattttggt gatcgtgtca ttttatttgt gaatggaatc attgtatgta    660
aatgaagcta gttcaggggt tatgatgtag ctggctttgt attctaaagg ctgctattat    720
tcatccatcg atttcaccta tatgtaatcc agagctttcg atgtgaaatt tgtctgatcc    780
ttcactagga aggacagaac attgttaata ttttggcaca tctgtcttat tctcatcctt    840
tgtttgaaca tgttagcctg ttcaaacaga tactgttgta atgtcctagt tatataggta    900
catatgtgtt ctctattgag tttatggact tttgtgtgtg aagttatatt tcattttgct    960
caaaactcat gtttgcaagc tttctgacat tattctattg ttctgaaaca ggtg          1014
```

```
<210> SEQ ID NO 114
<211> LENGTH: 2634
<212> TYPE: DNA
<213> ORGANISM: Setaria viridis

<400> SEQUENCE: 114

actgccgcga cacgcctcac tggcgggagg gctccgagcg ctctctcccc ggcggccggc     60
ggagcagcga tctggattgg agagaataga ggaaagagag ggaaaaggag agagatagcg    120
caaagagctg aaaagataag gttgtgcggg ctgtggtgat tagaggacca ctaatccctc    180
catctcctaa tgacgcggtg cccaagacca gtgccgcggc acaccagcgt ctaagtgaac    240
ttccgctaac cttccggtca ttgcgcctga aagatgtcat gtggcgaggc ccccctctca    300
gtagattgcc aactgcctac cgtgccactc ttccatgcat gattgctccc gtctatcccg    360
tttctcacaa cagatagaca acagtaagca tcactaaagc aagcatgtgt agaaccttaa    420
aaaaaggctt atactaccag tatactatca accagcatgc cgtttttgaa gtatccagga    480
ttagaagctt ctactgcgct tttatattat agctgtggac ctgtggtaac ctttctcttt    540
tggcgcttgc ttaatctcgg ccgtgctggt ccatgcttag gcactaggca gagatagagc    600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacag gtaactggcc ctgtaactac tcgttcggcc    780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag acatcggaac actggtgatt   1080
ggtggagccg gcagtatgcg ccccagcacg gccgaggtgg tggtggcccg tggccctgct   1140
```

```
gtctgcgcgg ctcgggacaa cttgaaactg ggccaccgcc tcgtcgcaac tcgcaacccg    1200

ttggcggaag aaaggaatgg ctcgtagggg cccgggtaga atccaagaat gttgcgctgg    1260

gcttcgattc acataacatg ggcctgaagc tctaaaacga cggcccggtc accgggcgat    1320

ggaaagagac cggatcctcc tcgtgaattc tggaaggcca cacgagagcg acccaccacc    1380

gacgcggagg agtcgtgcgt ggtccaacac ggccggcggg ctgggctgcg accttaacca    1440

gcaaggcacg ccacgacccg cctcgccctc gaggcataaa taccctccca tcccgttgcc    1500

gcaagactca gatcagattc cgatccccag ttcttcccca atcaccttgt ggtctctcgt    1560

gtcgcggttc ccagggacgc ctccggctcg tcgctcgaca gcgatctccg ccccagcaag    1620

gtatagattc agttccttgc tccgatccca atctggttga gatgttgctc cgatgcgact    1680

tgattatgtc atatatctgc ggtttgcacc gatctgaagc ctagggtttc tcgagcgacc    1740

cagttgtttg caatttgcga tttgctcgtt tgttgcgcat cgtagtttat gtttggagta    1800

atcgaggatt tgtatgcggc gtcggcgcta cctgcttaat cacgccatgt gacgcggtta    1860

cttgcagagg ctgggttagt gggttctgtt atgtcgtgat ctaagaatct agattaggct    1920

cagtcgttct tgctgtcgac tagtttgttt tgatatccat gtagtacaag ttacttaaaa    1980

tttaggtcca atatattttg catgcttttg gcctgttatt cttgccaaca agttgtcctg    2040

gtaaaaagta gatgtgaaag tcacgtattg ggacaaattg atggttaagt gctatagttc    2100

tatagttctg tgatacatct atctgatttt ttttggtcta ttggtgccta acttatctga    2160

aaatcatgga acatgaggct agtttgatca tggtttagtt cattgtgatt aataatgtat    2220

gatttagtag ctattttggt gatcgtgtca ttttatttgt gaatggaatc attgtatgta    2280

aatgaagcta gttcaggggt tatgatgtag ctggctttgt attctaaagg ctgctattat    2340

tcatccatcg atttcaccta tatgtaatcc agagctttcg atgtgaaatt tgtctgatcc    2400

ttcactagga aggacagaac attgttaata ttttggcaca tctgtcttat tctcatcctt    2460

tgtttgaaca tgttagcctg ttcaaacaga tactgttgta atgtcctagt tatataggta    2520

catatgtgtt ctctattgag tttatggact tttgtgtgtg aagttatatt tcattttgct    2580

caaaactcat gtttgcaagc tttctgacat tattctattg ttctgaaaca gggt          2634
```

<210> SEQ ID NO 115
<211> LENGTH: 1014
<212> TYPE: DNA
<213> ORGANISM: Setaria viridis

<400> SEQUENCE: 115

```
gtatagattc agttccttgc tccgatccca atctggttga gatgttgctc cgatgcgact      60

tgattatgtc atatatctgc ggtttgcacc gatctgaagc ctagggtttc tcgagcgacc     120

cagttgtttg caatttgcga tttgctcgtt tgttgcgcat cgtagtttat gtttggagta     180

atcgaggatt tgtatgcggc gtcggcgcta cctgcttaat cacgccatgt gacgcggtta     240

cttgcagagg ctgggttagt gggttctgtt atgtcgtgat ctaagaatct agattaggct     300

cagtcgttct tgctgtcgac tagtttgttt tgatatccat gtagtacaag ttacttaaaa     360

tttaggtcca atatattttg catgcttttg gcctgttatt cttgccaaca agttgtcctg     420

gtaaaaagta gatgtgaaag tcacgtattg ggacaaattg atggttaagt gctatagttc     480

tatagttctg tgatacatct atctgatttt ttttggtcta ttggtgccta acttatctga     540

aaatcatgga acatgaggct agtttgatca tggtttagtt cattgtgatt aataatgtat     600

gatttagtag ctattttggt gatcgtgtca ttttatttgt gaatggaatc attgtatgta     660
```

aatgaagcta gttcaggggt tatgatgtag ctggctttgt attctaaagg ctgctattat 720
tcatccatcg atttcaccta tatgtaatcc agagctttcg atgtgaaatt tgtctgatcc 780
ttcactagga aggacagaac attgttaata ttttggcaca tctgtcttat tctcatcctt 840
tgtttgaaca tgttagcctg ttcaaacaga tactgttgta atgtcctagt tatataggta 900
catatgtgtt ctctattgag tttatggact tttgtgtgtg aagttatatt tcattttgct 960
caaaactcat gtttgcaagc tttctgacat tattctattg ttctgaaaca gggt 1014

<210> SEQ ID NO 116
<211> LENGTH: 2176
<212> TYPE: DNA
<213> ORGANISM: Setaria viridis

<400> SEQUENCE: 116
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac aggtaactgg 300
ccctgtaact actcgttcgg ccatcatcaa acgacgacgt ccgctaggcg acgacacggg 360
taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agacatcgga acactggtga ttggtggagc cggcagtatg cgccccagca cggccgaggt 660
ggtggtggcc cgtggccctg ctgtctgcgc ggctcgggac aacttgaaac tgggccaccg 720
cctcgtcgca actcgcaacc cgttggcgga agaaaggaat ggctcgtagg ggcccgggta 780
gaatccaaga atgttgcgct gggcttcgat tcacataaca tgggcctgaa gctctaaaac 840
gacggcccgg tcaccgggcg atggaaagag accggatcct cctcgtgaat tctggaaggc 900
cacacgagag cgacccacca ccgacgcgga ggagtcgtgc gtggtccaac acggccggcg 960
ggctgggctg cgaccttaac cagcaaggca cgccacgacc cgcctcgccc tcgaggcata 1020
aataccctcc catcccgttg ccgcaagact cagatcagat tccgatcccc agttcttccc 1080
caatcacctt gtggtctctc gtgtcgcggt tcccagggac gcctccggct cgtcgctcga 1140
cagcgatctc cgccccagca aggtatagat tcagttcctt gctccgatcc caatctggtt 1200
gagatgttgc tccgatgcga cttgattatg tcatatatct gcggtttgca ccgatctgaa 1260
gcctagggtt tctcgagcga cccagttgtt tgcaatttgc gatttgctcg tttgttgcgc 1320
atcgtagttt atgtttggag taatcgagga tttgtatgcg gcgtcggcgc tacctgctta 1380
atcacgccat gtgacgcggt tacttgcaga ggctgggtta gtgggttctg ttatgtcgtg 1440
atctaagaat ctagattagg ctcagtcgtt cttgctgtcg actagtttgt tttgatatcc 1500
atgtagtaca agttacttaa aatttaggtc caatatattt tgcatgcttt tggcctgtta 1560
ttcttgccaa caagttgtcc tggtaaaaag tagatgtgaa agtcacgtat tgggacaaat 1620
tgatggttaa gtgctatagt tctatagttc tgtgatacat ctatctgatt tttttggtc 1680 tattggtgcc taacttatct gaaaatcatg gaacatgagg ctagtttgat catggtttag 1740

-continued

```
ttcattgtga ttaataatgt atgatttagt agctattttg gtgatcgtgt cattttattt   1800

gtgaatggaa tcattgtatg taaatgaagc tagttcaggg gttatgatgt agctggcttt   1860

gtattctaaa ggctgctatt attcatccat cgatttcacc tatatgtaat ccagagcttt   1920

cgatgtgaaa tttgtctgat ccttcactag gaaggacaga acattgttaa tattttggca   1980

catctgtctt attctcatcc tttgtttgaa catgttagcc tgttcaaaca gatactgttg   2040

taatgtccta gttatatagg tacatatgtg ttctctattg agtttatgga cttttgtgtg   2100

tgaagttata tttcattttg ctcaaaactc atgtttgcaa gctttctgac attattctat   2160

tgttctgaaa caggtg                                                   2176
```

```
<210> SEQ ID NO 117
<211> LENGTH: 1035
<212> TYPE: DNA
<213> ORGANISM: Setaria viridis

<400> SEQUENCE: 117

gccgtttttg aagtatccag gattagaagc ttctactgcg cttttatatt atagctgtgg     60

acctgtggta acctttctct tttggcgctt gcttaatctc ggccgtgctg gtccatgctt    120

aggcactagg cagagataga gccgggggtg aatggggcta aagctcagct gctcgagggg    180

ccgtgggctg gtttccacta gcctacagct gtgccacgtg cggccgcgca agccgaagca    240

agcacgctga gccgttggac agcttgtcat aatgccatta cgtggattac aggtaactgg    300

ccctgtaact actcgttcgg ccatcatcaa acgacgacgt ccgctaggcg acgacacggg    360

taatgcacgc agccacccag gcgcgcgcgc tagcggagca cggtcaggtg acacgggcgt    420

cgtgacgctt ccgagttgaa ggggttaacg ccagaaacag tgtttggcca gggtatgaac    480

ataacaaaaa atattcacac gaaagaatgg aagtatggag ctgctactgt gtaaatgcca    540

agcaggaaac tcacgcccgc taacatccaa cggccaacag ctcgacgtgc cggtcagcag    600

agacatcgga acactggtga ttggtggagc cggcagtatg cgccccagca cggccgaggt    660

ggtggtggcc cgtggccctg ctgtctgcgc ggctcgggac aacttgaaac tgggccaccg    720

cctcgtcgca actcgcaacc cgttggcgga agaaaggaat ggctcgtagg ggcccgggta    780

gaatccaaga atgttgcgct gggcttcgat tcacataaca tgggcctgaa gctctaaaac    840

gacggcccgg tcaccgggcg atggaaagag accggatcct cctcgtgaat tctggaaggc    900

cacacgagag cgacccacca ccgacgcgga ggagtcgtgc gtggtccaac acggccggcg    960

ggctgggctg cgaccttaac cagcaaggca cgccacgacc cgcctcgccc tcgaggcata   1020

aataccctcc catcc                                                    1035
```

```
<210> SEQ ID NO 118
<211> LENGTH: 1822
<212> TYPE: DNA
<213> ORGANISM: Setaria viridis

<400> SEQUENCE: 118

cacgggtaat gcacgcagcc acccaggcgc gcgcgctagc ggagcacggt caggtgacac     60

gggcgtcgtg acgcttccga gttgaagggg ttaacgccag aaacagtgtt tggccagggt    120

atgaacataa caaaaaatat tcacacgaaa gaatggaagt atggagctgc tactgtgtaa    180

atgccaagca ggaaactcac gcccgctaac atccaacggc caacagctcg acgtgccggt    240

cagcagagac atcggaacac tggtgattgg tggagccggc agtatgcgcc ccagcacggc    300

cgaggtggtg gtggcccgtg gccctgctgt ctgcgcggct cgggacaact tgaaactggg    360
```

-continued

```
ccaccgcctc gtcgcaactc gcaacccgtt ggcggaagaa aggaatggct cgtaggggcc    420

cgggtagaat ccaagaatgt tgcgctgggc ttcgattcac ataacatggg cctgaagctc    480

taaaacgacg gcccggtcac cgggcgatgg aaagagaccg gatcctcctc gtgaattctg    540

gaaggccaca cgagagcgac ccaccaccga cgcggaggag tcgtgcgtgg tccaacacgg    600

ccggcgggct gggctgcgac cttaaccagc aaggcacgcc acgacccgcc tcgccctcga    660

ggcataaata ccctcccatc ccgttgccgc aagactcaga tcagattccg atccccagtt    720

cttccccaat caccttgtgg tctctcgtgt cgcggttccc agggacgcct ccggctcgtc    780

gctcgacagc gatctccgcc ccagcaaggt atagattcag ttccttgctc cgatcccaat    840

ctggttgaga tgttgctccg atgcgacttg attatgtcat atatctgcgg tttgcaccga    900

tctgaagcct agggtttctc gagcgaccca gttgtttgca atttgcgatt tgctcgtttg    960

ttgcgcatcg tagtttatgt ttggagtaat cgaggatttg tatgcggcgt cggcgctacc   1020

tgcttaatca cgccatgtga cgcggttact tgcagaggct gggttagtgg gttctgttat   1080

gtcgtgatct aagaatctag attaggctca gtcgttcttg ctgtcgacta gtttgttttg   1140

atatccatgt agtacaagtt acttaaaatt taggtccaat atattttgca tgcttttggc   1200

ctgttattct tgccaacaag ttgtcctggt aaaaagtaga tgtgaaagtc acgtattggg   1260

acaaattgat ggttaagtgc tatagttcta tagttctgtg atacatctat ctgatttttt   1320

ttggtctatt ggtgcctaac ttatctgaaa atcatggaac atgaggctag tttgatcatg   1380

gtttagttca ttgtgattaa taatgtatga tttagtagct attttggtga tcgtgtcatt   1440

ttatttgtga atggaatcat tgtatgtaaa tgaagctagt tcaggggtta tgatgtagct   1500

ggctttgtat tctaaaggct gctattattc atccatcgat ttcacctata tgtaatccag   1560

agctttcgat gtgaaatttg tctgatcctt cactaggaag gacagaacat tgttaatatt   1620

ttggcacatc tgtcttattc tcatcctttg tttgaacatg ttagcctgtt caaacagata   1680

ctgttgtaat gtcctagtta tataggtaca tatgtgttct ctattgagtt tatggacttt   1740

tgtgtgtgaa gttatatttc attttgctca aaactcatgt ttgcaagctt tctgacatta   1800

ttctattgtt ctgaaacagg tg                                            1822
```

<210> SEQ ID NO 119
<211> LENGTH: 681
<212> TYPE: DNA
<213> ORGANISM: Setaria viridis

<400> SEQUENCE: 119

```
cacgggtaat gcacgcagcc acccaggcgc gcgcgctagc ggagcacggt caggtgacac     60

gggcgtcgtg acgcttccga gttgaagggg ttaacgccag aaacagtgtt tggccagggt    120

atgaacataa caaaaaatat tcacacgaaa gaatggaagt atggagctgc tactgtgtaa    180

atgccaagca ggaaactcac gcccgctaac atccaacggc caacagctcg acgtgccggt    240

cagcagagac atcggaacac tggtgattgg tggagccggc agtatgcgcc ccagcacggc    300

cgaggtggtg gtggcccgtg gccctgctgt ctgcgcggct cgggacaact tgaaactggg    360

ccaccgcctc gtcgcaactc gcaacccgtt ggcggaagaa aggaatggct cgtaggggcc    420

cgggtagaat ccaagaatgt tgcgctgggc ttcgattcac ataacatggg cctgaagctc    480

taaaacgacg gcccggtcac cgggcgatgg aaagagaccg gatcctcctc gtgaattctg    540

gaaggccaca cgagagcgac ccaccaccga cgcggaggag tcgtgcgtgg tccaacacgg    600
```

-continued

```
ccggcgggct gggctgcgac cttaaccagc aaggcacgcc acgacccgcc tcgccctcga    660

ggcataaata ccctcccatc c                                              681


<210> SEQ ID NO 120
<211> LENGTH: 1822
<212> TYPE: DNA
<213> ORGANISM: Setaria viridis

<400> SEQUENCE: 120

cacgggtaat gcacgcagcc acccaggcgc gcgcgctagc ggagcacggt caggtgacac     60

gggcgtcgtg acgcttccga gttgaagggg ttaacgccag aaacagtgtt tggccagggt    120

atgaacataa caaaaaatat tcacacgaaa gaatggaagt atggagctgc tactgtgtaa    180

atgccaagca ggaaactcac gcccgctaac atccaacggc caacagctcg acgtgccggt    240

cagcagagac atcggaacac tggtgattgg tggagccggc agtatgcgcc ccagcacggc    300

cgaggtggtg gtggcccgtg gccctgctgt ctgcgcggct cgggacaact tgaaactggg    360

ccaccgcctc gtcgcaactc gcaacccgtt ggcggaagaa aggaatggct cgtaggggcc    420

cgggtagaat ccaagaatgt tgcgctgggc ttcgattcac ataacatggg cctgaagctc    480

taaaacgacg gcccggtcac cgggcgatgg aaagagaccg gatcctcctt gtgaattctg    540

gaaggccaca cgagagcgac ccaccaccga cgcggaggag tcgtgcgtgg tccaacacgg    600

ccggcgggct gggctgcgac cttaaccagc aaggcacgcc acgacccgcc tcgccctcga    660

ggcataaata ccctcccatc ccgttgccgc aagactcaga tcagattccg atccccagtt    720

cttccccaat caccttgtgg tctctcgtgt cgcggttccc agggacgcct ccggctcgtc    780

gctcgacagc gatctccgcc ccagcaaggt atagattcag ttccttgctc cgatcccaat    840

ctggttgaga tgttgctccg atgcgacttg attatgtcat atatctgcgg tttgcaccga    900

tctgaagcct agggtttctc gagcgaccca gttgtttgca atttgcgatt tgctcgtttg    960

ttgcgcatcg tagtttatgt ttggagtaat cgaggatttg tatgcggcgt cggcgctacc   1020

tgcttaatca cgccatgtga cgcggttact tgcagaggct gggttagtgg gttctgttat   1080

gtcgtgatct aagaatctag attaggctca gtcgttcttg ctgtcgacta gtttgttttg   1140

atatccatgt agtacaagtt acttaaaatt taggtccaat atattttgca tgcttttggc   1200

ctgttattct tgccaacaag ttgtcctggt aaaaagtaga tgtgaaagtc acgtattggg   1260

acaaattgat ggttaagtgc tatagttcta tagttctgtg atacatctat ctgatttttt   1320

ttggtctatt ggtgcctaac ttatctgaaa atcatggaac atgaggctag tttgatcatg   1380

gtttagttca ttgtgattaa taatgtatga tttagtagct attttggtga tcgtgtcatt   1440

ttatttgtga atggaatcat tgtatgtaaa tgaagctagt tcaggggtta tgatgtagct   1500

ggctttgtat tctaaaggct gctattattc atccatcgat ttcacctata tgtaatccag   1560

agctttcgat gtgaaatttg tctgatcctt cactaggaag gacagaacat tgttaatatt   1620

ttggcacatc tgtcttattc tcatcctttg tttgaacatg ttagcctgtt caaacagata   1680

ctgttgtaat gtcctagtta tataggtaca tatgtgttct ctattgagtt tatggacttt   1740

tgtgtgtgaa gttatatttc attttgctca aaactcatgt ttgcaagctt tctgacatta   1800

ttctattgtt ctgaaacagg gt                                            1822


<210> SEQ ID NO 121
<211> LENGTH: 681
<212> TYPE: DNA
<213> ORGANISM: Setaria viridis
```

<400> SEQUENCE: 121
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctt gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc c 681

<210> SEQ ID NO 122
<211> LENGTH: 1925
<212> TYPE: DNA
<213> ORGANISM: Zea mays subsp. Mexicana

<400> SEQUENCE: 122
gtcgtgcccc tctctagaga taatgagcat tgcatgtcta agttataaaa aattaccaca 60
tatttttttt tgtcacactt gtgtttgaag tgcagtttat ctatctctat acatatattt 120
aaacttcact atatgaataa tatagtctat agtattaaaa taatatcaat gttttagatg 180
attatataac tgaactgcta gacatggtct aaaggacaac cgagtatttt gacaacatga 240
ctctacagtt ttatcttttt agtgtgcatg tgttcttttt acttttgcaa atagcttcac 300
ctatataata cttcatccat tttattagta catccattta ctaaattttt agtacatcta 360
ttttattcta ttttagcctc taaattaaga aaacttaaac tctattttag ttttttattt 420
aataatttag atataaaata gaataaaata aagtgactaa aaaataacta aatacctttt 480
aagaaataaa aaaactaagg aaccattttt cttgttccga gtagataatg acagcctgtt 540
caacgccgtc gacgagtcta acggacacca accagcgaac cagcagcgtc gcgtcgggcc 600
aagcgaagca gacggcacgg catctctgta gctgcctctg gacccctctc gagagttccg 660
ctccaccgtt ggacttgctc cgctgtcggc atccagaaat tgcgtggcgg agcggcagac 720
gtgagccggc acggcaggcg gcctcctctc acggcaccgg cagctacggg ggattccttt 780
cccaccgctc cttcgctttc ccttcctcgc ccgccgtaat aaatagaccc cctccacacc 840
ctctttcccc aacctcgtgt tcgttcggag cgcgcacaca cacaaccaga tctcccccaa 900
atccacccgt cggcacctcc gcttcaaggt acgccgctca tcctcctccc ccccctctct 960
ctaccttctc tagatcggcg tttcggtcca tggttagggc ccggtagttc tacttctgtt 1020
catgtttgtg ttagatccgt gtttgtgtta gatccgtgct gctagatttc gtacacggat 1080
gcgacctgta catcagacat gttctgattg ctaacttgcc agtgtttctc tttggggaat 1140
cctgggatgg ctctagccgt tccgcagacg ggatcgattt catgaatttt ttttgtttcg 1200
ttgcataggg tttggtttgc ccttttcctt tatttcaata tatgccgtgc acttgtttgt 1260
cgggtcatct tttcatgttt tttttggctt ggttgtgatg atgtggtctg gttgggcggt 1320
cgttctagat cggagtagaa tactgtttca aactacctgg tggatttatt aaaggatctg 1380
tatgtatgtg ccatacatct tcatagttac gagtttaaga tgatggatgg aaatatcgat 1440
ctaggatagg tatacatgtt gatgcgggtt ttactgatgc atatacagag atgctttttt 1500
ttcgcttggt tgtgatgatg tggtctggtc gggcggtcgt tctagatcgg agtagaatac 1560
tgtttcaaac tacctggtgg atttattaat tttggatctg tatgtgtgtc atacatcttc 1620
atagttacga gtttaagatc gatggaaata tcgatctagg ataggtatac atgttgatgt 1680
gggttttact gatgcatata catggcatat gcagcatcta ttcatatgct ctaaccttga 1740
gtacctatct attataataa acaagtatgt tttataatta ttttgatctt gatatacttg 1800
gatgatggca tatgcagcag ctatatgtgg attttttttag ccctgccttc atacgctatt 1860
tatttgcttg gtactgtttc ttttgtcgat gctcaccctg ttgtttggtg atacttctgc 1920
aggtc 1925

<210> SEQ ID NO 123
<211> LENGTH: 850
<212> TYPE: DNA
<213> ORGANISM: Zea mays subsp. Mexicana

<400> SEQUENCE: 123
gtcgtgcccc tctctagaga taatgagcat tgcatgtcta agttataaaa aattaccaca 60
tatttttttt tgtcacactt gtgtttgaag tgcagtttat ctatctctat acatatattt 120
aaacttcact atatgaataa tatagtctat agtattaaaa taatatcaat gttttagatg 180
attatataac tgaactgcta gacatggtct aaaggacaac cgagtatttt gacaacatga 240
ctctacagtt ttatcttttt agtgtgcatg tgttcttttt acttttgcaa atagcttcac 300
ctatataata cttcatccat tttattagta catccattta ctaaattttt agtacatcta 360
ttttattcta ttttagcctc taaattaaga aaacttaaac tctattttag ttttttattt 420
aataatttag atataaaata gaataaaata aagtgactaa aaaataacta aatacctttt 480
aagaaataaa aaaactaagg aaccattttt cttgttccga gtagataatg acagcctgtt 540
caacgccgtc gacgagtcta acggacacca accagcgaac cagcagcgtc gcgtcgggcc 600
aagcgaagca gacggcacgg catctctgta gctgcctctg gacccctctc gagagttccg 660
ctccaccgtt ggacttgctc cgctgtcggc atccagaaat tgcgtggcgg agcggcagac 720
gtgagccggc acggcaggcg gcctcctctc acggcaccgg cagctacggg ggattccttt 780
cccaccgctc cttcgctttc ccttcctcgc ccgccgtaat aaatagaccc cctccacacc 840
ctctttcccc 850

<210> SEQ ID NO 124
<211> LENGTH: 78
<212> TYPE: DNA
<213> ORGANISM: Zea mays subsp. Mexicana

<400> SEQUENCE: 124
aacctcgtgt tcgttcggag cgcgcacaca cacaaccaga tctcccccaa atccacccgt 60
cggcacctcc gcttcaag 78

<210> SEQ ID NO 125
<211> LENGTH: 997
<212> TYPE: DNA
<213> ORGANISM: Zea mays subsp. Mexicana

<400> SEQUENCE: 125

```
gtacgccgct catcctcctc cccccccctct ctctaccttc tctagatcgg cgtttcggtc     60
catggttagg gcccggtagt tctacttctg ttcatgtttg tgttagatcc gtgtttgtgt    120
tagatccgtg ctgctagatt tcgtacacgg atgcgacctg tacatcagac atgttctgat    180
tgctaacttg ccagtgtttc tctttgggga atcctgggat ggctctagcc gttccgcaga    240
cgggatcgat ttcatgaatt ttttttgttt cgttgcatag ggtttggttt gccctttttcc   300
tttatttcaa tatatgccgt gcacttgttt gtcgggtcat cttttcatgt ttttttggc     360
ttggttgtga tgatgtggtc tggttgggcg gtcgttctag atcggagtag aatactgttt    420
caaactacct ggtggattta ttaaaggatc tgtatgtatg tgccatacat cttcatagtt    480
acgagtttaa gatgatggat ggaaatatcg atctaggata ggtatacatg ttgatgcggg    540
ttttactgat gcatatacag agatgctttt ttttcgcttg gttgtgatga tgtggtctgg    600
tcgggcggtc gttctagatc ggagtagaat actgtttcaa actacctggt ggatttatta    660
attttggatc tgtatgtgtg tcatacatct tcatagttac gagtttaaga tcgatggaaa    720
tatcgatcta ggataggtat acatgttgat gtgggtttta ctgatgcata tacatggcat    780
atgcagcatc tattcatatg ctctaacctt gagtacctat ctattataat aaacaagtat    840
gttttataat tattttgatc ttgatatact tggatgatgg catatgcagc agctatatgt    900
ggattttttt agccctgcct tcatacgcta tttatttgct tggtactgtt tcttttgtcg    960
atgctcaccc tgttgtttgg tgatacttct gcaggtc                              997
```

<210> SEQ ID NO 126
<211> LENGTH: 1925
<212> TYPE: DNA
<213> ORGANISM: Zea mays subsp. Mexicana

<400> SEQUENCE: 126

```
gtcgtgcccc tctctagaga taatgagcat tgcatgtcta agttataaaa aattaccaca     60
tatttttttt tgtcacactt gtgtttgaag tgcagtttat ctatctctat acatatattt    120
aaacttcact atatgaataa tatagtctat agtattaaaa taatatcaat gttttagatg    180
attatataac tgaactgcta gacatggtct aaaggacaac cgagtatttt gacaacatga    240
ctctacagtt ttatcttttt agtgtgcatg tgttcttttt acttttgcaa atagcttcac    300
ctatataata cttcatccat tttattagta catccattta ctaaattttt agtacatcta    360
ttttattcta ttttagcctc taaattaaga aaacttaaac tctattttag tttttttattt   420
aataatttag atataaaata gaataaaata aagtgactaa aaaataacta aataccttttt   480
aagaaataaa aaaactaagg aaccattttt cttgttccga gtagataatg acagcctgtt    540
caacgccgtc gacgagtcta acggacacca accagcgaac cagcagcgtc gcgtcgggcc    600
aagcgaagca gacggcacgg catctctgta gctgcctctg gacccctctc gagagttccg    660
ctccaccgtt ggacttgctc cgctgtcggc atccagaaat tgcgtggcgg agcggcagac    720
gtgagccggc acggcaggcg gcctcctctc acggcaccgg cagctacggg ggattccttt    780
cccaccgctc cttcgctttc ccttcctcgc ccgccgtaat aaatagaccc cctccacacc    840
ctctttcccc aacctcgtgt tcgttcggag cgcgcacaca cacaaccaga tctcccccaa    900
atccacccgt cggcacctcc gcttcaaggt acgccgctca tcctcctccc ccccctctct    960
ctaccttctc tagatcggcg tttcggtcca tggttagggc ccggtagttc tacttctgtt   1020
catgtttgtg ttagatccgt gtttgtgtta gatccgtgct gctagatttc gtacacggat   1080
```

-continued gcgacctgta catcagacat gttctgattg ctaacttgcc agtgtttctc tttggggaat 1140
cctgggatgg ctctagccgt tccgcagacg ggatcgattt catgaatttt ttttgtttcg 1200
ttgcataggg tttggtttgc ccttttcctt tatttcaata tatgccgtgc acttgtttgt 1260
cgggtcatct tttcatgttt tttttggctt ggttgtgatg atgtggtctg gttgggcggt 1320
cgttctagat cggagtagaa tactgtttca aactacctgg tggatttatt aaaggatctg 1380
tatgtatgtg ccatacatct tcatagttac gagtttaaga tgatggatgg aaatatcgat 1440
ctaggatagg tatacatgtt gatgcgggtt ttactgatgc atatacagag atgctttttt 1500
ttcgcttggt tgtgatgatg tggtctggtc gggcggtcgt tctagatcgg agtagaatac 1560
tgtttcaaac tacctggtgg atttattaat tttggatctg tatgtgtgtc atacatcttc 1620
atagttacga gtttaagatc gatggaaata tcgatctagg ataggtatac atgttgatgt 1680
gggttttact gatgcatata catggcatat gcagcatcta ttcatatgct ctaaccttga 1740
gtacctatct attataataa acaagtatgt tttataatta ttttgatctt gatatacttg 1800
gatgatggca tatgcagcag ctatatgtgg atttttttag ccctgccttc atacgctatt 1860
tatttgcttg gtactgtttc ttttgtcgat gctcaccctg ttgtttggtg atacttctgc 1920
agggt 1925

<210> SEQ ID NO 127
<211> LENGTH: 997
<212> TYPE: DNA
<213> ORGANISM: Zea mays subsp. Mexicana

<400> SEQUENCE: 127
gtacgccgct catcctcctc cccccctct ctctaccttc tctagatcgg cgtttcggtc 60
catggttagg gcccggtagt tctacttctg ttcatgtttg tgttagatcc gtgtttgtgt 120
tagatccgtg ctgctagatt tcgtacacgg atgcgacctg tacatcagac atgttctgat 180
tgctaacttg ccagtgtttc tctttgggga atcctgggat ggctctagcc gttccgcaga 240
cgggatcgat ttcatgaatt ttttttgttt cgttgcatag ggtttggttt gcccttttcc 300
tttatttcaa tatatgccgt gcacttgttt gtcgggtcat cttttcatgt tttttttggc 360
ttggttgtga tgatgtggtc tggttgggcg gtcgttctag atcggagtag aatactgttt 420
caaactacct ggtggattta ttaaaggatc tgtatgtatg tgccatacat cttcatagtt 480
acgagtttaa gatgatggat ggaaatatcg atctaggata ggtatacatg ttgatgcggg 540
ttttactgat gcatatacag agatgctttt ttttcgcttg gttgtgatga tgtggtctgg 600
tcgggcggtc gttctagatc ggagtagaat actgtttcaa actacctggt ggatttatta 660
attttggatc tgtatgtgtg tcatacatct tcatagttac gagtttaaga tcgatggaaa 720
tatcgatcta ggataggtat acatgttgat gtgggtttta ctgatgcata tacatggcat 780
atgcagcatc tattcatatg ctctaacctt gagtacctat ctattataat aaacaagtat 840
gttttataat tattttgatc ttgatatact tggatgatgg catatgcagc agctatatgt 900
ggattttttt agccctgcct tcatacgcta tttatttgct tggtactgtt tcttttgtcg 960
atgctcaccc tgttgtttgg tgatacttct gcagggt 997

<210> SEQ ID NO 128
<211> LENGTH: 1974
<212> TYPE: DNA
<213> ORGANISM: Zea mays subsp. Mexicana

<400> SEQUENCE: 128

```
gtcgtgcccc tctctagaga taaagagcat tgcatgtcta agttataaaa aattaccaca     60
tatttttttt gtcacacttg tttgaagtgc agtttatcta tctttataca tatatttaaa    120
ctttactcta cgaataatat aatctatagt actacaataa tatcagtgtt ttagagaatc    180
atataaatga acagttagac atggtctaaa ggacaattga gtattttgac aacaggactc    240
tacagtttta tctttttagt gtgcatgtgt tctccttttt tttttgcaaa tagcttcacc    300
tatataatac ttcatccatt ttattagtac atccatttag ggtttagggt taatggtttt    360
tatagactaa tttttttagt acatctattt tattctattt tagcctctaa attaagaaaa    420
ctaaaactct attttagttt ttttatttaa taatttagat ataaaataga ataaaataaa    480
gtgactaaaa attaaacaaa taccctttaa gaaattaaaa aaactaagga aacatttttc    540
ttgtttcgag tagataatgc cagcctgtta aacgccgtcg acgagtctaa cggacaccaa    600
ccagcgaacc agcagcgtcg cgtcgggcca agcgaagcag acggcacggc atctctgtcg    660
ctgcctctgg accccctctcg agagttccgc tccaccgttg gacttgctcc gctgtcggca    720
tccagaaatt gcgtggcgga gcggcagacg tgagccggca cggcaggcgg cctcctcctc    780
ctctcacggc accggcagct acgggggatt cctttcccac cgctccttcg ctttcccttc    840
ctcgcccgcc gtaataaata gacacccccct ccacaccttc tttccccaac ctcgtgttgt    900
tcggagcgca cacacacaca accagatctc ccccaaatcc acccgtcggc acctccgctt    960
caaggtacgc cgctcatcct cccccccccc tctctacctt ctctagatcg gcgttccggt   1020
ccatggttag ggcccggtag ttctacttct gttcatgttt gtgttagatc cgtgtttgtg   1080
ttagatccgt gctgctagcg ttcgtacacg gatgcgacct gtacgtcaga cacgttctga   1140
ttgctaactt gccagtgttt ctctttgggg aatcctggga tggctctagc cgttccgcag   1200
acgggatcga tttcatgatt ttttttgttt cgttgcatag ggtttggttt gccctttttcc   1260
tttatttcaa tatatgccgt gcacttgttt gtcgggtcat cttttcatgc ttttttttgt   1320
cttggttgtg atgatgtggt ctggttgggc ggtcgttcta gatcggagaa gaattctgtt   1380
tcaaactacc tggtggattt attaattttg gatctgtatg tgtgtgccat acatattcat   1440
agttacgaat tgaagatgat ggatggaaat atcgatctag gataggtata catgttgatg   1500
cgggttttac tgatgcatat acagagatgc tttttgttcg cttggttgtg atgatgtggt   1560
ctggttgggc ggtcgttcat tcgttctaga tcggagtaga atactgtttc aaactacctg   1620
gtgtatttat taattttgga actgtatgtg tgtgtcatac atcttcatag ttacgagttt   1680
aagatggatg gaaatatcga tctaggatag gtatacatgt tgatgtgggt tttactgatg   1740
catatacatg atggcatatg cagcatctat tcatatgctc taaccttgag tacctatcta   1800
ttataataaa caagtatgtt ttataattat tttgatcttg atatacttgg atgatggcat   1860
atgcagcagc tatatgtgga tttttttagc cctgccttca tacgctattt atttgcttgg   1920
tactgtttct tttgtcgatg ctcaccctgt tgtttggtga tacttctgca ggtc          1974
```

<210> SEQ ID NO 129
<211> LENGTH: 887
<212> TYPE: DNA
<213> ORGANISM: Zea mays subsp. Mexicana

<400> SEQUENCE: 129

```
gtcgtgcccc tctctagaga taaagagcat tgcatgtcta agttataaaa aattaccaca     60
tatttttttt gtcacacttg tttgaagtgc agtttatcta tctttataca tatatttaaa    120
```

-continued

```
ctttactcta cgaataatat aatctatagt actacaataa tatcagtgtt ttagagaatc    180

atataaatga acagttagac atggtctaaa ggacaattga gtattttgac aacaggactc    240

tacagtttta tctttttagt gtgcatgtgt tctccttttt tttttgcaaa tagcttcacc    300

tatataatac ttcatccatt ttattagtac atccatttag ggtttagggt taatggtttt    360

tatagactaa ttttttagt acatctattt tattctattt tagcctctaa attaagaaaa    420

ctaaaactct attttagttt ttttatttaa taatttagat ataaaataga ataaaataaa    480

gtgactaaaa attaaacaaa taccctttaa gaaattaaaa aaactaagga aacatttttc    540

ttgtttcgag tagataatgc cagcctgtta aacgccgtcg acgagtctaa cggacaccaa    600

ccagcgaacc agcagcgtcg cgtcgggcca agcgaagcag acggcacggc atctctgtcg    660

ctgcctctgg acccctctcg agagttccgc tccaccgttg gacttgctcc gctgtcggca    720

tccagaaatt gcgtggcgga gcggcagacg tgagccggca cggcaggcgg cctcctcctc    780

ctctcacggc accggcagct acgggggatt cctttcccac cgctccttcg ctttcccttc    840

ctcgcccgcc gtaataaata gacacccccct ccacaccttc tttcccc                 887


<210> SEQ ID NO 130
<211> LENGTH: 77
<212> TYPE: DNA
<213> ORGANISM: Zea mays subsp. Mexicana

<400> SEQUENCE: 130

aacctcgtgt tgttcggagc gcacacacac acaaccagat ctcccccaaa tccacccgtc     60

ggcacctccg cttcaag                                                     77


<210> SEQ ID NO 131
<211> LENGTH: 1010
<212> TYPE: DNA
<213> ORGANISM: Zea mays subsp. Mexicana

<400> SEQUENCE: 131

gtacgccgct catcctcccc ccccctctc taccttctct agatcggcgt tccggtccat     60

ggttagggcc cggtagttct acttctgttc atgtttgtgt tagatccgtg tttgtgttag    120

atccgtgctg ctagcgttcg tacacggatg cgacctgtac gtcagacacg ttctgattgc    180

taacttgcca gtgtttctct ttggggaatc ctgggatggc tctagccgtt ccgcagacgg    240

gatcgatttc atgatttttt ttgtttcgtt gcatagggtt tggtttgccc ttttccttta    300

tttcaatata tgccgtgcac ttgtttgtcg ggtcatcttt tcatgctttt ttttgtcttg    360

gttgtgatga tgtggtctgg ttgggcggtc gttctagatc ggagaagaat tctgtttcaa    420

actacctggt ggatttatta attttggatc tgtatgtgtg tgccatacat attcatagtt    480

acgaattgaa gatgatggat ggaaatatcg atctaggata ggtatacatg ttgatgcggg    540

ttttactgat gcatatacag agatgctttt tgttcgcttg gttgtgatga tgtggtctgg    600

ttgggcggtc gttcattcgt tctagatcgg agtagaatac tgtttcaaac tacctggtgt    660

atttattaat tttggaactg tatgtgtgtg tcatacatct tcatagttac gagtttaaga    720

tggatggaaa tatcgatcta ggataggtat acatgttgat gtgggtttta ctgatgcata    780

tacatgatgg catatgcagc atctattcat atgctctaac cttgagtacc tatctattat    840

aataaacaag tatgttttat aattattttg atcttgatat acttggatga tggcatatgc    900

agcagctata tgtggatttt tttagccctg ccttcatacg ctatttattt gcttggtact    960

gtttcttttg tcgatgctca ccctgttgtt tggtgatact tctgcaggtc              1010
```

<210> SEQ ID NO 132
<211> LENGTH: 1974
<212> TYPE: DNA
<213> ORGANISM: Zea mays subsp. Mexicana

<400> SEQUENCE: 132
gtcgtgcccc tctctagaga taaagagcat tgcatgtcta agttataaaa aattaccaca 60 tattttttt gtcacacttg tttgaagtgc agtttatcta tctttataca tatatttaaa 120
ctttactcta cgaataatat aatctatagt actacaataa tatcagtgtt ttagagaatc 180
atataaatga acagttagac atggtctaaa ggacaattga gtattttgac aacaggactc 240
tacagtttta tctttttagt gtgcatgtgt tctccttttt tttttgcaaa tagcttcacc 300
tatataatac ttcatccatt ttattagtac atccatttag ggtttagggt taatggtttt 360
tatagactaa ttttttagt acatctattt tattctattt tagcctctaa attaagaaaa 420
ctaaaactct attttagttt ttttatttaa taatttagat ataaaataga ataaaataaa 480
gtgactaaaa attaaacaaa taccctttaa gaaattaaaa aaactaagga aacatttttc 540
ttgtttcgag tagataatgc cagcctgtta aacgccgtcg acgagtctaa cggacaccaa 600
ccagcgaacc agcagcgtcg cgtcgggcca agcgaagcag acggcacggc atctctgtcg 660
ctgcctctgg acccctctcg agagttccgc tccaccgttg gacttgctcc gctgtcggca 720
tccagaaatt gcgtggcgga gcggcagacg tgagccggca cggcaggcgg cctcctcctc 780
ctctcacggc accggcagct acgggggatt cctttcccac cgctccttcg ctttcccttc 840
ctcgcccgcc gtaataaata gacacccccct ccacaccttc tttccccaac ctcgtgttgt 900
tcggagcgca cacacacaca accagatctc ccccaaatcc acccgtcggc acctccgctt 960
caaggtacgc cgctcatcct cccccccccc tctctacctt ctctagatcg gcgttccggt 1020
ccatggttag ggcccggtag ttctacttct gttcatgttt gtgttagatc cgtgtttgtg 1080
ttagatccgt gctgctagcg ttcgtacacg gatgcgacct gtacgtcaga cacgttctga 1140
ttgctaactt gccagtgttt ctctttgggg aatcctggga tggctctagc cgttccgcag 1200
acgggatcga tttcatgatt ttttttgttt cgttgcatag ggtttggttt gccctttcc 1260 tttatttcaa tatatgccgt gcacttgttt gtcgggtcat cttttcatgc ttttttttgt 1320
cttggttgtg atgatgtggt ctggttgggc ggtcgttcta gatcggagaa gaattctgtt 1380
tcaaactacc tggtggattt attaattttg gatctgtatg tgtgtgccat acatattcat 1440
agttacgaat tgaagatgat ggatggaaat atcgatctag gataggtata catgttgatg 1500
cgggttttac tgatgcatat acagagatgc tttttgttcg cttggttgtg atgatgtggt 1560
ctggttgggc ggtcgttcat tcgttctaga tcggagtaga atactgtttc aaactacctg 1620
gtgtatttat taattttgga actgtatgtg tgtgtcatac atcttcatag ttacgagttt 1680
aagatggatg gaaatatcga tctaggatag gtatacatgt tgatgtgggt tttactgatg 1740
catatacatg atggcatatg cagcatctat tcatatgctc taaccttgag tacctatcta 1800
ttataataaa caagtatgtt ttataattat tttgatcttg atatacttgg atgatggcat 1860
atgcagcagc tatatgtgga tttttttagc cctgccttca tacgctattt atttgcttgg 1920
tactgtttct tttgtcgatg ctcaccctgt tgtttggtga tacttctgca gggt 1974

<210> SEQ ID NO 133
<211> LENGTH: 1010
<212> TYPE: DNA

<213> ORGANISM: Zea mays subsp. Mexicana

<400> SEQUENCE: 133

```
gtacgccgct catcctcccc ccccctctc taccttctct agatcggcgt tccggtccat     60
ggttagggcc cggtagttct acttctgttc atgtttgtgt tagatccgtg tttgtgttag    120
atccgtgctg ctagcgttcg tacacggatg cgacctgtac gtcagacacg ttctgattgc    180
taacttgcca gtgtttctct ttggggaatc ctgggatggc tctagccgtt ccgcagacgg    240
gatcgatttc atgatttttt ttgtttcgtt gcatagggtt tggtttgccc ttttccttta    300
tttcaatata tgccgtgcac ttgtttgtcg ggtcatcttt tcatgctttt ttttgtcttg    360
gttgtgatga tgtggtctgg ttgggcggtc gttctagatc ggagaagaat tctgtttcaa    420
actacctggt ggatttatta attttggatc tgtatgtgtg tgccatacat attcatagtt    480
acgaattgaa gatgatggat ggaaatatcg atctaggata ggtatacatg ttgatgcggg    540
ttttactgat gcatatacag agatgctttt tgttcgcttg gttgtgatga tgtggtctgg    600
ttgggcggtc gttcattcgt tctagatcgg agtagaatac tgtttcaaac tacctggtgt    660
atttattaat tttggaactg tatgtgtgtg tcatacatct tcatagttac gagtttaaga    720
tggatggaaa tatcgatcta ggataggtat acatgttgat gtgggtttta ctgatgcata    780
tacatgatgg catatgcagc atctattcat atgctctaac cttgagtacc tatctattat    840
aataaacaag tatgttttat aattattttg atcttgatat acttggatga tggcatatgc    900
agcagctata tgtggatttt tttagccctg ccttcatacg ctatttattt gcttggtact    960
gtttcttttg tcgatgctca ccctgttgtt tggtgatact tctgcagggt              1010
```

<210> SEQ ID NO 134
<211> LENGTH: 2008
<212> TYPE: DNA
<213> ORGANISM: Zea mays subsp. Mexicana

<400> SEQUENCE: 134

```
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatcttttt agtgtgcatg tgatctctct gtttttttttg caaatagctt gacctatata    300
atacttcatc cattttatta gtacatccat ttaggattta gggttgatgg tttctataga    360
ctaattttta gtacatccat tttattcttt ttagtctcta aatttttttaa aactaaaact    420
ctattttagt tttttattta ataatttaga tataaaatga aataaaaataa attgactaca    480
aataaaacaa ataccctttta agaaataaaa aaactaagca aacatttttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acgggggatt cctttcccac cgctccttcg ctttcccttc ctcgcccgcc    840
gtaataaata gacacccccct ccacaccctc tttccccaac ctcgtgttcg ttcggagcgc    900
acacacacgc aaccagatct cccccaaatc cagccgtcgg cacctccgct tcaaggtacg    960
ccgctcatcc tcccccccccc cctctctcta ccttctctag atcggcgatc cggtccatgg   1020
```

-continued

```
ttagggcccg gtagttctac ttctgttcat gtttgtgtta gagcaaacat gttcatgttc   1080

atgtttgtga tgatgtggtc tggttgggcg gtcgttctag atcggagtag gatactgttt   1140

caagctacct ggtggattta ttaattttgt atctgtatgt gtgtgccata catcttcata   1200

gttacgagtt taagatgatg gatggaaata tcgatctagg ataggtatac atgttgatgc   1260

gggttttact gatgcatata cagagatgct ttttttctcg cttggttgtg atgatatggt   1320

ctggttgggc ggtcgttcta gatcggagta gaatactgtt tcaaactacc tggtggattt   1380

attaaaggat aaagggtcgt tctagatcgg agtagaatac tgtttcaaac tacctggtgg   1440

atttattaaa ggatctgtat gtatgtgcct acatcttcat agttacgagt ttaagatgat   1500

ggatggaaat atcgatctag gataggtata catgttgatg cgggttttac tgatgcatat   1560

acagagatgc tttttttcgc ttggttgtga tgatgtggtc tggttgggcg gtcgttctag   1620

atcggagtag aatactgttt caaactacct ggtggattta ttaattttgt atctttatgt   1680

gtgtgccata catcttcata gttacgagtt taagatgatg gatggaaata ttgatctagg   1740

ataggtatac atgttgatgt gggttttact gatgcatata catgatggca tatgcggcat   1800

ctattcatat gctctaacct tgagtaccta tctattataa taaacaagta tgttttataa   1860

ttattttgat cttgatatac ttggatgatg gcatatgcag cagctatatg tggatttttt   1920

agccctgcct tcatacgcta tttatttgct tggtactgtt tcttttgtcc gatgctcacc   1980

ctgttgttgg gtgatacttc tgcaggtc                                      2008
```

<210> SEQ ID NO 135
<211> LENGTH: 877
<212> TYPE: DNA
<213> ORGANISM: Zea mays subsp. Mexicana

<400> SEQUENCE: 135

```
gtcgtgcccc tctctagaga taaagagcat tgcatgtcta aagtataaaa aattaccaca     60

tatttttttg tcacacttat ttgaagtgta gtttatctat ctctatacat atatttaaac    120

ttcactctac aaataatata gtctataata ctaaaataat attagtgttt tagaggatca    180

tataaataaa ctgctagaca tggtctaaag gataattgaa tattttgaca atctacagtt    240

ttatcttttt agtgtgcatg tgatctctct gttttttttg caaatagctt gacctatata    300

atacttcatc cattttatta gtacatccat ttaggattta gggttgatgg tttctataga    360

ctaattttta gtacatccat tttattcttt ttagtctcta aattttttaa aactaaaact    420

ctattttagt tttttattta ataatttaga tataaaatga aataaaataa attgactaca    480

aataaaacaa ataccctttta agaaataaaa aaactaagca aacatttttc ttgtttcgag    540

tagataatga caggctgttc aacgccgtcg acgagtctaa cggacaccaa ccagcgaacc    600

agcagcgtcg cgtcgggcca agcgaagcag acggcacggc atctctgtag ctgcctctgg    660

acccctctcg agagttccgc tccaccgttg gacttgctcc gctgtcggca tccagaaatt    720

gcgtggcgga gcggcagacg tgaggcggca cggcaggcgg cctcttcctc ctctcacggc    780

accggcagct acgggggatt cctttcccac cgctccttcg ctttcccttc ctcgcccgcc    840

gtaataaata gacacccccct ccacaccctc tttcccc                             877
```

<210> SEQ ID NO 136
<211> LENGTH: 78
<212> TYPE: DNA
<213> ORGANISM: Zea mays subsp. Mexicana

<400> SEQUENCE: 136

```
aacctcgtgt tcgttcggag cgcacacaca cgcaaccaga tctcccccaa atccagccgt     60
cggcacctcc gcttcaag                                                   78
```

<210> SEQ ID NO 137
<211> LENGTH: 1053
<212> TYPE: DNA
<213> ORGANISM: Zea mays subsp. Mexicana

<400> SEQUENCE: 137

```
gtacgccgct catcctcccc cccccctct ctctaccttc tctagatcgg cgatccggtc     60
catggttagg gcccggtagt tctacttctg ttcatgtttg tgttagagca aacatgttca    120
tgttcatgtt tgtgatgatg tggtctggtt gggcggtcgt tctagatcgg agtaggatac    180
tgtttcaagc tacctggtgg atttattaat tttgtatctg tatgtgtgtg ccatacatct    240
tcatagttac gagtttaaga tgatggatgg aaatatcgat ctaggatagg tatacatgtt    300
gatgcgggtt ttactgatgc atatacagag atgctttttt tctcgcttgg ttgtgatgat    360
atggtctggt tgggcggtcg ttctagatcg gagtagaata ctgtttcaaa ctacctggtg    420
gatttattaa aggataaagg gtcgttctag atcggagtag aatactgttt caaactacct    480
ggtggattta ttaaaggatc tgtatgtatg tgcctacatc ttcatagtta cgagtttaag    540
atgatggatg gaaatatcga tctaggatag gtatacatgt tgatgcgggt tttactgatg    600
catatacaga gatgcttttt ttcgcttggt tgtgatgatg tggtctggtt gggcggtcgt    660
tctagatcgg agtagaatac tgtttcaaac tacctggtgg atttattaat tttgtatctt    720
tatgtgtgtg ccatacatct tcatagttac gagtttaaga tgatggatgg aaatattgat    780
ctaggatagg tatacatgtt gatgtgggtt ttactgatgc atatacatga tggcatatgc    840
ggcatctatt catatgctct aaccttgagt acctatctat tataataaac aagtatgttt    900
tataattatt ttgatcttga tatacttgga tgatggcata tgcagcagct atatgtggat    960
tttttagccc tgccttcata cgctatttat ttgcttggta ctgtttcttt tgtccgatgc   1020
tcaccctgtt gttgggtgat acttctgcag gtc                                1053
```

<210> SEQ ID NO 138
<211> LENGTH: 2008
<212> TYPE: DNA
<213> ORGANISM: Zea mays subsp. Mexicana

<400> SEQUENCE: 138

```
gtcgtgcccc tctctagaga taaagagcat tgcatgtcta aagtataaaa aattaccaca     60
tattttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatcttttt agtgtgcatg tgatctctct gtttttttg caaatagctt gacctatata    300
atacttcatc cattttatta gtacatccat ttaggattta gggttgatgg tttctataga    360
ctaattttta gtacatccat tttattcttt ttagtctcta aattttttaa aactaaaact    420
ctattttagt tttttattta ataatttaga tataaaatga aataaaataa attgactaca    480
aataaaacaa ataccettta agaaataaaa aaactaagca aacatttttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
```

```
accccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acgggggatt cctttcccac cgctccttcg ctttcccttc ctcgcccgcc    840
gtaataaata gacacccccct ccacaccctc tttccccaac ctcgtgttcg ttcggagcgc    900
acacacacgc aaccagatct cccccaaatc cagccgtcgg cacctccgct tcaaggtacg    960
ccgctcatcc tcccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt taagatgatg gatggaaata tcgatctagg ataggtatac atgttgatgc   1260
gggttttact gatgcatata cagagatgct ttttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc tttttttcgc ttggttgtga tgatgtggtc tggttgggcg gtcgttctag   1620
atcggagtag aatactgttt caaactacct ggtggattta ttaattttgt atctttatgt   1680
gtgtgccata catcttcata gttacgagtt taagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggatttttt   1920
agccctgcct tcatacgcta tttatttgct tggtactgtt tcttttgtcc gatgctcacc   1980
ctgttgttgg gtgatacttc tgcagggt                                        2008
```

<210> SEQ ID NO 139
<211> LENGTH: 1053
<212> TYPE: DNA
<213> ORGANISM: Zea mays subsp. Mexicana

<400> SEQUENCE: 139

```
gtacgccgct catcctcccc cccccctct ctctaccttc tctagatcgg cgatccggtc      60
catggttagg gcccggtagt tctacttctg ttcatgtttg tgttagagca aacatgttca    120
tgttcatgtt tgtgatgatg tggtctggtt gggcggtcgt tctagatcgg agtaggatac    180
tgtttcaagc tacctggtgg atttattaat tttgtatctg tatgtgtgtg ccatacatct    240
tcatagttac gagtttaaga tgatggatgg aaatatcgat ctaggatagg tatacatgtt    300
gatgcgggtt ttactgatgc atatacagag atgctttttt tctcgcttgg ttgtgatgat    360
atggtctggt tgggcggtcg ttctagatcg gagtagaata ctgtttcaaa ctacctggtg    420
gatttattaa aggataaagg gtcgttctag atcggagtag aatactgttt caaactacct    480
ggtggattta ttaaaggatc tgtatgtatg tgcctacatc ttcatagtta cgagtttaag    540
atgatggatg gaaatatcga tctaggatag gtatacatgt tgatgcgggt tttactgatg    600
catatacaga gatgcttttt ttcgcttggt tgtgatgatg tggtctggtt gggcggtcgt    660
tctagatcgg agtagaatac tgtttcaaac tacctggtgg atttattaat tttgtatctt    720
```

```
tatgtgtgtg ccatacatct tcatagttac gagtttaaga tgatggatgg aaatattgat    780

ctaggatagg tatacatgtt gatgtgggtt ttactgatgc atatacatga tggcatatgc    840

ggcatctatt catatgctct aaccttgagt acctatctat tataataaac aagtatgttt    900

tataattatt ttgatcttga tatacttgga tgatggcata tgcagcagct atatgtggat    960

tttttagccc tgccttcata cgctatttat ttgcttggta ctgtttcttt tgtccgatgc   1020

tcaccctgtt gttgggtgat acttctgcag ggt                                1053


<210> SEQ ID NO 140
<211> LENGTH: 1635
<212> TYPE: DNA
<213> ORGANISM: Sorghum bicolor

<400> SEQUENCE: 140

ccaagtccaa atgtcaattc ccttgaagat gatctatttt tatcttttgc attttgttat     60

ggaagtttgc aaatagcaac aaatgctaag tcaatttgcc aaagtctttg gagatgctct    120

tagtctataa ttgaacaata tttgtaaaat acaaaaaaaa atagtactat ttttatttta    180

aaaaattttt ggaagtaaac aaggccgagg atggggaaac ggaagtccaa cacgtcgttt    240

tctaagttgg gctcaaaagc ccatcacgga actgacctgc tatgggtcgg aggagagcgc    300

gtccagatgg ttccagaggc tggtggtggt gggccaaacg cggaactccg ccaccgccac    360

ggcctcgtgc gcaagcgcag cgcgttgccg tgagccgtga cgtaaccctc cgttgcccac    420

gataaaagct ccacccccga ccccggcccc ccgatttccc ctacggacca gtctcccccc    480

gatcgcaatc gcgaattcgt cgcaccatcg gcacgcagac gaacgaagca aggctctccc    540

catcggctcg tcaaggtatg cgttccctag atttgttccc ttcctctctc ggtttgtcta    600

tatatatgca tgtatggtcg attcccgatc tcgtcgattc tcggtttcgc cttccgtacg    660

aagattcgtt tagattgttc atatgttctg ttgtgttacc agattgatcg gatcaacttg    720

atccagttat cttcgctcct ccgattagat ccgtttctat ttcagtatat atatactagt    780

atagtatcta gggttcacac tgttgaccga ctggttactt ggaattgatc cgtgctgagt    840

tcagttgttg ccgtccataa aggcccgtgc tattgtctgt tctgaaacga aatcctgtag    900

atttcttagg gttagtgttc aattcatcaa aaggttgatt agtgaattat caaatttgag    960

agggttaaat cattctcatc atgttgtctc gaatgtaatc ccaaagatat tatagactgt   1020

gtttcgattt gatggattga tttgtgtatc atctaaatca acaaggctaa gtcatcagtt   1080

catagaatca tgtttaggtt tccgttcaat agactagttt tatcaatata taaaattata   1140

agaagggtag ggtaaatcac gttgcctcaa atgccatcct gtatggtttg gtttcaattc   1200

aattagtttg gttgattagg gtatgctctg gattaagatg gttaaatctt ccctagcatc   1260

ttccctgcct atccttactt gatccgtttc ggatatgttg gaagtacagc gagcttattt   1320

catgttgata gtgacccctt tcagattata ctattgaata ttgtatgttt gccacttctg   1380

tatgttgaat tatcctgcta aattagcaat ggaattagca tattggcaat tggtatgcat   1440

ggacctaatc aggacggatg tggttatgtt agtttcaatt cattgtcaat tcattgttca   1500

cctgcgttag atatatatga tgatttttac gtgtagttca tagttcttga gttttggatc   1560

tttcttatct gatatatgct ttcctgtgcc tgtgctttat tgtgtcttac catgcgattt   1620

ttgtctatgc aggtc                                                    1635


<210> SEQ ID NO 141
<211> LENGTH: 401
```

<212> TYPE: DNA
<213> ORGANISM: Sorghum bicolor

<400> SEQUENCE: 141
ccaagtccaa atgtcaattc ccttgaagat gatctatttt tatcttttgc attttgttat 60
ggaagtttgc aaatagcaac aaatgctaag tcaatttgcc aaagtctttg gagatgctct 120
tagtctataa ttgaacaata tttgtaaaat acaaaaaaaa atagtactat ttttatttta 180
aaaaattttt ggaagtaaac aaggccgagg atggggaaac ggaagtccaa cacgtcgttt 240
tctaagttgg gctcaaaagc ccatcacgga actgacctgc tatgggtcgg aggagagcgc 300
gtccagatgg ttccagaggc tggtggtggt gggccaaacg cggaactccg ccaccgccac 360
ggcctcgtgc gcaagcgcag cgcgttgccg tgagccgtga c 401

<210> SEQ ID NO 142
<211> LENGTH: 154
<212> TYPE: DNA
<213> ORGANISM: Sorghum bicolor

<400> SEQUENCE: 142
gtaaccctcc gttgcccacg ataaaagctc cacccccgac cccggccccc cgatttcccc 60
tacggaccag tctccccccg atcgcaatcg cgaattcgtc gcaccatcgg cacgcagacg 120
aacgaagcaa ggctctcccc atcggctcgt caag 154

<210> SEQ ID NO 143
<211> LENGTH: 1080
<212> TYPE: DNA
<213> ORGANISM: Sorghum bicolor

<400> SEQUENCE: 143
gtatgcgttc cctagatttg ttcccttcct ctctcggttt gtctatatat atgcatgtat 60
ggtcgattcc cgatctcgtc gattctcggt ttcgccttcc gtacgaagat tcgtttagat 120
tgttcatatg ttctgttgtg ttaccagatt gatcggatca acttgatcca gttatcttcg 180
ctcctccgat tagatccgtt tctatttcag tatatatata ctagtatagt atctagggtt 240
cacactgttg accgactggt tacttggaat tgatccgtgc tgagttcagt tgttgccgtc 300
cataaaggcc cgtgctattg tctgttctga aacgaaatcc tgtagatttc ttagggttag 360
tgttcaattc atcaaaaggt tgattagtga attatcaaat ttgagagggt taaatcattc 420
tcatcatgtt gtctcgaatg taatcccaaa gatattatag actgtgtttc gatttgatgg 480
attgatttgt gtatcatcta aatcaacaag gctaagtcat cagttcatag aatcatgttt 540
aggtttccgt tcaatagact agttttatca atatataaaa ttataagaag ggtagggtaa 600
atcacgttgc ctcaaatgcc atcctgtatg gtttggtttc aattcaatta gtttggttga 660
ttagggtatg ctctggatta agatggttaa atcttcccta gcatcttccc tgcctatcct 720
tacttgatcc gtttcggata tgttggaagt acagcgagct tatttcatgt tgatagtgac 780
ccctttcaga ttatactatt gaatattgta tgtttgccac ttctgtatgt tgaattatcc 840
tgctaaatta gcaatggaat tagcatattg gcaattggta tgcatggacc taatcaggac 900
ggatgtggtt atgttagttt caattcattg tcaattcatt gttcacctgc gttagatata 960
tatgatgatt tttacgtgta gttcatagtt cttgagtttt ggatctttct tatctgatat 1020
atgctttcct gtgcctgtgc tttattgtgt cttaccatgc gatttttgtc tatgcaggtc 1080

<210> SEQ ID NO 144

<211> LENGTH: 2067
<212> TYPE: DNA
<213> ORGANISM: Sorghum bicolor

<400> SEQUENCE: 144

```
cattaaaagt cattatgtgc atgcgtcgta actaacatgg atatgttgct gcactatctc     60
ctcgcactag ctgcgcatga taaagccaca agccaaaatt aattattatg ggtgagaata    120
aatacgtacc agcaccggcc atagaaaaag tacattatta aaggtctaat ttggaaacag    180
tctgaaaacg acgtgcgctg cagaggtaaa tgtaattttc ggcactaaaa ccattatcaa    240
ctaattcatt caataacagt tatttagaaa atgtatagct cgctctaaaa aaacagttta    300
gaaaaacagt caaaataatt cgaccaacaa acagttaata aggttcatta aatatataat    360
gcacggtgct atttgatctt ttaaaggaaa aagaggaata gtcgtgggcg ccaggcggga    420
attggggcgc gggagtctgc cggacgacgc gttccgtccg aacggccgga cccgacgagg    480
ccccccgcc gccccacgtc gcagaaccgt ccgtgggtgg taatctggcc gggtacacca    540
gccgtcccct tgggcggcct cacagcactg ggctcacacg tgagttttgt tctgggcttc    600
ggatcgcacc atatgggcct cggcatcaga aagacggggc ccgtctggga tagaagagac    660
aggaacctcc tcgtggattc cagaagccag ccacgagcga ccaccgacgc ggaggatact    720
cgtcgtccaa gtccaacacg gcgggcgggc gggcggacgc gtgggctggg ctaactgcct    780
aaccttaacc tccaaggcac gccaaggccc gcttctccca cccgacataa atatccccc    840
atccaggcaa ggcgcagagc ctcagaccag attccgatca atcacccata agctcccccc    900
aaatctgttc ctcgtctccc gtctcgcggt ttcctacttc cctcggacgc ctccggcaag    960
tcgctcgacc gcgcgattcc gcccgctcaa ggtatcaact cggttcacca ctccaatcta   1020
cgtctgattt agatgttact tccatctatg tctaatttag atgttactcc gatgcgattg   1080
gattatgttt atgcggtttg cactgctctg gaaactggaa tctagggttt cgagtgattt   1140
gatcgatcgc gatctgtgat ttcgttgcgc cttgtgtatg cttggagtga tctaggcttg   1200
tatatgcggc atcgcgatct gacgcggttg ctttgtagag gctgggggtc taggctgtga   1260
ttttagaatc aaataaagct gttccttacc gtagatgttt cctacatgtt ctgtccagta   1320
ctccagtgct atattcacat tgtttgaggc ttgagttttg tcgatcagtg gtcatgagaa   1380
aaatatatct catgatttta gaggcaccta ttgggaaagg tagatggttc cgttttacat   1440
gttttataga ccttgtggca tggctccttt gttctatggg tgctttattt tcctgaataa   1500
cagtaatgcg agactggtct atgggtgctt tgaccagtaa tgcgagacta gttatttgat   1560
catggtgcag ttcctagtga ttacgaacaa caatttggta gctcagttca ttcagcattg   1620
gtttctacga tccttatcat tttacttctg aatgaattta tttatttaag atattacagt   1680
gcaataaact gctgtataat atcagtaaca aactgctatt actagtaaat gcctagattc   1740
ataataattc attattctac ttgaaaatga tcttaggcct ttttatgcgg tcctacgcat   1800
ccttccacag gacttgctgt ttgtttgttt tttgtaatcc ctcgctggga cgcagaatgg   1860
ttcatctgtg ctaataattt ttttgcatat ataagtttat agttctcatt attcatgtgg   1920
ctatggtagc ctgtaaaatc tattgtaata acatattagt cagccataca tctgttccaa   1980
cttgctcaat tgcaaatcat atctccactt aaagcacatg tttgcaagct ttctgacaag   2040
tttctttgtg tttgattgaa acaggtg                                       2067
```

<210> SEQ ID NO 145
<211> LENGTH: 855

<212> TYPE: DNA
<213> ORGANISM: Sorghum bicolor

<400> SEQUENCE: 145
cattaaaagt cattatgtgc atgcgtcgta actaacatgg atatgttgct gcactatctc 60
ctcgcactag ctgcgcatga taaagccaca agccaaaatt aattattatg ggtgagaata 120
aatacgtacc agcaccggcc atagaaaaag tacattatta aaggtctaat ttggaaacag 180
tctgaaaacg acgtgcgctg cagaggtaaa tgtaattttc ggcactaaaa ccattatcaa 240
ctaattcatt caataacagt tatttagaaa atgtatagct cgctctaaaa aaacagttta 300
gaaaaacagt caaaataatt cgaccaacaa acagttaata aggttcatta aatatataat 360
gcacggtgct atttgatctt ttaaaggaaa aagaggaata gtcgtgggcg ccaggcggga 420
attggggcgc gggagtctgc cggacgacgc gttccgtccg aacggccgga cccgacgagg 480
cccccccgcc gccccacgtc gcagaaccgt ccgtgggtgg taatctggcc gggtacacca 540
gccgtcccct tgggcggcct cacagcactg ggctcacacg tgagttttgt tctgggcttc 600
ggatcgcacc atatgggcct cggcatcaga aagacggggc ccgtctggga tagaagagac 660
aggaacctcc tcgtggattc cagaagccag ccacgagcga ccaccgacgc ggaggatact 720
cgtcgtccaa gtccaacacg gcgggcgggc gggcggacgc gtgggctggg ctaactgcct 780
aaccttaacc tccaaggcac gccaaggccc gcttctccca cccgacataa atatcccccc 840
atccaggcaa ggcgc 855

<210> SEQ ID NO 146
<211> LENGTH: 136
<212> TYPE: DNA
<213> ORGANISM: Sorghum bicolor

<400> SEQUENCE: 146
agagcctcag accagattcc gatcaatcac ccataagctc cccccaaatc tgttcctcgt 60
ctcccgtctc gcggtttcct acttccctcg gacgcctccg gcaagtcgct cgaccgcgcg 120
attccgcccg ctcaag 136

<210> SEQ ID NO 147
<211> LENGTH: 1076
<212> TYPE: DNA
<213> ORGANISM: Sorghum bicolor

<400> SEQUENCE: 147
gtatcaactc ggttcaccac tccaatctac gtctgattta gatgttactt ccatctatgt 60
ctaatttaga tgttactccg atgcgattgg attatgttta tgcggtttgc actgctctgg 120
aaactggaat ctagggtttc gagtgatttg atcgatcgcg atctgtgatt tcgttgcgcc 180
ttgtgtatgc ttggagtgat ctaggcttgt atatgcggca tcgcgatctg acgcggttgc 240
tttgtagagg ctgggggtct aggctgtgat tttagaatca aataaagctg ttccttaccg 300
tagatgtttc ctacatgttc tgtccagtac tccagtgcta tattcacatt gtttgaggct 360
tgagttttgt cgatcagtgg tcatgagaaa aatatatctc atgattttag aggcacctat 420
tgggaaaggt agatggttcc gttttacatg ttttatagac cttgtggcat ggctcctttg 480
ttctatgggt gctttatttt cctgaataac agtaatgcga gactggtcta tgggtgcttt 540
gaccagtaat gcgagactag ttatttgatc atggtgcagt tcctagtgat tacgaacaac 600
aatttggtag ctcagttcat tcagcattgg tttctacgat ccttatcatt ttacttctga 660
atgaatttat ttatttaaga tattacagtg caataaactg ctgtataata tcagtaacaa 720
actgctatta ctagtaaatg cctagattca taataattca ttattctact tgaaaatgat 780
cttaggcctt tttatgcggt cctacgcatc cttccacagg acttgctgtt tgtttgtttt 840
ttgtaatccc tcgctgggac gcagaatggt tcatctgtgc taataatttt tttgcatata 900
taagtttata gttctcatta ttcatgtggc tatggtagcc tgtaaaatct attgtaataa 960
catattagtc agccatacat ctgttccaac ttgctcaatt gcaaatcata tctccactta 1020
aagcacatgt ttgcaagctt tctgacaagt ttctttgtgt ttgattgaaa caggtg 1076

<210> SEQ ID NO 148
<211> LENGTH: 2067
<212> TYPE: DNA
<213> ORGANISM: Sorghum bicolor

<400> SEQUENCE: 148
cattaaaagt cattatgtgc atgcgtcgta actaacatgg atatgttgct gcactatctc 60
ctcgcactag ctgcgcatga taaagccaca agccaaaatt aattattatg ggtgagaata 120
aatacgtacc agcaccggcc atagaaaaag tacattatta aaggtctaat ttggaaacag 180
tctgaaaacg acgtgcgctg cagaggtaaa tgtaattttc ggcactaaaa ccattatcaa 240
ctaattcatt caataacagt tatttagaaa atgtatagct cgctctaaaa aaacagttta 300
gaaaaacagt caaaataatt cgaccaacaa acagttaata aggttcatta aatatataat 360
gcacggtgct atttgatctt ttaaaggaaa aagaggaata gtcgtgggcg ccaggcggga 420
attggggcgc gggagtctgc cggacgacgc gttccgtccg aacggccgga cccgacgagg 480 ccccccgcc gccccacgtc gcagaaccgt ccgtgggtgg taatctggcc gggtacacca 540
gccgtcccct tgggcggcct cacagcactg ggctcacacg tgagttttgt tctgggcttc 600
ggatcgcacc atatgggcct cggcatcaga aagacggggc ccgtctggga tagaagagac 660
aggaacctcc tcgtggattc cagaagccag ccacgagcga ccaccgacgc ggaggatact 720
cgtcgtccaa gtccaacacg gcgggcgggc gggcggacgc gtgggctggg ctaactgcct 780
aaccttaacc tccaaggcac gccaaggccc gcttctccca cccgacataa atatcccccc 840
atccaggcaa ggcgcagagc ctcagaccag attccgatca atcacccata agctcccccc 900
aaatctgttc ctcgtctccc gtctcgcggt ttcctacttc cctcggacgc ctccggcaag 960
tcgctcgacc gcgcgattcc gcccgctcaa ggtatcaact cggttcacca ctccaatcta 1020
cgtctgattt agatgttact tccatctatg tctaatttag atgttactcc gatgcgattg 1080
gattatgttt atgcggtttg cactgctctg gaaactggaa tctagggttt cgagtgattt 1140
gatcgatcgc gatctgtgat ttcgttgcgc cttgtgtatg cttggagtga tctaggcttg 1200
tatatgcggc atcgcgatct gacgcggttg ctttgtagag gctgggggtc taggctgtga 1260
ttttagaatc aaataaagct gttccttacc gtagatgttt cctacatgtt ctgtccagta 1320
ctccagtgct atattcacat tgtttgaggc ttgagttttg tcgatcagtg gtcatgagaa 1380
aaatatatct catgatttta gaggcaccta ttgggaaagg tagatggttc cgttttacat 1440
gttttataga ccttgtggca tggctccttt gttctatggg tgctttattt tcctgaataa 1500
cagtaatgcg agactggtct atgggtgctt tgaccagtaa tgcgagacta gttatttgat 1560
catggtgcag ttcctagtga ttacgaacaa caatttggta gctcagttca ttcagcattg 1620
gtttctacga tccttatcat tttacttctg aatgaattta tttatttaag atattacagt 1680
gcaataaact gctgtataat atcagtaaca aactgctatt actagtaaat gcctagattc 1740

-continued ataataattc attattctac ttgaaaatga tcttaggcct ttttatgcgg tcctacgcat 1800
ccttccacag gacttgctgt ttgtttgttt tttgtaatcc ctcgctggga cgcagaatgg 1860
ttcatctgtg ctaataattt ttttgcatat ataagtttat agttctcatt attcatgtgg 1920
ctatggtagc ctgtaaaatc tattgtaata acatattagt cagccataca tctgttccaa 1980
cttgctcaat tgcaaatcat atctccactt aaagcacatg tttgcaagct ttctgacaag 2040
tttctttgtg tttgattgaa acagggt 2067

<210> SEQ ID NO 149
<211> LENGTH: 1076
<212> TYPE: DNA
<213> ORGANISM: Sorghum bicolor

<400> SEQUENCE: 149
gtatcaactc ggttcaccac tccaatctac gtctgattta gatgttactt ccatctatgt 60
ctaatttaga tgttactccg atgcgattgg attatgttta tgcggtttgc actgctctgg 120
aaactggaat ctagggtttc gagtgatttg atcgatcgcg atctgtgatt tcgttgcgcc 180
ttgtgtatgc ttggagtgat ctaggcttgt atatgcggca tcgcgatctg acgcggttgc 240
tttgtagagg ctgggggtct aggctgtgat tttagaatca aataaagctg ttccttaccg 300
tagatgtttc ctacatgttc tgtccagtac tccagtgcta tattcacatt gtttgaggct 360
tgagttttgt cgatcagtgg tcatgagaaa aatatatctc atgattttag aggcacctat 420
tgggaaaggt agatggttcc gttttacatg ttttatagac cttgtggcat ggctcctttg 480
ttctatgggt gctttatttt cctgaataac agtaatgcga gactggtcta tgggtgcttt 540
gaccagtaat gcgagactag ttatttgatc atggtgcagt tcctagtgat tacgaacaac 600
aatttggtag ctcagttcat tcagcattgg tttctacgat ccttatcatt ttacttctga 660
atgaatttat ttatttaaga tattacagtg caataaactg ctgtataata tcagtaacaa 720
actgctatta ctagtaaatg cctagattca taataattca ttattctact tgaaaatgat 780
cttaggcctt tttatgcggt cctacgcatc cttccacagg acttgctgtt tgtttgtttt 840
ttgtaatccc tcgctgggac gcagaatggt tcatctgtgc taataatttt tttgcatata 900
taagtttata gttctcatta ttcatgtggc tatggtagcc tgtaaaatct attgtaataa 960
catattagtc agccatacat ctgttccaac ttgctcaatt gcaaatcata tctccactta 1020
aagcacatgt ttgcaagctt tctgacaagt ttctttgtgt ttgattgaaa cagggt 1076

<210> SEQ ID NO 150
<211> LENGTH: 2003
<212> TYPE: DNA
<213> ORGANISM: Sorghum bicolor

<400> SEQUENCE: 150
agaagtaaaa aaaaagttcg tttcagaatc ataaaggtaa gttaaaaaaa gaccatacaa 60
aaaagaggta tttaatgata aactataatc cagaatttgt taggatagta tataagaata 120
agaccttgtt tagtttcaaa aaaatttgca aaattttcca gattcctcgt cacatcaaat 180
ctttagaggt atgcatggag tattaaatat agacaagacc taaataagaa aacatgaaat 240
gttcacgaaa aaaatcaagc caatgcatga tcgaagcaaa cggtatagta acggtgttaa 300
cctgatccat tgatctttgt aatctttaac ggccacctac cgcgggcagc aaacggcgtc 360
cccctcctcg atatctccgc ggcggcctct ggctttttcc gcggaattgc gcggtgggga 420

```
cggattccac gagaccgcaa cgcaaccgcc tctcgccgct gggccccaca ccgctcggtg    480

ccgtagcccg tagcctcacg ggattctttc tccctcctcc cccgtgtata aattggcttc    540

atcccctccc tgcctcatcc atccaaatcc cactccccaa tcccatcccg tcggagaaat    600

tcatcgaagc gaagcgaagc gaatcctccc gatcctctca aggtacgcga gttttcgaat    660

cccctccaga cccctcgtat gctttccctg ttcgttttcg tcgtagcgtt tgattaggta    720

tgctttccct gttcgtgttc gtcgtagggt tcgattaggt cgtgtgaggc catggcctgc    780

tgtgataaat ttatttgttg ttatatcgga tctgtagtcg atttgggggt cgtggtgtag    840

atccgcgggc tgtgatgaag ttatttggtg tgattgtgct cgcgtgattc tgcgcgttga    900

gctcgagtag atctgatggt tggacgaccg attggttcgt tggctggctg cgctaaggtt    960

gggctgggct catgttgcgt tcgctgttgc gcgtgattcc gcggatggac ttgcgcttga   1020

ttgccgccag atcacgttac gattatgtga tttcgtttgg aactttttag atttgtagct   1080

tctgcttatt atatgacaga tgcgcctact gctcatatgc ctgtggtaaa taatggatgg   1140

ctgtgggtca aactagttga ttgtcgagtc atgtatcata tacaggtgta tagacttgcg   1200

tctaattgtt tgcatgttgc agttatatga tttgttttag attgtttgtt ccactcatct   1260

aggctgtaaa agggacacta cttattagct tgttgtttaa tctttttatt agtagattat   1320

attggtaatg ttttactaat tattattatg ttatatgtga cttctgctca tgcctgatta   1380

taatcataga tcactgtagt tgattgttga atcatgtgtc aaatacccgt atacataaca   1440

ctacacattt gcttagttgt ttccttaact catgcaaatt gaacaccatg tatgatttgc   1500

atggtgctgt aatgttaaat actacagtcc tgttggtact tgtttagtaa gaatctgctt   1560

catacaacta tatgctatgc ctgatgataa tcatatatct ttgtgtaatt aataattagt   1620

tgactgttga ataatgtatc gagtacatac catggcacaa ttgcttagtc acttccttaa   1680

ccatgcatat tgaactgacc ccttcatgtt ctgctgaatt gttctattct gattagacca   1740

tacatcatgt attgcaatct ttatttgcaa ttgtaatgta atggttcggt tctcaaatgt   1800

taaatgctat agttgtgcta ctttctaatg ttaaatgcta tagctgtgct acttgtaaga   1860

tctgcttcat agtttagtta aattaggatg atgagctttg atgctgtaac tttgtttgat   1920

tatgttcata gttgatcagt ttttgttaga ctcacagtaa cttatggtct cactcttctt   1980

ctggtctttg atgtttgcag cgg                                           2003
```

<210> SEQ ID NO 151
<211> LENGTH: 565
<212> TYPE: DNA
<213> ORGANISM: Sorghum bicolor

<400> SEQUENCE: 151

```
agaagtaaaa aaaaagttcg tttcagaatc ataaaggtaa gttaaaaaaa gaccatacaa     60

aaaagaggta tttaatgata aactataatc cagaatttgt taggatagta tataagaata    120

agaccttgtt tagtttcaaa aaaatttgca aaattttcca gattcctcgt cacatcaaat    180

ctttagaggt atgcatggag tattaaatat agacaagacc taaataagaa aacatgaaat    240

gttcacgaaa aaaatcaagc caatgcatga tcgaagcaaa cggtatagta acggtgttaa    300

cctgatccat tgatctttgt aatctttaac ggccacctac cgcgggcagc aaacggcgtc    360

cccctcctcg atatctccgc ggcggcctct ggctttttcc gcggaattgc gcggtgggga    420

cggattccac gagaccgcaa cgcaaccgcc tctcgccgct gggccccaca ccgctcggtg    480

ccgtagcccg tagcctcacg ggattctttc tccctcctcc cccgtgtata aattggcttc    540
```

atcccctccc tgcctcatcc atcca 565

<210> SEQ ID NO 152
<211> LENGTH: 77
<212> TYPE: DNA
<213> ORGANISM: Sorghum bicolor

<400> SEQUENCE: 152
aatcccactc cccaatccca tcccgtcgga gaaattcatc gaagcgaagc gaagcgaatc 60
ctcccgatcc tctcaag 77

<210> SEQ ID NO 153
<211> LENGTH: 1361
<212> TYPE: DNA
<213> ORGANISM: Sorghum bicolor

<400> SEQUENCE: 153
gtacgcgagt tttcgaatcc cctccagacc cctcgtatgc tttccctgtt cgttttcgtc 60
gtagcgtttg attaggtatg ctttccctgt tcgtgttcgt cgtagggttc gattaggtcg 120
tgtgaggcca tggcctgctg tgataaattt atttgttgtt atatcggatc tgtagtcgat 180
ttgggggtcg tggtgtagat ccgcgggctg tgatgaagtt atttggtgtg attgtgctcg 240
cgtgattctg cgcgttgagc tcgagtagat ctgatggttg gacgaccgat tggttcgttg 300
gctggctgcg ctaaggttgg gctgggctca tgttgcgttc gctgttgcgc gtgattccgc 360
ggatggactt gcgcttgatt gccgccagat cacgttacga ttatgtgatt tcgtttggaa 420
ctttttagat ttgtagcttc tgcttattat atgacagatg cgcctactgc tcatatgcct 480
gtggtaaata atggatggct gtgggtcaaa ctagttgatt gtcgagtcat gtatcatata 540
caggtgtata gacttgcgtc taattgtttg catgttgcag ttatatgatt tgttttagat 600
tgtttgttcc actcatctag gctgtaaaag ggacactact tattagcttg ttgtttaatc 660
tttttattag tagattatat tggtaatgtt ttactaatta ttattatgtt atatgtgact 720
tctgctcatg cctgattata atcatagatc actgtagttg attgttgaat catgtgtcaa 780
atacccgtat acataacact acacatttgc ttagttgttt ccttaactca tgcaaattga 840
acaccatgta tgatttgcat ggtgctgtaa tgttaaatac tacagtcctg ttggtacttg 900
tttagtaaga atctgcttca tacaactata tgctatgcct gatgataatc atatatcttt 960
gtgtaattaa taattagttg actgttgaat aatgtatcga gtacatacca tggcacaatt 1020
gcttagtcac ttccttaacc atgcatattg aactgacccc ttcatgttct gctgaattgt 1080
tctattctga ttagaccata catcatgtat tgcaatcttt atttgcaatt gtaatgtaat 1140
ggttcggttc tcaaatgtta aatgctatag ttgtgctact ttctaatgtt aaatgctata 1200
gctgtgctac ttgtaagatc tgcttcatag tttagttaaa ttaggatgat gagctttgat 1260
gctgtaactt tgtttgatta tgttcatagt tgatcagttt ttgttagact cacagtaact 1320
tatggtctca ctcttcttct ggtctttgat gtttgcagcg g 1361

<210> SEQ ID NO 154
<211> LENGTH: 1812
<212> TYPE: DNA
<213> ORGANISM: Artificial sequence
<220> FEATURE:
<223> OTHER INFORMATION: Codon optimized coding sequence.

<400> SEQUENCE: 154

-continued

```
atggtccgtc ctgtagaaac cccaacccgt gaaatcaaaa aactcgacgg cctgtgggca     60
ttcagtctgg atcgcgaaaa ctgtggaatt gatcagcgtt ggtgggaaag cgcgttacaa    120
gaaagccggg caattgctgt gccaggcagt tttaacgatc agttcgccga tgcagatatt    180
cgtaattatg cgggcaacgt ctggtatcag cgcgaagtct ttataccgaa aggttgggca    240
ggccagcgta tcgtgctgcg tttcgatgcg gtcactcatt acggcaaagt gtgggtcaat    300
aatcaggaag tgatggagca tcagggcggc tatacgccat ttgaagccga tgtcacgccg    360
tatgttattg ccgggaaaag tgtacgtatc accgtttgtg tgaacaacga actgaactgg    420
cagactatcc cgccgggaat ggtgattacc gacgaaaacg gcaagaaaaa gcagtcttac    480
ttccatgatt tctttaacta tgccggaatc catcgcagcg taatgctcta caccacgccg    540
aacacctggg tggacgatat caccgtggtg acgcatgtcg cgcaagactg taaccacgcg    600
tctgttgact ggcaggtggt ggccaatggt gatgtcagcg ttgaactgcg tgatgcggat    660
caacaggtgg ttgcaactgg acaaggcact agcgggactt tgcaagtggt gaatccgcac    720
ctctggcaac cgggtgaagg ttatctctat gaactgtgcg tcacagccaa aagccagaca    780
gagtgtgata tctacccgct tcgcgtcggc atccggtcag tggcagtgaa gggcgaacag    840
ttcctgatta accacaaacc gttctacttt actggctttg gtcgtcatga agatgcggac    900
ttgcgtggca aaggattcga taacgtgctg atggtgcacg accacgcatt aatggactgg    960
attggggcca actcctaccg tacctcgcat tacccttacg ctgaagagat gctcgactgg   1020
gcagatgaac atggcatcgt ggtgattgat gaaactgctg ctgtcggctt taacctctct   1080
ttaggcattg gtttcgaagc gggcaacaag ccgaaagaac tgtacagcga agaggcagtc   1140
aacggggaaa ctcagcaagc gcacttacag gcgattaaag agctgatagc gcgtgacaaa   1200
aaccacccaa gcgtggtgat gtggagtatt gccaacgaac cggatacccg tccgcaaggt   1260
gcacgggaat atttcgcgcc actggcggaa gcaacgcgta aactcgaccc gacgcgtccg   1320
atcacctgcg tcaatgtaat gttctgcgac gctcacaccg ataccatcag cgatctcttt   1380
gatgtgctgt gcctgaaccg ttattacgga tggtatgtcc aaagcggcga tttggaaacg   1440
gcagagaagg tactggaaaa agaacttctg gcctggcagg agaaactgca tcagccgatt   1500
atcatcaccg aatacggcgt ggatacgtta gccgggctgc actcaatgta caccgacatg   1560
tggagtgaag agtatcagtg tgcatggctg gatatgtatc accgcgtctt tgatcgcgtc   1620
agcgccgtcg tcggtgaaca ggtatggaat ttcgccgatt ttgcgacctc gcaaggcata   1680
ttgcgcgttg gcggtaacaa gaaagggatc ttcactcgcg accgcaaacc gaagtcggcg   1740
gcttttctgc tgcaaaaacg ctggactggc atgaacttcg gtgaaaaacc gcagcaggga   1800
ggcaaacaat ga                                                       1812
```

<210> SEQ ID NO 155
<211> LENGTH: 2001
<212> TYPE: DNA
<213> ORGANISM: Artificial sequence
<220> FEATURE:
<223> OTHER INFORMATION: Chimeric coding sequence with processable intron.

<400> SEQUENCE: 155

```
atggtccgtc ctgtagaaac cccaacccgt gaaatcaaaa aactcgacgg cctgtgggca     60
ttcagtctgg atcgcgaaaa ctgtggaatt gatcagcgtt ggtgggaaag cgcgttacaa    120
gaaagccggg caattgctgt gccaggcagt tttaacgatc agttcgccga tgcagatatt    180
```

-continued

```
cgtaattatg cgggcaacgt ctggtatcag cgcgaagtct ttataccgaa aggttgggca    240

ggccagcgta tcgtgctgcg tttcgatgcg gtcactcatt acggcaaagt gtgggtcaat    300

aatcaggaag tgatggagca tcagggcggc tatacgccat ttgaagccga tgtcacgccg    360

tatgttattg ccgggaaaag tgtacgtaag tttctgcttc tacctttgat atatatataa    420

taattatcat taattagtag taatataata tttcaaatat ttttttcaaa ataaaagaat    480

gtagtatata gcaattgctt ttctgtagtt tataagtgtg tatattttaa tttataactt    540

ttctaatata tgaccaaaat ttgttgatgt gcaggtatca ccgtttgtgt gaacaacgaa    600

ctgaactggc agactatccc gccgggaatg gtgattaccg acgaaaacgg caagaaaaag    660

cagtcttact tccatgattt ctttaactat gccggaatcc atcgcagcgt aatgctctac    720

accacgccga acacctgggt ggacgatatc accgtggtga cgcatgtcgc gcaagactgt    780

aaccacgcgt ctgttgactg gcaggtggtg gccaatggtg atgtcagcgt tgaactgcgt    840

gatgcggatc aacaggtggt tgcaactgga caaggcacta gcgggacttt gcaagtggtg    900

aatccgcacc tctggcaacc gggtgaaggt tatctctatg aactgtgcgt cacagccaaa    960

agccagacag agtgtgatat ctacccgctt cgcgtcggca tccggtcagt ggcagtgaag   1020

ggcgaacagt tcctgattaa ccacaaaccg ttctacttta ctggctttgg tcgtcatgaa   1080

gatgcggact tgcgtggcaa aggattcgat aacgtgctga tggtgcacga ccacgcatta   1140

atggactgga ttggggccaa ctcctaccgt acctcgcatt acccttacgc tgaagagatg   1200

ctcgactggg cagatgaaca tggcatcgtg gtgattgatg aaactgctgc tgtcggcttt   1260

aacctctctt taggcattgg tttcgaagcg ggcaacaagc cgaaagaact gtacagcgaa   1320

gaggcagtca acggggaaac tcagcaagcg cacttacagg cgattaaaga gctgatagcg   1380

cgtgacaaaa accacccaag cgtggtgatg tggagtattg ccaacgaacc ggatacccgt   1440

ccgcaaggtg cacgggaata tttcgcgcca ctggcggaag caacgcgtaa actcgacccg   1500

acgcgtccga tcacctgcgt caatgtaatg ttctgcgacg ctcacaccga taccatcagc   1560

gatctctttg atgtgctgtg cctgaaccgt tattacggat ggtatgtcca aagcggcgat   1620

ttggaaacgg cagagaaggt actggaaaaa gaacttctgg cctggcagga gaaactgcat   1680

cagccgatta tcatcaccga atacggcgtg gatacgttag ccgggctgca ctcaatgtac   1740

accgacatgt ggagtgaaga gtatcagtgt gcatggctgg atatgtatca ccgcgtcttt   1800

gatcgcgtca gcgccgtcgt cggtgaacag gtatggaatt tcgccgattt tgcgacctcg   1860

caaggcatat tgcgcgttgg cggtaacaag aaagggatct tcactcgcga ccgcaaaccg   1920

aagtcggcgg cttttctgct gcaaaaacgc tggactggca tgaacttcgg tgaaaaaccg   1980

cagcagggag gcaaacaatg a                                             2001
```

<210> SEQ ID NO 156
<211> LENGTH: 1653
<212> TYPE: DNA
<213> ORGANISM: Artificial sequence
<220> FEATURE:
<223> OTHER INFORMATION: Codon optimized coding sequence.

<400> SEQUENCE: 156

```
atggaagacg ccaaaaacat aaagaaaggc ccggcgccat tctatcctct agaggatgga     60

accgctggag agcaactgca taaggctatg aagagatacg ccctggttcc tggaacaatt    120

gcttttacag atgcacatat cgaggtgaac atcacgtacg cggaatactt cgaaatgtcc    180

gttcggttgg cagaagctat gaaacgatat gggctgaata caaatcacag aatcgtcgta    240
```

```
tgcagtgaaa actctcttca attctttatg ccggtgttgg gcgcgttatt tatcggagtt    300

gcagttgcgc ccgcgaacga catttataat gaacgtgaat tgctcaacag tatgaacatt    360

tcgcagccta ccgtagtgtt tgtttccaaa aaggggttgc aaaaaatttt gaacgtgcaa    420

aaaaaattac caataatcca gaaaattatt atcatggatt ctaaaacgga ttaccaggga    480

tttcagtcga tgtacacgtt cgtcacatct catctacctc ccggttttaa tgaatacgat    540

tttgtaccag agtcctttga tcgtgacaaa acaattgcac tgataatgaa ttcctctgga    600

tctactgggt tacctaaggg tgtggccctt ccgcatagaa ctgcctgcgt cagattctcg    660

catgccagag atcctatttt tggcaatcaa atcattccgg atactgcgat tttaagtgtt    720

gttccattcc atcacggttt tggaatgttt actacactcg gatatttgat atgtggattt    780

cgagtcgtct taatgtatag atttgaagaa gagctgtttt tacgatccct tcaggattac    840

aaaattcaaa gtgcgttgct agtaccaacc ctattttcat tcttcgccaa aagcactctg    900

attgacaaat acgatttatc taatttacac gaaattgctt ctgggggcgc acctctttcg    960

aaagaagtcg gggaagcggt tgcaaaacgc ttccatcttc cagggatacg acaaggatat   1020

gggctcactg agactacatc agctattctg attacacccg agggggatga taaaccgggc   1080

gcggtcggta aagttgttcc atttttttgaa gcgaaggttg tggatctgga taccgggaaa   1140

acgctgggcg ttaatcagag aggcgaatta tgtgtcagag gacctatgat tatgtccggt   1200

tatgtaaaca atccggaagc gaccaacgcc ttgattgaca aggatggatg gctacattct   1260

ggagacatag cttactggga cgaagacgaa cacttcttca tagttgaccg cttgaagtct   1320

ttaattaaat acaaaggata tcaggtggcc cccgctgaat tggaatcgat attgttacaa   1380

caccccaaca tcttcgacgc gggcgtggca ggtcttcccg acgatgacgc cggtgaactt   1440

cccgccgccg ttgttgtttt ggagcacgga aagacgatga cggaaaaaga gatcgtggat   1500

tacgtcgcca gtcaagtaac aaccgcgaaa aagttgcgcg gaggagttgt gtttgtggac   1560

gaagtaccga aaggtcttac cggaaaactc gacgcaagaa aaatcagaga gatcctcata   1620

aaggccaaga agggcggaaa gtccaaattg taa                                1653
```

<210> SEQ ID NO 157
<211> LENGTH: 936
<212> TYPE: DNA
<213> ORGANISM: Artificial sequence
<220> FEATURE:
<223> OTHER INFORMATION: Codon optimized coding sequence.

<400> SEQUENCE: 157

```
atggcttcca aggtgtacga ccccgagcaa cgcaaacgca tgatcactgg gcctcagtgg     60

tgggctcgct gcaagcaaat gaacgtgctg gactccttca tcaactacta tgattccgag    120

aagcacgccg agaacgccgt gatttttctg catggtaacg ctgcctccag ctacctgtgg    180

aggcacgtcg tgcctcacat cgagcccgtg gctagatgca tcatccctga tctgatcgga    240

atgggtaagt ccggcaagag cgggaatggc tcatatcgcc tcctggatca ctacaagtac    300

ctcaccgctt ggttcgagct gctgaacctt ccaaagaaaa tcatctttgt gggccacgac    360

tggggggctt gtctggcctt tcactactcc tacgagcacc aagacaagat caaggccatc    420

gtccatgctg agagtgtcgt ggacgtgatc gagtcctggg acgagtggcc tgacatcgag    480

gaggatatcg ccctgatcaa gagcgaagag ggcgagaaaa tggtgcttga gaataacttc    540

ttcgtcgaga ccatgctccc aagcaagatc atgcggaaac tggagcctga ggagttcgct    600
```

-continued gcctacctgg agccattcaa ggagaagggc gaggttagac ggcctaccct ctcctggcct 660
cgcgagatcc ctctcgttaa gggaggcaag cccgacgtcg tccagattgt ccgcaactac 720
aacgcctacc ttcgggccag cgacgatctg cctaagatgt tcatcgagtc cgaccctggg 780
ttcttttcca acgctattgt cgagggagct aagaagttcc ctaacaccga gttcgtgaag 840
gtgaagggcc tccacttcag ccaggaggac gctccagatg aaatgggtaa gtacatcaag 900
agcttcgtgg agcgcgtgct gaagaacgag cagtaa 936

<210> SEQ ID NO 158
<211> LENGTH: 253
<212> TYPE: DNA
<213> ORGANISM: Agrobacterium tumefaciens

<400> SEQUENCE: 158
gatcgttcaa acatttggca ataaagtttc ttaagattga atcctgttgc cggtcttgcg 60
atgattatca tataatttct gttgaattac gttaagcatg taataattaa catgtaatgc 120
atgacgttat ttatgagatg ggtttttatg attagagtcc cgcaattata catttaatac 180
gcgatagaaa acaaaatata gcgcgcaaac taggataaat tatcgcgcgc ggtgtcatct 240
atgttactag atc 253

<210> SEQ ID NO 159
<211> LENGTH: 210
<212> TYPE: DNA
<213> ORGANISM: Triticum aestivum

<400> SEQUENCE: 159
ctgcatgcgt ttggacgtat gctcattcag gttggagcca atttggttga tgtgtgtgcg 60
agttcttgcg agtctgatga gacatctctg tattgtgttt ctttccccag tgttttctgt 120
acttgtgtaa tcggctaatc gccaacagat tcggcgatga ataaatgaga aataaattgt 180
tctgattttg agtgcaaaaa aaaaggaatt 210

<210> SEQ ID NO 160
<211> LENGTH: 300
<212> TYPE: DNA
<213> ORGANISM: Oryza sativa

<400> SEQUENCE: 160
attaatcgat cctccgatcc cttaattacc ataccattac accatgcatc aatatccata 60
tatatataaa ccctttcgca cgtacttata ctatgttttg tcatacatat atatgtgtcg 120
aacgatcgat ctatcactga tatgatatga ttgatccatc agcctgatct ctgtatcttg 180
ttatttgtat accgtcaaat aaaagtttct tccacttgtg ttaataatta gctactctca 240
tctcatgaac cctatatata actagtttaa tttgctgtca attgaacatg atgatcgatg 300

<210> SEQ ID NO 161
<211> LENGTH: 1204
<212> TYPE: DNA
<213> ORGANISM: Artificial sequence
<220> FEATURE:
<223> OTHER INFORMATION: Chimeric transcriptional regulatory expression element group.

<400> SEQUENCE: 161
ggtccgattg agacttttca acaaagggta atatccggaa acctcctcgg attccattgc 60
ccagctatct gtcactttat tgtgaagata gtggaaaagg aaggtggctc ctacaaatgc 120
catcattgcg ataaaggaaa ggccatcgtt gaagatgcct ctgccgacag tggtcccaaa 180
gatggacccc cacccacgag gagcatcgtg gaaaaagaag acgttccaac cacgtcttca 240
aagcaagtgg attgatgtga tggtccgatt gagacttttc aacaaagggt aatatccgga 300
aacctcctcg gattccattg cccagctatc tgtcacttta ttgtgaagat agtggaaaag 360
gaaggtggct cctacaaatg ccatcattgc gataaaggaa aggccatcgt tgaagatgcc 420
tctgccgaca gtggtcccaa agatggaccc ccacccacga ggagcatcgt ggaaaaagaa 480
gacgttccaa ccacgtcttc aaagcaagtg gattgatgtg atatctccac tgacgtaagg 540
gatgacgcac aatcccacta tccttcgcaa gacccttcct ctatataagg aagttcattt 600
catttggaga ggacacgctg acaagctgac tctagcagat cctctagaac catcttccac 660
acactcaagc cacactattg gagaacacac agggacaaca caccataaga tccaagggag 720
gcctccgccg ccgccggtaa ccaccccgcc cctctcctct ttctttctcc gttttttttt 780
ccgtctcggt ctcgatcttt ggccttggta gtttgggtgg gcgagaggcg gcttcgtgcg 840
cgcccagatc ggtgcgcggg aggggcggga tctcgcggct ggggctctcg ccggcgtgga 900
tccggcccgg atctcgcggg gaatggggct ctcggatgta gatctgcgat ccgccgttgt 960
tgggggagat gatggggggt ttaaaatttc cgccgtgcta aacaagatca ggaagagggg 1020
aaaagggcac tatggtttat atttttatat atttctgctg cttcgtcagg cttagatgtg 1080
ctagatcttt ctttcttctt tttgtgggta gaatttgaat ccctcagcat tgttcatcgg 1140
tagtttttct tttcatgatt tgtgacaaat gcagcctcgt gcggagcttt tttgtaggta 1200
gaag 1204

<210> SEQ ID NO 162
<211> LENGTH: 1396
<212> TYPE: DNA
<213> ORGANISM: Oryza sativa

<400> SEQUENCE: 162
tcgaggtcat tcatatgctt gagaagagag tcgggatagt ccaaaataaa acaaaggtaa 60
gattacctgg tcaaaagtga aaacatcagt taaaaggtgg tataaagtaa aatatcggta 120
ataaaaggtg gcccaaagtg aaatttactc ttttctacta ttataaaaat tgaggatgtt 180
tttgtcggta ctttgatacg tcatttttgt atgaattggt ttttaagttt attcgctttt 240
ggaaatgcat atctgtattt gagtcgggtt ttaagttcgt ttgcttttgt aaatacagag 300
ggatttgtat aagaaatatc tttagaaaaa cccatatgct aatttgacat aatttttgag 360
aaaaatatat attcaggcga attctcacaa tgaacaataa taagattaaa atagctttcc 420
cccgttgcag cgcatgggta ttttttctag taaaaataaa agataaactt agactcaaaa 480
catttacaaa aacaacccct aaagttccta aagcccaaag tgctatccac gatccatagc 540
aagcccagcc caacccaacc caacccagcc caccccagtc cagccaactg gacaatagtc 600
tccacacccc cccactatca ccgtgagttg tccgcacgca ccgcacgtct cgcagccaaa 660
aaaaaaaaga aagaaaaaaa agaaaaagaa aaaacagcag gtgggtccgg gtcgtggggg 720
ccggaaacgc gaggaggatc gcgagccagc gacgaggccg gccctccctc cgcttccaaa 780
gaaacgcccc ccatcgccac tatatacata ccccccccctc tcctcccatc cccccaaccc 840
taccaccacc accaccacca cctccacctc ctcccccctc gctgccggac gacgagctcc 900 tccccccctcc ccctccgccg ccgccgcgcc ggtaaccacc ccgcccctct cctctttctt 960
tctccgtttt tttttccgtc tcggtctcga tctttggcct tggtagtttg ggtgggcgag 1020

-continued

```
aggcggcttc gtgccgccca gatcggtgcg cgggaggggc gggatctcgc ggctggctct   1080

cgcccccgtg gatccggccc ggatctcgcg gggaatgggg ctctcggatg tagatctgcg   1140

atccgccgtt gttggggccg atgatggggc ccttaaaatt tccgccgtgc taaacaagat   1200

caggaagagg ggaaaagggc actatggttt atattttat atatttctgc tgcttcgtca    1260

ggcttagatg tgctagatct ttctttcttc tttttgtggg tagaatttaa tccctcagca   1320

ttgttcatcg gtagtttttc ttttcatgat tcgtgacaaa tgcagcctcg tgcggacgtt   1380

tttttgtagg tagaag                                                   1396
```

<210> SEQ ID NO 163
<211> LENGTH: 1446
<212> TYPE: DNA
<213> ORGANISM: Artificial sequence
<220> FEATURE:
<223> OTHER INFORMATION: Chimeric transcriptional regulatory expression element group.

<400> SEQUENCE: 163

```
ggtccgattg agacttttca acaaagggta atatccggaa acctcctcgg attccattgc     60

ccagctatct gtcactttat tgtgaagata gtggaaaagg aaggtggctc ctacaaatgc    120

catcattgcg ataaaggaaa ggccatcgtt gaagatgcct ctgccgacag tggtcccaaa    180

gatggacccc cacccacgag gagcatcgtg gaaaaagaag acgttccaac cacgtcttca    240

aagcaagtgg attgatgtga tggtccgatt gagacttttc aacaaagggt aatatccgga    300

aacctcctcg gattccattg cccagctatc tgtcacttta ttgtgaagat agtggaaaag    360

gaaggtggct cctacaaatg ccatcattgc gataaaggaa aggccatcgt tgaagatgcc    420

tctgccgaca gtggtcccaa agatggaccc ccacccacga ggagcatcgt ggaaaaagaa    480

gacgttccaa ccacgtcttc aaagcaagtg gattgatgtg atatctccac tgacgtaagg    540

gatgacgcac aatcccacta tccttcgcaa gacccttcct ctatataagg aagttcattt    600

catttggaga ggacacgctg acaagctgac tctagcagat ctaccgtctt cggtacgcgc    660

tcactccgcc ctctgccttt gttactgcca cgtttctctg aatgctctct tgtgtggtga    720

ttgctgagag tggtttagct ggatctagaa ttacactctg aaatcgtgtt ctgcctgtgc    780

tgattacttg ccgtcctttg tagcagcaaa atatagggac atggtagtac gaaacgaaga    840

tagaacctac acagcaatac gagaaatgtg taatttggtg cttagcggta tttatttaag    900

cacatgttgg tgttataggg cacttggatt cagaagtttg ctgttaattt aggcacaggc    960

ttcatactac atgggtcaat agtataggga ttcatattat aggcgatact ataataattt   1020

gttcgtctgc agagcttatt atttgccaaa attagatatt cctattctgt ttttgtttgt   1080

gtgctgttaa attgttaacg cctgaaggaa taaatataaa tgacgaaatt ttgatgttta   1140

tctctgctcc tttattgtga ccataagtca agatcagatg cacttgtttt aaatattgtt   1200

gtctgaagaa ataagtactg acagtatttt gatgcattga tctgcttgtt tgttgtaaca   1260

aaatttaaaa ataaagagtt tcctttttgt tgctctcctt acctcctgat ggtatctagt   1320

atctaccaac tgacactata ttgcttctct ttacatacgt atcttgctcg atgccttctc   1380

cctagtgttg accagtgtta ctcacatagt ctttgctcat ttcattgtaa tgcagatacc   1440

aagcgg                                                              1446
```

<210> SEQ ID NO 164
<211> LENGTH: 675

<212> TYPE: DNA
<213> ORGANISM: Artificial sequence
<220> FEATURE:
<223> OTHER INFORMATION: Chimeric transcriptional regulatory expression element group.

<400> SEQUENCE: 164
ggtccgatgt gagacttttc aacaaagggt aatatccgga aacctcctcg gattccattg 60
cccagctatc tgtcacttta ttgtgaagat agtggaaaag gaaggtggct cctacaaatg 120
ccatcattgc gataaaggaa aggccatcgt tgaagatgcc tctgccgaca gtggtcccaa 180
agatggaccc ccacccacga ggagcatcgt ggaaaaagaa gacgttccaa ccacgtcttc 240
aaagcaagtg gattgatgtg atggtccgat gtgagacttt tcaacaaagg gtaatatccg 300
gaaacctcct cggattccat tgcccagcta tctgtcactt tattgtgaag atagtggaaa 360
aggaaggtgg ctcctacaaa tgccatcatt gcgataaagg aaaggccatc gttgaagatg 420
cctctgccga cagtggtccc aaagatggac ccccacccac gaggagcatc gtggaaaaag 480
aagacgttcc aaccacgtct tcaaagcaag tggattgatg tgatatctcc actgacgtaa 540
gggatgacgc acaatcccac tatccttcgc aagacccttc ctctatataa ggaagttcat 600
ttcatttgga gaggaaccat cttccacaca ctcaagccac actattggag aacacacagg 660
gacaacacac cataa 675

<210> SEQ ID NO 165
<211> LENGTH: 804
<212> TYPE: DNA
<213> ORGANISM: Zea mays

<400> SEQUENCE: 165
accgtcttcg gtacgcgctc actccgccct ctgcctttgt tactgccacg tttctctgaa 60
tgctctcttg tgtggtgatt gctgagagtg gtttagctgg atctagaatt acactctgaa 120
atcgtgttct gcctgtgctg attacttgcc gtcctttgta gcagcaaaat atagggacat 180
ggtagtacga aacgaagata gaacctacac agcaatacga gaaatgtgta atttggtgct 240
tagcggtatt tatttaagca catgttggtg ttatagggca cttggattca gaagtttgct 300
gttaatttag gcacaggctt catactacat gggtcaatag tatagggatt catattatag 360
gcgatactat aataatttgt tcgtctgcag agcttattat ttgccaaaat tagatattcc 420
tattctgttt ttgtttgtgt gctgttaaat tgttaacgcc tgaaggaata aatataaatg 480
acgaaatttt gatgtttatc tctgctcctt tattgtgacc ataagtcaag atcagatgca 540
cttgttttaa atattgttgt ctgaagaaat aagtactgac agtattttga tgcattgatc 600
tgcttgtttg ttgtaacaaa atttaaaaat aaagagtttc ctttttgttg ctctccttac 660
ctcctgatgg tatctagtat ctaccaactg acactatatt gcttctcttt acatacgtat 720
cttgctcgat gccttctccc tagtgttgac cagtgttact cacatagtct ttgctcattt 780
cattgtaatg cagataccaa gcgg 804

<210> SEQ ID NO 166
<211> LENGTH: 623
<212> TYPE: DNA
<213> ORGANISM: Cauliflower mosaic virus

<400> SEQUENCE: 166
ggtccgatgt gagacttttc aacaaagggt aatatccgga aacctcctcg gattccattg 60
cccagctatc tgtcacttta ttgtgaagat agtggaaaag gaaggtggct cctacaaatg 120
ccatcattgc gataaaggaa aggccatcgt tgaagatgcc tctgccgaca gtggtcccaa 180
agatggaccc ccacccacga ggagcatcgt ggaaaaagaa gacgttccaa ccacgtcttc 240
aaagcaagtg gattgatgtg atggtccgat gtgagacttt tcaacaaagg gtaatatccg 300
gaaacctcct cggattccat tgcccagcta tctgtcactt tattgtgaag atagtggaaa 360
aggaaggtgg ctcctacaaa tgccatcatt gcgataaagg aaaggccatc gttgaagatg 420
cctctgccga cagtggtccc aaagatggac ccccacccac gaggagcatc gtggaaaaag 480
aagacgttcc aaccacgtct tcaaagcaag tggattgatg tgatatctcc actgacgtaa 540
gggatgacgc acaatcccac tatccttcgc aagacccttc ctctatataa ggaagttcat 600
ttcatttgga gaggacacgc tga 623

<210> SEQ ID NO 167
<211> LENGTH: 8
<212> TYPE: DNA
<213> ORGANISM: Cauliflower mosaic virus

<400> SEQUENCE: 167 acacgctg 8

<210> SEQ ID NO 168
<211> LENGTH: 1790
<212> TYPE: DNA
<213> ORGANISM: Coix lacryma-jobi

<400> SEQUENCE: 168
gtgatgttca agatattgta atggtgttta ttttctatca aatagccata aaatgatata 60
caaaatgtta ttcatgattg atcctagtta cattcaaagt attaaatagc ttgcagatag 120
taaatagaca gtcattgtat aacctgtttt tttgactgtc tatgttcagt tccaagaact 180
tacagacaag aggttatgtg tagattgaac gtgcccttga cggcatccaa ctagcgaacc 240
acgagggaag cagatggtgg ccgttgaggg gctgttgacg caaagcatct ctctcggctg 300
ctctcgaaag ctccattgcg ggtggcggtc tggtggcacc aggaaattgc gtgagccaag 360
gcgggctcgt ctcggtctca caacacggca cgaaaccgtc acggcacacg gcaccaggat 420
ttccttcccc tcccctgccg ttctcctcat cataaatagc cacccccctcc tcgcctcttt 480 tccccaactc atctgttctt cgtctcacac agccagatcc caatccctct cctcgcgaac 540
ttcgtcgatc tcccttccct cgcctcgctt caaggtacgg cgatcatcct cccgctttcc 600
ctcctcctcc tctagatgta gtacggagta cttgccatca tgcatcatgc tacatcacgc 660
tcgtgcgagc tctgggtcct cgatctggga acggaactgt gggatgctgc tcgtgcgatt 720
tattattggg gatctgggtt ctcgatctgg gaacggaact gtgggatgct gctcgtgcga 780
tttattattg gggatctggg ttctcgatct gggaacggaa ctgtgggatg cttgtaggca 840
ggtcggagat gggtcggatc gttgcttagg gttcgatctg ctcgtggttt tcttttaatc 900
cctgatgcat gatttatcgg tcatcctatt agatggaacc agtagggtga ctctgatccg 960
atatacttaa cctcgatctg gttcgatgtt cctggctagg cttgtgcgtc tgtttcgtca 1020
gaccagtttt gctgtttttg gtatggttgt gatgcccgtc caaatatgac taagcgagtg 1080
tagaatcatt ttatgaacta actgctggtc ttattaaatc tagatctgca tacgttgatg 1140
tactacgttc atagttgata cagtatgtat gaactagttg ctggtcgtat taattttgga 1200
tctgcatgtg tggtagcata taatgttcat aatacaattg atacagtatg atgtatgaac 1260

```
tatctgctgg tttattaaat ttggatctgc ttgtggtaaa aaatatgttt tttatatagt   1320

taccatgatg gattaatcta tacttctgat gtatatgctg cagttttctg ctgaggctgt   1380

agttttttcc agattaaaat acagcatgca tatttgctaa gctctgggcg tgtgaacgcc   1440

caccatggca ttgtccagta atagtaatga atttttttgt ttgcctgatg tgggagaaaa   1500

cacgcattgt ccagttattt tgttccatat gcattgtcct gttttgttgg atatgcatgc   1560

ttagaaaaca tatgcagcca ctgtttgata atgctttagc atctgcctgt tgaacatgca   1620

tgatctacct atctttattt tgtatgtact tgggtagtgg catgttgcta gttttccttg   1680

attctgtggc gtctacatgt tgagcttgca tatatgtttg ttgtccttct tttcctcctt   1740

ggtctactgc tatatgctta cccttttgtt tggctaattt tcaggtgcag              1790
```

<210> SEQ ID NO 169
<211> LENGTH: 481
<212> TYPE: DNA
<213> ORGANISM: Coix lacryma-jobi

<400> SEQUENCE: 169

```
gtgatgttca agatattgta atggtgttta ttttctatca aatagccata aaatgatata     60

caaaatgtta ttcatgattg atcctagtta cattcaaagt attaaatagc ttgcagatag    120

taaatagaca gtcattgtat aacctgtttt tttgactgtc tatgttcagt tccaagaact    180

tacagacaag aggttatgtg tagattgaac gtgcccttga cggcatccaa ctagcgaacc    240

acgagggaag cagatggtgg ccgttgaggg gctgttgacg caaagcatct ctctcggctg    300

ctctcgaaag ctccattgcg ggtggcggtc tggtggcacc aggaaattgc gtgagccaag    360

gcgggctcgt ctcggtctca caacacggca cgaaaccgtc acggcacacg gcaccaggat    420

ttccttcccc tcccctgccg ttctcctcat cataaatagc cacccccctcc tcgcctcttt    480

t                                                                    481
```

<210> SEQ ID NO 170
<211> LENGTH: 93
<212> TYPE: DNA
<213> ORGANISM: Coix lacryma-jobi

<400> SEQUENCE: 170

```
ccccaactca tctgttcttc gtctcacaca gccagatccc aatccctctc ctcgcgaact     60

tcgtcgatct cccttccctc gcctcgcttc aag                                  93
```

<210> SEQ ID NO 171
<211> LENGTH: 1216
<212> TYPE: DNA
<213> ORGANISM: Coix lacryma-jobi

<400> SEQUENCE: 171

```
gtacggcgat catcctcccg ctttccctcc tcctcctcta gatgtagtac ggagtacttg     60

ccatcatgca tcatgctaca tcacgctcgt gcgagctctg ggtcctcgat ctgggaacgg    120

aactgtggga tgctgctcgt gcgatttatt attggggatc tgggttctcg atctgggaac    180

ggaactgtgg gatgctgctc gtgcgattta ttattgggga tctgggttct cgatctggga    240

acggaactgt gggatgcttg taggcaggtc ggagatgggt cggatcgttg cttagggttc    300

gatctgctcg tggttttctt ttaatccctg atgcatgatt tatcggtcat cctattagat    360

ggaaccagta gggtgactct gatccgatat acttaacctc gatctggttc gatgttcctg    420

gctaggcttg tgcgtctgtt tcgtcagacc agttttgctg tttttggtat ggttgtgatg    480
```

-continued

```
cccgtccaaa tatgactaag cgagtgtaga atcattttat gaactaactg ctggtcttat    540

taaatctaga tctgcatacg ttgatgtact acgttcatag ttgatacagt atgtatgaac    600

tagttgctgg tcgtattaat tttggatctg catgtgtggt agcatataat gttcataata    660

caattgatac agtatgatgt atgaactatc tgctggttta ttaaatttgg atctgcttgt    720

ggtaaaaaat atgtttttta tatagttacc atgatggatt aatctatact tctgatgtat    780

atgctgcagt tttctgctga ggctgtagtt ttttccagat taaaatacag catgcatatt    840

tgctaagctc tgggcgtgtg aacgcccacc atggcattgt ccagtaatag taatgaattt    900

ttttgtttgc ctgatgtggg agaaaacacg cattgtccag ttattttgtt ccatatgcat    960

tgtcctgttt tgttggatat gcatgcttag aaaacatatg cagccactgt ttgataatgc   1020

tttagcatct gcctgttgaa catgcatgat ctacctatct ttattttgta tgtacttggg   1080

tagtggcatg ttgctagttt tccttgattc tgtggcgtct acatgttgag cttgcatata   1140

tgtttgttgt ccttcttttc ctccttggtc tactgctata tgcttaccct tttgtttggc   1200

taattttcag gtgcag                                                   1216
```